United States Patent
Zhao et al.

(10) Patent No.: US 11,920,130 B2
(45) Date of Patent: Mar. 5, 2024

(54) MODIFIED IMMUNE CELLS HAVING ENHANCED FUNCTION AND METHODS FOR SCREENING FOR SAME

(71) Applicant: THE TRUSTEES OF THE UNIVERSITY OF PENNSYLVANIA, Philadelphia, PA (US)

(72) Inventors: Yangbing Zhao, Lumberton, NJ (US); Jiangtao Ren, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 135 days.

(21) Appl. No.: 17/743,183

(22) Filed: May 12, 2022

(65) Prior Publication Data

US 2023/0032532 A1 Feb. 2, 2023

Related U.S. Application Data

(62) Division of application No. 16/365,326, filed on Mar. 26, 2019, now Pat. No. 11,447,769.

(60) Provisional application No. 62/648,722, filed on Mar. 27, 2018.

(51) Int. Cl.
| | | |
|---|---|---|
| *C12N 15/11* | (2006.01) | |
| *C12N 5/0783* | (2010.01) | |
| *C12N 9/22* | (2006.01) | |
| *C12N 15/10* | (2006.01) | |

(52) U.S. Cl.
CPC ............ *C12N 15/11* (2013.01); *C12N 5/0636* (2013.01); *C12N 9/22* (2013.01); *C12N 15/1082* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 11,203,758 B2 | 12/2021 | Zhao |
| 2015/0275209 A1 | 10/2015 | Ji |
| 2016/0272999 A1 | 9/2016 | Duchateau |
| 2017/0253933 A1 | 9/2017 | Wang |

FOREIGN PATENT DOCUMENTS

| | | |
|---|---|---|
| WO | 2017069958 | 4/2017 |
| WO | 2018035387 | 2/2018 |
| WO | 2018048828 | 3/2018 |
| WO | 2018049025 | 3/2018 |

OTHER PUBLICATIONS

Ren et al., "Multiplex genome editing to generate universal CAR T cells resistant to PD1 inhibition", Clin Cancer Res. May 1, 2017, 23(9), 2255-2266.
Pauken et al., "Epigenetic stability of exhausted T cells limits durability of reinvigoration by PD-1 blockade", Science, Dec. 2, 2016, 354, 6316, 1160-1165.
International Search Report dated Sep. 13, 2019 for International Application No. PCT/US2019/024096.
Supplementary European Search Report dated Oct. 29, 2021 for European Application No. 19774693.6.

*Primary Examiner* — Suzanne M Noakes
*Assistant Examiner* — Jae W Lee
(74) *Attorney, Agent, or Firm* — Saul Ewing LLP; Kathryn Doyle

(57) ABSTRACT

The present disclosure provides gene edited modified immune cells or precursors thereof (e.g., gene edited modified T cells) comprising an exogenous T cell receptor (TCR) and/or a chimeric antigen receptor (CAR) having specificity for a target antigen, and an insertion and/or deletion in one or more endogenous gene loci, wherein the endogenous gene loci encode regulators of T cell function, thereby resulting in immune cells having enhanced function. Compositions and methods of treatment are also provided. The present invention provides methods of screening for TCR- or CAR-T cells with enhanced immune function (e.g., T cell efficacy, T cell memory, and/or T cell persistence).

19 Claims, 52 Drawing Sheets

Specification includes a Sequence Listing.

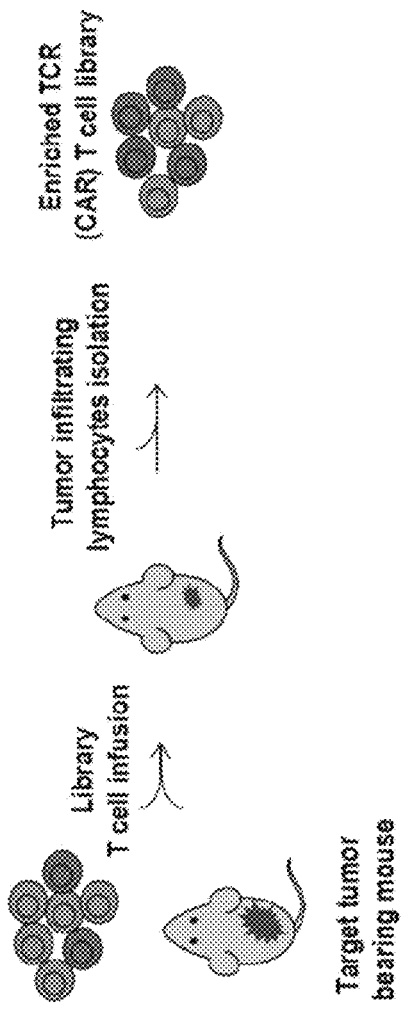
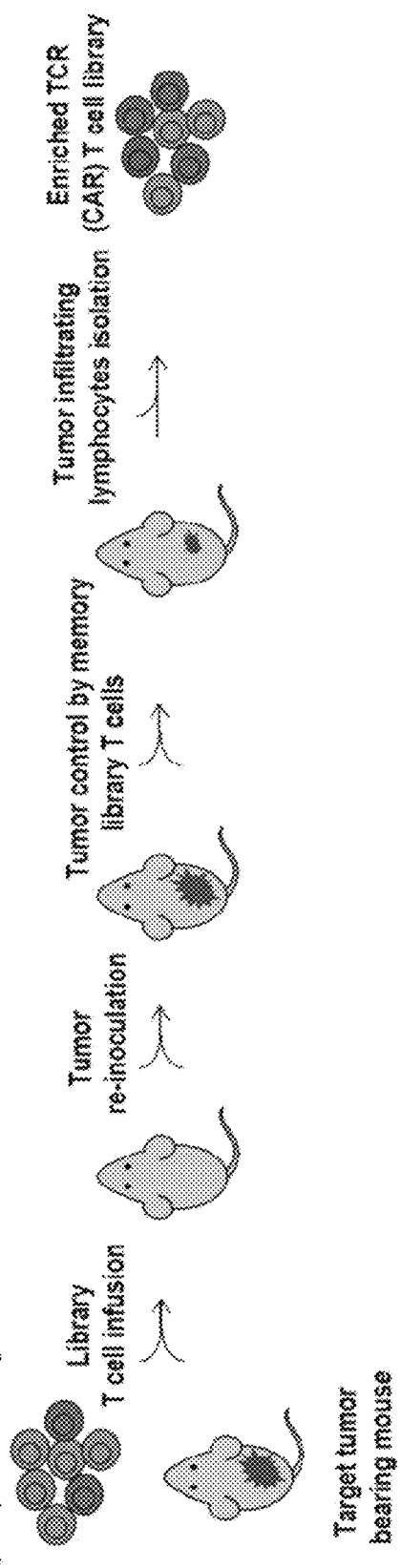

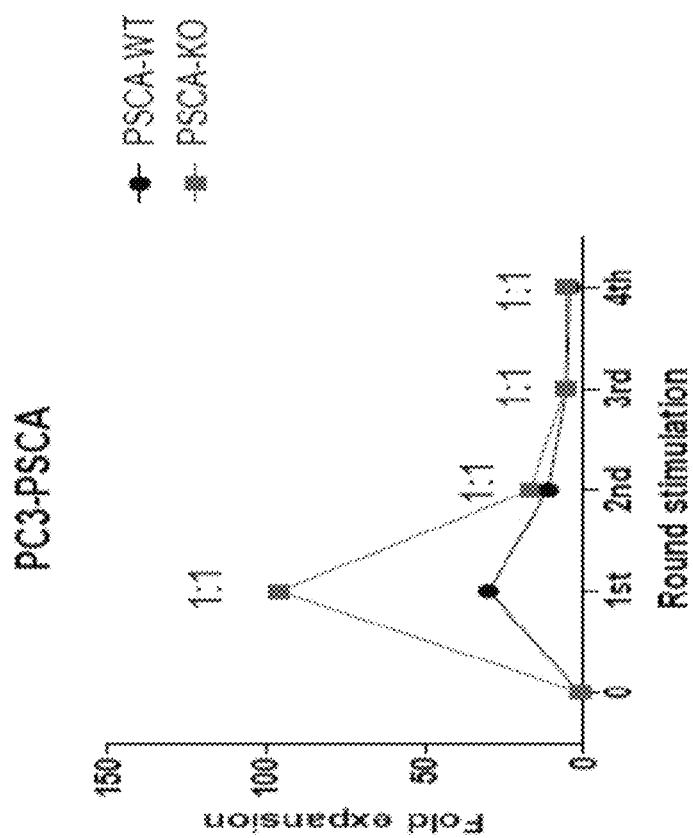
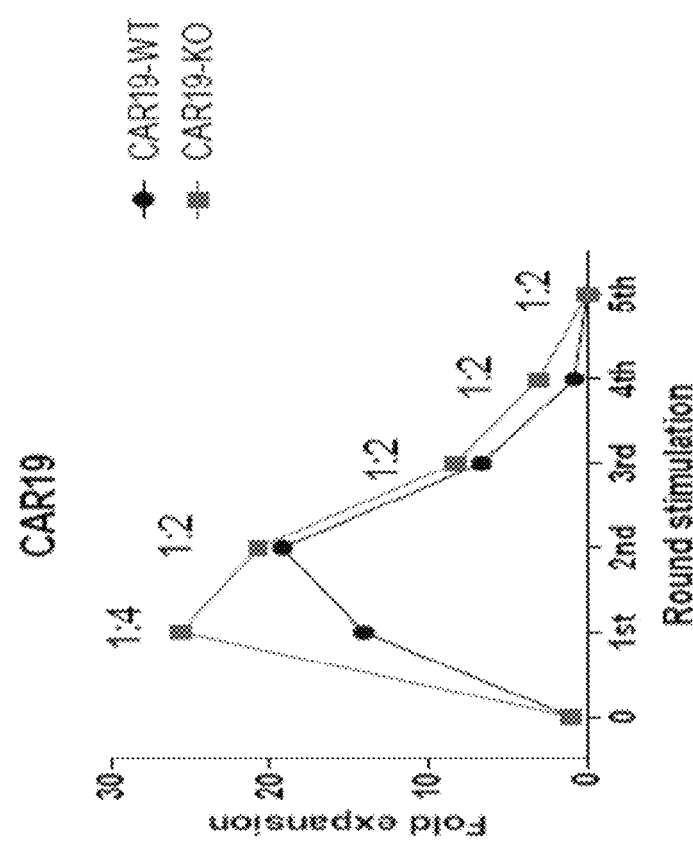

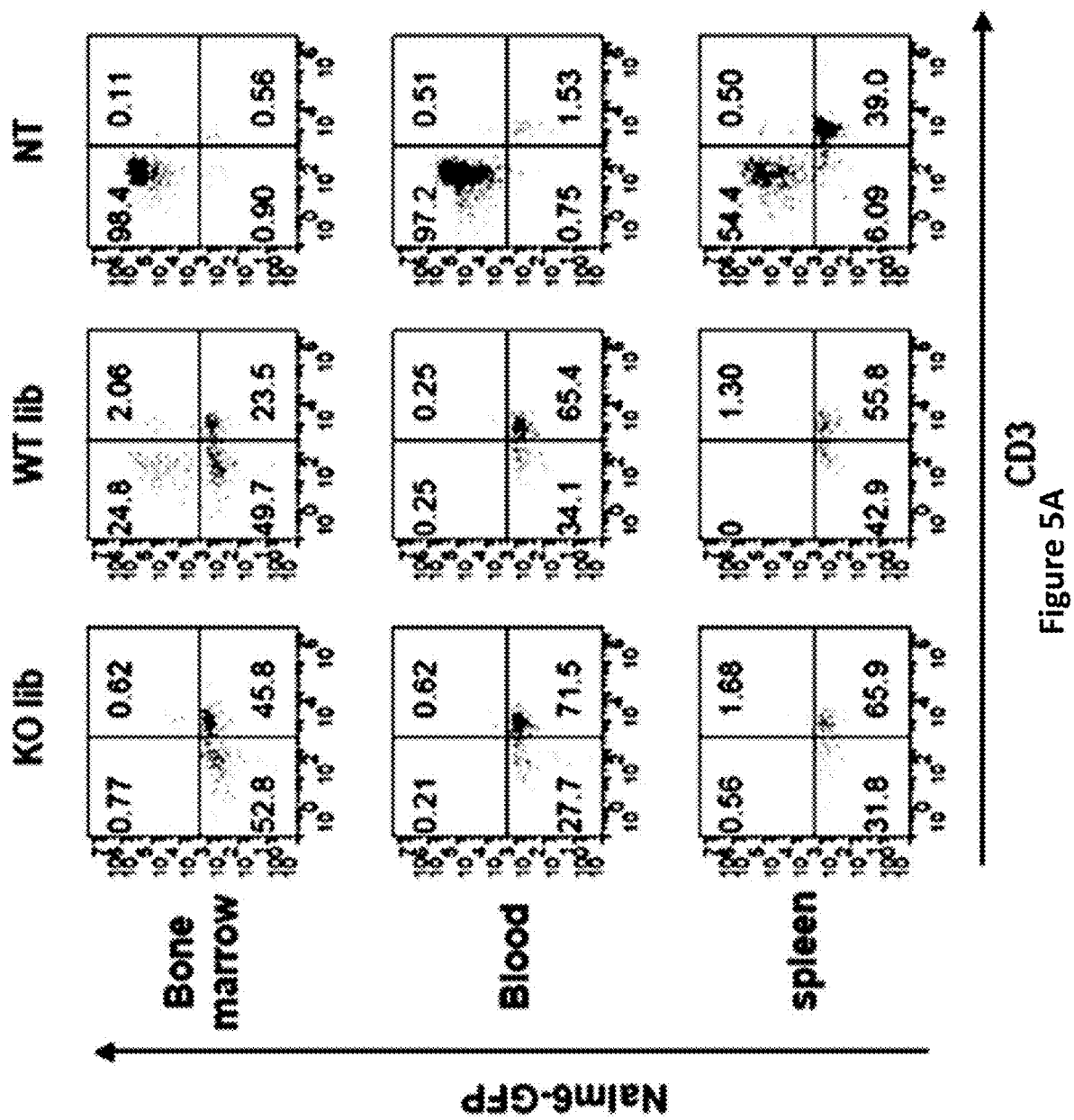

Figure 7

| TOP Genes | |
|---|---|
| Signal transduction | 5 |
| Metabolism | 4 |
| Cell-cell contact | 3 |
| Cell cycle regulation | 3 |
| Mitochondria | 3 |
| Transmembrane transport | 3 |
| Cytoskeleton maintanance | 3 |
| Programmed cell death | 2 |
| Gene expression regulation | 2 |
| Autoantigen | 1 |
| Immunosenescence | 1 |
| Metabolism of protein | 1 |
| Total | 31 |

| Enriched gRNA mapped Genes | |
|---|---|
| 5~20 folds | 200 |
| 10~20 folds | 30 |
| 20~40 folds | 7 |
| 40~80 folds | 2 |
| >80 folds | 1 |
| Total | 240 |

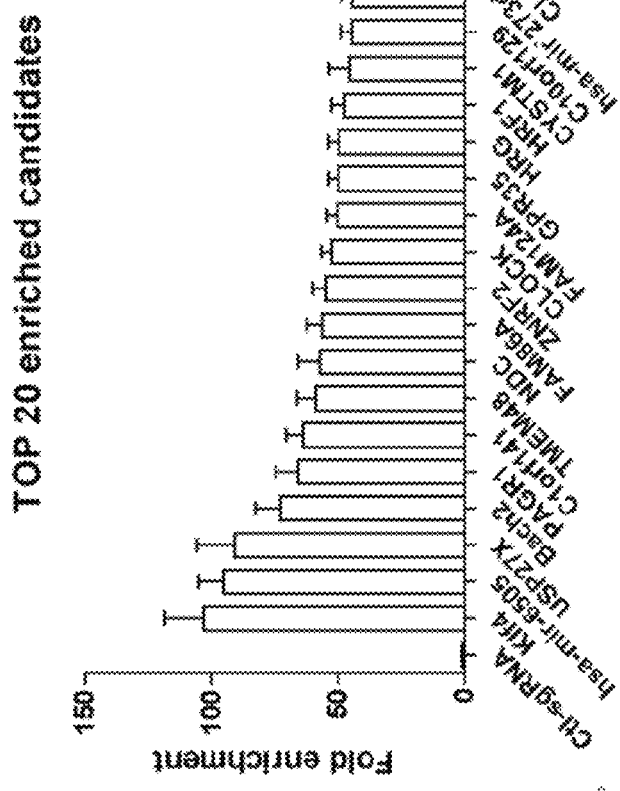
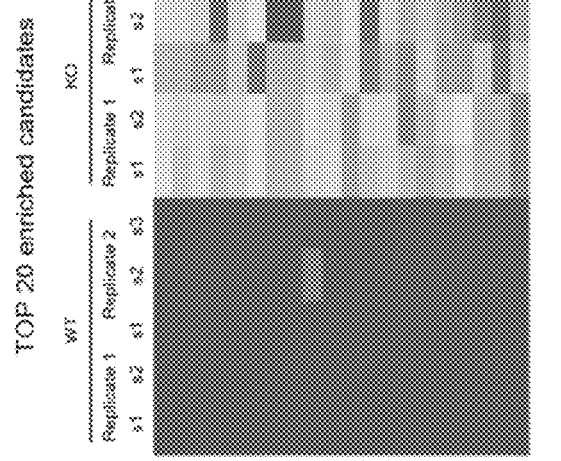

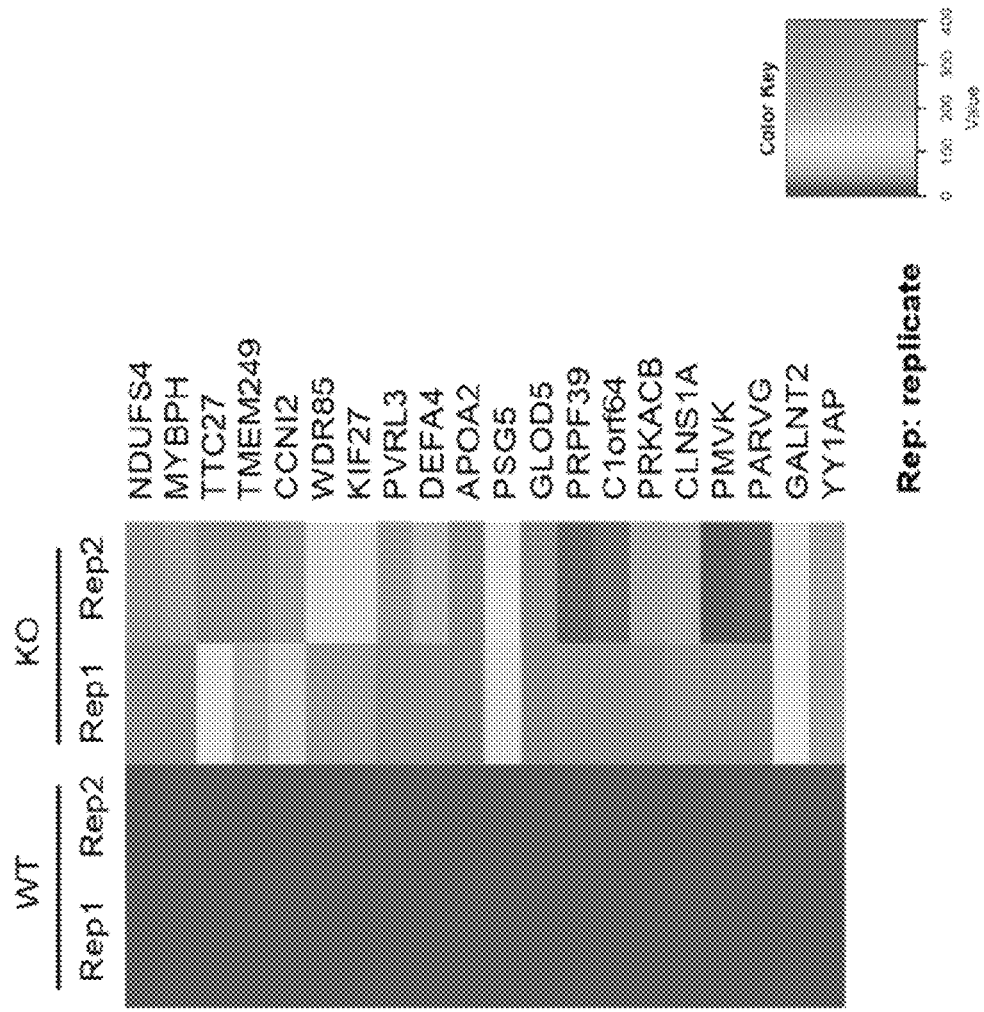

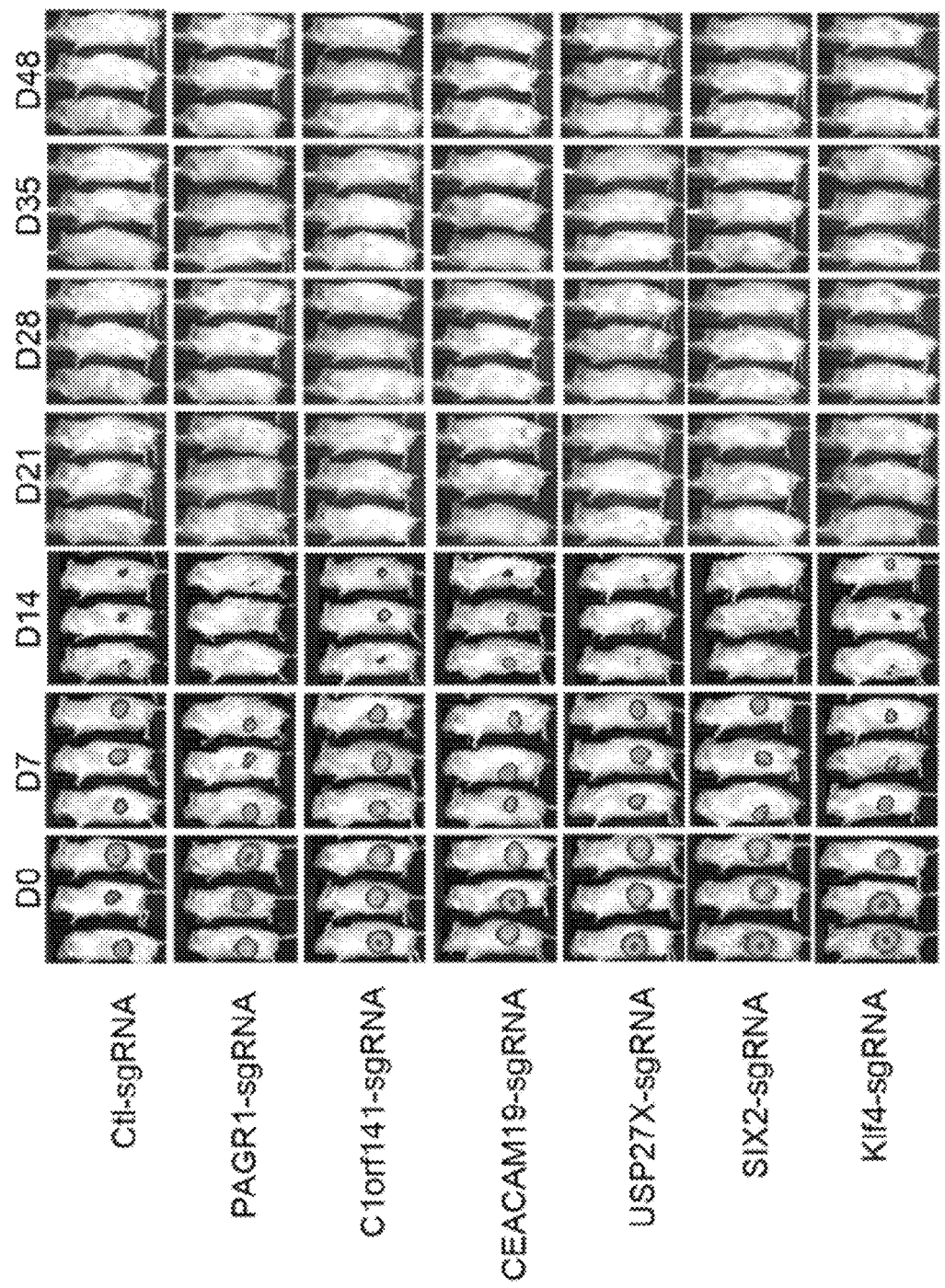

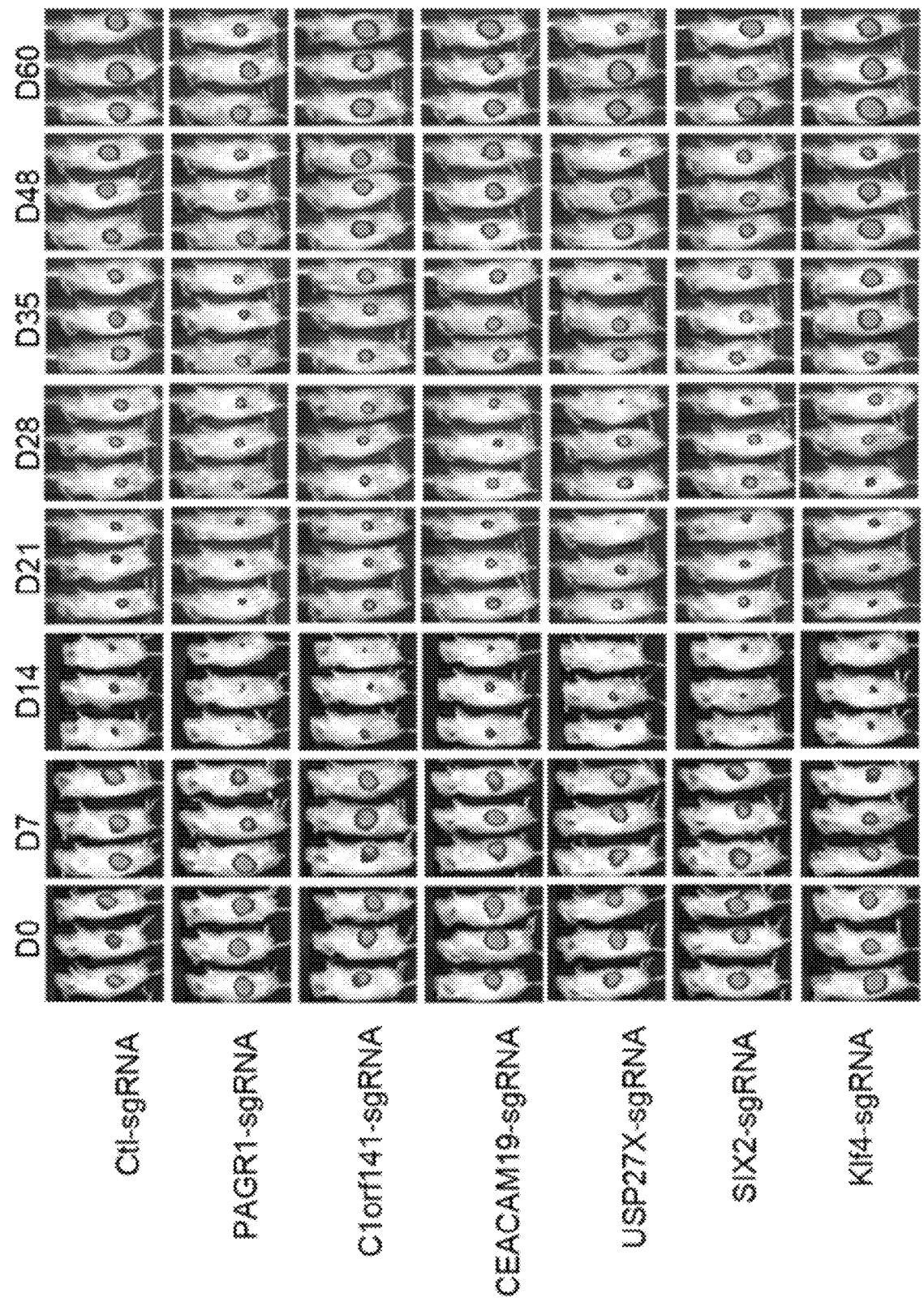
Figure 13.A

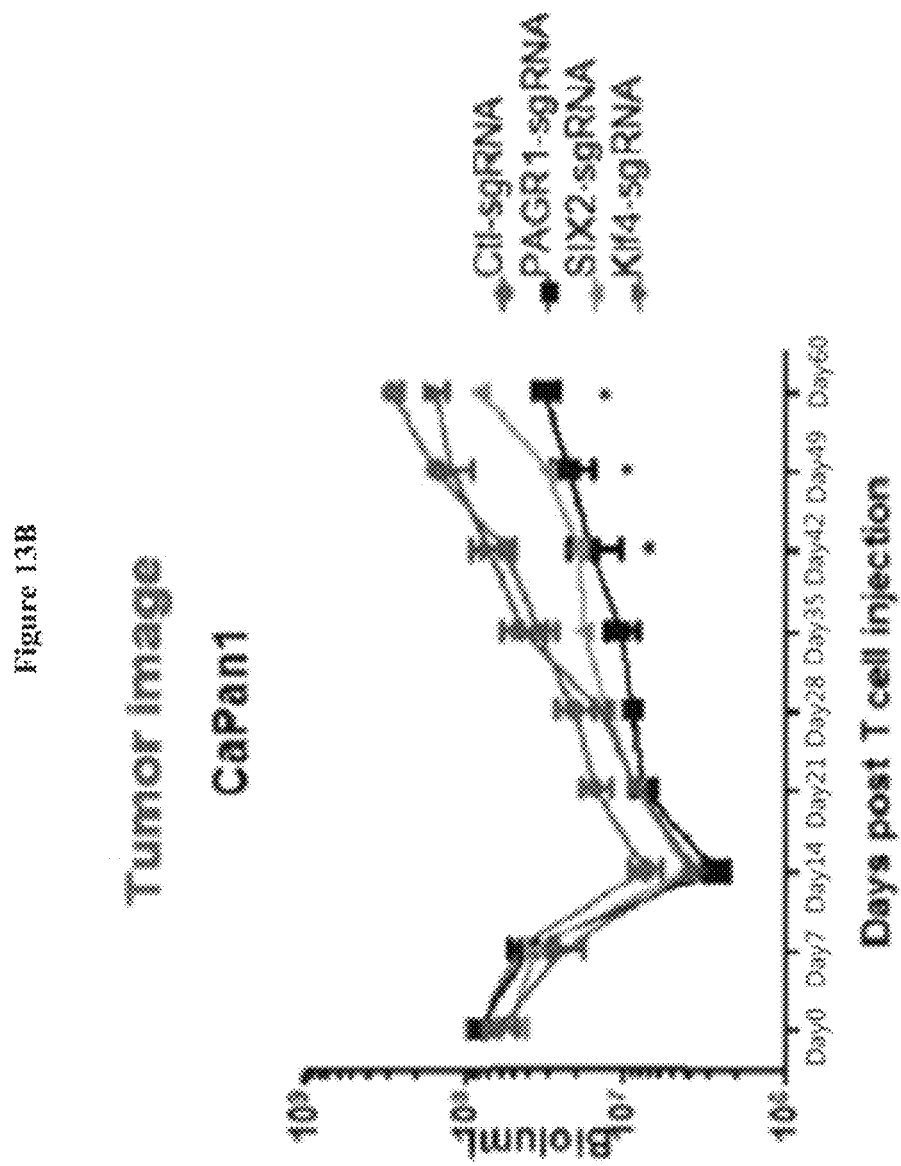

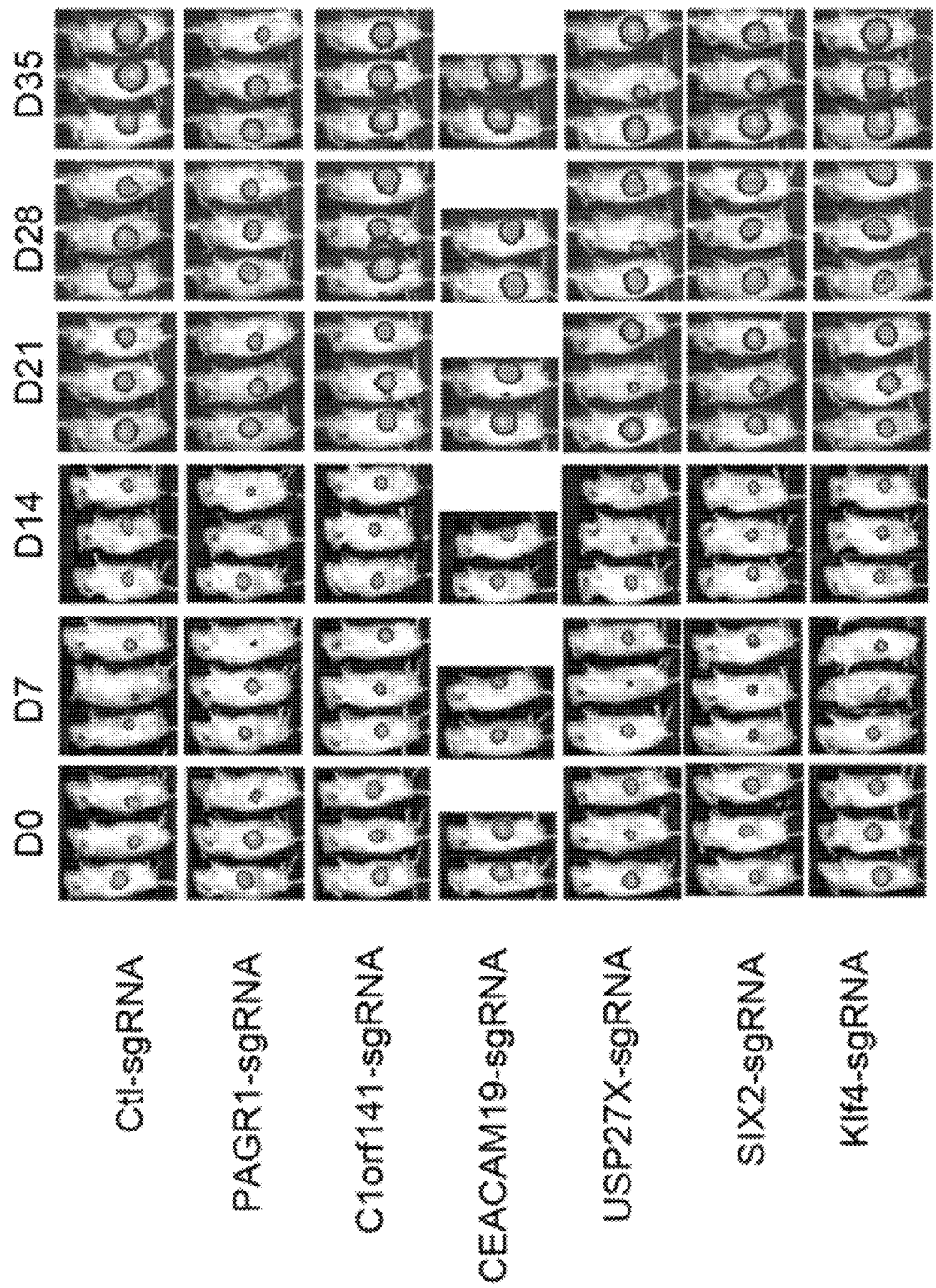

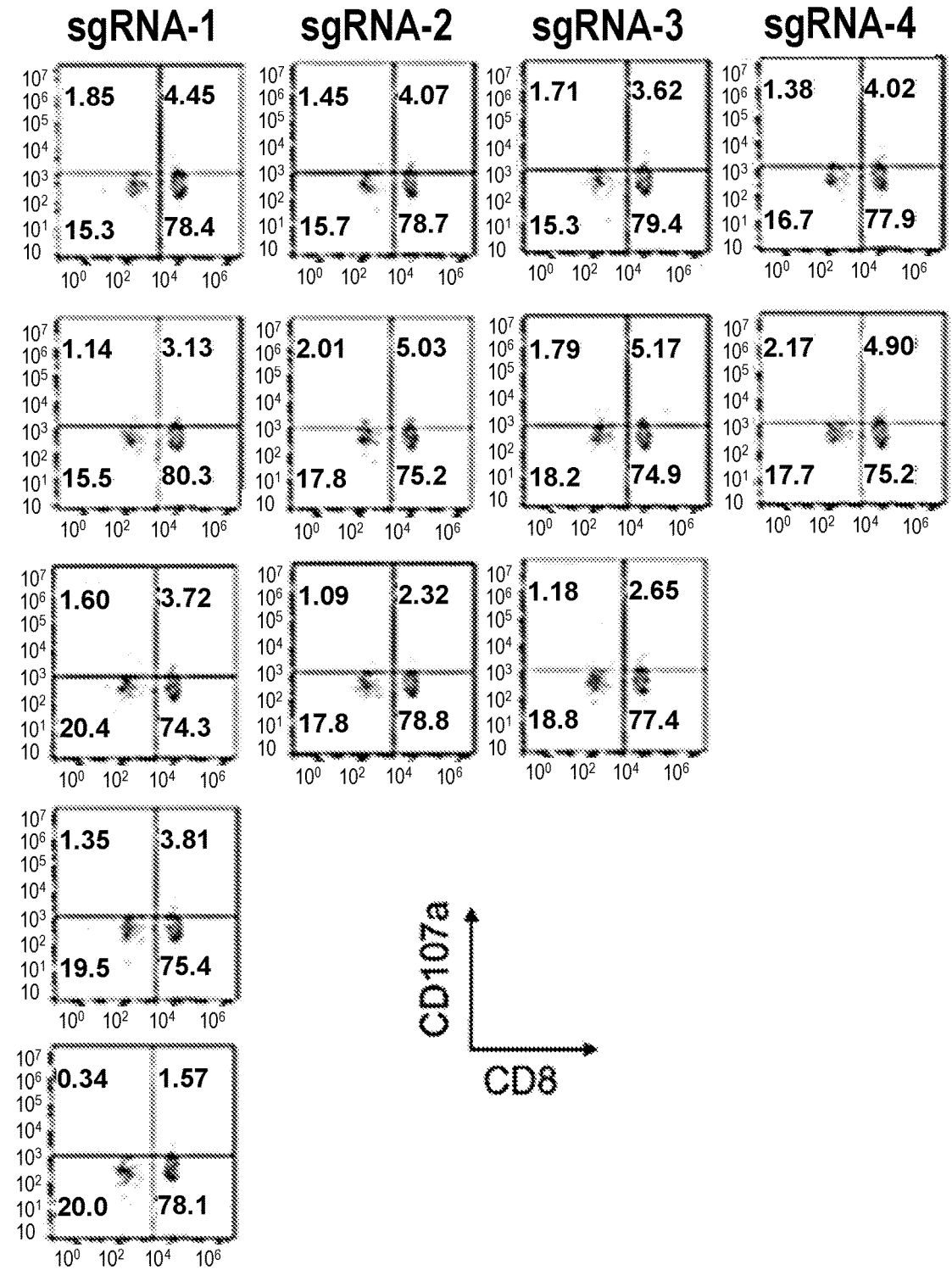
Figure 15A, continued

Tumor Volume
PC3-PSCA

Tumor Image
PC3-PSCA

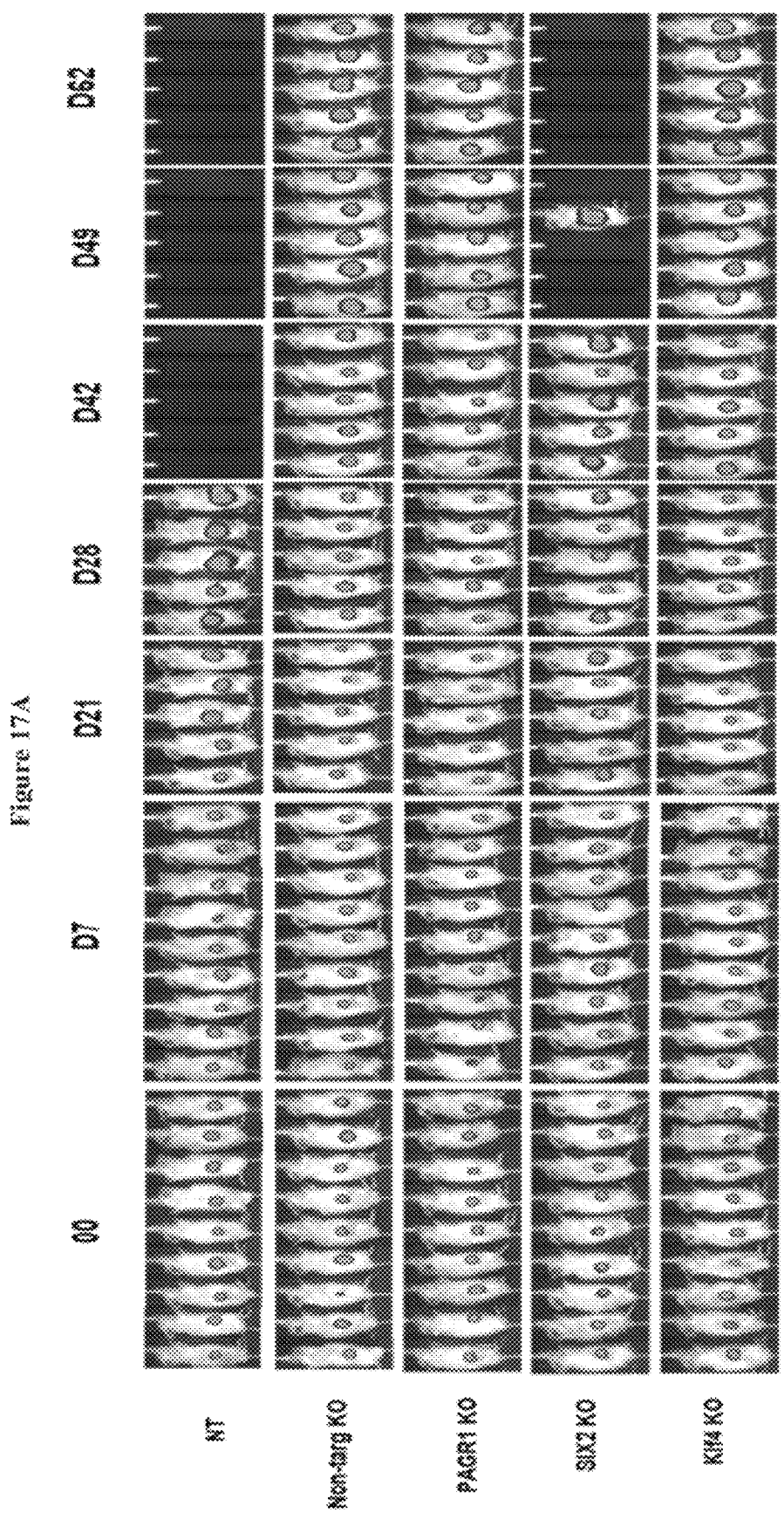

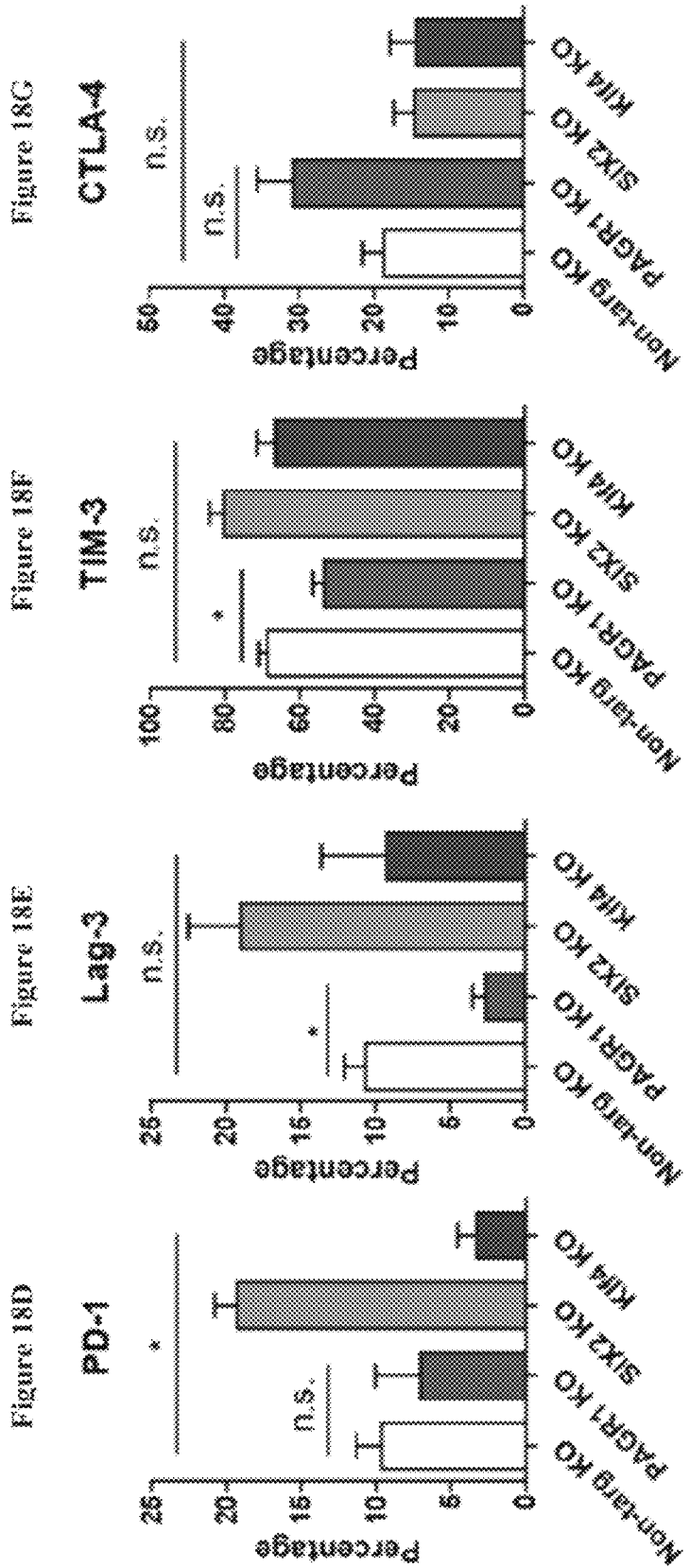

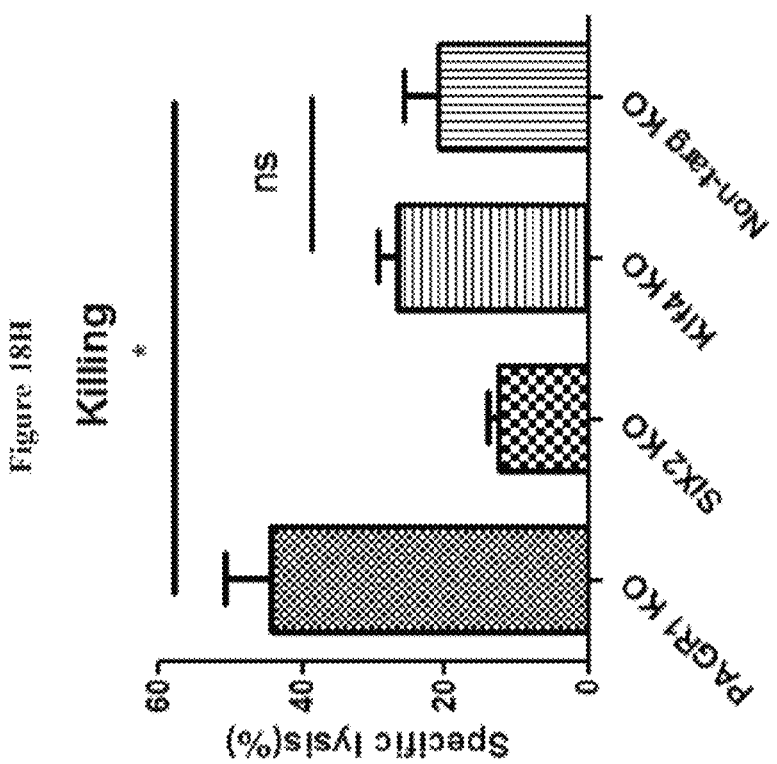

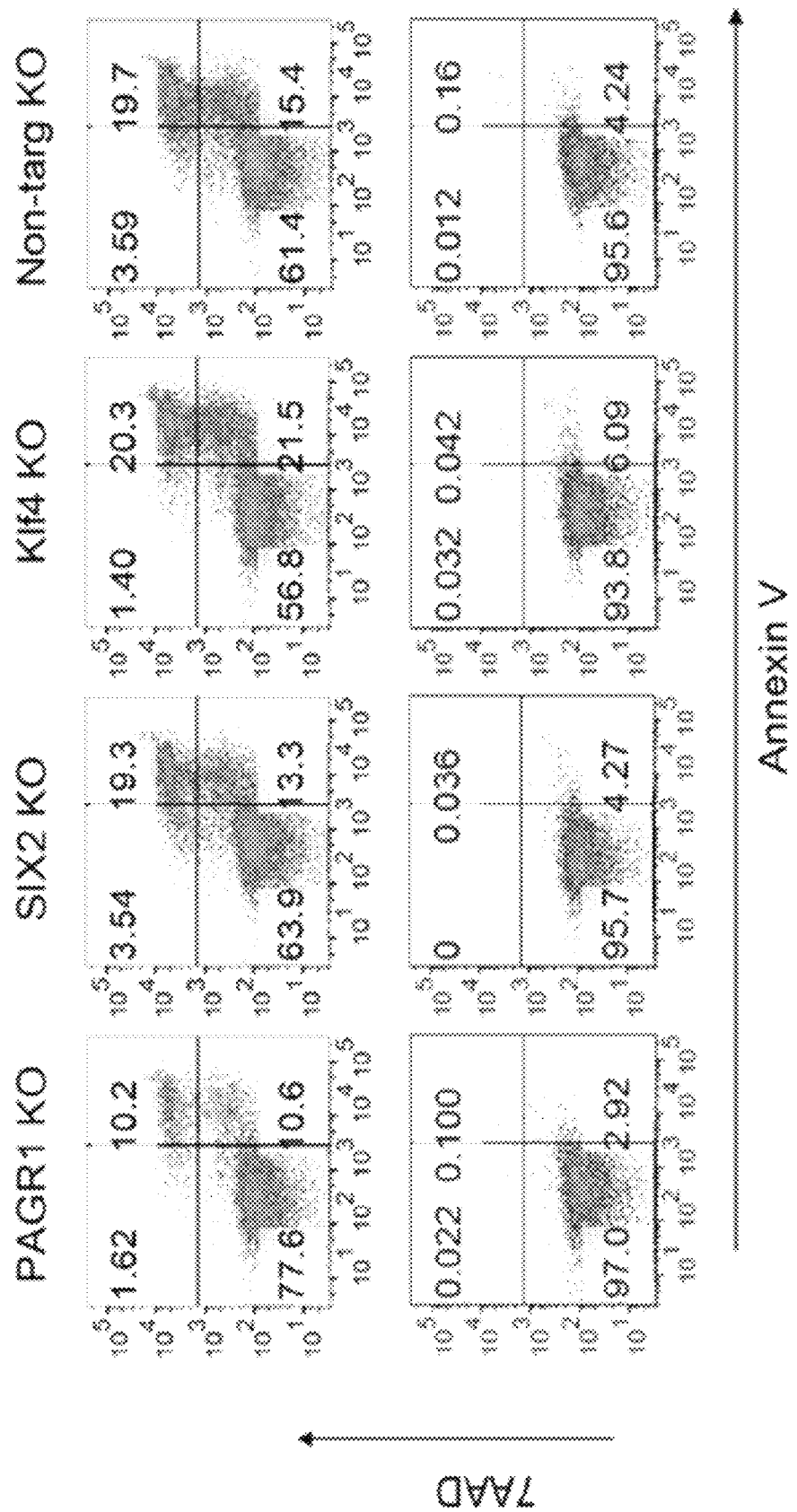

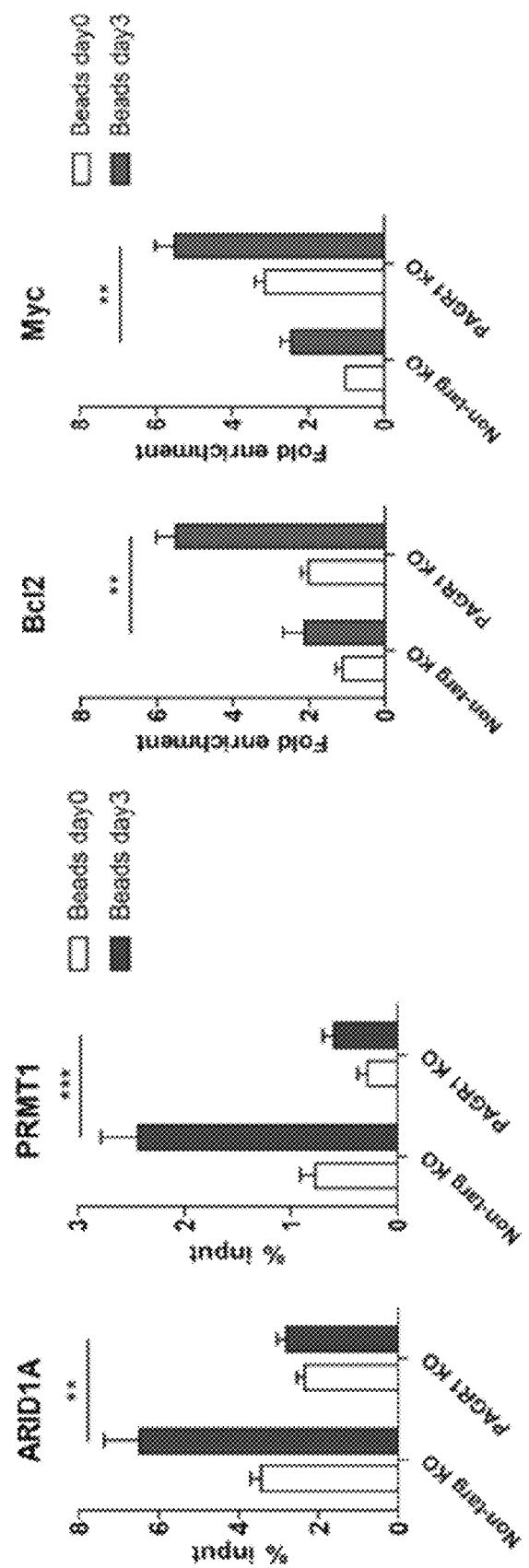

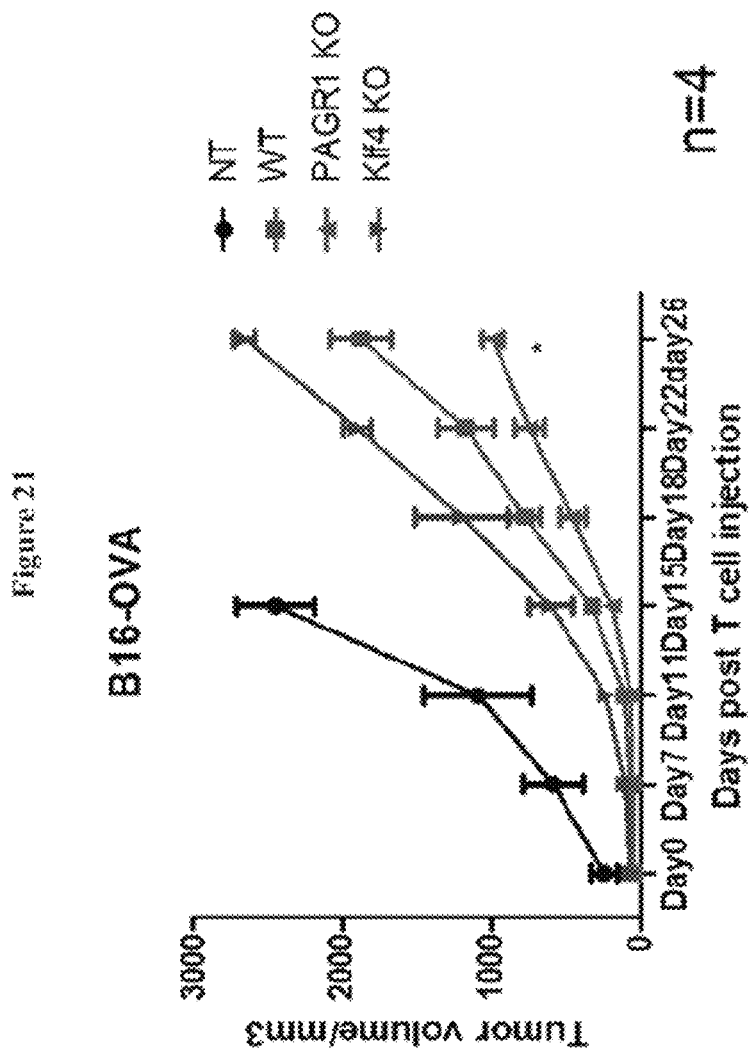

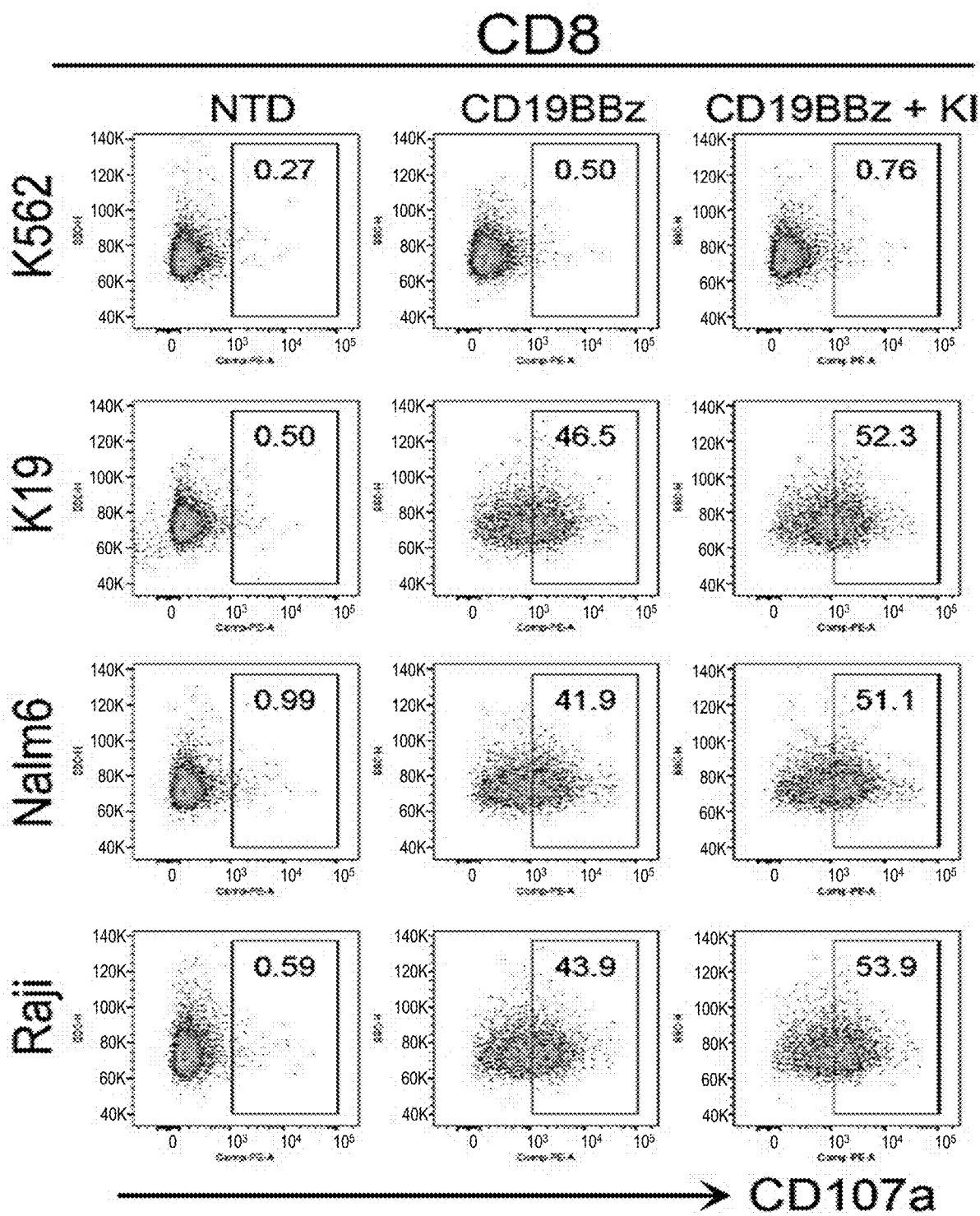
Figure 28, continued

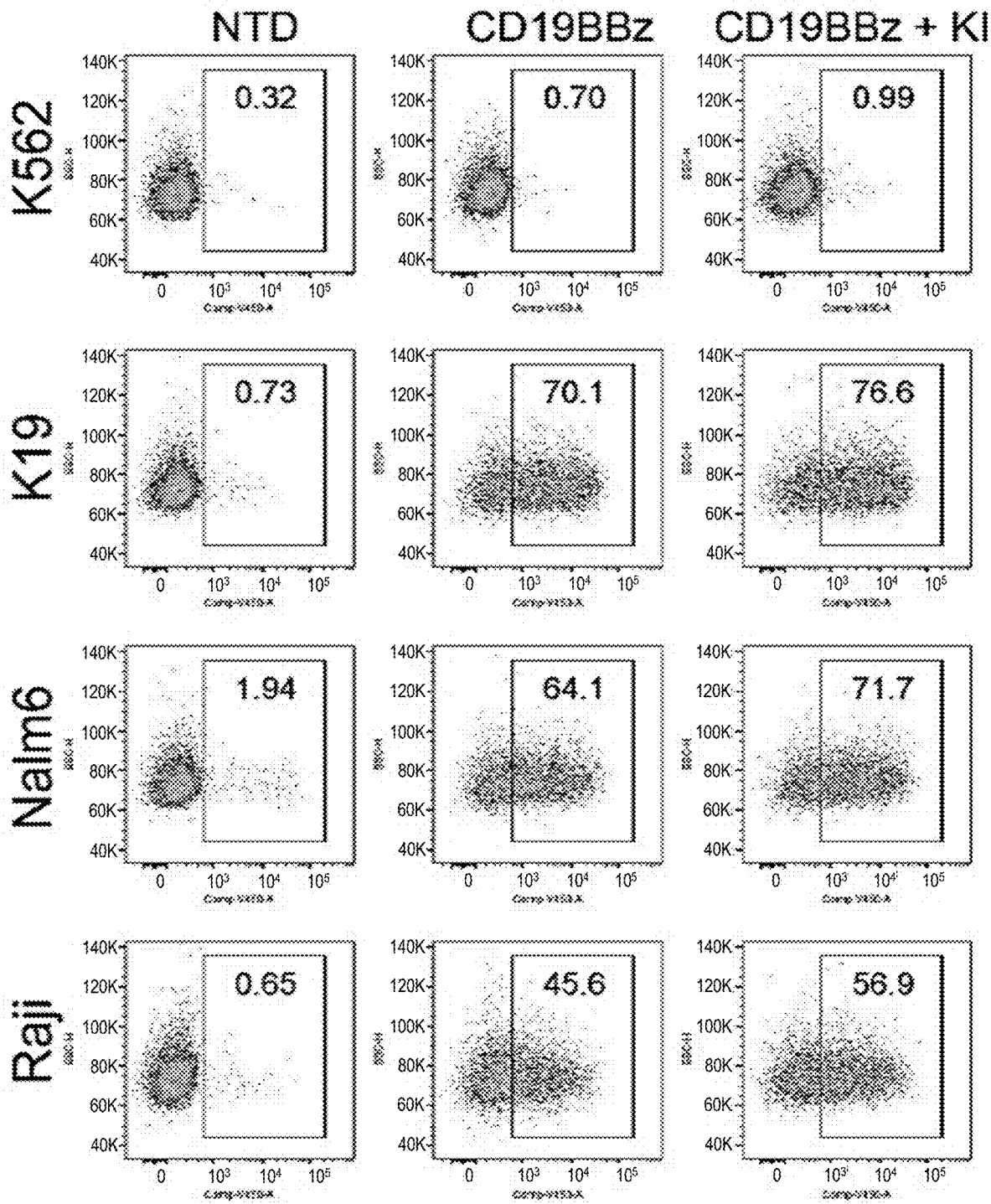
Figure 29, continued

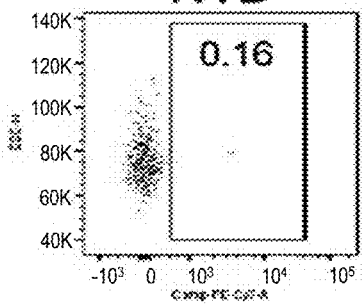
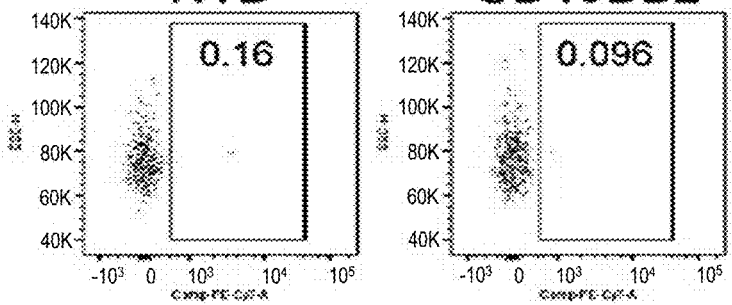
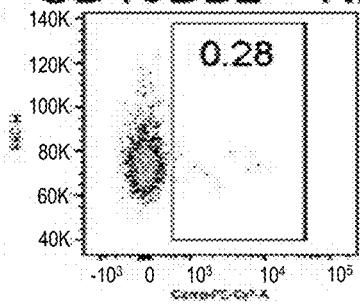
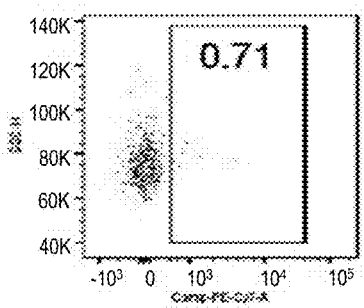
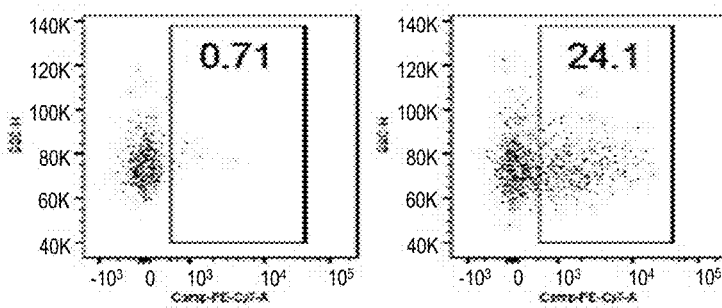
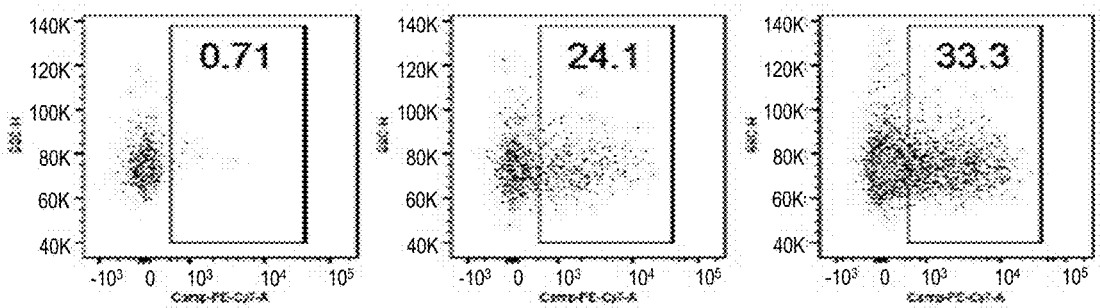
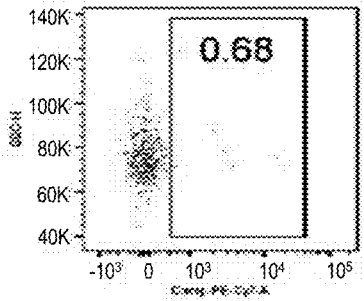
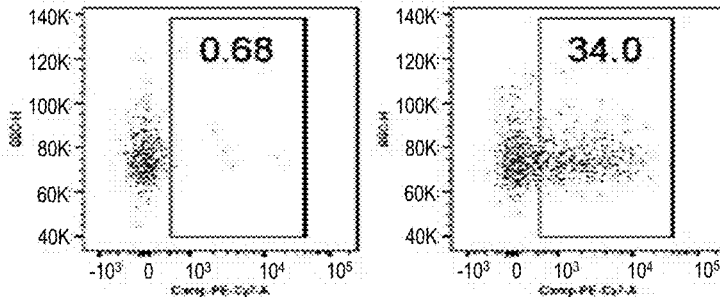
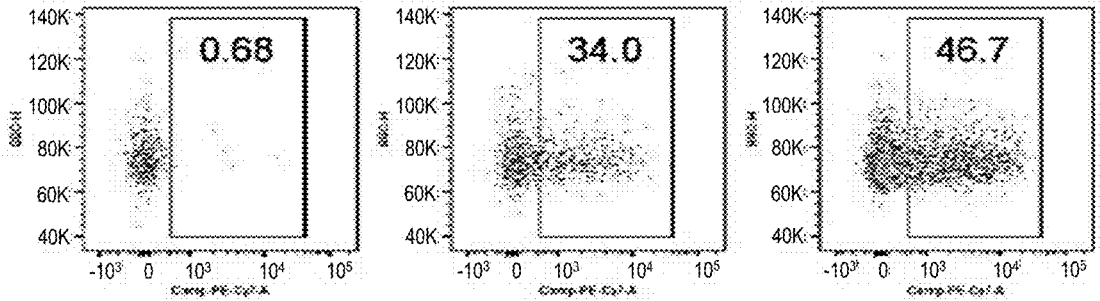
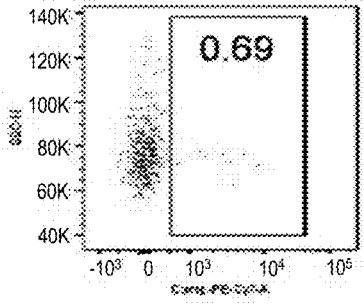
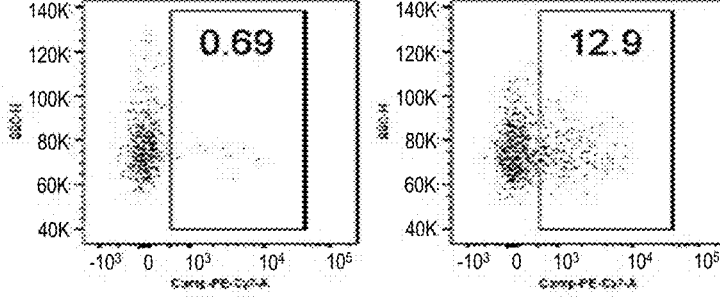
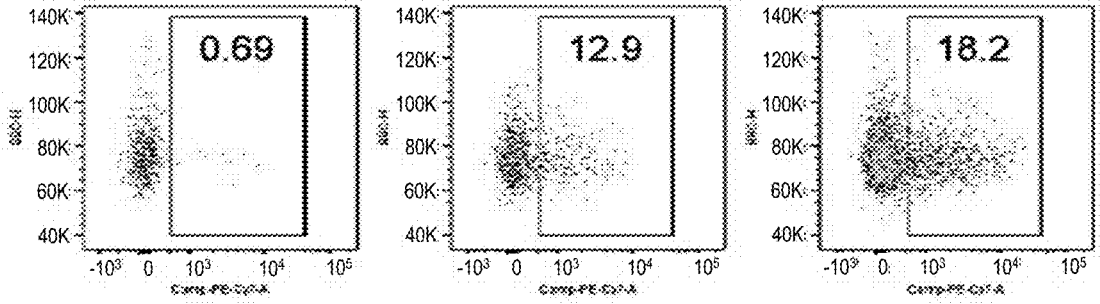
Figure 30

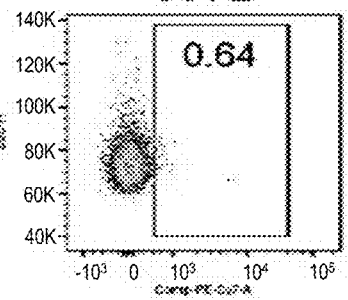
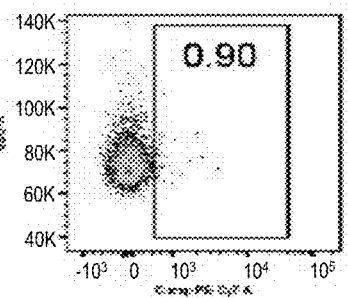
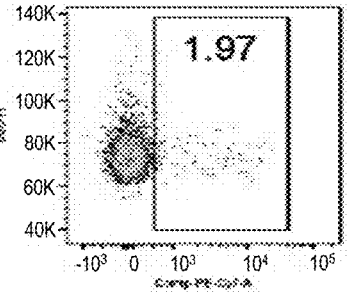
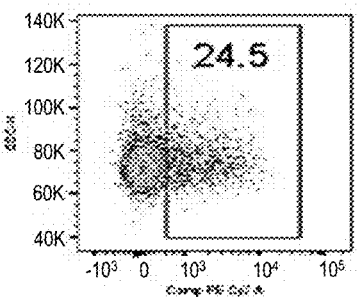
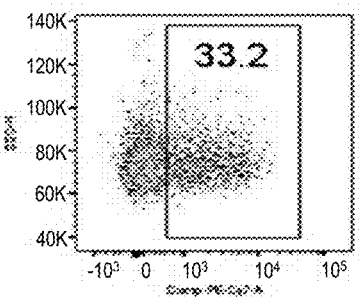
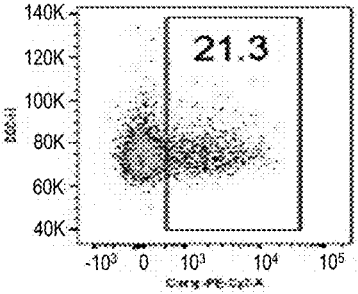
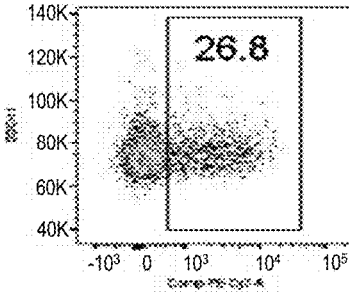
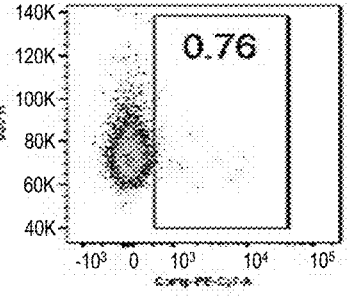
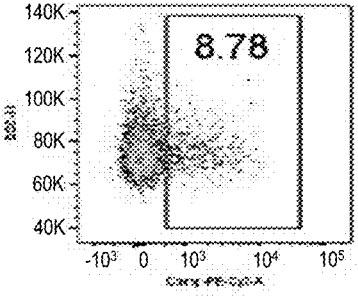
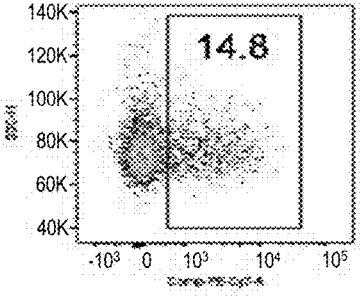
Figure 30, continued

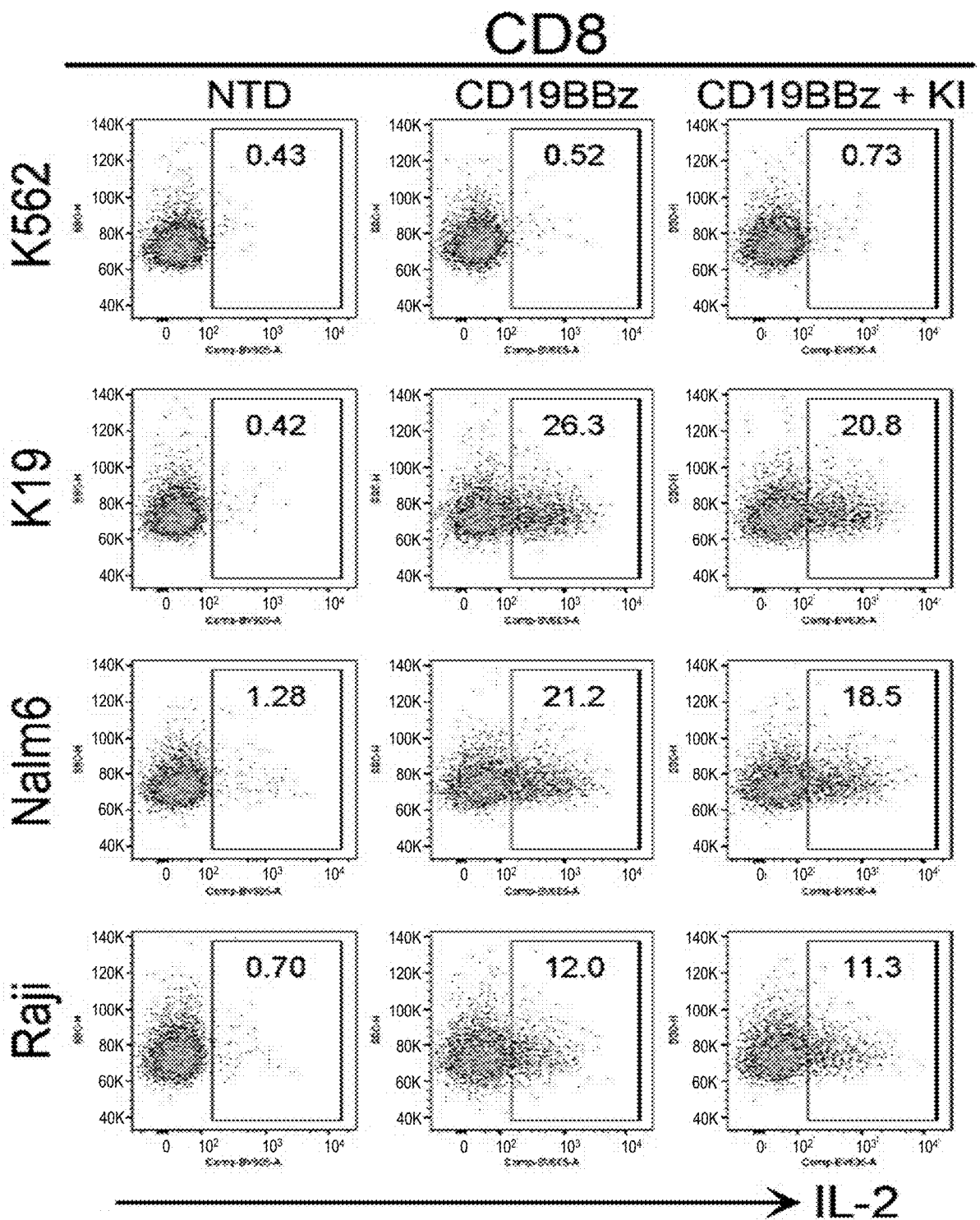
Figure 31, continued

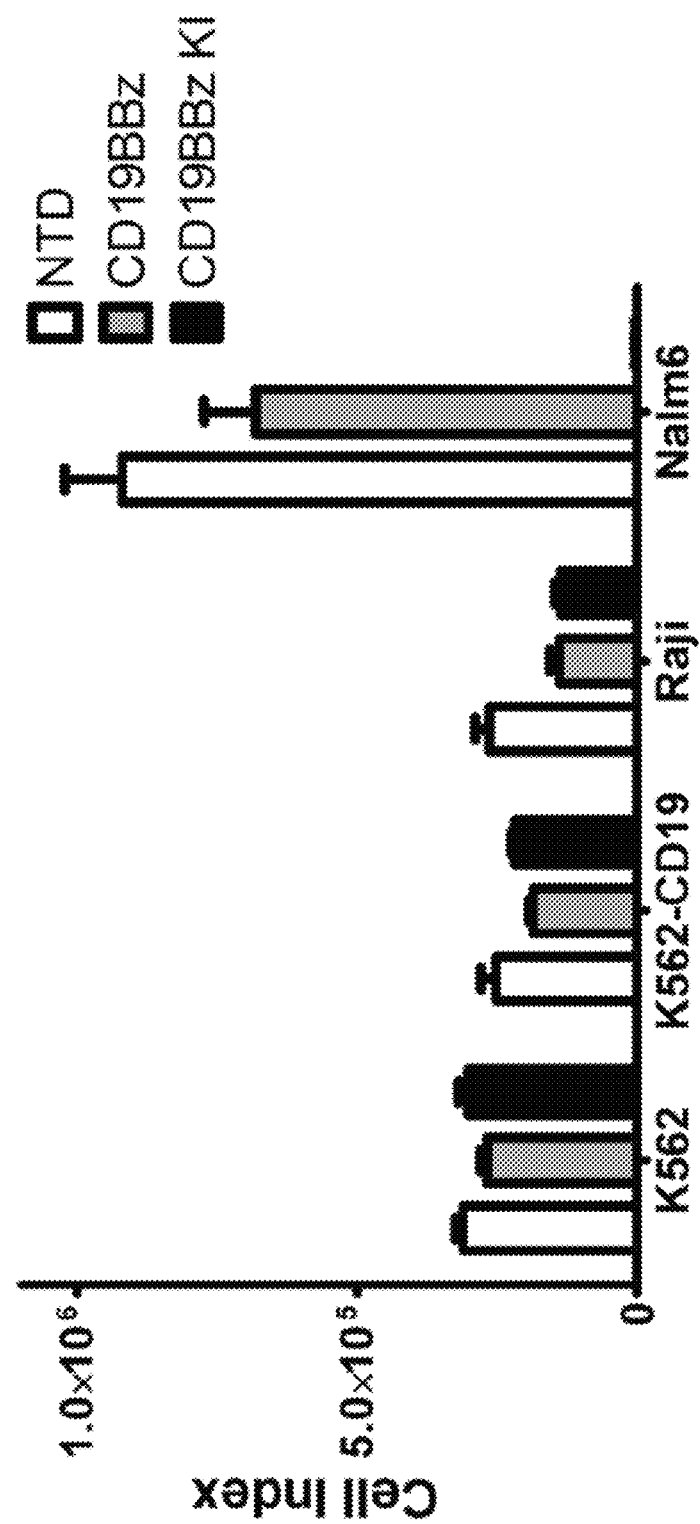

MODIFIED IMMUNE CELLS HAVING ENHANCED FUNCTION AND METHODS FOR SCREENING FOR SAME

CROSS-REFERENCE TO RELATED APPLICATIONS

This application is a Divisional of, and claims priority to, U.S. patent application Ser. No. 16/365,326, filed Mar. 26, 2019, which claims priority to U.S. Provisional Application No. 62/648,722, filed Mar. 27, 2018, each of which application is hereby incorporated herein by reference in its entirety.

STATEMENT REGARDING FEDERALLY SPONSORED RESEARCH OR DEVELOPMENT

This invention was made with government support under grant CA120409 awarded by the National Institutes of Health (NIH). The government has certain rights in the invention.

REFERENCE TO SEQUENCE LISTING

The Sequence Listing concurrently submitted herewith as a text file named "046483_7202US2_Sequence_Listing.txt," created on May 6, 2022 and having a size of 40,037 bytes is herein incorporated by reference pursuant to 37 C.F.R. § 1.52(e)(5).

BACKGROUND OF THE INVENTION

The field of adoptive cell therapy is currently comprised of CAR- and TCR-engineered T cells and has emerged from principles of basic immunology to paradigm-shifting clinical immunotherapy. Adoptive cell therapy of T cells engineered to express artificial receptors that target cells of choice has provided an exciting new approach for attacking cancer, and holds equal promise for chronic infection and autoimmunity. Using principles of synthetic biology, advances in immunology and genetic engineering have made it possible to generate human T-cells that display desired specificities and enhanced functionalities. For example, clinical trials in patients with advanced B cell leukemias and lymphomas treated with CD19-specific CAR T cells have induced durable remissions in adults and children.

T cell exhaustion is a state of T cell dysfunction that arises during many chronic infections and cancer. It is defined by poor effector function, sustained expression of inhibitory receptors and a transcriptional state distinct from that of functional effector or memory T cells. Exhaustion prevents optimal control of infection and tumors. Another barrier to efficient T cell based therapy is that T cells are susceptible to immunosuppression by the microenvironment of the targeted cell. For example, PD-L1 in the microenvironment of prostate cancer cells inhibits the function of TCR- or CAR-engineered T cells.

Thus, there is a need in the art to identify genes that regulate the function of T cells. In particular, there is a need in the art to identify genes that regulate the function of TCR- or CAR-engineered T cell function.

SUMMARY OF THE INVENTION

The present invention is based on the discovery that an unbiased, in vivo genome-wide screen can identify genes that regulate T cell function (e.g., T cell efficacy, T cell memory, and/or T cell persistence). The present invention provides a method of screening for TCR- or CAR-T cells with enhanced immune function (e.g., target cell killing). A screening method of the invention resulted in the identification of several genes that when downregulated, result in TCR- or CAR-T cells with enhanced immune function. Accordingly, the present invention provides modified immune cells comprising an exogenous TCR and/or CAR, and an insertion and/or deletion in an endogenous gene locus, wherein the endogenous gene locus encodes regulator of T cell function.

In another aspect, a modified immune cell or precursor cell thereof, comprising an insertion and/or deletion in a gene locus encoding for a transcriptional modulator, wherein the insertion and/or deletion is capable of downregulating gene expression of the endogenous transcriptional modulator; and an exogenous T cell receptor (TCR) and/or chimeric antigen receptor (CAR) comprising affinity for an antigen on a target cell, is provided.

In certain exemplary embodiments, the insertion and/or deletion in a gene locus is mediated by a CRISPR-related system. In certain exemplary embodiments, the insertion and/or deletion in a gene locus is mediated by CRISPR/Cas9. In certain exemplary embodiments, the transcriptional modulator is a transcription factor or an epigenetic regulator.

In certain exemplary embodiments, the transcription factor is SIX2 or KLF4. In certain exemplary embodiments, the transcription factor is SIX2. In certain exemplary embodiments, the insertion and/or deletion in the gene locus encoding for SIX2 is capable of downregulating expression of SIX2, and/or downregulating gene expression of one or more downstream targets of SIX2. In certain exemplary embodiments, the transcription factor is KLF4. In certain exemplary embodiments, the insertion and/or deletion in the gene locus encoding for KLF4 is capable of downregulating expression of KLF4, and/or downregulating gene expression of one or more downstream targets of KLF4.

In certain exemplary embodiments, the epigenetic regulator is a modulator of histone methylation. In certain exemplary embodiments, the modulator of histone methylation is a component of a histone methyltransferase complex. In certain exemplary embodiments, the component of a histone methyltransferase complex is histone-lysine-N-methyltransferase 2D (KMT2D).

In certain exemplary embodiments, the component of a histone methyltransferase complex is PAGR1. In certain exemplary embodiments, the insertion and/or deletion in the gene locus encoding for PAGR1 is capable of downregulating gene expression of one or more downstream targets of the PAGR1-associated hi stone methyltransferase complex. In certain exemplary embodiments, the one or more downstream targets of the PAGR1-associated histone methyltransferase complex is selected from the group consisting of ARID1A, ARID3B, ASXL1, DNMT3A, DUSP1, MAP3K8, PAXIP1, PRMT1, SOCS3, and TNFAIP3.

In certain exemplary embodiments, the exogenous TCR is selected from the group consisting of a wild-type TCR, a high affinity TCR, and a chimeric TCR. In certain exemplary embodiments, the exogenous TCR comprises at least one disulfide bond. In certain exemplary embodiments, the exogenous TCR comprises a TCR alpha chain and a TCR beta chain.

In certain exemplary embodiments, the exogenous CAR comprises an antigen-binding domain, a transmembrane domain, and an intracellular domain. In certain exemplary embodiments, the antigen-binding domain is selected from the group consisting of an antibody, an scFv, and a Fab. In certain exemplary embodiments, the exogenous CAR further comprises a hinge domain. In certain exemplary embodiments, the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof. In certain exemplary embodiments, the transmembrane domain is selected from the group consisting of an artificial hydrophobic sequence and transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, CD134, CD137, and CD154. In certain exemplary embodiments, the intracellular domain comprises at least one co-stimulatory domain selected from the group consisting of co-stimulatory domains of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3. In certain exemplary embodiments, the intracellular domain comprises an intracellular domain selected from the group consisting of cytoplasmic signaling domains of a human CD3 zeta chain, FcγRIII, FcεRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

In another aspect, a modified immune cell or precursor cell thereof, comprising: an insertion and/or deletion in one or more gene loci encoding for a protein selected from the group consisting of AZI2, C1orf141, CCDC33, CCL7, CEACAM19, KLF4, MFSD5, PAGR1, SIX2, and USP27X, wherein the insertion and/or deletion is capable of downregulating gene expression of the one or more endogenous genes; and an exogenous T cell receptor (TCR) or chimeric antigen receptor (CAR) comprising affinity for an antigen on a target cell, is provided.

In another aspect, a modified immune cell or precursor cell thereof, comprising: an insertion and/or deletion in one or more gene loci encoding for a protein selected from the group consisting of C1orf141, CCDC33, CCL7, CEACAM19, KLF4, MFSD5, PAGR1, SIX2, and USP27X, wherein the insertion and/or deletion is capable of downregulating gene expression of the one or more endogenous genes; and an exogenous T cell receptor (TCR) and/or chimeric antigen receptor (CAR) comprising affinity for an antigen on a target cell, is provided.

In another aspect, a modified immune cell or precursor cell thereof, comprising: an insertion and/or deletion in one or more gene loci encoding for a protein selected from the group consisting of KLF4, PAGR1, and SIX2, wherein the insertion and/or deletion is capable of downregulating gene expression of the one or more endogenous genes; and an exogenous T cell receptor (TCR) and/or chimeric antigen receptor (CAR) comprising affinity for an antigen on a target cell, is provided.

In another aspect, a modified immune cell or precursor cell thereof, comprising: an insertion and/or deletion in a gene locus encoding for KLF4, wherein the insertion and/or deletion is capable of downregulating gene expression of endogenous KLF4; and an exogenous T cell receptor (TCR) and/or chimeric antigen receptor (CAR) comprising affinity for an antigen on a target cell, is provided.

In another aspect, a modified immune cell or precursor cell thereof, comprising: an insertion and/or deletion in a gene locus encoding for SIX2, wherein the insertion and/or deletion is capable of downregulating gene expression of endogenous SIX2; and an exogenous T cell receptor (TCR) and/or chimeric antigen receptor (CAR) comprising affinity for an antigen on a target cell, is provided.

In another aspect, a modified immune cell or precursor cell thereof, comprising: an insertion and/or deletion in a gene locus encoding for PAGR1, wherein the insertion and/or deletion is capable of downregulating gene expression of endogenous PAGR1; and an exogenous T cell receptor (TCR) and/or chimeric antigen receptor (CAR) comprising affinity for an antigen on a target cell, is provided.

In certain exemplary embodiments, the antigen on a target cell is a tumor associated antigen (TAA). In some embodiments, the modified cell is an autologous cell. In certain exemplary embodiments, the modified cell is derived from a human. In certain exemplary embodiments, the modified cell is a modified T cell.

In another aspect, a method for generating a modified immune cell or precursor cell thereof, comprising: a) introducing into the immune cell a first nucleic acid comprising a nucleic acid sequence encoding an exogenous T cell receptor (TCR) and/or a chimeric antigen receptor (CAR) comprising affinity for an antigen on a target cell; and b) introducing into the immune cell one or more polypeptides and/or nucleic acids capable of downregulating gene expression of an endogenous transcriptional modulator, is provided.

In certain exemplary embodiments, the endogenous transcriptional modulator is a transcription factor or an epigenetic regulator. In certain exemplary embodiments, the transcription factor is SIX2 or KLF4. In certain exemplary embodiments, downregulating gene expression of the transcription factor results in downregulated gene expression of SIX2, and/or downregulated gene expression of one or more downstream targets of SIX2. In certain exemplary embodiments, downregulating gene expression of the transcription factor results in downregulated gene expression of KLF4, and/or downregulated gene expression of one or more downstream targets of KLF4.

In certain exemplary embodiments, the epigenetic regulator is a modulator of histone methylation. In certain exemplary embodiments, the modulator of histone methylation is a component of a histone methyltransferase complex. In certain exemplary embodiments, the component of a histone methyltransferase complex is a histone-lysine-N-methyltransferase 2D (KMT2D). In certain exemplary embodiments, the component of a histone methyltransferase complex is PAGR1. In certain exemplary embodiments, downregulating gene expression of the component of a histone methyltransferase complex results in downregulated gene expression of PAGR1, and/or downregulated gene expression of one or more downstream targets of the PAGR1-associated histone methyltransferase complex. In certain exemplary embodiments, the one or more downstream targets of the PAGR1-associated histone methyltransferase complex is selected from the group consisting of ARID1A, ARID3B, ASXL1, DNMT3A, DUSP1, MAP3K8, PAXIP1, PRMT1, SOCS3, and TNFAIP3.

In another aspect, a method for generating a modified immune cell or precursor cell thereof, comprising: a) introducing into the immune cell a first nucleic acid comprising a nucleic acid sequence encoding an exogenous T cell receptor (TCR) and/or a chimeric antigen receptor (CAR)

comprising affinity for an antigen on a target cell; and b) introducing into the immune cell one or more polypeptides and/or nucleic acids capable of downregulating gene expression of one or more endogenous genes selected from the group consisting of AZI2, C1orf141, CCDC33, CCL7, CEACAM19, KLF4, MFSD5, PAGR1, SIX2, and USP27X, is provided.

In another aspect, a method for generating a modified immune cell or precursor cell thereof, comprising: a) introducing into the immune cell a first nucleic acid comprising a nucleic acid sequence encoding an exogenous T cell receptor (TCR) and/or a chimeric antigen receptor (CAR) comprising affinity for an antigen on a target cell; and b) introducing into the immune cell one or more polypeptides and/or nucleic acids capable of downregulating gene expression of one or more endogenous genes selected from the group consisting of C1orf141, CCDC33, CCL7, CEACAM19, KLF4, MFSD5, PAGR1, SIX2, and USP27X, is provided.

In another aspect, a method for generating a modified immune cell or precursor cell thereof, comprising: a) introducing into the immune cell a first nucleic acid comprising a nucleic acid sequence encoding an exogenous T cell receptor (TCR) and/or a chimeric antigen receptor (CAR) comprising affinity for an antigen on a target cell; and b) introducing into the immune cell one or more polypeptides and/or nucleic acids capable of downregulating gene expression of one or more endogenous genes selected from the group consisting of KLF4, PAGR1, and SIX2, is provided.

In another aspect, a method for generating a modified immune cell or precursor cell thereof, comprising: a) introducing into the immune cell a first nucleic acid comprising a nucleic acid sequence encoding an exogenous T cell receptor (TCR) and/or a chimeric antigen receptor (CAR) comprising affinity for an antigen on a target cell; and b) introducing into the immune cell one or more polypeptides and/or nucleic acids capable of downregulating gene expression of endogenous KLF4, is provided.

In another aspect, a method for generating a modified immune cell or precursor cell thereof, comprising: a) introducing into the immune cell a first nucleic acid comprising a nucleic acid sequence encoding an exogenous T cell receptor (TCR) and/or a chimeric antigen receptor (CAR) comprising affinity for an antigen on a target cell; and b) introducing into the immune cell one or more polypeptides and/or nucleic acids capable of downregulating gene expression of endogenous SIX2, is provided.

In another aspect, a method for generating a modified immune cell or precursor cell thereof, comprising: a) introducing into the immune cell a first nucleic acid comprising a nucleic acid sequence encoding an exogenous T cell receptor (TCR) and/or a chimeric antigen receptor (CAR) comprising affinity for an antigen on a target cell; and b) introducing into the immune cell one or more polypeptides and/or nucleic acids capable of downregulating gene expression of endogenous PAGR1, is provided.

In certain exemplary embodiments, the first nucleic acid is introduced by viral transduction. In certain exemplary embodiments, the viral transduction comprises contacting the cell with a viral vector comprising the first nucleic acid. In certain exemplary embodiments, the viral vector is selected from the group consisting of a retroviral vector, a lentiviral vector, an adenoviral vector, and an adeno-associated viral vector.

In certain exemplary embodiments, each of the one or more polypeptides and/or nucleic acids capable of downregulating gene expression comprises a CRISPR-related system. In certain exemplary embodiments, the CRISPR-related system comprises a CRISPR nuclease and a guide RNA. In certain exemplary embodiments, the guide RNA comprises a guide sequence that is sufficiently complementary to a target sequence of an endogenous gene. In certain exemplary embodiments, the guide sequence comprises a nucleic acid sequence set forth in any one of SEQ ID NOs: 31-66. In certain exemplary embodiments, the CRISPR nuclease and the guide RNA comprise a ribonucleoprotein (RNP) complex.

In certain exemplary embodiments, the target sequence is within the PAGR1 gene and comprises a nucleic acid sequence set forth in any one of SEQ ID NOs: 31-36. In certain exemplary embodiments, the target sequence is within the SIX2 gene and wherein the guide RNA comprises a nucleic acid sequence set forth in any one of SEQ ID NOs: 43-48. In certain exemplary embodiments, the target sequence is within the USP27X gene and wherein the guide RNA comprises a nucleic acid sequence set forth in any one of SEQ ID NOs:49-54. In certain exemplary embodiments, the target sequence is within the CEACAM19 gene and wherein the guide RNA comprises a nucleic acid sequence set for the in any one of SEQ ID NOs:55-60. In certain exemplary embodiments, the target sequence is within the C1orf141 gene and wherein the guide RNA comprises a nucleic acid sequence set forth in any one of SEQ ID NOs: 61-66.

In certain exemplary embodiments, the CRISPR nuclease and/or the guide RNA are encoded by a polynucleotide. In certain exemplary embodiments, the polynucleotide comprises a vector and/or a synthetic mRNA.

In certain exemplary embodiments, each of the one or more polypeptides and/or nucleic acids capable of downregulating gene expression is introduced by electroporation. In certain exemplary embodiments, the antigen on a target cell is a tumor associated antigen (TAA). In certain exemplary embodiments, the modified cell is an autologous cell. In certain exemplary embodiments, the modified cell is derived from a human. In certain exemplary embodiments, the modified cell is a modified T cell.

In another aspect, a method for enhancing a function of a modified immune cell or precursor cell thereof, wherein the modified cell comprises an exogenous T cell receptor (TCR) and/or chimeric antigen receptor (CAR) comprising affinity for an antigen on a target cell, comprising: introducing into the immune cell one or more polypeptides and/or nucleic acids capable of downregulating gene expression of an endogenous transcriptional modulator, is provided.

In another aspect, a method for enhancing a function of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of one or more endogenous genes selected from the group consisting of AZI2, C1orf141, CCDC33, CCL7, CEACAM19, KLF4, MFSD5, PAGR1, SIX2, and USP27X, is provided.

In another aspect, a method for enhancing a function of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of one or more endogenous genes selected from the group consisting of C1orf141, CCDC33, CCL7, CEACAM19, KLF4, MFSD5, PAGR1, SIX2, and USP27X, is provided.

In another aspect, a method for enhancing a function of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of one or more endogenous genes selected from the group consisting of KLF4, PAGR1, and SIX2, is provided.

In another aspect, a method for enhancing a function of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of endogenous KLF4, is provided.

In another aspect, a method for enhancing a function of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of endogenous SIX2, is provided.

In another aspect, a method for enhancing a function of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of endogenous PAGR1, is provided.

In certain exemplary embodiments, the function is tumor infiltration. In certain exemplary embodiments, the function is tumor killing. In certain exemplary embodiments, the function is immunosuppression. In certain exemplary embodiments, the function is resistance to immunosuppression by PD-1, LAG-3, TIM-3, and/or CTLA-4.

In another aspect, a method for inhibiting activation-induced cell death of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of an endogenous transcriptional modulator, is provided.

In another aspect, a method for inhibiting activation-induced cell death of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of one or more endogenous genes selected from the group consisting of AZI2, C1orf141, CCDC33, CCL7, CEACAM19, KLF4, MFSD5, PAGR1, SIX2, and USP27X, is provided.

In another aspect, a method for inhibiting activation-induced cell death of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of one or more endogenous genes selected from the group consisting of C1orf141, CCDC33, CCL7, CEACAM19, KLF4, MFSD5, PAGR1, SIX2, and USP27X, is provided.

In another aspect, a method for inhibiting activation-induced cell death of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of one or more endogenous genes selected from the group consisting of KLF4, PAGR1, and SIX2, is provided.

In another aspect, a method for inhibiting activation-induced cell death of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of endogenous KLF4, is provided.

In another aspect, a method for inhibiting activation-induced cell death of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of endogenous SIX2, is provided.

In another aspect, a method for inhibiting activation-induced cell death of a modified immune cell or precursor cell thereof, wherein the modified cell comprises an exogenous T cell receptor (TCR) and/or a chimeric antigen receptor (CAR) comprising affinity for an antigen on a target cell, comprising: introducing into the immune cell one or more polypeptides and/or nucleic acids capable of downregulating gene expression of endogenous PAGR1, is provided.

In certain exemplary embodiments, the antigen on a target cell is a tumor associated antigen (TAA). In certain exemplary embodiments, the modified cell is an autologous cell. In certain exemplary embodiments, the modified cell is derived from a human. In certain exemplary embodiments, the modified cell is a modified T cell.

In another aspect, a method for identifying a gene that when downregulated, results in an enhanced function of an immune cell or precursor cell thereof, comprising the steps of: a) introducing into a plurality of immune cells a library of nucleic acids encoding for an exogenous T cell receptor (TCR) and/or a chimeric antigen receptor (CAR) having affinity for an antigen, thereby generating a plurality of modified immune cells; b) introducing into the plurality of modified immune cells a plurality of agents that target a plurality of endogenous genes, thereby generating a plurality of edited immune cells; c) contacting the plurality of edited immune cells with a tumor cell; d) selecting one or more edited immune cells that exhibit an enhanced function of an immune cell; and e) identifying the endogenous gene that is downregulated in the one or more edited immune cells of step d), thereby identifying the gene that when downregulated, results in an enhanced function of an immune cell or precursor cell thereof, is provided.

In certain exemplary embodiments, the steps of a) and b) are carried out simultaneously. In certain exemplary embodiments, the plurality of agents in step b) each comprise a nucleic acid encoding a unique guide RNA that targets each of the plurality of endogenous genes. In certain exemplary embodiments, the plurality of agents in step b) each comprise a CRISPR nuclease polypeptide or a nucleic acid that encodes for a CRISPR nuclease. In certain exemplary embodiments, the plurality of agents in step b) each comprise a CRISPR-related system. In certain exemplary embodiments, the CRISPR-related system comprises a CRISPR nuclease and a guide RNA. In certain exemplary embodiments, the guide RNA comprises a guide sequence that is sufficiently complementary with a target sequence of a gene that regulates a function of the immune cell. In certain exemplary embodiments, the CRISPR nuclease and the guide RNA comprise a ribonucleoprotein (RNP) complex. In certain exemplary embodiments, the identifying step in e) comprises identifying the unique guide RNA that targets the downregulated gene.

In another aspect, a method for identifying a gene that when downregulated, results in an enhanced function of an immune cell or precursor cell thereof, comprising the steps of: a) introducing into a plurality of immune cells a library of nucleic acids encoding for an exogenous T cell receptor (TCR) and/or a chimeric antigen receptor (CAR) having affinity for an antigen, and encoding for a plurality of guide RNAs that each target a unique region of each of a plurality of endogenous genes, thereby generating a plurality of modified immune cells; b) introducing into the plurality of modified immune cells a CRISPR nuclease or a nucleic acid that encodes for a CRISPR nuclease, thereby generating a plurality of edited immune cells wherein gene expression of the plurality of endogenous genes is downregulated; c) contacting the plurality of edited immune cells with a tumor cell; d) selecting one or more edited immune cells that exhibit an enhanced function of an immune cell; and e) identifying the endogenous gene that is downregulated in the one or more edited immune cells of step d), thereby identifying the gene that when downregulated, results in an enhanced function of an immune cell or precursor cell thereof, is provided.

In certain exemplary embodiments, the step of contacting c) comprises contacting the plurality of edited immune cells with a tumor cell line comprising the tumor cell. In certain exemplary embodiments, the step of contacting comprises administering the plurality of edited immune cells into a tumor-bearing organism comprising the tumor cell.

In another aspect, a nucleic acid library comprising one or more nucleic acids, wherein each of the one or more nucleic acids comprise: a first nucleic acid encoding for a unique guide RNA; and a second nucleic acid encoding for an exogenous T cell receptor (TCR) and/or chimeric antigen receptor (CAR) having affinity for an antigen, is provided.

In certain exemplary embodiments, the first nucleic acid comprises guide sequences that are sufficiently complementary with target sequences of an endogenous gene. In certain exemplary embodiments, each of the one or more nucleic acids is a vector. In certain exemplary embodiments, each of the vectors comprise a first expression cassette comprising a first promoter operably linked to the first nucleic acid, and a second expression cassette comprising a second promoter operably linked to the second nucleic acid. In certain exemplary embodiments, the second expression cassette further comprises a polynucleotide sequence that encodes for a selectable marker. In certain exemplary embodiments, the selectable marker is a fluorescent protein.

In another aspect, the modified immune cell or precursor cell thereof of any one of the preceding aspects and/or embodiments, for use in the method of any one of the preceding aspects and/or embodiments, is provided.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1A depicts a schematic of the design of a one-shot CRISPR construct. FIG. 1B depicts a schematic illustrating the preparation of a gene modified TCR- or CAR-T cell library.

FIGS. 3A-3B depict a schematic showing the design of an in vivo genome wide screen using TCR- or CAR-T cell libraries according to an embodiment of the present invention. FIG. 3A depicts a schematic showing the screening of genes that regulate T cell function. FIG. 3B depicts a schematic showing the screening of genes that regulate T cell memory and persistence.

FIGS. 4A-4B depict graphs showing the fold expansion of CAR-T cell libraries in vitro stimulated with irradiated target tumor cells. FIG. 4A depicts a graph showing the fold expansion of a CD19 directed CAR-T cell library (CAR19). FIG. 4B depicts a graph showing the fold expansion of a PSCA directed CAR-T cell library stimulated with PC3-PSCA tumor cells.

FIGS. 5A-5B depict flow cytometry analysis showing tumor control and function of isolated tumor infiltrating lymphocytes. FIG. 5A shows the elimination of Nalm6-GFP tumor cells by CAR19 library T cells. FIG. 5B shows the upregulation of T cell activation marker CD137 after co-culture of PC3-PSCA tumor cells with PSCA-CAR library T cells.

FIG. 7 depicts the genes identified from deep sequencing and relative enrichment of single guide RNAs and possible functions of the TOP candidates.

FIGS. 8A-8B depict top 20 candidates in a PC3-PSCA prostate cancer in vivo CRISPR screen. FIG. 8A depicts a heatmap of top 20 potential therapeutic targets identified by the CRISPR screen in PC3-PSCA model. FIG. 8B depicts the fold enrichment of the top 20 potential therapeutic targets.

FIG. 9 depicts a heatmap showing the top 20 candidates in a CaPan1 pancreatic cancer in vivo CRISPR screen.

FIG. 10A depicts the overlapping genes among top 100, 200, and 500 hits screen from different tumors.

FIG. 10B depicts fold enrichment of the overlapping candidates.

FIGS. 12A-12C depict the validation of candidates in a PC3-PSCA prostate cancer model. FIG. 12A depicts bioluminescent tumor images of candidate validation in the PC3-PSCA prostate cancer model. PC3-PSCA tumors were established in the flank of NSG mice (n=3). After three weeks, the mice were treated with 1×10⁶ WT or KO PSCA CAR-T cells (i.v.). Bioluminiscent imaging was conducted before (day 0) and after the mice were treated with a single T cell injection. FIG. 12B depicts quantitative image data. FIG. 12C depicts tumor volume data.

FIGS. 13A-13C depict the validation of candidates in a CaPan1 pancreatic cancer model. FIG. 13A depicts bioluminescent tumor images of candidate validation in the CaPan1 pancreatic cancer model. CaPan1 tumors were established in the flank of NSG mice (n=3). After three weeks, the mice were treated with 1×10⁶ WT or KO PSCA CAR-T cells (i.v.). Bioluminescent imaging was conducted before (day 0) and after the mice were treated with a single T cell injection. FIG. 13B depicts quantitative image data. FIG. 13C depicts tumor volume data.

FIGS. 14A-14C depict the validation of candidates in an A549-NY-ESO lung cancer model. FIG. 14A depicts bioluminescent tumor images of candidate validation in the A549-NY-ESO lung cancer model. A549-NY-ESO tumors were established in the flank of NSG mice (n=3). After one week, the mice were treated with 1×10⁷ WT or KO NY-ESO TCR-T cells (i.v.). Bioluminiscent imaging was conducted before (day 0) and after the mice were treated with a single T cell injection. FIG. 14B depicts quantitative image data. FIG. 14C depicts tumor volume data.

FIG. 15A depicts a CD107a assay of PAGR1, Klf4, and SIX2 KO CAR-T cells co-cultured with PC3-PSCA and A375 tumor. FIG. 15B depicts a CD107A assay of PAGR1, Klf4, and SIX2 KO CAR-T cells co-cultured with CaPan1 tumor. FIGS. 15C and 15D depict the killing ability of gene knockout CAR-T cells. FIG. 15E depicts results of a CFSE proliferation assay of gene knockout CAR-T cells.

FIG. 16A depicts bioluminescent tumor imaging of candidate validation in a PC3-PSCA prostate cancer model. PC3-PSCA tumors were established in the flank of NSG mice (n=3). After three weeks, the mice were treated with 1×10⁶ WT or KO PSCA CAR-T cells (i.v.). Bioluminescent imaging was conducted before (day 0) and after the mice were treated with a single T cell injection. FIG. 16B depicts quantitative image data. FIG. 16C depicts tumor volume data.

FIGS. 17A-17B depict results showing that PAGR1 KO enhances CaPan1 tumor control. FIG. 17A depicts bioluminescent tumor images of candidate validation in the CaPan1 pancreatic cancer model. CaPan1 tumors were established in the flank of NSG mice (n=3). After three weeks, the mice were treated with 1×10⁶ WT or KO PSCA CAR-T cells (i.v.). Bioluminescent imaging was conducted before (day 0) and after the mice were treated with a single T cell injection. FIG. 17B depicts tumor volume data.

FIGS. 18A-18H depict results showing that PAGR1 enhances CAR-T cell tumor accumulation and suppression resistance. FIG. 18A depicts the number of tumor infiltrating CAR-T cells in PC3-PSCA model. FIG. 18B depicts the number of tumor infiltrating CAR-T cells in CaPan1 model. FIG. 18C depicts the percentage killing of target tumor cells by different CAR-T cells isolated from the tumor. FIGS. 18D-18G depict the level of expression of the indicated inhibitory molecule on different tumor infiltrating CAR-T cells. FIG. 18H depicts results showing that PAGR1 KO enhances killing ability of the tumor infiltrating cells.

FIGS. 19A-19B depict results showing that PAGR1 KO reduces apoptosis of CAR-T cells. FIG. 19A depicts plots showing the apoptosis of different KO CAR-T cells after activation induced cell death. FIG. 19B depicts plots showing the apoptosis of different KO CAR-T cells after co-culture with target tumor cells.

FIGS. 20A-20D depict results showing that PAGR1 KO enhances CAR-T cell function by epigenetic regulation. FIG. 20A depicts Western blots showing H3K4 mono-methylation and di-methylation in gene KO T cells before and after bead stimulation. FIG. 20B depicts real-time PCT results of KMT2D downstream genes in PAGR1 KO and wild type T cells. FIG. 20C depicts results of a ChIP assay of H3K4 mono-methylation on negative regulators ARID1A and PRMT1. FIG. 20D shows the mRNA level of pro-survival genes Bcl2 and Myc measured by real-time PCR.

FIG. 21 depicts results showing that PAGR1 KO enhances adoptive T cell therapy in a syngeneic model. Volume of B16-OVA tumor after adoptive transfer of wild type, PAGR1 and Klf4 KO OT-I T cells. B16-OVA tumors were established in the flank of C57/BL6 mice (n=4). After eight days, the mice were treated with 1×10⁶ WT or KO OT-I T cells (i.v.). Tumor measurement conducted before (day 0) and after the mice were treated with a single T cell injection.

FIG. 30 depicts results showing that TNFα is expressed at significant levels in both CD4 and CD8 CD19BBz+KI cells.

FIG. 33 depicts results showing the number of survived cancer cells at the end of a sequential killing assay.

DETAILED DESCRIPTION

Figure 1A:
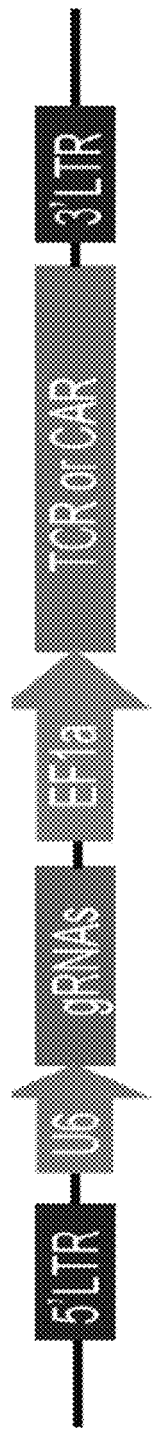
FIGS. 1A-1B depict a schematic showing the generation of gene modified TCR- or CAR-T cell libraries with the one-shot CRISPR system.

The present invention provides compositions and methods for modified immune cells or precursors thereof (e.g., modified T cells) comprising an exogenous (e.g., recombinant, transgenic or engineered) T cell receptor (TCR) and/or chimeric antigen receptor (CAR). In some embodiments, the modified immune cells are genetically edited such that the expression of one or more endogenous genes is downregulated. These genetically edited modified immune cells have enhanced immune function. In some embodiments, the genetically edited modified immune cells of the present invention are resistant to immunosuppression, e.g., to immunosuppressive factors of a tumor microenvironment. In certain embodiments, the immune cells have a genetic disruption of a gene encoding an endogenous gene that regulates immune cell function. In certain embodiments, the endogenous gene negatively regulates immune cell function, such that when the endogenous gene is downregulated, the immune cell has enhanced immune cell function.

In some embodiments, the provided immune cells, compositions and methods alter or reduce the effects of T cell inhibitory pathways or signals in the tumor microenvironment. The modified immune cells of the invention counteract the upregulation and/or expression of inhibitory receptors or ligands that can negatively control T cell activation and T cell function. For example, expression of certain immune checkpoint proteins (e.g., PD-1 or PD-L1) on T cells and/or in the tumor microenvironment can reduce the potency and efficacy of adoptive T cell therapy. Such inhibitory pathways may otherwise impair certain desirable effector functions in the context of adoptive cell therapy. Tumor cells and/or cells in the tumor microenvironment often upregulate certain inhibitory proteins (such as PD-L1 and PD-L2) delivering an inhibitory signal. Such proteins may also be upregulated on T cells in the tumor microenvironment, e.g., on tumor-infiltrating T cells, which can occur following signaling through the antigen receptor (e.g., TCR and/or CAR) or certain other activating signals. Such events may contribute to genetically engineered immune cells (e.g., TCR- or CAR-T cells) acquiring an exhausted phenotype, such as when present in proximity with other cells that express such protein, which in turn can lead to reduced functionality. Thus, the modified immune cells of the invention address the T cell exhaustion and/or the lack of T cell persistence that is a barrier to the efficacy and therapeutic outcomes of conventional adoptive cell therapies.

The present invention also provides in vitro and in vivo screening methods to identify genes involved in T cell inhibitory pathways or signals in the tumor microenvironment. The present invention also provides in vitro and in vivo screening methods to identify genes that regulate T cell memory and persistence. T cell memory is conferred by a subset of T cells called memory T cells. Memory T cells are T cells that have previously encountered and responded to a target antigen. At a second encounter of the same target antigen, memory T cells can reproduce to mount a faster and stronger immune response than the first time the immune system responded to the target antigen. Certain inhibitory pathways or signals are known in the art to prevent T cell memory. Thus, the modified immune cells of the present invention may have stronger persistence and efficacy.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Insertion/deletion", commonly abbreviated "indel," is a type of genetic polymorphism in which a specific nucleotide sequence is present (insertion) or absent (deletion) in a genome.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockin" as used herein refers to an exogenous nucleic acid sequence that has been inserted into a target sequence (e.g., endogenous gene locus). For example, a CAR/TCR knockin into a target site (e.g., endogenous gene locus) refers to a nucleic acid sequence encoding a chimeric antigen receptor (CAR) or T cell receptor (TCR) that has been inserted into a target location within the targeted gene sequence. In some embodiments, where the target sequence is a gene, a knockin is generated resulting in the exogenous nucleic acid sequence being in operable linkage with any upstream and/or downstream regulatory elements controlling expression of the target gene. In some embodiments, the knockin is generated resulting in the exogenous nucleic acid sequence not being in operable linkage with any upstream and/or downstream regulatory elements controlling expression of the target gene.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. T Cell Receptors

The present invention provides compositions and methods for modified immune cells or precursors thereof (e.g., modified T cells) comprising an exogenous T cell receptor (TCR). Thus, in some embodiments, the target cell has been altered to contain specific T cell receptor (TCR) genes (e.g., a nucleic acid encoding an alpha/beta TCR). TCRs or antigen-binding portions thereof include those that recognize a peptide epitope or T cell epitope of a target polypeptide, such as an antigen of a tumor, viral or autoimmune protein. In some embodiments, the TCR has binding specificity for a tumor associated antigen, e.g., human NY-ESO-1.

In some embodiments, a modified T cell comprising an exogenous T cell receptor (TCR) can be used in a screening method of the present invention, e.g., to identify genetic targets that when modulated, enhance the function of the TCR-T cell.

A TCR is a disulfide-linked heterodimeric protein comprised of six different membrane bound chains that participate in the activation of T cells in response to an antigen. There exists alpha/beta TCRs and gamma/delta TCRs. An alpha/beta TCR comprises a TCR alpha chain and a TCR beta chain. T cells expressing a TCR comprising a TCR alpha chain and a TCR beta chain are commonly referred to as alpha/beta T cells. Gamma/delta TCRs comprise a TCR gamma chain and a TCR delta chain. T cells expressing a TCR comprising a TCR gamma chain and a TCR delta chain are commonly referred to as gamma/delta T cells. A TCR of the present disclosure is a TCR comprising a TCR alpha chain and a TCR beta chain.

The TCR alpha chain and the TCR beta chain are each comprised of two extracellular domains, a variable region and a constant region. The TCR alpha chain variable region and the TCR beta chain variable region are required for the affinity of a TCR to a target antigen. Each variable region comprises three hypervariable or complementarity-determining regions (CDRs) which provide for binding to a target antigen. The constant region of the TCR alpha chain and the constant region of the TCR beta chain are proximal to the cell membrane. A TCR further comprises a transmembrane region and a short cytoplasmic tail. CD3 molecules are assembled together with the TCR heterodimer. CD3 molecules comprise a characteristic sequence motif for tyrosine phosphorylation, known as immunoreceptor tyrosine-based activation motifs (ITAMs). Proximal signaling events are mediated through the CD3 molecules, and accordingly, TCR-CD3 complex interaction plays an important role in mediating cell recognition events.

Stimulation of TCR is triggered by major histocompatibility complex molecules (MHCs) on antigen presenting cells that present antigen peptides to T cells and interact with TCRs to induce a series of intracellular signaling cascades. Engagement of the TCR initiates both positive and negative signaling cascades that result in cellular proliferation, cytokine production, and/or activation-induced cell death.

A TCR of the present invention can be a wild-type TCR, a high affinity TCR, and/or a chimeric TCR. A high affinity TCR may be the result of modifications to a wild-type TCR that confers a higher affinity for a target antigen compared to the wild-type TCR. A high affinity TCR may be an affinity-matured TCR. Methods for modifying TCRs and/or the affinity-maturation of TCRs are known to those of skill in the art. Techniques for engineering and expressing TCRs include, but are not limited to, the production of TCR heterodimers which include the native disulphide bridge which connects the respective subunits (Garboczi, et al., (1996), Nature 384(6605): 134-41; Garboczi, et al., (1996), J Immunol 157(12): 5403-10; Chang et al., (1994), PNAS USA 91: 11408-11412; Davodeau et al., (1993), J. Biol. Chem. 268(21): 15455-15460; Golden et al., (1997), J. Imm. Meth. 206: 163-169; U.S. Pat. No. 6,080,840).

In some embodiments, the exogenous TCR is a full TCR or an antigen-binding portion or antigen-binding fragment thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable a chain and variable β chain of a TCR, sufficient to form a binding site for binding to a specific MHC-peptide complex. Generally, the variable chains of a TCR contain complementarity determining regions (CDRs) involved in recognition of the peptide, MHC and/or MHC-peptide complex.

In some embodiments, the variable domains of the TCR contain hypervariable loops, or CDRs, which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al, Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR contains a variable alpha domain ($V_a$) and/or a variable beta domain ($V_β$) or antigen-binding fragments thereof. In some embodiments, the a-chain and/or β-chain of a TCR also can contain a constant domain, a transmembrane domain and/or a short cytoplasmic tail (see, e.g., Janeway et al., Immunobiology: The Immune System in Health and Disease, 3 Ed., Current Biology Publications, p. 4:33, 1997). In some embodiments, the a chain constant domain is encoded by the TRAC gene (IMGT nomenclature) or is a variant thereof. In some embodiments, the (3 chain constant region is encoded by TRBC1 or TRBC2 genes (IMGT nomenclature) or is a variant thereof. In some embodiments, the constant domain is adjacent to the cell membrane. For example, in some cases, the extracellular portion of the TCR formed by the two chains contains two membrane-proximal constant domains, and two membrane-distal variable domains, which variable domains each contain CDRs.

It is within the level of a skilled artisan to determine or identify the various domains or regions of a TCR. In some aspects, residues of a TCR are known or can be identified according to the International Immunogenetics Information System (IMGT) numbering system (see e.g. www.imgt.org; see also, Lefranc et al. (2003) Developmental and Comparative Immunology, 2&; 55-77; and The T Cell Factsbook 2nd Edition, Lefranc and LeFranc Academic Press 2001). Using this system, the CDR1 sequences within a TCR Va chains and/or vβ chain correspond to the amino acids present between residue numbers 27-38, inclusive, the CDR2 sequences within a TCR Vα chain and/or vβ chain correspond to the amino acids present between residue numbers 56-65, inclusive, and the CDR3 sequences within a TCR Va chain and/or vβ chain correspond to the amino acids present between residue numbers 105-117, inclusive. The IMGT numbering system should not be construed as limiting in any way, as there are other numbering systems known to those of skill in the art, and it is within the level of the skilled artisan to use any of the numbering systems available to identify the various domains or regions of a TCR.

In some embodiments, the TCR may be a heterodimer of two chains α and β (or optionally γ and δ) that are linked, such as by a disulfide bond or disulfide bonds. In some embodiments, the constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains. In some embodiments, each of the constant and variable domains contain disulfide bonds formed by cysteine residues.

In some embodiments, the TCR for engineering cells as described is one generated from a known TCR sequence(s), such as sequences of vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the T-cells can be a cultured T-cell hybridoma or clone. In some embodiments, the TCR or antigen-binding portion thereof can be synthetically generated from knowledge of the sequence of the TCR. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15: 169-180 and Cohen et al. (2005) J Immunol. 175:5799-5808. In some embodiments, phage display is used to isolate TCRs against a target antigen (see, e.g., Varela-Rohena et al. (2008) Nat Med. 14: 1390-1395 and Li (2005) Nat Biotechnol. 23:349-354.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments as described, the TCR can contain an introduced disulfide bond or bonds. In some embodiments, the native disulfide bonds are not present. In some embodiments, the one or more of the native cysteines (e.g. in the constant domain of the α chain and β chain) that form a native interchain disulfide bond are substituted with another residue, such as with a serine or alanine. In some embodiments, an introduced disulfide bond can be formed by mutating non-cysteine residues on the alpha and beta chains, such as in the constant domain of the α chain and β chain, to cysteine. Exemplary non-native disulfide bonds of a TCR are described in published International PCT No. WO2006/000830 and WO2006/037960. In some embodiments, cysteines can be introduced at residue Thr48 of the α chain and Ser57 of the β chain, at residue Thr45 of the α chain and Ser77 of the β chain, at residue Tyr10 of the α chain and Ser17 of the β chain, at residue Thr45 of the α chain and Asp59 of the β chain and/or at residue Ser15 of the α chain and Glu15 of the β chain. In some embodiments, the presence of non-native cysteine residues (e.g. resulting in one or more non-native disulfide bonds) in a recombinant TCR can favor production of the desired recombinant TCR in a cell in which it is introduced over expression of a mismatched TCR pair containing a native TCR chain.

In some embodiments, the TCR chains contain a transmembrane domain. In some embodiments, the transmembrane domain is positively charged. In some cases, the TCR chain contains a cytoplasmic tail. In some aspects, each chain (e.g. alpha or beta) of the TCR can possess one N-terminal immunoglobulin variable domain, one immunoglobulin constant domain, a transmembrane region, and a short cytoplasmic tail at the C-terminal end. In some embodiments, a TCR, for example via the cytoplasmic tail, is associated with invariant proteins of the CD3 complex involved in mediating signal transduction. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or IT AM that are involved in the signaling capacity of the TCR complex.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). A TCR may be cell-bound or in soluble form. In some embodiments, for purposes of the provided methods, the TCR is in cell-bound form expressed on the surface of a cell. In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR chain variable region sequence is fused to the N terminus a sequence corresponding to a TCR chain constant region extracellular sequence, the first and second polypeptides being linked by a disulfide bond. In some embodiments, the bond can correspond to the native interchain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane. In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR, which is a single amino acid strand containing an α chain and a β chain that is able to bind to MHC-peptide complexes. Typically, a scTCR can be generated using methods known to those of skill in the art, See e.g., International published PCT Nos. WO 96/13593, WO 96/18105, WO99/18129, WO04/033685, WO2006/037960, WO2011/044186; U.S. Pat. No. 7,569,664; and Schlueter, C. J. et al. J. Mol. Biol. 256, 859 (1996). In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment. In some embodiments, a scTCR contains a first segment constituted by an amino acid sequence corresponding to a TCR β chain variable region, a second segment constituted by an amino acid sequence corresponding to a TCR α chain variable region sequence fused to the N terminus of an amino acid sequence corresponding to a TCR α chain constant domain extracellular sequence, and a linker sequence linking the C terminus of the first segment to the N terminus of the second segment. In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment. In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence comprising an α chain extracellular constant domain sequence and transmembrane sequence, and, optionally, a linker sequence linking the C terminus of the first segment to the N terminus of the second segment. In some embodiments, for the scTCR to bind an WIC-peptide complex, the α and β chains must be paired so that the variable region sequences thereof are orientated for such binding. Various methods of promoting pairing of an α and β in a scTCR are well known in the art. In some embodiments, a linker sequence is included that links the a and β chains to form the single polypeptide strand. In some embodiments, the linker should have sufficient length to span the distance between the C terminus of the α chain and the N terminus of the β chain, or vice versa, while also ensuring that the linker length is not so long so that it blocks or reduces bonding of the scTCR to the target peptide-WIC complex. In some embodiments, the linker of a scTCRs that links the first and second TCR segments can be any linker capable of forming a single polypeptide strand, while retaining TCR binding specificity. In some embodiments, the linker sequence may, for example, have the formula —P-AA-P—, wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, a scTCR contains a disulfide bond between residues of the single amino acid strand, which, in some cases, can promote stability of the pairing between the α and β regions of the single chain molecule (see e.g. U.S. Pat. No. 7,569,664). In some embodiments, the scTCR contains a covalent disulfide bond linking a residue of the immunoglobulin region of the constant domain of the α chain to a residue of the immunoglobulin region of the constant domain of the β chain of the single chain molecule. In some embodiments, the disulfide bond corresponds to the native disulfide bond present in a native dTCR. In some embodiments, the disulfide bond in a native TCR is not present. In some embodiments, the disulfide bond is an introduced non-native disulfide bond, for example, by incorporating one or more cysteines into the constant region extracellular sequences of the first and second chain regions of the scTCR polypeptide. Exemplary cysteine mutations include any as described above. In some cases, both a native and a non-native disulfide bond may be present.

In some embodiments, any of the TCRs, including a dTCR or scTCR, can be linked to signaling domains that yield an active TCR on the surface of a T cell. In some embodiments, the TCR is expressed on the surface of cells. In some embodiments, the TCR does contain a sequence corresponding to a transmembrane sequence. In some embodiments, the transmembrane domain can be a Ca or CP transmembrane domain. In some embodiments, the transmembrane domain can be from a non-TCR origin, for example, a transmembrane region from CD3z, CD28 or B7.1. In some embodiments, the TCR does contain a sequence corresponding to cytoplasmic sequences. In some embodiments, the TCR contains a CD3z signaling domain. In some embodiments, the TCR is capable of forming a TCR complex with CD3. In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal.

In some embodiments, the TCR comprises affinity to a target antigen on a target cell. The target antigen may include any type of protein, or epitope thereof, associated with the target cell. For example, the TCR may comprise affinity to a target antigen on a target cell that indicates a particular disease state of the target cell. In some embodiments, the target antigen is processed and presented by MHCs.

In one embodiment, the target cell antigen is a New York esophageal-1 (NY-ESO-1) peptide. NY-ESO-1 belongs to the cancer-testis (CT) antigen group of proteins. NY-ESO-1 is a highly immunogenic antigen in vitro and is presented to T cells via the MHC. CTLs recognizing the A2 presented epitope NY-ESO$_{157-165}$, SLLMWITQC (SEQ ID NO:1), have been grown from the blood and lymph nodes of myeloma patients. T cell clones specific for this epitope have been shown to kill tumor cells. A high affinity TCR recognizing the NY-E50157-165 epitope may recognize HLA-A2-positive, NY-ESO-1 positive cell lines (but not to cells that lack either HLA-A2 or NY-ESO). Accordingly, a TCR of the present disclosure may be a HLA-A2-restricted NY-ESO-1 (SLLMWITQC; SEQ ID NO:1)-specific TCR. In one embodiment, an NY-ESO-1 TCR of the present disclosure is a wild-type NY-ESO-1 TCR. A wild-type NY-ESO-1 TCR may include, without limitation, the 8F NY-ESO-1 TCR (also referred to herein as "8F" or "8F TCR"), and the 1G4 NY-ESO-1 TCR (also referred to herein as "1G4" or "1G4 TCR"). In one embodiment, an NY-ESO-1 TCR of the present disclosure is an affinity enhanced 1G4 TCR, also called Ly95. 1G4 TCR and affinity enhanced 1G4 TCR is described in U.S. Pat. No. 8,143,376. This should not be construed as limiting in any way, as a TCR having affinity for any target antigen is suitable for use in a composition or method of the present invention. In some embodiments, a modified immune cell comprising an exogenous T cell receptor (TCR) having affinity for NY-ESO-1 can be used in a screening method of the present invention, e.g., to identify genetic targets that when modulated, enhance the function of the NY-ESO-1 TCR-T cell. A genetic target that is identified in a screening method of the present invention is not limited to a genetic target that when modified, modulates the function of a TCR-T cell having affinity for a specific antigen target. A genetic target that is identified in a screening method of the present invention may be a genetic target that when modified, modulates the function of any TCR-T cell (i.e., having affinity for any antigen target). In some embodiments, genetic targets identified in a screening method of the present invention comprising the use of a TCR-T cell, may be global regulators of TCR-T cell function that is independent of the specificity of the TCR comprised therein.

In some embodiments, the genetic target that is identified in a screening method of the present invention may be a genetic target that when modified, modulates the function of any TCR-T cell (i.e., having affinity for any target antigen). In some embodiments, the genetic target that is identified in a screening method of the present invention may be a genetic target that when modified, modulates the function of any CAR-T cell (i.e., having affinity for any target antigen). In some embodiments, the genetic target may be a regulator of T cell function. As such, the genetic target, when modified, modulates the function of any TCR- or CAR-T cell having affinity for any target antigen.

Accordingly, a modified immune cell comprising an exogenous TCR and/or CAR may be edited to modify a genetic target that is a regulator of T cell function. Such modified immune cells may possess enhanced immune cell function (e.g., target cell killing).

C. Chimeric Antigen Receptors

The present invention provides compositions and methods for modified immune cells or precursors thereof, e.g., modified T cells, comprising a chimeric antigen receptor (CAR). Thus, in some embodiments, the immune cell has been genetically modified to express the CAR. CARs of the present invention comprise an antigen binding domain, a transmembrane domain, a hinge domain, and an intracellular signaling domain.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains described herein, any of the intracellular domains or cytoplasmic domains described herein, or any of the other domains described herein that may be included in a CAR of the present invention. A subject CAR of the present invention may also include a spacer domain as described herein. In some embodiments, each of the antigen binding domain, transmembrane domain, and intracellular domain is separated by a linker.

Antigen Binding Domain

The antigen binding domain of a CAR is an extracellular region of the CAR for binding to a specific target antigen including proteins, carbohydrates, and glycolipids. In some embodiments, the CAR comprises affinity to a target antigen on a target cell. The target antigen may include any type of protein, or epitope thereof, associated with the target cell. For example, the CAR may comprise affinity to a target antigen on a target cell that indicates a particular disease state of the target cell.

In one embodiment, the target cell antigen is a prostate stem cell antigen (PSCA). As such, in one embodiment, a CAR of the present disclosure has affinity for PSCA on a target cell. In one embodiment, the target cell antigen is CD19. As such, in one embodiment, a CAR of the present disclosure has affinity for CD19 on a target cell. This should not be construed as limiting in any way, as a CAR having affinity for any target antigen is suitable for use in a composition or method of the present invention.

As described herein, a CAR of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin. In one embodiment, a CAR of the present disclosure having affinity for PSCA on a target cell may comprise a PSCA binding domain. In one embodiment, a CAR of the present disclosure having affinity for CD19 on a target cell may comprise a CD19 binding domain.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

In some embodiments, the antigen binding domain is selected from the group consisting of an antibody, an antigen binding fragment (Fab), and a single-chain variable fragment (scFv). In some embodiments, a PSCA binding domain of the present invention is selected from the group consisting of a PSCA-specific antibody, a PSCA-specific Fab, and a PSCA-specific scFv. In one embodiment, a PSCA binding domain is a PSCA-specific antibody. In one embodiment, a PSCA binding domain is a PSCA-specific Fab. In one embodiment, a PSCA binding domain is a PSCA-specific scFv. In some embodiments, a PSCA binding domain of the present invention is selected from the group consisting of a CD19-specific antibody, a CD19-specific Fab, and a CD19-specific scFv. In one embodiment, a CD19binding domain is a CD19-specific antibody. In one embodiment, a CD19 binding domain is a CD19-specific Fab. In one embodiment, a CD19 binding domain is a CD19-specific scFv.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., PSCA binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO:2), $(GGGS)_n$ (SEQ ID NO:3), and $(GGGGS)_n$ (SEQ ID NO:4), where n represents an integer of at least 1. Exemplary linker sequences can comprise amino acid sequences including, without limitation, GGSG (SEQ ID NO:5), GGSGG (SEQ ID NO:6), GSGSG (SEQ ID NO:7), GSGGG (SEQ ID NO:8), GGGSG (SEQ ID NO:9), GSSSG (SEQ ID NO:10), GGGGS (SEQ ID NO:11), GGGGSGGGGSGGGGS (SEQ ID NO:12) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:12), which may be encoded by the nucleic acid sequence (SEQ ID NO: 13)
GGTGGCGGTGGCTCGGGCGGTGGTGGGTCGGGTGGCGGCGGATCT Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Immunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody or a fragment thereof. In some embodiments, the antigen binding domain may be derived from a different species in which the CAR will ultimately be used. For example, for use in humans, the antigen binding domain of the CAR may comprise a murine antibody or a fragment thereof Transmembrane Domain CARs of the present invention may comprise a transmembrane domain that connects the antigen binding domain of the CAR to the intracellular domain of the CAR. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. A subject CAR of the present invention may also include a hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ (SEQ ID NO:2) and $(GGGS)_n$ (SEQ ID NO:3), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, GGSG (SEQ ID NO:5), GGSGG (SEQ ID NO:6), GSGSG (SEQ ID NO:7), GSGGG (SEQ ID NO:8), GGGSG (SEQ ID NO:9), GSSSG (SEQ ID NO:10), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res*. (1986) 14(4): 1779-1789. As non-limiting examples, an immunoglobulin hinge region can include one of the following amino acid sequences: DKTHT (SEQ ID NO:14); CPPC (SEQ ID NO:15); CPEPKSCDTPPPCPR (SEQ ID NO:16) (see, e.g., Glaser et al., *J. Biol. Chem.* (2005) 280:41494-41503); ELKTPLGDTTHT (SEQ ID NO:17); KSCDKTHTCP (SEQ ID NO:18); KCCVDCP (SEQ ID NO:19); KYGPPCP (SEQ ID NO:20); EPKSCDKTHTCPPCP (SEQ ID NO:21) (human IgG1 hinge); ERKCCVECPPCP (SEQ ID NO:22) (human IgG2 hinge); ELKTPLGDTTHTCPRCP (SEQ ID NO:23) (human IgG3 hinge); SPNMVPHAHHAQ (SEQ ID NO:24) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:25); see, e.g., Yan et al., *J. Biol. Chem.* (2012) 287: 5891-5897. In one embodiment, the hinge region can comprise an amino acid sequence derived from human CD8, or a variant thereof.

Intracellular Signaling Domain

A subject CAR of the present invention also includes an intracellular signaling domain. The terms "intracellular signaling domain" and "intracellular domain" is used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcεRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcεRI, cytoplasmic tails of Fc receptors, an immunoreceptor tyrosine-based activation motif (ITAM) bearing cytoplasmic receptors, and combinations thereof.

In one embodiment, the intracellular signaling domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP 12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD 96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceRl gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the antigen binding domains described herein, any of the transmembrane domains described herein, or any of the other domains described herein that may be included in the CAR.

D. Nucleic Acids and Expression Vectors

The present disclosure provides a nucleic acid encoding an exogenous TCR and/or CAR. In one embodiment, a nucleic acid of the present disclosure comprises a nucleic acid sequence encoding an exogenous TCR (e.g., an NY-ESO-1 TCR). In one embodiment, a nucleic acid of the present disclosure comprises a nucleic acid sequence encoding an exogenous CAR (e.g., a PSCA CAR).

In some embodiments, a nucleic acid of the present disclosure is provided for the production of a TCR and/or CAR as described herein, e.g., in a mammalian cell. In some embodiments, a nucleic acid of the present disclosure provides for amplification of the TCR- or CAR-encoding nucleic acid.

As described herein, a TCR of the present disclosure comprises a TCR alpha chain and a TCR beta chain. Accordingly, the present disclosure provides a nucleic acid encoding a TCR alpha chain, and a nucleic acid encoding a TCR beta chain. In some embodiments, the nucleic acid encoding a TCR alpha chain is separate from the nucleic acid encoding a TCR beta chain. In an exemplary embodiment, the nucleic acid encoding a TCR alpha chain, and the nucleic acid encoding a TCR beta chain, resides within the same nucleic acid.

In some embodiments, a nucleic acid of the present disclosure comprises a nucleic acid comprising a TCR alpha chain coding sequence and a TCR beta chain coding sequence. In some embodiments, a nucleic acid of the present disclosure comprises a nucleic acid comprising a TCR alpha chain coding sequence and a TCR beta chain coding sequence that is separated by a linker. A linker for use in the present disclosure allows for multiple proteins to be encoded by the same nucleic acid sequence (e.g., a multicistronic or bicistronic sequence), which are translated as a polyprotein that is dissociated into separate protein components. For example, a linker for use in a nucleic acid of the present disclosure comprising a TCR alpha chain coding sequence and a TCR beta chain coding sequence, allows for the TCR alpha chain and TCR beta chain to be translated as a polyprotein that is dissociated into separate TCR alpha chain and TCR beta chain components.

In some embodiments, the linker comprises a nucleic acid sequence that encodes for an internal ribosome entry site (IRES). As used herein, "an internal ribosome entry site" or "IRES" refers to an element that promotes direct internal ribosome entry to the initiation codon, such as ATG, of a protein coding region, thereby leading to cap-independent translation of the gene. Various internal ribosome entry sites are known to those of skill in the art, including, without limitation, IRES obtainable from viral or cellular mRNA sources, e.g., immunogloublin heavy-chain binding protein (BiP); vascular endothelial growth factor (VEGF); fibroblast growth factor 2; insulin-like growth factor; translational initiation factor eIF4G; yeast transcription factors TFIID and HAP4; and IRES obtainable from, e.g., cardiovirus, rhinovirus, aphthovirus, HCV, Friend murine leukemia virus (FrMLV), and Moloney murine leukemia virus (MoMLV). Those of skill in the art would be able to select the appropriate IRES for use in the present invention.

In some embodiments, the linker comprises a nucleic acid sequence that encodes for a self-cleaving peptide. As used herein, a "self-cleaving peptide" or "2A peptide" refers to an oligopeptide that allow multiple proteins to be encoded as polyproteins, which dissociate into component proteins upon translation. Use of the term "self-cleaving" is not intended to imply a proteolytic cleavage reaction. Various self-cleaving or 2A peptides are known to those of skill in the art, including, without limitation, those found in members of the Picornaviridae virus family, e.g., foot-and-mouth disease virus (FMDV), equine rhinitis A virus (ERAVO, Thosea asigna virus (TaV), and porcine tescho virus-1 (PTV-1); and carioviruses such as Theilovirus and encephalomyocarditis viruses. 2A peptides derived from FMDV, ERAV, PTV-1, and TaV are referred to herein as "F2A," "E2A," "P2A," and "T2A," respectively. Those of skill in the art would be able to select the appropriate self-cleaving peptide for use in the present invention.

In some embodiments, a linker further comprises a nucleic acid sequence that encodes a furin cleavage site. Furin is a ubiquitously expressed protease that resides in the trans-golgi and processes protein precursors before their secretion. Furin cleaves at the COOH— terminus of its consensus recognition sequence. Various furin consensus recognition sequences (or "furin cleavage sites") are known to those of skill in the art, including, without limitation, Arg-X1-Lys-Arg (SEQ ID NO:26) or Arg-X1-Arg-Arg (SEQ ID NO:27), X2-Arg-X1-X3-Arg (SEQ ID NO:28) and Arg-X1-X1-Arg (SEQ ID NO:29), such as an Arg-Gln-Lys-Arg (SEQ ID NO:30), where X1 is any naturally occurring amino acid, X2 is Lys or Arg, and X3 is Lys or Arg. Those of skill in the art would be able to select the appropriate Furin cleavage site for use in the present invention.

In some embodiments, the linker comprises a nucleic acid sequence encoding a combination of a Furin cleavage site and a 2A peptide. Examples include, without limitation, a linker comprising a nucleic acid sequence encoding Furin and F2A, a linker comprising a nucleic acid sequence encoding Furin and E2A, a linker comprising a nucleic acid sequence encoding Furin and P2A, a linker comprising a nucleic acid sequence encoding Furin and T2A. Those of skill in the art would be able to select the appropriate combination for use in the present invention. In such embodiments, the linker may further comprise a spacer sequence between the Furin and 2A peptide. Various spacer sequences are known in the art, including, without limitation, glycine serine (GS) spacers such as (GS)n, (GSGGS)n (SEQ ID NO:2) and (GGGS)n (SEQ ID NO:3), where n represents an integer of at least 1. Exemplary spacer sequences can comprise amino acid sequences including, without limitation, GGSG (SEQ ID NO:5), GGSGG (SEQ ID NO:6), GSGSG (SEQ ID NO:7), GSGGG (SEQ ID NO:8), GGGSG (SEQ ID NO:9), GSSSG (SEQ ID NO:10), and the like. Those of skill in the art would be able to select the appropriate spacer sequence for use in the present invention.

In some embodiments, a nucleic acid of the present disclosure may be operably linked to a transcriptional control element, e.g., a promoter, and enhancer, etc. Suitable promoter and enhancer elements are known to those of skill in the art.

For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/

17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a TCR and/or CAR inducible expression cassette. In one embodiment, the TCR and/or CAR inducible expression cassette is for the production of a transgenic polypeptide product that is released upon TCR and/or CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the TCR and/or CAR into an immune cell or precursor thereof (e.g., a T cell). Accordingly, an expression vector (e.g., a lentiviral vector) of the present invention may comprise a nucleic acid encoding for a TCR and/or CAR. In some embodiments, the expression vector (e.g., lentiviral vector) will comprise additional elements that will aid in the functional expression of the TCR and/or CAR encoded therein. In some embodiments, an expression vector comprising a nucleic acid encoding for a TCR and/or CAR further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a TCR and/or CAR encoding nucleic acid sequence). Physiologic promoters (e.g., an EF-1a promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a TCR and/or CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a TCR and/or CAR of the present disclosure. Methods for introducing RNA into a host cell are known in the art. See, e.g., Zhao et al. Cancer Res. (2010) 15: 9053. Introducing RNA comprising a nucleotide sequence encoding a TCR and/or CAR of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a TCR and/or CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

E. Modified Immune Cells

The present invention provides a modified immune cell or precursor thereof (e.g., a T cell) comprising an exogenous TCR and/or CAR as described herein. Accordingly, such modified cells possess the specificity directed by the TCR and/or CAR that is expressed therein. For example, a modified cell of the present disclosure comprising a NY-ESO-1 TCR possesses specificity for NY-ESO-1 on a target cell.

Gene Edited Immune Cells

The present disclosure provides gene edited modified cells. In some embodiments, a modified cell (e.g., a modified cell comprising an exogenous TCR and/or CAR) of the present disclosure is genetically edited to disrupt the expression of one or more endogenously expressed genes. In some embodiments, the gene-edited immune cells (e.g., T cells) have a reduction, deletion, elimination, knockout or disruption in expression of one or more endogenously expressed genes In some embodiments, the modified cell of the present disclosure is genetically edited to disrupt the expression of one or more of an endogenous gene selected from the group consisting of Apolipoprotein A2 (APOA2), 5-Azacytidine Induced 2 (AZI2), BTB Domain And CNC Homolog 2 (Bach2), C10orf129 (also known as Acyl-CoA Synthetase Medium Chain Family Member 6; ACSM6), C1orf141, C1orf64 (also known as Steroid Receptor Associated And Regulated Protein; SRARP), C—C Motif Chemokine Ligand 7 (CCL7), Cyclin I Family Member 2 (CCNI2), Chloride Channel Accessory 1 (CLCA1), Chloride Nucleotide-Sensitive Channel 1A (CLNS1A), Clock Circadian Regulator (CLOCK), Cysteine Rich Transmembrane Module Containing 1 (CYSTM1), Defensin Alpha 4 (DEFA4), Family With Sequence Similarity 124 Member A (FAM124A), FAM86A (also known as Eukaryotic Elongation Factor 2 Lysine Methyltransferase; EEF2KMT), Polypeptide N-Acetylgalactosaminyltransferase 2 (GALNT2), Glyoxalase Domain Containing 5 (GLOD5), G Protein-Coupled Receptor 35 (GPR35), Hypoxia-Regulated Factor-1 (HRF1), Histidine Rich Glycoprotein (HRG), hsa-mir1273d, hsa-mir-6505, Kinesin Family Member 27 (KIF27), Kruppel Like Factor 4 (Klf4), Myosin Binding Protein H (MYBPH), NDC, NADH:Ubiquinone Oxidoreductase Subunit S4 (NDUFS4), PAXIP1 Associated Glutamate Rich Protein 1 (PAGR1), Parvin Gamma (PARVG), Phosphomevalonate Kinase (PMVK), Protein Kinase CAMP-Activated Catalytic Subunit Beta (PRKACB), Pre-MRNA Processing Factor 39 (PRPF39), Pregnancy Specific Beta-1-Glycoprotein 5 (PSG5), Prostaglandin I2 Receptor (PTGIR), Poliovirus Receptor-Related 3 (PVRL3), SIX Homeobox 2 (SIX2), Transmembrane Protein 249 (TMEM249), Transmembrane Protein 48 (TMEM48), Tetratricopeptide Repeat Domain 27 (TTC27), Ubiquitin Specific Peptidase 27, X-Linked (USP27X), WD Repeat-Containing Protein 85 (WDR85), YY1 Associated Protein 1 (YY1AP), and Zinc And Ring Finger 2 (ZNRF2).

Immunotherapies using CAR (chimeric antigen receptors) T cells and TCR redirected T cells have shown various efficacies in the treatment of cancer patients. One of the major problems limiting their effects is that T cells are exhausted after persistent stimulation by tumor cells. Exhausted T cells have reduced effector functions such as production of cytokines and cytotoxicity against tumor cells, and they express higher levels of checkpoint inhibitory molecules, such as PD-1 and CTLA-4. PD-1 and CTLA-4 antibodies have been used clinically to treat multiple types of cancers. However, the majority of patients do not benefit significantly from these therapies. It has been shown that the genome-wide epigenetic landscape of exhausted T cells is different from that of effector T cells and memory T cells, and these exhausted T cells cannot be remodeled/reinvigorated by, e.g., PD-L1 blockade (see, Pauken et al. (2016) Science, 354(6316):1160-1165). Without being bound to any theory, the altered epigenetic landscape may be limiting the exhausted T cell from being fully reinvigorated by checkpoint antibodies.

In certain embodiments, the modified cell of the present disclosure is genetically edited to disrupt the expression of a transcriptional modulator. As described elsewhere herein, disruption of a transcriptional modulator (e.g., a transcription factor or an epigenetic regulator) is shown by the present disclosure to enhance immune cell (e.g., T cell) function. Without being bound to any theory, disrupting the expression of a transcriptional modulator (e.g., a transcription factor or an epigenetic regulator) may result in reduced expression of genes involved in negatively regulating immune cell function (e.g., T cell survival) and/or enhanced expression of genes involved in positively regulating immune cell function (e.g., pro-survival factors), thus increasing efficacy of the gene edited immune cells.

Accordingly, a modified cell of the present disclosure with disrupted expression of a transcriptional modulator (e.g., a modified T cell with disrupted expression of a transcription factor or an epigenetic regulator), may be resistant to exhaustion, and in some embodiments, may additionally be reinvigorated by checkpoint antibodies (e.g., anti-PD-1, anti-CTLA-4, anti-PDL1 antibodies).

For example, the present disclosure identifies PAGR1, Klf4, and SIX2 as genes that when expression is disrupted, enhances immune cell (e.g., T cell) function. In an exemplary embodiment, a modified cell of the present disclosure is genetically edited to disrupt the expression of PAGR1. In an exemplary embodiment, a modified cell of the present disclosure is genetically edited to disrupt the expression of Klf4. In an exemplary embodiment, a modified cell of the present disclosure is genetically edited to disrupt the expression of SIX2. In some embodiments, a modified cell of the present disclosure is genetically edited to disrupt the expression of one or more genes selected from the group consisting of PAGR1, Klf4, and SIX2.

Where disruption of the expression of a transcriptional modulator (e.g., a transcription factor or an epigenetic regulator) results in the downregulation of the expression of one or more genes that act downstream of the transcriptional modulator, a modified cell of the present invention can be genetically edited to disrupt the expression of one or more of the downstream acting genes. For example, Klf4 and SIX2 are transcription factors that regulate the expression of one or more downstream genes that are known in the art. Accordingly, the present invention provides a modified cell genetically edited to disrupt the expression of one or more of the genes that are regulated by Klf4 and/or SIX2. In another example, PAGR1 is a known component of the epigenetic regulator histone-lysine-N-methyltransferase 2D (KMT2D). As described elsewhere herein, disruption of PAGR1 results in the reduced expression of one or more of AT-Rich Interaction Domain 1A (ARID1A), AT-Rich Interaction Domain 3B (ARID3B), Additional Sex Combs Like 1 (ASXL1), DNA Methyltransferase 3 Alpha (DNMT3A), Dual Specificity Phosphatase 1 (DUSP1), Mitogen-Activated Protein Kinase Kinase Kinase 8 (MAP3K8), PAX Interacting Protein 1 (PAXIP1), Protein Arginine Methyltransferase 1 (PRMT1), Suppressor Of Cytokine Signaling 3 (SOCS3), and/or TNF Alpha Induced Protein 3 (TNFAIP3). Accordingly, the present invention provides a modified cell genetically edited to disrupt the expression of one or more of the genes selected from the group consisting of ARID1A, ARID3B, ASXL1, DNMT3A, DUSP1, MAP3K8, PAXIP1, PRMT1, SOCS3, and TNFAIP3.

In other embodiments, the modified cell of the present disclosure is genetically edited to disrupt the expression of endogenous PDCD1 gene products (Programmed Death 1 receptor; PD-1). Disrupting the expression of endogenous PD-1 may create "checkpoint" resistant modified cells, resulting in increased tumor control. Checkpoint resistant modified cells may also be created by disrupting the expression of, for example, without limitation, the Adenosine A2A receptor (A2AR), B7-H3 (CD276), B7-H4 (VTCN1), the B and T Lymphocyte Attenuator protein (BTLA/CD272), CD96, the Cytotoxic T-Lymphocyte Associated protein 4 (CTLA-4/CD152), Indoleamine 2,3-dioxygenase (IDO), the Killer-cell Immunoglobulin-like Receptor (KIR), the Lymphocyte Activation Gene-3 (LAG3), the T cell immunoreceptor with Ig and ITIM domains (TIGIT), T-cell Immunoglobulin domain and Mucin domain 3 (TIM-3), or the V-domain Ig suppressor of T cell activation (VISTA).

Accordingly, the modified cell of the present invention is genetically edited to disrupt the expression of any of the endogenous genes described herein. Accordingly, in some embodiments, a modified cell (e.g., a modified cell comprising an exogenous TCR and/or CAR) of the present invention is genetically edited to disrupt the expression of one or more of the endogenous genes described herein.

Various gene editing technologies are known to those skilled in the art. Gene editing technologies include, without limitation, homing endonucleases, zinc-finger nucleases (ZFNs), transcription activator-like effector (TALE) nucleases (TALENs), and clustered regularly interspaced short palindromic repeats (CRISPR)-CRISPR-associated protein 9 (Cas9). Homing endonucleases generally cleave their DNA substrates as dimers, and do not have distinct binding and cleavage domains. ZFNs recognize target sites that consist of two zinc-finger binding sites that flank a 5- to 7-base pair (bp) spacer sequence recognized by the FokI cleavage domain. TALENs recognize target sites that consist of two TALE DNA-binding sites that flank a 12- to 20-bp spacer sequence recognized by the FokI cleavage domain. The Cas9 nuclease is targeted to DNA sequences complementary to the targeting sequence within the single guide RNA (gRNA) located immediately upstream of a compatible protospacer adjacent motif (PAM). Accordingly, one of skill in the art would be able to select the appropriate gene editing technology for the present invention.

In some aspects, the disruption is carried out by gene editing using an RNA-guided nuclease such as a CRISPR-Cas system, such as CRISPR-Cas9 system, specific for the gene (e.g., PAGR1, Klf4, SIX2) being disrupted. In some embodiments, an agent containing a Cas9 and a guide RNA (gRNA) containing a targeting domain, which targets a region of the genetic locus, is introduced into the cell. In some embodiments, the agent is or comprises a ribonucleoprotein (RNP) complex of a Cas9 polypeptide and a gRNA (Cas9/gRNA RNP). In some embodiments, the introduction includes contacting the agent or portion thereof with the cells in vitro, which can include cultivating or incubating the cell and agent for up to 24, 36 or 48 hours or 3, 4, 5, 6, 7, or 8 days. In some embodiments, the introduction further can include effecting delivery of the agent into the cells. In various embodiments, the methods, compositions and cells according to the present disclosure utilize direct delivery of ribonucleoprotein (RNP) complexes of Cas9 and gRNA to cells, for example by electroporation. In some embodiments, the RNP complexes include a gRNA that has been modified to include a 3' poly-A tail and a 5' Anti-Reverse Cap Analog (ARCA) cap.

The CRISPR/Cas9 system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/Cas9 system can thereby be engineered to cleave virtually any DNA sequence by redesigning the gRNA in cell lines (such as 293T cells), primary cells, and TCR T cells. The CRISPR/Cas9 system can simultaneously target multiple genomic loci by co-expressing a single Cas9 protein with two or more gRNAs, making this system suited for multiple gene editing or synergistic activation of target genes.

The Cas9 protein and guide RNA form a complex that identifies and cleaves target sequences. Cas9 is comprised of six domains: REC I, REC II, Bridge Helix, PAM interacting, HNH, and RuvC. The REC I domain binds the guide RNA, while the Bridge helix binds to target DNA. The HNH and RuvC domains are nuclease domains. Guide RNA is engineered to have a 5' end that is complementary to the target DNA sequence. Upon binding of the guide RNA to the Cas9 protein, a conformational change occurs activating the protein. Once activated, Cas9 searches for target DNA by binding to sequences that match its protospacer adjacent motif (PAM) sequence. A PAM is a two or three nucleotide base sequence within one nucleotide downstream of the region complementary to the guide RNA. In one non-limiting example, the PAM sequence is 5'-NGG-3'. When the Cas9 protein finds its target sequence with the appropriate PAM, it melts the bases upstream of the PAM and pairs them with the complementary region on the guide RNA. Then the RuvC and HNH nuclease domains cut the target DNA after the third nucleotide base upstream of the PAM.

One non-limiting example of a CRISPR/Cas system used to inhibit gene expression, CRISPRi, is described in U.S. Patent Appl. Publ. No. US20140068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In certain embodiments, the CRISPR/Cas system comprises an expression vector, such as, but not limited to, a pAd5F35-CRISPR vector. In other embodiments, the Cas expression vector induces expression of Cas9 endonuclease. Other endonucleases may also be used, including but not limited to, Cas12a (Cpf1), T7, Cas3, Cas8a, Cas8b, Cas10d, Cse1, Csy1, Csn2, Cas4, Cas10, Csm2, Cmr5, Fok1, other nucleases known in the art, and any combinations thereof.

In certain embodiments, inducing the Cas expression vector comprises exposing the cell to an agent that activates an inducible promoter in the Cas expression vector. In such embodiments, the Cas expression vector includes an inducible promoter, such as one that is inducible by exposure to an antibiotic (e.g., by tetracycline or a derivative of tetracycline, for example doxycycline). Other inducible promoters known by those of skill in the art can also be used. The inducing agent can be a selective condition (e.g., exposure to an agent, for example an antibiotic) that results in induction of the inducible promoter. This results in expression of the Cas expression vector.

As used herein, the term "guide RNA" or "gRNA" refer to any nucleic acid that promotes the specific association (or "targeting") of an RNA-guided nuclease such as a Cas9 to a target sequence (e.g., a genomic or episomal sequence) in a cell.

As used herein, a "modular" or "dual RNA" guide comprises more than one, and typically two, separate RNA molecules, such as a CRISPR RNA (crRNA) and a trans-activating crRNA (tracrRNA), which are usually associated with one another, for example by duplexing. gRNAs and their component parts are described throughout the literature (see, e.g., Briner et al. Mol. Cell, 56(2), 333-339 (2014), which is incorporated by reference).

As used herein, a "unimolecular gRNA," "chimeric gRNA," or "single guide RNA (sgRNA)" comprises a single RNA molecule. The sgRNA may be a crRNA and tracrRNA linked together. For example, the 3' end of the crRNA may be linked to the 5' end of the tracrRNA. A crRNA and a tracrRNA may be joined into a single unimolecular or chimeric gRNA, for example, by means of a four nucleotide (e.g., GAAA) "tetraloop" or "linker" sequence bridging complementary regions of the crRNA (at its 3' end) and the tracrRNA (at its 5' end).

As used herein, a "repeat" sequence or region is a nucleotide sequence at or near the 3' end of the crRNA which is complementary to an anti-repeat sequence of a tracrRNA.

As used herein, an "anti-repeat" sequence or region is a nucleotide sequence at or near the 5' end of the tracrRNA which is complementary to the repeat sequence of a crRNA.

Additional details regarding guide RNA structure and function, including the gRNA/Cas9 complex for genome editing may be found in, at least, Mali et al. Science, 339(6121), 823-826 (2013); Jiang et al. Nat. Biotechnol. 31(3). 233-239 (2013); and Jinek et al. Science, 337(6096), 816-821 (2012); which are incorporated by reference herein.

As used herein, a "guide sequence" or "targeting sequence" refers to the nucleotide sequence of a gRNA, whether unimolecular or modular, that is fully or partially complementary to a target domain or target polynucleotide within a DNA sequence in the genome of a cell where editing is desired. Guide sequences are typically 10-30 nucleotides in length, preferably 16-24 nucleotides in length (for example, 16, 17, 18, 19, 20, 21, 22, 23 or 24 nucleotides in length), and are at or near the 5' terminus of a Cas9 gRNA.

As used herein, a "target domain" or "target polynucleotide sequence" or "target sequence" is the DNA sequence in a genome of a cell that is complementary to the guide sequence of the gRNA.

In the context of formation of a CRISPR complex, "target sequence" refers to a sequence to which a guide sequence is designed to have some complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In certain embodiments, a target sequence is located in the nucleus or cytoplasm of a cell. In other embodiments, the target sequence may be within an organelle of a eukaryotic cell, for example, mitochondrion or nucleus. Typically, in the context of a CRISPR system, formation of a CRISPR complex (comprising a guide sequence hybridized to a target sequence and complexed with one or more Cas proteins) results in cleavage of one or both strands in or near (e.g., within about 1, 2, 3, 4, 5, 6, 7, 8, 9, 10, 20, 50 or more base pairs) the target sequence. As with the target sequence, it is believed that complete complementarity is not needed, provided this is sufficient to be functional.

In certain embodiments, one or more vectors driving expression of one or more elements of a CRISPR system are introduced into a host cell, such that expression of the elements of the CRISPR system direct formation of a CRISPR complex at one or more target sites. For example, a Cas nuclease, a crRNA, and a tracrRNA could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In certain embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In certain embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Additional domains that may form part of a fusion protein comprising a CRISPR enzyme are described in U.S. Patent Appl. Publ. No. US20110059502, incorporated herein by reference. In certain embodiments, a tagged CRISPR enzyme is used to identify the location of a target sequence.

Conventional viral and non-viral based gene transfer methods can be used to introduce nucleic acids in mammalian and non-mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell (Anderson, 1992, Science 256:808-813; and Yu, et al., 1994, Gene Therapy 1:13-26).

In some embodiments, the CRISPR/Cas is derived from a type II CRISPR/Cas system. In other embodiments, the CRISPR/Cas system is derived from a Cas9 nuclease. Exemplary Cas9 nucleases that may be used in the present invention include, but are not limited to, *S. pyogenes* Cas9 (SpCas9), *S. aureus* Cas9 (SaCas9), *S. thermophilus* Cas9

(StCas9), *N. meningitidis* Cas9 (NmCas9), *C. jejuni* Cas9 (CjCas9), and *Geobacillus* Cas9 (GeoCas9).

In general, Cas proteins comprise at least one RNA recognition and/or RNA binding domain. RNA recognition and/or RNA binding domains interact with the guiding RNA. Cas proteins can also comprise nuclease domains (i.e., DNase or RNase domains), DNA binding domains, helicase domains, RNAse domains, protein-protein interaction domains, dimerization domains, as well as other domains. The Cas proteins can be modified to increase nucleic acid binding affinity and/or specificity, alter an enzymatic activity, and/or change another property of the protein. In certain embodiments, the Cas-like protein of the fusion protein can be derived from a wild type Cas9 protein or fragment thereof. In other embodiments, the Cas can be derived from modified Cas9 protein. For example, the amino acid sequence of the Cas9 protein can be modified to alter one or more properties (e.g., nuclease activity, affinity, stability, and so forth) of the protein. Alternatively, domains of the Cas9 protein not involved in RNA-guided cleavage can be eliminated from the protein such that the modified Cas9 protein is smaller than the wild type Cas9 protein. In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-stranded break in DNA. (Jinek, et al., 2012, Science, 337:816-821). In certain embodiments, the Cas9-derived protein can be modified to contain only one functional nuclease domain (either a RuvC-like or a HNH-like nuclease domain). For example, the Cas9-derived protein can be modified such that one of the nuclease domains is deleted or mutated such that it is no longer functional (i.e., the nuclease activity is absent). In some embodiments in which one of the nuclease domains is inactive, the Cas9-derived protein is able to introduce a nick into a double-stranded nucleic acid (such protein is termed a "nickase"), but not cleave the double-stranded DNA. In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In one non-limiting embodiment, a vector drives the expression of the CRISPR system. The art is replete with suitable vectors that are useful in the present invention. The vectors to be used are suitable for replication and, optionally, integration in eukaryotic cells. Typical vectors contain transcription and translation terminators, initiation sequences, and promoters useful for regulation of the expression of the desired nucleic acid sequence. The vectors of the present invention may also be used for nucleic acid standard gene delivery protocols. Methods for gene delivery are known in the art (U.S. Pat. Nos. 5,399,346, 5,580,859 & 5,589,466, incorporated by reference herein in their entireties).

Further, the vector may be provided to a cell in the form of a viral vector. Viral vector technology is well known in the art and is described, for example, in Sambrook et al. (4th Edition, Molecular Cloning: A Laboratory Manual, Cold Spring Harbor Laboratory, New York, 2012), and in other virology and molecular biology manuals. Viruses, which are useful as vectors include, but are not limited to, retroviruses, adenoviruses, adeno-associated viruses, herpes viruses, Sindbis virus, gammaretrovirus and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

In some embodiments, guide RNA(s) and Cas9 can be delivered to a cell as a ribonucleoprotein (RNP) complex (e.g., a Cas9/RNA-protein complex). RNPs are comprised of purified Cas9 protein complexed with gRNA and are well known in the art to be efficiently delivered to multiple types of cells, including but not limited to stem cells and immune cells (Addgene, Cambridge, MA, Minis Bio LLC, Madison, WI). In some embodiments, the Cas9/RNA-protein complex is delivered into a cell by electroporation.

In some embodiments, a gene edited modified cell of the present disclosure is edited using CRISPR/Cas9 to disrupt one or more endogenous genes in a modified cell (e.g., a modified T cell). In some embodiments, CRISPR/Cas9 is used to disrupt one or more of endogenous TRAC, TRBC, PDCD1, A2AR, B7-H3 (CD276), B7-H4 (VTCN1), BTLA (CD272), CD96, CTLA-4 (CD152), IDO, KIR, LAG3, TIGIT, TIM-3, and/or VISTA loci, thereby resulting in the downregulation of TRAC, TRBC, PD-1, A2AR, B7-H3 (CD276), B7-H4 (VTCN1), BTLA (CD272), CD96, CTLA-4 (CD152), IDO, KIR, LAG3, TIGIT, TIM-3, and/or VISTA. In some embodiments, CRISPR/Cas9 is used to disrupt one or more of endogenous TRAC, TRBC, PDCD1, and/or TIM-3.

In some embodiments, CRISPR/Cas9 is used to disrupt one or more of endogenous APOA2, AZI2, Bach2, C10orf129, C1orf141, C1orf64, CCL7, CCNI2, CLCA1, CLNS1A, CLOCK, CYSTM1, DEFA4, FAM124A, FAM86A, GALNT2, GLOD5, GPR35, HRF1, HRG, hsa-mir1273d, hsa-mir-6505, KIF27, Klf4, MYBPH, NDC, NDUFS4, PAGR1, PARVG, PMVK, PRKACB, PRPF39, PSG5, PTGIR, PVRL3, TMEM249, TMEM48, TTC27, USP27X, WDR85, YY1AP, and/or ZNRF2 loci, thereby resulting in the downregulation of APOA2, AZI2, Bach2, C10orf129, C1orf141, C1orf64, CCL7, CCNI2, CLCA1, CLNS1A, CLOCK, CYSTM1, DEFA4, FAM124A, FAM86A, GALNT2, GLOD5, GPR35, HRF1, HRG, hsa-mir1273d, hsa-mir-6505, KIF27, Klf4, MYBPH, NDC, NDUFS4, PAGR1, PARVG, PMVK, PRKACB, PRPF39, PSG5, PTGIR, PVRL3, TMEM249, TMEM48, TTC27, USP27X, WDR85, YY1AP, and/or ZNRF2. In certain exemplary embodiments, CRISPR/Cas9 is used to disrupt one or more of endogenous PAGR1, SIX2, KLF4, USP27X, CEACAM19 and/or C1orf14 loci, thereby resulting in the downregulation of PAGR1, SIX2, KLF4, USP27X, CEACAM19 and/or C1orf14. Suitable gRNAs for use in disrupting one or more of endogenous PAGR1, SIX2, KLF4, USP27X, CEACAM19 and/or C1orf141 is set forth in Table 1.

TABLE 1

| gRNA name | gRNA sequence | SEQ ID NO: |
|---|---|---|
| PAGR1 | AATCAGTATTTCCGCTGCCG | 31 |
| PAGR1 | TTGTACCTGGGGTGCGTCTC | 32 |
| PAGR1 | AGGAGCAGATCCTTCGTACC | 33 |
| PAGR1 | CCGGTAAGGCCGAGGACGAG | 34 |
| PAGR1 | CCCCTCGTCCTCGGCCTTAC | 35 |
| PAGR1 | ATTGACCGGAGACGCACCCC | 36 |
| SIX2 | GCGGGAATTTGCGGCGCACG | 37 |

TABLE 1-continued

| gRNA name | gRNA sequence | SEQ ID NO: |
|---|---|---|
| SIX2 | ACCCCGCGAGAAGCGTGAGC | 38 |
| SIX2 | GAGTGGTCTGGCGTCCCCGA | 39 |
| SIX2 | AACAGCCACAACCCGCTGAA | 40 |
| SIX2 | TTGCTCCTGCGTGAAGCCGA | 41 |
| SIX2 | CAAGGCACACTACATCGAGG | 42 |
| KLF4 | GTGGTGGCGCCCTACAACGG | 43 |
| KLF4 | AGCCCGCGTAATCACAAGTG | 44 |
| KLF4 | GCGCGGCGGCCCGCCGTTGT | 45 |
| KLF4 | TCTTTCTCCACGTTCGCGTC | 46 |
| KLF4 | CACCCACACTTGTGATTACG | 47 |
| KLF4 | GAGAAGACACTGCGTCAAGC | 48 |
| USP27X | CGCGGCGCACGACTGCGACG | 49 |
| USP27X | GTGAGATGTCGTCGCTGTTT | 50 |
| USP27X | CTCGATGCCAGTTGTAGTAT | 51 |
| USP27X | GTCCAGTACGTCCTTAATAC | 52 |
| USP27X | TCTTAAACCGATCGTAAAGC | 53 |
| USP27X | ACTGCTTGCGGAGGTTTACG | 54 |
| CEACAM19 | CTCTGAGGCCGTTGTATCCC | 55 |
| CEACAM19 | ATACAACGGCCTCAGAGGGA | 56 |
| CEACAM19 | GATCCCTGGCCCCTCGGAGC | 57 |
| CEACAM19 | CATGTGCTGGGCGTCACTGA | 58 |
| CEACAM19 | GGCCGCCAGGATCCCAGCGT | 59 |
| CEACAM19 | ATCCTGGCGGCCACCATCAT | 60 |
| C1orf141 | TCTTGCTACATCCGCGTCTA | 61 |
| C1orf141 | CTTTGATATTGCCTTAGACG | 62 |
| C1orf141 | GATTCTGTTGGTCTCTTAGA | 63 |
| C1orf141 | AATAAAGAAAGTGAGTCAAC | 64 |
| C1orf141 | AAGAGACCAACAGAATCCAA | 65 |
| C1orf141 | ACATTTGTTTGAATAAAGAA | 66 |

It will be understood to those of skill in the art that guide RNA sequences may be recited with a thymidine (T) or a uridine (U) nucleotide.

In some embodiments, the present invention provides a modified immune cell or precursor cell thereof, comprising: an insertion and/or deletion in a gene locus encoding for a transcriptional modulator, wherein the insertion and/or deletion is capable of downregulating gene expression of the endogenous transcriptional modulator. In some embodiments, the insertion and/or deletion in a gene locus is a CRISPR-mediated insertion and/or deletion in the gene locus. In some embodiments, the gene locus is any one of the endogenous target genes described herein. Accordingly, the present invention provides a modified immune cell or precursor cell thereof, comprising: a CRISPR-mediated insertion and/or deletion in a gene locus encoding for any one of the genes described herein, wherein the CRISPR-mediated insertion and/or deletion is capable of downregulating gene expression of the gene.

In some embodiments, the present invention provides a modified immune cell or precursor cell thereof, comprising: an insertion and/or deletion in a gene locus encoding for a transcriptional modulator, wherein the insertion and/or deletion is capable of downregulating gene expression of the endogenous transcriptional modulator; and an exogenous T cell receptor (TCR) and/or chimeric antigen receptor (CAR) comprising affinity for an antigen on a target cell. In some embodiments, the insertion and/or deletion in a gene locus is a CRISPR-mediated insertion and/or deletion in the gene locus. In some embodiments, the gene locus is any one of the endogenous target genes described herein. Accordingly, the present invention provides a modified immune cell or precursor cell thereof, comprising: a CRISPR-mediated insertion and/or deletion in a gene locus encoding for any one of the genes described herein, wherein the CRISPR-mediated insertion and/or deletion is capable of downregulating gene expression of the gene; and an exogenous T cell receptor (TCR) and/or chimeric antigen receptor (CAR) comprising affinity for an antigen on a target cell.

In some embodiments, the present invention provides a modified immune cell or precursor cell thereof, comprising: a CRISPR-mediated insertion and/or deletion in a gene locus encoding for an endogenous APOA2, AZI2, Bach2, C10orf129, C1orf141, C1orf64, CCL7, CCNI2, CLCA1, CLNS1A, CLOCK, CYSTM1, DEFA4, FAM124A, FAM86A, GALNT2, GLOD5, GPR35, HRF1, HRG, hsa-mir1273d, hsa-mir-6505, KIF27, Klf4, MYBPH, NDC, NDUFS4, PAGR1, PARVG, PMVK, PRKACB, PRPF39, PSG5, PTGIR, PVRL3, TMEM249, TMEM48, TTC27, USP27X, WDR85, YY1AP, and/or ZNRF2 loci, wherein the CRISPR-mediated insertion and/or deletion is capable of downregulating gene expression of APOA2, AZI2, Bach2, C10orf129, C1orf141, C1orf64, CCL7, CCNI2, CLCA1, CLNS1A, CLOCK, CYSTM1, DEFA4, FAM124A, FAM86A, GALNT2, GLOD5, GPR35, HRF1, HRG, hsa-mir1273d, hsa-mir-6505, KIF27, Klf4, MYBPH, NDC, NDUFS4, PAGR1, PARVG, PMVK, PRKACB, PRPF39, PSG5, PTGIR, PVRL3, TMEM249, TMEM48, TTC27, USP27X, WDR85, YY1AP, and/or ZNRF2.

In some embodiments, the present invention provides a modified immune cell or precursor cell thereof, comprising: a CRISPR-mediated insertion and/or deletion in a gene locus encoding for an endogenous APOA2, AZI2, Bach2, C10orf129, C1orf141, C1orf64, CCL7, CCNI2, CLCA1, CLNS1A, CLOCK, CYSTM1, DEFA4, FAM124A, FAM86A, GALNT2, GLOD5, GPR35, HRF1, HRG, hsa-mir1273d, hsa-mir-6505, KIF27, Klf4, MYBPH, NDC, NDUFS4, PAGR1, PARVG, PMVK, PRKACB, PRPF39, PSG5, PTGIR, PVRL3, TMEM249, TMEM48, TTC27, USP27X, WDR85, YY1AP, and/or ZNRF2 loci, wherein the CRISPR-mediated insertion and/or deletion is capable of downregulating gene expression of APOA2, AZI2, Bach2, C10orf129, C1orf141, C1orf64, CCL7, CCNI2, CLCA1, CLNS1A, CLOCK, CYSTM1, DEFA4, FAM124A, FAM86A, GALNT2, GLOD5, GPR35, HRF1, HRG, hsa-mir1273d, hsa-mir-6505, KIF27, Klf4, MYBPH, NDC, NDUFS4, PAGR1, PARVG, PMVK, PRKACB, PRPF39, PSG5, PTGIR, PVRL3, TMEM249, TMEM48, TTC27, USP27X, WDR85, YY1AP, and/or ZNRF2; and an exogenous T cell receptor (TCR) and/or chimeric antigen receptor (CAR) comprising affinity for an antigen on a target cell.

Accordingly, a method of genetically editing a modified cell of the present disclosure comprises introducing into the cell one or more nucleic acids capable of downregulating gene expression of one or more endogenous genes selected from APOA2, AZI2, Bach2, C10orf129, C1orf141, C1orf64, CCL7, CCNI2, CLCA1, CLNS1A, CLOCK, CYSTM1, DEFA4, FAM124A, FAM86A, GALNT2, GLOD5, GPR35, HRF1, HRG, hsa-mir1273d, hsa-mir-6505, KIF27, Klf4, MYBPH, NDC, NDUFS4, PAGR1, PARVG, PMVK, PRKACB, PRPF39, PSG5, PTGIR, PVRL3, TMEM249, TMEM48, TTC27, USP27X, WDR85, YY1AP, and/or ZNRF2. In one embodiment, a method of genetically editing a modified cell of the present disclosure comprises introducing into the cell one or more nucleic acids capable of downregulating gene expression of one or more endogenous genes selected from PAGR1, SIX2, KLF4, USP27X, CEACAM19 and C1orf141. In one embodiment, a method of genetically editing a modified cell of the present disclosure comprises introducing into the cell one or more nucleic acids capable of downregulating gene expression of one or more endogenous genes selected from PAGR1, Klf4, and SIX2. In one embodiment, a method of genetically editing a modified cell of the present invention comprises introducing into the cell one or more nucleic acids capable of downregulating gene expression of endogenous PAGR1. In one embodiment, a method of genetically editing a modified cell of the present invention comprises introducing into the cell one or more nucleic acids capable of downregulating gene expression of endogenous Klf4. In one embodiment, a method of genetically editing a modified cell of the present invention comprises introducing into the cell one or more nucleic acids capable of downregulating gene expression of endogenous SIX2.

In one embodiment, a method for generating a modified cell of the present disclosure comprises 1) introducing into the cell a nucleic acid comprising a nucleic acid sequence encoding an exogenous TCR and/or CAR; and 2) introducing into the cell one or more nucleic acids capable of downregulating gene expression of one or more endogenous genes selected from PAGR1, SIX2, KLF4, USP27X, CEACAM19 and C1orf141. In an exemplary embodiment, a method for generating a modified cell of the present disclosure comprises 1) introducing into the cell a nucleic acid comprising a nucleic acid sequence encoding an exogenous TCR and/or CAR; and 2) introducing into the cell a nucleic acid capable of downregulating gene expression of PAGR1, SIX2, KLF4, USP27X, CEACAM19 and/or C1orf141 (e.g., SEQ ID NOs:31-66). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of PAGR1, SIX2, KLF4, USP27X, CEACAM19 and/or C1orf141, wherein the nucleic acid capable of downregulating gene expression comprises a targeting sequence that is any one of SEQ ID NOs:31-66.

In one embodiment, a method for generating a modified cell of the present disclosure comprises 1) introducing into the cell a nucleic acid comprising a nucleic acid sequence encoding an exogenous TCR and/or CAR; and 2) introducing into the cell one or more nucleic acids capable of downregulating gene expression of one or more endogenous genes selected from PAGR1, K14, and SIX2.

In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of PAGR1, Klf4, and/or SIX2 (e.g., SEQ ID NOs: 31-38). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of PAGR1, Klf4, and/or SIX2, wherein the nucleic acid capable of downregulating gene expression comprises a targeting sequence that is any one of SEQ ID NOs:31-48.

In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of PAGR1 (e.g., SEQ ID NOs:31-36). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of PAGR1, wherein the nucleic acid capable of downregulating gene expression comprises a targeting sequence that is any one of SEQ ID NOs:31-36.

In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of SIX2 (e.g., SEQ ID NOs:37-42). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of SIX2, wherein the nucleic acid capable of downregulating gene expression comprises a targeting sequence that is any one of SEQ ID NOs:37-42.

In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of Klf4 (e.g., SEQ ID NOs:43-48). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of Klf4, wherein the nucleic acid capable of downregulating gene expression comprises a targeting sequence that is any one of SEQ ID NOs:43-48.

In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of USP27X (e.g., SEQ ID NOs:49-54). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of USP27X, wherein the nucleic acid capable of downregulating gene expression comprises a targeting sequence that is any one of SEQ ID NOs:49-54.

In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of CEACAM19 (e.g., SEQ ID NOs:55-60). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of CEACAM19, wherein the nucleic acid capable of downregulating gene expression comprises a targeting sequence that is any one of SEQ ID NOs: 55-60.

In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of C1orf141 (e.g., SEQ ID NOs:61-66). In an exemplary embodiment, a method for generating a modified T cell of the present disclosure comprises 1) introducing into the T cell a nucleic acid comprising a nucleic acid sequence encoding an exogenous TCR and/or CAR; 2) introducing into the cell a nucleic acid capable of downregulating gene expression of C1orf141, wherein the nucleic acid capable of downregulating gene expression comprises a targeting sequence that is any one of SEQ ID NOs:61-66.

Non-limiting types of CRISPR-mediated modifications include a substitution, an insertion, a deletion, and an insertion/deletion (INDEL). The modification can be located in any part of the target site (e.g., an endogenous gene locus of any one of the targeted genes described herein), including but not limited to an exon, a splice donor, or a splice acceptor.

In some aspects, the provided compositions and methods include those in which at least or greater than about 50%, 60%, 65%, 70%, 75%, 80%, 85%, 90% or 95% of immune cells in a composition of immune cells contain the desired genetic modification. For example, about 50%, 60%, 65%, 70%, 75%, 80%, 85%, 90% or 95% of immune cells in a composition of cells into which an agent (e.g. gRNA/Cas9) for knockout or genetic disruption of endogenous gene (e.g., PAGR1, KLF4, or SIX2) was introduced contain the genetic disruption; do not express the targeted endogenous polypeptide, do not contain a contiguous and/or functional copy of the targeted gene. In some embodiments, the methods, compositions and cells according to the present disclosure include those in which at least or greater than about 50%, 60%, 65%, 70%. 75%, 80%, 85%, 90% or 95% of cells in a composition of cells into which an agent (e.g. gRNA/Cas9) for knockout or genetic disruption of a targeted gene was introduced do not express the targeted polypeptide, such as on the surface of the immune cells. In some embodiments, at least or greater than about 50%, 60%, 65%, 70%, 75%, 80%, 85%, 90% or 95% of cells in a composition of cells into which an agent (e.g. gRNA/Cas9) for knockout or genetic disruption of the targeted gene was introduced are knocked out in both alleles, i.e. comprise a biallelic deletion, in such percentage of cells.

In some embodiments, provided are compositions and methods in which the Cas9-mediated cleavage efficiency (% indel) in or near the targeted gene (e.g. within or about within 100 base pairs, within or about within 50 base pairs, or within or about within 25 base pairs or within or about within 10 base pairs upstream or downstream of the cut site) is at least or greater than about 50%, 60%, 65%, 70%, 75%, 80%, 85%, 90% or 95% in cells of a composition of cells into which an agent (e.g. gRNA/Cas9) for knockout or genetic disruption of a targeted gene has been introduced.

In some embodiments, the provided cells, compositions and methods results in a reduction or disruption of signals delivered via the endogenous in at least or greater than about 50%, 60%, 65%, 70%, 75%, 80%, 85%, 90% or 95% of cells in a composition of cells into which an agent (e.g. gRNA/Cas9) for knockout or genetic disruption of a targeted gene was introduced.

In some embodiments, compositions according to the provided disclosure that comprise cells engineered with a recombinant receptor and comprise the reduction, deletion, elimination, knockout or disruption in expression of an endogenous receptor (e.g. genetic disruption of PAGR1, KLF4, or SIX2) retain the functional property or activities of the receptor compared to the receptor expressed in engineered cells of a corresponding or reference composition comprising the receptor but do not comprise the genetic disruption of a gene or express the polypeptide when assessed under the same conditions. In some embodiments, the engineered cells of the provided compositions retain a functional property or activity compared to a corresponding or reference composition comprising engineered cells in which such are engineered with the recombinant receptor but do not comprise the genetic disruption or express the targeted polypeptide when assessed under the same conditions. In some embodiments, the cells retain cytotoxicity, proliferation, survival or cytokine secretion compared to such a corresponding or reference composition.

In some embodiments, the immune cells in the composition retain a phenotype of the immune cell or cells compared to the phenotype of cells in a corresponding or reference composition when assessed under the same conditions. In some embodiments, cells in the composition include naive cells, effector memory cells, central memory cells, stem central memory cells, effector memory cells, and long-lived effector memory cells. In some embodiments, the percentage of T cells, or T cells expressing the recombinant receptor (e.g. TCR and/or CAR), and comprising the genetic disruption of a targeted gene (e.g., PAGR1, KLF4, or SIX2) exhibit a non-activated, long-lived memory or central memory phenotype that is the same or substantially the same as a corresponding or reference population or composition of cells engineered with the recombinant receptor but not containing the genetic disruption. In some embodiments, such property, activity or phenotype can be measured in an in vitro assay, such as by incubation of the cells in the presence of an antigen targeted by the TCR and/or CAR, a cell expressing the antigen and/or an antigen-receptor activating substance. In some embodiments, any of the assessed activities, properties or phenotypes can be assessed at various days following electroporation or other introduction of the agent, such as after or up to 3, 4, 5, 6, 7 days. In some embodiments, such activity, property or phenotype is retained by at least 80%, 85%, 90%, 95% or 100% of the cells in the composition compared to the activity of a corresponding composition containing cells engineered with the recombinant receptor but not comprising the genetic disruption of the targeted gene when assessed under the same conditions.

As used herein, reference to a "corresponding composition" or a "corresponding population of immune cells" (also called a "reference composition" or a "reference population of cells") refers to immune cells (e.g., T cells) obtained, isolated, generated, produced and/or incubated under the same or substantially the same conditions, except that the immune cells or population of immune cells were not introduced with the agent. In some aspects, except for not containing introduction of the agent, such immune cells are treated identically or substantially identically as immune cells that have been introduced with the agent, such that any one or more conditions that can influence the activity or properties of the cell, including the upregulation or expression of the inhibitory molecule, is not varied or not substantially varied between the cells other than the introduction of the agent.

Methods and techniques for assessing the expression and/or levels of T cell markers are known in the art. Antibodies and reagents for detection of such markers are well known in the art, and readily available. Assays and methods for detecting such markers include, but are not limited to, flow cytometry, including intracellular flow cytometry, ELISA, ELISPOT, cytometric bead array or other multiplex methods, Western Blot and other immunoaffinity-based methods. In some embodiments, antigen receptor (e.g. TCR and/or CAR)-expressing cells can be detected by flow cytometry or other immunoaffinity based method for expression of a marker unique to such cells, and then such cells can be co-stained for another T cell surface marker or markers.

In some embodiments, the cells, compositions and methods provide for the deletion, knockout, disruption, or reduction in expression of the target gene in immune cells (e.g. T cells) to be adoptively transferred (such as cells engineered to express an exogenous TCR and/or CAR). In some embodiments, the methods are performed ex vivo on primary cells, such as primary immune cells (e.g. T cells) from a subject. In some aspects, methods of producing or generating such genetically engineered T cells include introducing into a population of cells containing immune cells (e.g. T cells) one or more nucleic acid encoding a recombinant receptor (e.g. exogenous TCR and/or CAR) and an agent or agents that is capable of disrupting, a gene that encode the endogenous receptor to be targeted. As used herein, the term "introducing" encompasses a variety of methods of introducing DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

The population of cells containing T cells can be cells that have been obtained from a subject, such as obtained from a peripheral blood mononuclear cells (PBMC) sample, an unfractionated T cell sample, a lymphocyte sample, a white blood cell sample, an apheresis product, or a leukapheresis product. In some embodiments, T cells can be separated or selected to enrich T cells in the population using positive or negative selection and enrichment methods. In some embodiments, the population contains CD4+, CD8+ or CD4+ and CD8+ T cells. In some embodiments, the step of introducing the nucleic acid encoding a genetically engineered antigen receptor and the step of introducing the agent (e.g. Cas9/gRNA RNP) can occur simultaneously or sequentially in any order. In some embodiments, subsequent to introduction of the exogenous receptor and one or more gene editing agents (e.g. Cas9/gRNA RNP), the cells are cultured or incubated under conditions to stimulate expansion and/or proliferation of cells.

Thus, provided are cells, compositions and methods that enhance immune cell, such as T cell, function in adoptive cell therapy, including those offering improved efficacy, such as by increasing activity and potency of administered genetically engineered cells, while maintaining persistence or exposure to the transferred cells over time. In some embodiments, the genetically engineered cells, exhibit increased expansion and/or persistence when administered in vivo to a subject, as compared to certain available methods. In some embodiments, the provided immune cells exhibit increased persistence when administered in vivo to a subject. In some embodiments, the persistence of genetically engineered immune cells, in the subject upon administration is greater as compared to that which would be achieved by alternative methods, such as those involving administration of cells genetically engineered by methods in which T cells were not introduced with an agent that reduces expression of or disrupts a gene encoding an endogenous receptor. In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the exogenous receptor (e.g., TCR and/or CAR) in the blood or serum or organ or tissue (e.g., disease site) of the subject. In some aspects, persistence is quantified as copies of DNA or plasmid encoding the exogenous receptor per microgram of DNA, or as the number of receptor-expressing cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the exogenous receptor (e.g. exogenous TCR and/or CAR) can be used to distinguish the administered cells from endogenous cells in a subject.

F. Methods of Producing Genetically Modified Immune Cells

The present disclosure provides methods for producing or generating a modified immune cell or precursor thereof (e.g., a T cell) of the invention for tumor immunotherapy, e.g., adoptive immunotherapy. The cells generally are engineered by introducing one or more genetically engineered nucleic acid encoding the exogenous receptors (e.g., a TCR and/or CAR). In some embodiments, the cells also are introduced, either simultaneously or sequentially with the nucleic acid encoding the exogenous receptor, with an agent (e.g. Cas9/ gRNA RNP) that is capable of disrupting a targeted gene (e.g., a gene encoding for PAGR1).

In some embodiments, the nucleic acid encoding an exogenous TCR and/or CAR is inserted into a target site (e.g., endogenous gene locus of any one of the targeted genes described herein) using homology directed repair.

As used herein, "homology-directed repair" or "HDR" is a mechanism to repair double stranded DNA breaks in cells. HDR generally relies on the process of homologous recombination, whereby stretches of nucleic acid sequence homology are used to repair the double stranded DNA break. During HDR, a strand of the homologous sequence of a nucleic acid donor invades, or hybridizes, with a resected portion of the cut DNA. A DNA polymerase, using the resected DNA as a primer, elongates the cut DNA, using the invaded donor sequence as a template. After elongation and break repair, the new sequence at the site of the cut possess whatever sequence was present in the nucleic acid donor used in the repair process. The process of HDR is further described in Jasin et al. (Cold Spring Harb. Perspect. Biol. 2013 November; 5(11): a012740), incorporated herein by reference.

In some embodiments, the nucleic acid donor template (e.g., for insertion of a nucleic acid sequence encoding a TCR and/or CAR) may be employed with gene editing complexes (e.g., CRISPR/Cas system) to enable genome engineering at specific nucleotide positions in a homologous target nucleic acid of a host cell (e.g., homologous chromosomes that are compound heterozygous at a particular allele). In some aspects, the disclosure provides a method for targeted gene editing, the method comprising delivering to a cell (e.g., a cell of a disease subject) at least one component of a recombinant gene-editing complex together with the nucleic acid donor template, under conditions such that the recombinant gene editing complex induces a genetic lesion (e.g., nick or double stranded break) in a target site in the chromosome, and the donor template of the invention mediates a repair mechanism (e.g., HDR), thereby repairing the lesion.

In certain embodiments, the nucleic acid donor template (also referred to herein as an exogenous donor DNA sequence) facilitates insertion of a nucleic acid sequence encoding a TCR and/or CAR into a target site (e.g., an endogenous gene locus) via homologous recombination. Accordingly, in certain embodiments, the nucleic acid sequence encoding a TCR and/or CAR is inserted into the target site (e.g., an endogenous gene locus) via homologous recombination using an exogenous donor DNA sequence. In certain embodiments, the exogenous donor DNA sequence comprises a 5' homologous arm comprising the nucleotide sequence set forth in SEQ ID NO: 162. In certain embodiments, the exogenous donor DNA sequence comprises the nucleotide sequence set forth in SEQ ID NO: 163. In certain embodiments, the exogenous donor DNA sequence comprises a 3' homologous arm comprising the nucleotide sequence set forth in SEQ ID NO: 164. In certain embodiments, the exogenous donor DNA sequence comprises the nucleotide sequence set forth in SEQ ID NO: 165.

```
5' homologous arm (SEQ ID NO: 162):
AAGGCACCCGCTGGGTCATGTGGTTCGGAGACGGACATTGAGGCTCCCACAGGAGATGCAGATGTCTG

GAAAGCAGAGGGAGGGGATGGGGTGAGAGTGCCAGAGTTCCCAGGCAACAAACTTACCCTCAATGTT

CCGGCACTTCTGCCGCACCTCGTACACCAGCCGCTCTGCAAGGGGAGGAGAGCTGGCGTCAGAGGTGC

CACCCTCTCCAGAAGCAGGCCAACTACCTCTTGTGCGCTCATCAATAATCTCCTTGACCTTGGGCTTCT

CCGCTGTGCTCTTCCGGGGCTTTTTGGCTGGTGGAGGTGGTGCGTAGGCAGCTGCCTCAGGTTCCACCC

ACATGTCCGTGTACACTTCTTTGTAGGGATTCTTCTCTTCTGGAGGAGGAAAGCAGGTGCCAAGGTCA

GGGTCCCAGAAAGCTGGGTGCCCTCATTTACCTTCTGGTGGCTCCAGGCCCTTAGGGCCAGAAGGCTG

GAAGCCCCCAGGGCCCATTCAATCATGGGCTTGTTCTGCACCTCCACGGCCTTGGCAGTGTCACTCTC

ATCGCTGTCGTGGCACACCGGGAACAGCTTCCCCGCGCGGCTGCTGGCCACCTGGAGGGTGACACGCC

AGGGTTGGGGTTGCTCCTCCGAGCTCCCAGCAGGGACACTCACCTGCAGGACCTCGTAGATGGCTTTG

CGGTACATGGGCTGCTTGTTGTACGTGGCCTGGTGGAACGCACTGCAAAACGAGCTCAGCGGCATCAG

CTTCTCAACACACACCTGGGGGGACAAGCCAGGCCTTGTTTGCCGCCCAGGCTACTGCCAAACCCCAC

AACTTACCACTGAGAAT hPGK promoter-eGFP-WPRE-BghPolyA (SEQ ID NO: 163):
GGGGTTGGGGTTGCGCCTTTTCCAAGGCAGCCCTGGGTTTGCGCAGGGACGCGGCTGCTCTGGGCGTG

GTTCCGGGAAACGCAGCGGCGCCGACCCTGGGTCTCGCACATTCTTCACGTCCGTTCGCAGCGTCACC

CGGATCTTCGCCGCTACCCTTGTGGGCCCCCGGCGACGCTTCCTGCTCCGCCCCTAAGTCGGGAAGGT

TCCTTGCGGTTCGCGGCGTGCCGGACGTGACAAACGGAAGCCGCACGTCTCACTAGTACCCTCGCAGA

CGGACAGCGCCAGGGAGCAATGGCAGCGCGCCGACCGCGATGGGCTGTGGCCAATAGCGGCTGCTCA

GCAGGGCGCGCCGAGAGCAGCGGCCGGGAAGGGGCGGTGCGGGAGGCGGGGTGTGGGCGGTAGTG

TGGGCCCTGTTCCTGCCCGCGCGGTGTTCCGCATTCTGCAAGCCTCCGGAGCGCACGTCGGCAGTCGG

CTCCCTCGTTGACCGAATCACCGACCTCTCTCCCCAGGGGGATCATCGAATTACCTCTAGAGCCACCAT
```

-continued

GGTGAGCAAGGGCGAGGAGCTGTTCACCGGGGTGGTGCCCATCCTGGTCGAGCTGGACGGCGACGTA

AACGGCCACAAGTTCAGCGTGTCCGGCGAGGGCGAGGGCGATGCCACCTACGGCAAGCTGACCCTGA

AGTTCATCTGCACCACCGGCAAGCTGCCCGTGCCCTGGCCCACCCTCGTGACCACCCTGACCTACGGC

GTGCAGTGCTTCAGCCGCTACCCCGACCACATGAAGCAGCACGACTTCTTCAAGTCCGCCATGCCCGA

AGGCTACGTCCAGGAGCGCACCATCTTCTTCAAGGACGACGGCAACTACAAGACCCGCGCCGAGGTG

AAGTTCGAGGGCGACACCCTGGTGAACCGCATCGAGCTGAAGGGCATCGACTTCAAGGAGGACGGCA

ACATCCTGGGGCACAAGCTGGAGTACAACTACAACAGCCACAACGTCTATATCATGGCCGACAAGCA

GAAGAACGGCATCAAGGTGAACTTCAAGATCCGCCACAACATCGAGGACGGCAGCGTGCAGCTCGCC

GACCACTACCAGCAGAACACCCCCATCGGCGACGGCCCCGTGCTGCTGCCCGACAACCACTACCTGAG

CACCCAGTCCGCCCTGAGCAAAGACCCCAACGAGAAGCGCGATCACATGGTCCTGCTGGAGTTCGTGA

CCGCCGCCGGGATCACTCTCGGCATGGACGAGCTGTACAAGTAAGTCGACATCAACCTCTGGATTACA

AAATTTGTGAAAGATTGACTGGTATTCTTAACTATGTTGCTCCTTTTACGCTATGTGGATACGCTGCTTT

AATGCCTTTGTATCATGCTATTGCTTCCCGTATGGCTTTCATTTTCTCCTCCTTGTATAAATCCTGGTTG

CTGTCTCTTTATGAGGAGTTGTGGCCCGTTGTCAGGCAACGTGGCGTGGTGTGCACTGTGTTTGCTGAC

GCAACCCCCACTGGTTGGGGCATTGCCACCACCTGTCAGCTCCTTTCCGGGACTTTCGCTTTCCCCCTC

CCTATTGCCACGGCGGAACTCATCGCCGCCTGCCTTGCCCGCTGCTGGACAGGGGCTCGGCTGTTGGG

CACTGACAATTCCGTGGTGTTGTCGGGGAAGCTGACGTCCTTTCCTTGGCTGCTCGCCTGTGTTGCCAC

CTGGATTCTGCGCGGGACGTCCTTCTGCTACGTCCCTTCGGCCCTCAATCCAGCGGACCTTCCTTCCCG

CGGCCTGCTGCCGGCTCTGCGGCCTCTTCCGCGTCTTCGCCTTCGCCCTCAGACGAGTCGGATCTCCCT

TTGGGCCGCCTCCCCGCCTGCTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGAGGAAATTGCATCGCATTGT

CTGAGTAGGTGTCATTCTATTCTGGGGGGTGGGGTGGGGCAGGACAGCAAGGGGGAGGATTGGGAAG

ACAATAGCAGGCATGCTGGGGATGCGGTGGGCTCTATG

3' homologous arm (SEQ ID NO: 164):
GACCCAGCGGGTGCCTTCAGCTGCTCGGCTCCGGCCCGTCATCCACCAAGACACAATGCGGCCTGGCC

ACCAGGAGAAGCCCCGCAGTTTCCCCCACACCAGCTCCCCAATGCCAAAGCCCCGGCCGTCCTGGAGC

CCCAAGGAGCAGAAATCATTACACTGGCCACGGCTGGTGAAGAAGCCGCTCACCTCGTACTCTGGCTC

GTCATCGCCTGCTTTGGTGGCATTCTTGTCCCCAGCATCGGACCCCACGGGCTCAGGCGTGGTAGCCAC

AGTGGGGGATGCGGGGTCAGTGGGCTGCTGCACAGCAGGAGGGCTGGCCTCCTCCACCTTCTGAGACT

CCCCGGGCCCCTGGTTTTCTTCCACAGCATTCATTCCTGCAATGACCTTGGCTTTCTTCTCAGCCTGGGG

AAACAAAAAACAAAAAGTCACCTTGGCTGGGGCCCAGGCCAGAAGGCGCCTCACCTCCCTTTTCCAGC

GTGCCAGCCACTCGTCCCGCTTGCGCTTGCTGATGTAGTAGGGGTCCCCGCCTGGAAGGTGAGCCTC

GGCATGGGCCGCTGACGGAGGCTGGACTCCCAGCCCAAGCCACCCCGCAGCCGGCCCCGGGAGCCCT

AGGACAGAGAGACAGACATTAGGGCATTCCACAGAGCCCCTGGGGGTGGAACACTTGCCTCCATTTTC

ATGGATTCGATGTTGGTCTCCTTCTGTTCTTTGCCTGTGGAGAGGGAAGAACAAAGGGACCAGTAAGA

GGCTGCCCCTGGTGCTGAGGACTCACCCGCTTCTGCAGGGGCTCCTCGGCCCGTCTCCGAACCACATG

ACCCAGCGGGTGCCTT complete sequence of 5' homologous arm-hPGK promoter-eGFP-WPRE-
BghPolyA-3' homologous arm (SEQ ID NO: 165):
AAGGCACCCGCTGGGTCATGTGGTTCGGAGACGGACATTGAGGCTCCCACAGGAGATGCAGATGTCTG

GAAAGCAGAGGGAGGGGATGGGGTGAGAGTGCCAGAGTTCCCAGGCAACAAACTTACCCTCAATGTT

CCGGCACTTCTGCCGCACCTCGTACACCAGCCGCTCTGCAAGGGGAGGAGAGCTGGCGTCAGAGGTGC

-continued

```
CACCCTCTCCAGAAGCAGGCCAACTACCTCTTGTGCGCTCATCAATAATCTCCTTGACCTTGGGCTTCT
CCGCTGTGCTCTTCCGGGGCTTTTTGGCTGGTGGAGGTGGTGCGTAGGCAGCTGCCTCAGGTTCCACCC
ACATGTCCGTGTACACTTCTTTGTAGGGATTCTTCTCTTCTGGAGGAGGAAAGCAGGTGCCAAGGTCA
GGGTCCCAGAAAGCTGGGTGCCCTCATTTACCTTCTGGTGGCTCCAGGCCCTTAGGGCCAGAAGGCTG
GAAGCCCCCAGGGCCCATTCAATCATGGGCTTGTTCTGCACCTCCACGGCCTTGGCAGTGTCACTCTC
ATCGCTGTCGTGGCACACCGGGAACAGCTTCCCCGCGCGGCTGCTGGCCACCTGGAGGGTGACACGCC
AGGGTTGGGGTTGCTCCTCCGAGCTCCCAGCAGGGACACTCACCTGCAGGACCTCGTAGATGGCTTTG
CGGTACATGGGCTGCTTGTTGTACGTGGCCTGGTGGAACGCACTGCAAAACGAGCTCAGCGGCATCAG
CTTCTCAACACACACCTGGGGGACAAGCCAGGCCTTGTTTGCCGCCCAGGCTACTGCCAAACCCCAC
AACTTACCACTGAGAATGCGATCGCGGGGTTGGGGTTGCGCCTTTTCCAAGGCAGCCCTGGGTTTGCG
CAGGGACGCGGCTGCTCTGGGCGTGGTTCCGGGAAACGCAGCGGCGCCGACCCTGGGTCTCGCACATT
CTTCACGTCCGTTCGCAGCGTCACCCGGATCTTCGCCGCTACCCTTGTGGGCCCCCGGCGACGCTTCC
TGCTCCGCCCCTAAGTCGGGAAGGTTCCTTGCGGTTCGCGGCGTGCCGGACGTGACAAACGGAAGCCG
CACGTCTCACTAGTACCCTCGCAGACGGACAGCGCCAGGGAGCAATGGCAGCGCGCCGACCGCGATG
GGCTGTGGCCAATAGCGGCTGCTCAGCAGGGCGCGCCGAGAGCAGCGGCCGGGAAGGGGCGGTGCGG
GAGGCGGGGTGTGGGGCGGTAGTGTGGGCCCTGTTCCTGCCCGCGCGGTGTTCCGCATTCTGCAAGCC
TCCGGAGCGCACGTCGGCAGTCGGCTCCCTCGTTGACCGAATCACCGACCTCTCTCCCCAGGGGGATC
ATCGAATTACCTCTAGAGCCACCATGGTGAGCAAGGGCGAGGAGCTGTTCACCGGGGTGGTGCCCATC
CTGGTCGAGCTGGACGGCGACGTAAACGGCCACAAGTTCAGCGTGTCCGGCGAGGGCGAGGGCGATG
CCACCTACGGCAAGCTGACCCTGAAGTTCATCTGCACCACCGGCAAGCTGCCCGTGCCCTGGCCCACC
CTCGTGACCACCCTGACCTACGGCGTGCAGTGCTTCAGCCGCTACCCCGACCACATGAAGCAGCACGA
CTTCTTCAAGTCCGCCATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGCATCGAGCTGAAGGG
CATCGACTTCAAGGAGGACGGCAACATCCTGGGGCACAAGCTGGAGTACAACTACAACAGCCACAAC
GTCTATATCATGGCCGACAAGCAGAAGAACGGCATCAAGGTGAACTTCAAGATCCGCCACAACATCG
AGGACGGCAGCGTGCAGCTCGCCGACCACTACCAGCAGAACACCCCCATCGGCGACGGCCCCGTGCT
GCTGCCCGACAACCACTACCTGAGCACCCAGTCCGCCCTGAGCAAAGACCCCAACGAGAAGCGCGAT
CACATGGTCCTGCTGGAGTTCGTGACCGCCGCCGGGATCACTCTCGGCATGGACGAGCTGTACAAGTA
AGTCGACATCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGGCTTTCATTT
TCTCCTCCTTGTATAAATCCTGGTTGCTGTCTCTTTATGAGGAGTTGTGGCCCGTTGTCAGGCAACGTG
GCGTGGTGTGCACTGTGTTTGCTGACGCAACCCCCACTGGTTGGGGCATTGCCACCACCTGTCAGCTCC
TTTCCGGGACTTTCGCTTTCCCCCTCCCTATTGCCACGGCGGAACTCATCGCCGCCTGCCTTGCCCGCTG
CTGGACAGGGGCTCGGCTGTTGGGCACTGACAATTCCGTGGTGTTGTCGGGGAAGCTGACGTCCTTTC
CTTGGCTGCTCGCCTGTGTTGCCACCTGGATTCTGCGCGGGACGTCCTTCTGCTACGTCCCTTCGGCCCT
CAATCCAGCGGACCTTCCTTCCCGCGGCCTGCTGCCGGCTCTGCGGCCTCTTCCGCGTCTTCGCCTTCG
CCCTCAGACGAGTCGGATCTCCCTTTGGGCCGCCTCCCCGCCTGCTGTGCCTTCTAGTTGCCAGCCATC
TGTTGTTTGCCCCTCCCCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGTGGGGTGGGGCAGGA
CAGCAAGGGGGAGGATTGGGAAGACAATAGCAGGCATGCTGGGGATGCGGTGGGCTCTATGGACCCA
GCGGGTGCCTTCAGCTGCTCGGCTCCGGCCCGTCATCCACCAAGACACAATGCGGCCTGGCCACCAGG
```

-continued

```
AGAAGCCCCGCAGTTTCCCCCACACCAGCTCCCCAATGCCAAAGCCCCGGCCGTCCTGGAGCCCCAAG

GAGCAGAAATCATTACACTGGCCACGGCTGGTGAAGAAGCCGCTCACCTCGTACTCTGGCTCGTCATC

GCCTGCTTTGGTGGCATTCTTGTCCCCAGCATCGGACCCCACGGGCTCAGGCGTGGTAGCCACAGTGG

GGGATGCGGGGTCAGTGGGCTGCTGCACAGCAGGAGGGCTGGCCTCCTCCACCTTCTGAGACTCCCCG

GGCCCCTGGTTTTCTTCCACAGCATTCATTCCTGCAATGACCTTGGCTTTCTTCTCAGCCTGGGGAAAC

AAAAAACAAAAGTCACCTTGGCTGGGGCCCAGGCCAGAAGGCGCCTCACCTCCCTTTTCCAGCGTGC

CAGCCACTCGTCCCGCTTGCGCTTGCTGATGTAGTAGGGGTCCCCCGCCTGGAAGGTGAGCCTCGGCA

TGGGCCGCTGACGGAGGCTGGACTCCCAGCCCAAGCCACCCCGCAGCCGGCCCCGGGAGCCCTAGGA

CAGAGAGACAGACATTAGGGCATTCCACAGAGCCCTGGGGGTGGAACACTTGCCTCCATTTTCATGG

ATTCGATGTTGGTCTCCTTCTGTTCTTTGCCTGTGGAGAGGGAAGAACAAAGGGACCAGTAAGAGGCT

GCCCCTGGTGCTGAGGACTCACCCGCTTCTGCAGGGGCTCCTCGGCCCGTCTCCGAACCACATGACCC

AGCGGGTGCCTT
```

In some embodiments, the donor DNA sequence can comprise transcriptional control elements such as, without limitation, a MND promoter, a CMB promoter, a EF-1alpha promoter, a PGK promoter. In some embodiments, the donor DNA sequence can comprise a reporter molecule such as, without limitation, a fluorescent marker (e.g., GFP), an epidermal growth factor receptor (EGFR), a nerve growth factor receptor (NGFR), an inducible caspase. Where the donor DNA sequence comprises both the primary insertion element (e.g., a nucleic acid sequence encoding a TCR and/or CAR) and a secondary element (e.g., a reporter molecule), coordinated expression may be desired. Various methods of coordinated expression of one or more genes are known in the art. In some embodiments, the primary insertion element (e.g., a nucleic acid sequence encoding a TCR and/or CAR) and the secondary insertion element (e.g., GFP) is separated by a linker. A linker for use in the present disclosure allows for multiple proteins to be encoded by the same nucleic acid sequence (e.g., a multicistronic or bicistronic sequence), which are translated as a polyprotein that is dissociated into separate protein components. For example, a linker for use in a donor nucleic acid of the present disclosure comprising a nucleic acid sequence encoding a TCR and/or CAR and a reporter gene, allows for the TCR and/or CAR and the reporter gene product to be translated as a polyprotein that is dissociated into separate TCR and/or CAR and reporter gene product components. Various linkers that can be used are disclosed elsewhere herein, e.g., IRES, or a 2A peptide.

In some embodiments, the exogenous receptor (e.g., TCR and/or CAR) is introduced into a cell by an expression vector. Expression vectors comprising a nucleic acid sequence encoding a TCR and/or CAR of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the TCR and/or CAR in the host cell. In some embodiments, the adenovirus genome is a 36 kb, linear, double stranded DNA, where a foreign DNA sequence (e.g., a nucleic acid encoding an exogenous TCR and/or CAR) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus, which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retroviral vector is constructed by inserting a nucleic acid (e.g., a nucleic acid encoding an exogenous TCR and/or CAR) into the viral genome at certain locations to produce a virus that is replication defective. Though the retroviral vectors are able to infect a broad variety of cell types, integration and stable expression of the TCR and/or CAR requires the division of host cells.

Lentiviral vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are capable of infecting non-dividing cells and can be used for both in vivo and ex vivo gene transfer and expression, e.g., of a nucleic acid encoding a TCR and/or CAR (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides genetically engineered cells which include and stably express a TCR and/or CAR of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

Modified cells (e.g., comprising a TCR and/or CAR) may be produced by stably transfecting host cells with an expression vector including a nucleic acid of the present disclosure. Additional methods for generating a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a TCR and/or CAR of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified.

"Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a TCR and/or CAR of the present disclosure will be RNA, e.g., in vitro synthesized RNA. Methods for in vitro synthesis of RNA are known in the art; any known method can be used to synthesize RNA comprising a sequence encoding a TCR and/or CAR. Methods for introducing RNA into a host cell are known in the art. See, e.g., Zhao et al. Cancer Res. (2010) 15: 9053. Introducing RNA comprising a nucleotide sequence encoding a TCR and/or CAR into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a TCR and/or CAR.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the immune cells (e.g. T cells) can be incubated or cultivated prior to, during and/or subsequent to introducing the nucleic acid molecule encoding the exogenous receptor (e.g., the TCR and/or CAR) and the gene editing agent (e.g. Cas9/gRNA RNP). In some embodiments, the cells (e.g. T cells) can be incubated or cultivated prior to, during or subsequent to the introduction of the nucleic acid molecule encoding the exogenous receptor, such as prior to, during or subsequent to the transduction of the cells with a viral vector (e.g. lentiviral vector) encoding the exogenous receptor. In some embodiments, the cells (e.g. T cells) can be incubated or cultivated prior to, during or subsequent to the introduction of the gene editing agent (e.g. Cas9/gRNA RNP), such as prior to, during or subsequent to contacting the cells with the agent or prior to, during or subsequent to delivering the agent into the cells, e.g. via electroporation. In some embodiments, the incubation can be both in the context of introducing the nucleic acid molecule encoding the exogenous receptor and introducing the gene editing agent, e.g. Cas9/gRNA RNP. In some embodiments, the method includes activating or stimulating cells with a stimulating or activating agent (e.g. anti-CD3/anti-CD28 antibodies) prior to introducing the nucleic acid molecule encoding the exogenous receptor and the gene editing agent, e.g. Cas9/gRNA RNP.

In some embodiments, introducing the gene editing agent, e.g. Cas9/gRNA RNP, is done after introducing the nucleic acid molecule encoding the exogenous receptor. In some embodiments, prior to the introducing of the agent, the cells are allowed to rest, e.g. by removal of any stimulating or activating agent. In some embodiments, prior to introducing the agent, the stimulating or activating agent and/or cytokines are not removed. Those of skill in the art will be able to determine the order in which each of the one or more nucleic acid sequences are introduced into the host cell.

G. Sources of Immune Cells

Prior to expansion, a source of immune cells is obtained from a subject for ex vivo manipulation. Sources of target cells for ex vivo manipulation may also include, e.g., autologous or heterologous donor blood, cord blood, or bone marrow. For example the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker −) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNA-BEADS® M-450 CD3/CD28 T Cell Expander).

In some embodiments, T cells are separated from a PBMC sample by negative selection of markers expressed on non-T cells, such as B cells, monocytes, or other white blood cells, such as CD 14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

H. Expansion of Immune Cells

Whether prior to or after modification of cells to express a TCR and/or CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

I. Methods of Treatment

The modified cells (e.g., T cells) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells.

Also included is a method of treating a disease or condition in a subject in need thereof comprising administering to the subject a genetically edited modified cell (e.g., genetically edited modified T cell). In one embodiment, the method of treating a disease or condition in a subject in need thereof comprises administering to the subject a genetically edited modified cell comprising an exogenous TCR and/or CAR.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undertermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ cells, and/or is based on a desired fixed or minimum dose of CD4$^+$ and/or CD8$^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ CD4$^+$ and/or CD8$^+$ cells/kilograms (kg) body weight, such as between $10^5$ and $10^6$ CD4$^+$ and/or CD8$^+$ cells/kg body weight, for example, at or about $1\times10^5$ CD4$^+$ and/or CD8$^+$ cells/kg, $1.5\times10^5$ CD4$^+$ and/or CD8$^+$ cells/kg, $2\times10^5$ CD4$^+$ and/or CD8$^+$ cells/kg, or $1\times10^6$ CD4$^+$ and/or CD8$^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ CD4$^+$ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ CD4$^+$ cells, and/or between about $10^8$ and $10^{12}$ or between about $10^{10}$ and $10^{11}$ CD8$^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents includes a cytokine, such as IL-2, for example, to enhance persistence. In some embodiments, the methods comprise administration of a chemotherapeutic agent.

In certain embodiments, the modified cells of the invention (e.g., a modified cell comprising a TCR and/or CAR) may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment.

In some embodiments, the subject can be administered conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In certain embodiments, the subject is provided a secondary treatment. Secondary treatments include but are not limited to chemotherapy, radiation, surgery, and medications.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0. In an exemplary embodiment, for a subject having cancer, the subject receives lymphodepleting chemotherapy including 300 mg/m$^2$ of cyclophosphamide by intravenous infusion 3 days prior to administration of the modified T cells. In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with CRS. The presence of CRS generally correlates with expansion and progressive immune activation of adoptively transferred cells. It has been demonstrated that the degree of CRS severity is dictated by disease burden at the time of infusion as patients with high tumor burden experience a more severe CRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology*, 15:47; Teachey et al. (2016) *Cancer Discov*, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

The modified immune cells comprising an exogenous TCR and/or CAR of the present invention may be used in a method of treatment as described herein. In some embodiments, the modified immune cells comprise an insertion and/or deletion in a gene locus that is capable of downregulating gene expression of the endogenous gene. In some embodiments, the endogenous gene is a gene that when downregulated, enhances a function of the immune cell comprising an exogenous TCR and/or CAR. For example, without limitation, the endogenous gene is a gene that when downregulated, enhances tumor infiltration, tumor killing, and/or resistance to immunosuppression of the immune cell comprising an exogenous TCR and/or CAR.

In some embodiments, the insertion and/or deletion in a gene locus is capable of downregulating the expression of one or more genes selected from the group consisting of C1orf141, CCDC33, CCL7, CEACAM19, KLF4, MFSD5, PAGR1, SIX2, and USP27X. In some embodiments, the insertion and/or deletion in a gene locus is capable of downregulating the expression of one or more genes selected from the group consisting of AZI2, C1orf141, CCDC33, CCL7, CEACAM19, KLF4, MFSD5, PAGR1, SIX2, and USP27X. In some embodiments, the insertion and/or deletion in a gene locus is capable of downregulating the expression of one or more genes selected from the group consisting of KLF4, PAGR1, and SIX2. In some embodiments, the insertion and/or deletion in a gene locus is capable of downregulating the expression of PAGR1. In some embodiments, the insertion and/or deletion in a gene locus is capable of downregulating the expression of a PAGR1-associated gene, e.g., ARID1A, ARID3B, ASXL1, DNMT3A, DUSP1, MAP3K8, PAXIP1, PRMT1, SOCS3, or TNFAIP3.

As such, the modified immune cells comprising an exogenous TCR and/or CAR of the present invention when used in a method of treatment as described herein, enhances the ability of the modified immune cells in carrying out their function. Accordingly, the present invention provides a method for enhancing a function of a modified immune cell for use in a method of treatment as described herein.

J. Pharmaceutical Compositions and Formulations

Also provided are populations of immune cells of the invention, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

K. Nucleic Acid and Immune Cell Libraries

The present invention provides a nucleic acid library for use in a method of screening described elsewhere herein. The nucleic acid library comprises one or more nucleic acids. In some embodiments, the library comprises one or more nucleic acids each comprising a first nucleic acid encoding a unique targeting sequence. The unique targeting sequence may be any sequence that is capable of targeting any region of an endogenous gene locus. In one embodiment, the unique targeting sequence is capable of targeting an endogenous gene locus and generating an insertion and/or deletion in the targeted sequence of the endogenous gene locus. In one embodiment, the nucleic acid library of the present invention comprises one or more nucleic acids, wherein each of the one or more nucleic acids comprises a first nucleic acid encoding a unique targeting sequence. In some embodiments, the nucleic acid library of the present invention comprises one or more nucleic acids, wherein each of the one or more nucleic acids comprises a first nucleic acid encoding a unique targeting sequence, and the library comprises at least one nucleic acid encoding a unique targeting sequence that targets each gene (e.g., open reading frame) of a human genome.

There is an estimated 19,000-20,000 genes in the human genome. As such, in some embodiments, a nucleic acid library of the present invention comprises at least 19,000-20,000 nucleic acids, each comprising a first nucleic acid encoding a unique targeting sequence that targets each of the 19,000-20,000 genes of the human genome. For example, a nucleic acid library of the present invention comprises over 100 nucleic acids, each comprising a first nucleic acid encoding a unique targeting sequence that targets at least 100 unique genes (e.g., open reading frames) of the human genome. For example, a nucleic acid library of the present invention comprises over 200, e.g., over 300, 400, 500, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, nucleic acids, each comprising a first nucleic acid encoding a unique targeting sequence that targets at least 200, e.g., 300, 400, 500, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000 unique genes of the human genome.

Yet in another embodiment, the nucleic acid library of the present invention comprises one or more nucleic acids comprising a first nucleic acid encoding a unique targeting sequence that targets one or more portions of each of the 19,000-20,000 genes of the human genome. In such embodiments, the nucleic acid library of the present invention is said to have one or more times coverage of the human genome. For example, each gene of the human genome may be targeted one or more times, e.g., 2 or more times, 3 or more times, 4 or more times, 5 or more times, 10 or more times, 15 or more times, 20 or more times, and the nucleic acid library of the present invention comprises at least 2 times coverage, e.g. at least 3 times coverage, at least 4 times coverage, at least 5 times coverage, at least 10 times coverage, at least 15 times coverage, at least 20 times coverage of the human genome. For example, in one embodiment, a nucleic acid library of the present invention that comprises at least 3 times coverage of the human genome comprises over 600, e.g., over 900, 1200, 1500, 3000, 4500, 6000, 9000, 12,000, 15,000, 18,000, 21,000, 24,000, 27,000, 30,000, 33,000, 36,000, 39,000, 42,000, 45,000, 48,000, 51,000, 54,000, 57,000, 60,000, nucleic acids, each comprising a first nucleic acid encoding a unique targeting sequence that targets at least 200, e.g., 300, 400, 500, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000 unique genes of the human genome, at least three times. In such an embodiment, the targeting sequences that target the same gene target unique regions of the same gene. In another example, in one embodiment, a nucleic acid library of the present invention that comprises at least 6 times coverage of the human genome comprises over 1200, e.g., over 1800, 2400, 3000, 6000, 9000, 12,000, 18,000, 24,000, 30,000, 36,000, 42,000, 48,000, 54,000, 60,000, 66,000, 72,000, 78,000, 84,000, 90,000, 96,000, 102,000, 108,000, 114,000, 120,000, nucleic acids, each comprising a first nucleic acid encoding a unique targeting sequence that targets at least 200, e.g., 300, 400, 500, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000 unique genes of the human genome, at least six times. In this example, at least six unique targeting sequences target at least six unique regions of the same gene (e.g., open reading frame). The skilled artisan would readily be able to determine the appropriate level of coverage and the appropriate size of the library (e.g., number of unique targets) for use in a screen of interest.

The first nucleic acid of a subject nucleic acid library may further comprise a promoter sequence in operable linkage with the unique targeting sequence. For example, the first nucleic acid of a subject nucleic acid library may further comprise a U6 promoter sequence in operable linkage with the unique targeting sequence. The U6 promoter recruits RNA polymerase III which transcribes, amongst others, small RNAs, and is useful for driving transcription of a unique targeting sequence. Any promoter sequence that is suitable for driving transcription of small RNAs can be operably linked to the unique targeting sequence of a first nucleic acid of a subject nucleic acid library. Another example of such a promoter is the H1 promoter. Accordingly, in one embodiment, a nucleic acid library of the present invention comprises one or more nucleic acids, each comprising a first nucleic acid comprising a U6 promoter operably linked to a nucleic acid sequence encoding a unique targeting sequence. A variety of promoters suitable for driving transcription of unique targeting sequences are known in the art. The skilled artisan would readily be able to determine which promoter to use that suits the needs of the screen of interest.

In some embodiments, a subject nucleic acid library of the present invention comprises one or more nucleic acids each comprising a first nucleic acid encoding for a unique targeting sequence, e.g., a unique guide RNA. The unique guide RNA comprises a sequence that is sufficiently complementary with a target region of an endogenous gene. In one embodiment, a nucleic acid library of the present invention that comprises at least 6 times coverage of the human genome comprises over 1200, e.g., over 1800, 2400, 3000, 6000, 9000, 12,000, 18,000, 24,000, 30,000, 36,000, 42,000, 48,000, 54,000, 60,000, 66,000, 72,000, 78,000, 84,000, 90,000, 96,000, 102,000, 108,000, 114,000, 120,000, nucleic acids, each comprising a first nucleic acid encoding a unique guide RNA that targets (e.g., is sufficiently complementary to) a unique target region of at least 200, e.g., 300, 400, 500, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000 unique genes of the human genes, at least six times.

In some embodiments, the library comprises a second nucleic acid that encodes for an exogenous T cell receptor (TCR) and/or chimeric antigen receptor (CAR). In some embodiments, the exogenous TCR and/or CAR encoded by the second nucleic acid comprises affinity for a target antigen, e.g., a known target antigen. In some embodiments, the exogenous TCR and/or CAR encoded by the second nucleic acid comprises affinity for, e.g., NY-ESO-1 or PSCA.

In some embodiments, the second nucleic acid of a subject nucleic acid library may further comprise an elongation-factor-1-alpha promoter (EF-1α promoter) in operable linkage with the nucleic acid encoding the exogenous TCR and/or CAR. Use of an EF-1α promoter may increase the efficiency in expression of downstream transgenes (e.g., a TCR and/or CAR encoding nucleic acid sequence). Any promoter sequence that is suitable for driving expression of a downstream transgene, e.g., a TCR and/or CAR, can be operably linked to the nucleic acid encoding for the exogenous TCR and/or CAR. In one embodiment, a nucleic acid library of the present invention comprises a second nucleic acid comprising an EF-1α promoter operably linked to a nucleic acid sequence encoding for an exogenous TCR and/or CAR. A variety promoters suitable for driving expression of downstream transgenes are known in the art. The skilled artisan would readily be able to determine which promoter to use that suits the needs of the screen of interest.

In some embodiments, the first and the second nucleic acid of a subject nucleic acid library each reside on separate nucleic acids. In such embodiments, a selection marker, e.g., a detectable label or a resistance gene, may be incorporated into the first and/or the second nucleic acid. In embodiments where the first and the second nucleic acid each reside on separate nucleic acids, when the library is introduced into a population of cells, the selectable marker may be used to determine which cells comprise both the first and the second nucleic acid. In some embodiments, the first and the second nucleic acid reside on the same nucleic acid. A selectable marker may be incorporated into such a nucleic acid comprising the first and the second nucleic acids. In one embodiment, the selectable marker is a reporter gene, e.g., comprises a nucleic acid sequence encoding for a reporter protein, e.g., a fluorescent protein. Such a selectable marker is useful for determining which cells have been successfully transformed or transduced with a nucleic acid of a subject nucleic acid library.

In an exemplary embodiment, the first and the second nucleic acid of a subject nucleic acid library resides on the same nucleic acid. For example, see FIG. 1. In one embodiment, a subject nucleic acid library comprises one or more nucleic acids, wherein each nucleic acid comprises a first nucleic acid encoding a unique targeting sequence, and a second nucleic acid comprising a nucleic acid sequence encoding for an exogenous TCR and/or CAR. In one embodiment, a subject nucleic acid library comprises one or more nucleic acids, wherein each nucleic acid comprises a first nucleic acid comprising a U6 promoter sequence in operable linkage to a nucleic acid sequence encoding a unique targeting sequence, and an EF-1α promoter sequence in operable linkage to a nucleic acid sequence encoding for an exogenous TCR and/or CAR.

In those embodiments employing viral vectors in a subject nucleic acid library, members of the nucleic acid library are present as viral particles that house a viral genomic nucleic acid, where the viral genomic nucleic acid of a given particle member of the library includes both a vector domain and a subject nucleic acid (e.g., a nucleic acid comprising a first nucleic acid encoding a unique targeting sequence, and a second nucleic acid comprising a nucleic acid sequence encoding for an exogenous TCR and/or CAR). Such libraries may be referred to as packaged viral nucleic acid libraries. Of particular interest in certain embodiments is the use of packaged viral nucleic acid libraries that employ viral vector domains that provide for entry of a single member of a nucleic acid library into a given target cell (e.g., a target immune cell).

Within a packaged viral nucleic acid library of the invention, the viral genomic nucleic acids of different library members will share common vector domains. Accordingly, the nucleic acid library members will share a common vector sequence, such that the sequence of the encapsidated viral genomic nucleic acids in the library will be substantially, if not completely, identical, but for the different members of the subject nucleic acid library. The sequence of the vector domain may vary greatly, depending on the nature of the vector. In some instances, the vector domain includes sequences necessary for the production of recombinant viral constructs in a packaging cell, transduction and replication of a member of the nucleic acid library in the target cells (e.g., immune cells) and expression of the member of the nucleic acid library (e.g., expression of a guide RNA and a TCR and/or CAR), reporters or other effectors and genes. Generation of the vector domain, as well as subject nucleic acid libraries including the same, can be accomplished using any suitable genetic engineering techniques, including without limitation, the standard techniques of PCR, oligonucleotide synthesis, restriction endonuclease digestion, site-specific digestion, site-specific recombination, ligation, transformation, plasmid purification, and DNA sequencing.

In some instances, the vector domain is selected from a viral genome of a virus selected from the group of adenoviral, adeno-associated, vaccinia, herpes, foamy, etc. viruses, where such viruses are commonly used for gene transfer applications. In some instances, the vector domain is a retroviral vector region, such that it is a domain derived from a retrovirus. Retroviruses are any virus belonging to the family Retroviridae, comprising single-stranded RNA animal viruses characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus may then be capable of integrating into the host genome (e.g., the genome of the target immune cell). Accordingly, in certain aspects, each member of a subject nucleic acid library is configured to integrate into the genome of the target immune cell. The integration may be non-specific or specific to a particular chromosomal location. In certain aspects, the viral vector is designed to integrate at a specific chromosomal site using site-specific recombination (e.g., using a Cre-Lox or other recombination system), zinc finger endonuclease, CRISPR endonuclease, at a specific site at which the virus from which the vector is derived naturally integrates, or the like.

In certain aspects, the members of a subject nucleic acid library are non-integrating vectors, e.g., where each member of a subject nucleic acid library is based on a non-integrating lentiviral, adenoviral or adeno-associated viral vector.

According to certain embodiments, the retroviral vector region is an adeno-associated viral vector region, e.g., a vector derived from an adeno-associated virus (AAV). Any suitable AAV-based vector with any serotype of interest may be used, including AAV-based vectors described, e.g., in McCarty (2008) Mol. Therapy 16:1648-1656; Nonnenmacher (2012) Gene Therapy 19:649-658; and Jayandharan et al. (2008) Gene Therapy 15:1287-1293.

In some embodiments, the retroviral vector region is a lentiviral vector region, e.g., a vector derived from a lentivirus. Lentiviruses are members of the retrovirus family. Lentivirus vectors may be pseudotyped with VSV-G, and have been derived from the human immunodeficiency virus (HIV), the etiologic agent of the human acquired immunodeficiency syndrome (AIDS); visan-maedi, which causes encephalitis (visna) or pneumonia in sheep; the caprine arthritis-encephalitis virus, which causes immune deficiency, arthritis, and encephalopathy in goats; equine infectious anemia virus (EIAV), which causes autoimmune hemolytic anemia and encephalopathy in horses; feline immunodeficiency virus (Hy), which causes immune deficiency in cats; bovine immune deficiency virus (BIV) which causes lymphadenopathy and lymphocytosis in cattle; and simian immunodeficiency virus (SIV), which causes immune deficiency and encephalopathy in non-human primates. Vectors that are based on HIV may retain <5% of the parental genome, and <25% of the genome may be incorporated into packaging constructs, which minimizes the possibility of the generation of revertant replication-competent HIV. The vector region may include sequences form the 5' and 3' LTRs of a lentivirus. In some instances, the vector domain includes the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Where desired, the subject viral nucleic acid library may be made up of self-inactivating vectors that contain deletions of the regulatory elements in the downstream long-terminal-repeat sequence, eliminating transcription of the packaging signal that is required for vector mobilization. As such, the vector region may include an inactivated or self-inactivating 3' LTR. The 3' LTR may be made self-inactivating by any convenient method. For example, the U3 element of the 3' LTR may contain a deletion of its enhancer sequence, such as the TATA box, Sp1 and NF-kappa B sites. As a result of the self-inactivating 3' LTR, the provirus that is integrated into the host cell genome will comprise an inactivated 5' LTR. Optionally, the U3 sequence from the lentiviral 5' LTR may be replaced with a promoter sequence in the viral construct. This may increase the titer of virus recovered from the packaging cell line. An enhancer sequence may also be included.

The viral genomic nucleic acids of a subject viral nucleic acid library may contain additional elements, where such elements may vary greatly. For example, a reporter gene may be placed in functional relationship with the internal promoter, such as the gene for a fluorescent marker protein. The additional genetic elements can be operably linked with and controlled by an independent promoter/enhancer.

In some embodiments, each member of a subject viral nucleic acid library may include an effector cassette, e.g., as described in more detail below and in co-pending U.S. Provisional Patent Application No. 61/644,324 filed on May 8, 2012, the disclosure of which is herein incorporated by reference. The term "effector" is used to refer to a biochemical molecule that can effect the transcription, translation, expression, processing or function of another molecule or molecules, such as a target gene or the product of a target gene. Effectors may be full-length proteins, protein domains, peptides, single-stranded or double-stranded deoxy- or ribo-oligonucleotides, siRNAs, micro RNAs, CRISPR RNAs, ribozymes, antisense RNAs, regulatory RNAs including small RNAs and non-coding RNAs, or mimetics or analogues thereof. Effector cassettes of interest include at least an effector sequence, where the effector sequence may be operationally-linked to a promoter, e.g., for expression of the effector sequence in a cell that includes the effector construct. Optionally, an effector cassette may include an effector-specific barcode, e.g., to facilitate identification of effector sequence.

The libraries employed in embodiments of the subject methods can be produced using any convenient protocol. For example, the subject nucleic acid libraries can be generated synthetically or enzymatically by a number of different protocols, and the appropriate oligonucleotide and polynucleotide vectors may be purified using standard recombinant DNA techniques as described in, for example, Sambrook et al., Molecular Cloning: A Laboratory Manual, 3rd Ed., Cold Spring Harbor Press, Cold Spring Harbor, N.Y. (2000), and under regulations described in, e.g., United States Dept. of HHS, National Institute of Health (NIH) Guidelines for Recombinant DNA Research.

In some embodiments, preparing the subject nucleic acid libraries includes combining a each member of the nucleic acid library with a vector construct comprising a vector domain or vector sequence under conditions sufficient to produce transfection plasmids which, upon transfection of a packaging cell, result in the production of viral particles containing the subject nucleic acid library as part of genomic nucleic acids encapsidated in viral protein shells. To prepare the product transfection plasmids used for transfection, each member of a subject nucleic acid library may be inserted into a vector nucleic acid, where any suitable protocol may be employed. Examples of suitable protocols include, but are not limited to: DNA ligase mediated joining, recombination enzyme mediate joining, using In-Fusion® PCR protocols (Clontech Laboratories, Mountain View, Calif.), Gateway® cloning technology (Life Technologies, Carlsbad, Calif.), and the like.

The resultant product transfection plasmids may then be used to transfect a suitable packaging cell line for production of subject nucleic acid library viral particles. The packaging cell line provides the viral proteins that are required in trans for the packaging of the viral genomic RNA into viral particles. The packaging cell line may be any cell line that is capable of expressing retroviral proteins, including HEK293, HeLa, D17, MDCK, BHK, NIH3T3, CHO, CrFK, and Cf2Th. In some embodiments, each member of a subject viral nucleic acid library is used together with a viral reporter construct which may comprise one or more reporter genes under the control of a constitutive or conditional (regulatable) promoter. The packaging cell line may stably express necessary viral proteins. Such a packaging cell line is described, for example, in U.S. Pat. No. 6,218,181. Alternatively, a packaging cell line may be transiently transfected with plasmids comprising nucleic acids that encode the necessary viral proteins. In another embodiment, a packaging cell line that does not stably express the necessary viral proteins is co-transfected with two or more plasmids. One of the plasmids comprises the viral construct a member of a subject nucleic acid library. The other plasmid(s) comprises nucleic acids encoding the proteins necessary to allow the cells to produce functional virus that is able to infect the desired host cell. The packaging cell line may not express envelope gene products. In this case, the packaging cell line will package the viral genome into particles that lack an envelope protein. As the envelope protein is responsible, in part, for the host range of the viral particles, the viruses preferably are pseudotyped. A "pseudo-typed" retrovirus is a retroviral particle having an envelope protein that is from a virus other than the virus from which the RNA genome is derived. The envelope protein may be from a different retrovirus or a non-retrovirus. One envelope protein is the vesicular stomatitis virus G (VSV-G) protein. Thus, the packaging cell line may be transfected with a plasmid that includes sequences encoding a membrane-associated protein, such as VSV-G, that will permit entry of the virus into a target cell. One of skill in the art can choose an appropriate pseudo type specific and/or more efficient for the target cell used. In addition to conferring a specific host range, a chosen pseudotype may permit the virus to be concentrated to a very high titer. Viruses alternatively can be pseudotyped with ecotropic envelope proteins that limit infection to a specific species.

The present invention also provides a plurality of immune cells comprising a subject nucleic acid library. In one embodiment, each of the plurality of immune cells comprise a member of the subject nucleic acid library, e.g., a single member of the subject nucleic acid library comprising a nucleic acid comprising a first nucleic acid encoding for a single unique targeting sequence, and a second nucleic acid encoding for a TCR and/or CAR. The plurality of immune cells are contacted with the subject nucleic acid library under transduction conditions.

Transduction of one or more target cells in the plurality of immune cells with a subject viral nucleic acid library may be accomplished by any convenient protocol and may depend, at least in part, on the target cell type and the viral vectors employed. For example, transduction may include thawing a frozen subject viral nucleic acid library, suspending the cellular sample in a cell culture medium (e.g., D-MEM) which may be supplemented with serum (e.g., 10% FBS) and/or a transduction enhancing agent (e.g., hexadimethrine bromide (Polybrene®)), combining the library and cell suspension in a cell culture plate, and placing the plate at 37° C. in a $CO^2$ incubator for a suitable period of time. In certain aspects, the cells are incubated for between 1 and 24 hours, such as between 4 and 16 hours, e.g., between 8 and 12 hours.

The transduction conditions may be optimized in order to achieve delivery and expression of a single member of a subject nucleic acid library into a given target cell. For example, in certain aspects, transducing any given target cell with a single member of a subject viral nucleic acid library is achieved by employing a sufficiently complex packaged viral nucleic acid library and carrying out the transduction step at a suitable multiplicity of infection (MOI), which is the ratio of infectious agents (e.g., viral particles) to target cells (e.g., target immune cells). In some embodiments, the transduction is carried out at an MOI of 1 or less, 0.9 or less, 0.8 or less, 0.7 or less, 0.6 or less, 0.5 or less, 0.4 or less, 0.3 or less, 0.2 or less, or 0.1 or less. Of particular interest are transduction conditions that result in each of the plurality of immune cells containing one single member of a subject viral nucleic acid library. In such an embodiment, each immune cell comprises a nucleic acid comprising a first nucleic acid encoding for a single unique targeting sequence (e.g., a single unique guide RNA), and second nucleic acid encoding for a TCR and/or CAR.

In some embodiments, each of a plurality of immune cells comprising a subject nucleic acid library is contacted with an editing agent. As used herein, an "editing agent" refers to any agent that introduces an insertion and/or deletion in an endogenous gene locus based on a unique targeting sequence comprised by the subject nucleic acid library. In one embodiment, the editing agent is a CRISPR nuclease polypeptide, or a nucleic acid that encodes for a CRISPR nuclease. In embodiments where the first and the second nucleic acid of a subject nucleic acid library reside on the same nucleic acid, the editing agent may be a CRISPR nuclease, or a nucleic acid encoding a CRISPR nuclease. In embodiments, where the first and the second nucleic acid of a subject nucleic acid library reside on separate nucleic acids, the editing agent may be a CRISPR-related system. In such an embodiment, the CRISPR-related system comprises the first nucleic acid of a subject nucleic acid library, e.g., the CRISPR-related system comprises a unique targeting sequence. Where each of a plurality of immune cells comprises a member of a subject nucleic acid library and has been contacted with an editing agent, each of the plurality of immune cells comprise an insertion and/or deletion in an endogenous gene locus (as dictated by the unique targeting sequence), and an exogenous TCR and/or CAR. Such a plurality of gene edited, modified immune cells may be referred to herein as a gene modified TCR/CAR immune cell (e.g., T cell) library.

In some embodiments, whether the screening method is performed in vitro or in vivo (as described elsewhere herein), the cells are derived from cell lines, e.g., T cell lines. The cells in some embodiments are obtained from a host organism source, for example, without limitation, from a mouse, a rat, a non-human primate, and a pig.

L. Methods of Screening

The present invention provides a method for identifying a gene (e.g., a method of screening for a gene) that regulates immune cell function (e.g., a gene that when downregulated, results in an enhanced function of an immune cell or precursor cell thereof). For example, such a gene may, without limitation, be a gene that normally acts to inhibit a function of the immune cell, or may be a gene that normally acts to enhance an inhibitor of a function of the immune cell, or may be a gene that normally acts to inhibit an enhancer of a function of the immune cell. The present invention also provides a method for identifying a gene that regulates immune cell memory and persistence (e.g., T cell memory and T cell persistence). In one embodiment, the present invention provides a method for identifying a gene that when downregulated, enhances immune cell memory and/or enhances immune cell persistence. In one embodiment, the present invention provides a method for identifying a gene that when downregulated, enhances T cell memory and/or enhances T cell persistence.

In some embodiments, the present invention provides a method for identifying a gene that regulates immune cell function (e.g., a gene that when downregulated, results in an enhanced function of an immune cell or precursor cell thereof comprising an exogenous T cell receptor (TCR) and/or chimeric antigen receptor (CAR)). Any of the endogenous genes described elsewhere herein, when downregulated, may result in an enhanced function of an immune cell comprising an exogenous TCR and/or CAR. The identification method comprises introducing into a plurality of immune cells (e.g., population of T cells) a subject nucleic acid library as described elsewhere herein. In some embodiments, the plurality of immune cells is a plurality of T cells modified to express an exogenous TCR and/or CAR having affinity for an antigen. In some embodiments, the plurality of modified immune cells cells are modified T-lymphocytes (T cells), naive T cells (TN), memory T cells (for example, central memory T cells (TCM), effector memory cells (TEM)), natural killer cells (NK cells), and macrophages. In one embodiment, the genetically engineered cells are autologous cells. In such embodiments, the plurality of modified immune cells is further modified by introducing a plurality of agents (e.g., gene editing agents) that target a plurality of endogenous genes, thereby generating a plurality of edited immune cells.

In an exemplary embodiment, the plurality of immune cells is a plurality of T cells modified by a subject nucleic acid library to express an exogenous TCR and/or CAR having affinity for an antigen, and to express a unique targeting sequence (e.g., unique guide RNA). In such an embodiment, the plurality of modified immune cells is further modified by introducing a plurality of gene editing agents (e.g., a CRISPR nuclease) that results in an insertion and/or deletion in the endogenous gene that the unique target sequence targets, thereby generating a plurality of edited immune cells. Each of the edited immune cells comprises an insertion and/or deletion in a endogenous gene locus (as dictated by the unique targeting sequence) and an exogenous TCR and/or CAR.

Figure 2:
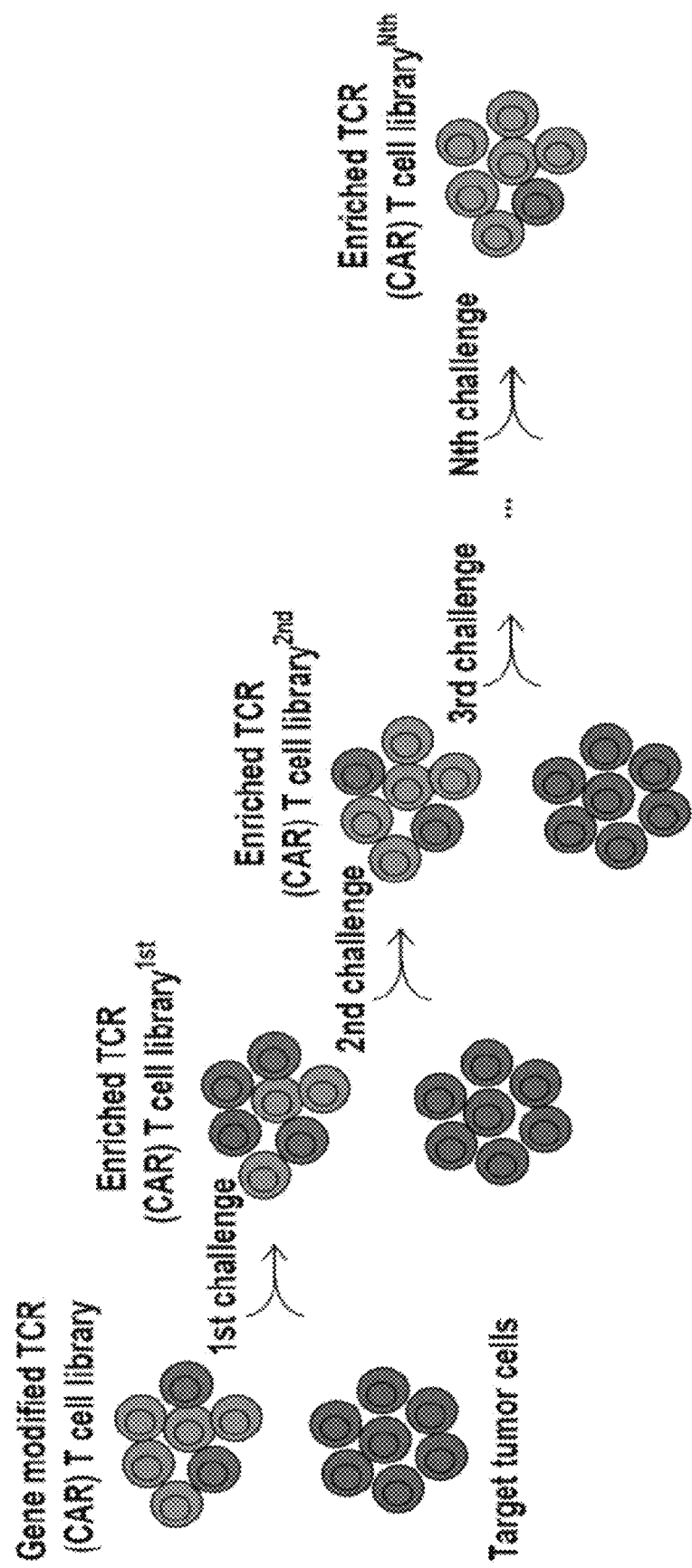
FIG. 2 depicts a schematic of the design of an in vitro genome wide screen using TCR- or CAR-T cell libraries according to an embodiment of the present invention.

A method for identifying a gene that regulates immune cell function (e.g., a gene that when downregulated, results in an enhanced function of an immune cell or precursor cell thereof), may be performed in vitro or in vivo. In one embodiment, the identification method is performed in vitro. An in vitro method for identifying a gene that regulates immune cell function (e.g., a gene that when downregulated, results in an enhanced function of an immune cell or precursor cell thereof (e.g., T cell)) is schematically illustrated in FIG. 2. As illustrated, an in vitro screening method comprises contacting a gene edited, modified TCR/CAR immune cell library (e.g., gene edited, modified TCR/CAR T cell library) with target tumor cells. In such an embodiment, the TCR/CAR that is comprised by the immune cells comprises affinity for the target tumor cell. For example, the gene edited, modified TCR/CAR T cell library comprises T cells that express a TCR/CAR having affinity for a specific antigen (e.g., a PSCA CAR), and the T cell library is contacted with target tumor cells expressing the specific antigen (e.g., PSCA-expressing target tumor cells). The step of contacting the T cell library with target tumor cells represents a "challenge," e.g., a tumor cell challenge. Each challenge results in an enriched TCR/CAR T cell library. For example, upon a first challenge, a first enriched TCR/CAR T cell library may be isolated. Upon one or more challenges, e.g., two or more challenges, three or more challenges, four or more challenges, five or more challenges, a second or more, e.g., a third or more, a fourth or more, a fifth or more, sixth or more enriched TCR/CAR T cell library may be isolated. Upon successive challenges, the final enriched TCR/CAR T cell library may comprise T cells wherein an endogenous gene has been edited to confer enhanced T cell functions (e.g., T cell persistence, T cell efficacy).

In one embodiment, the identification method is performed in vivo. An in vivo method for identifying a gene that regulates immune cell function (e.g., a gene that when downregulated, results in an enhanced function of an immune cell or precursor cell thereof (e.g., T cell)) is schematically illustrated in FIG. 3A. As illustrated, an in vivo screening method comprises infusing a gene edited, modified TCR/CAR immune cell library (e.g., a gene edited, modified TCR/CAR T cell library) into a target tumor-bearing model organism. For example, the gene edited, modified TCR/CAR T cell library comprises T cells that express a TCR/CAR having affinity for a specific antigen (e.g., a PSCA CAR), and the T cell library is infused into a tumor-bearing organism, wherein the organism has a tumor that expresses the specific antigen (e.g., PSCA expressing tumor). Tumor infiltrating lymphocytes are then isolated from the infused, tumor-bearing organism, thereby resulting in an enriched TCR/CAR T cell library. The infusion step is akin to the "challenge" step of an in vitro screening method as described herein. As such, in some embodiments, multiple infusions ("challenges") can be performed successively to further enrich the resulting isolated TCR/CAR T cell library.

A suitable model organism for use in an in vivo screening method of the present invention includes, without limitation, a mouse, a rat, a non-human primate, and a pig. A suitable model organism generally includes an organism that has a natural immune cell repertoire (e.g., T cell repertoire). In some embodiments, where the identification method is performed in vivo, the gene edited, modified TCR/CAR immune cell (e.g., T cell) library is generated from a population of immune cells (e.g., T cells) that are obtained from the same animal as the subject of infusion. For example, where the in vivo screening method includes infusing a subject gene edited, modified TCR/CAR T cell library into a tumor-bearing mouse, the gene edited, modified TCR/CAR T cell library may be generated from a population of mouse T cells. In some embodiments, where the identification method is performed in vivo, the gene edited, modified TCR/CAR immune cell (e.g., T cell) library is generated from a population of immune cells (e.g., T cells) that are obtained from a different animal as the subject of infusion. For example, where the in vivo screening method includes infusing a subject gene edited, modified TCR/CAR T cell library into a tumor-bearing mouse, the gene edited, modified TCR/CAR T cell library may be generated from a population of human T cells. The skilled artisan would readily be able to determine the appropriate source of immune cells and the appropriate infusion subject.

An in vivo method for identifying a gene that regulates immune cell memory and/or immune cell persistence (e.g., a gene that when that when downregulated, results in enhanced T cell memory and/or T cell persistence) is schematically illustrated in FIG. 3A. As illustrated, an in vivo screening method comprises infusing a gene edited, modified TCR/CAR immune cell library (e.g., a gene edited, modified TCR/CAR T cell library) into a target tumor-bearing model organism. For example, the gene edited, modified TCR/CAR T cell library comprises T cells that express a TCR/CAR having affinity for a specific antigen (e.g., a PSCA CAR), and the T cell library is infused into a tumor-bearing organism, wherein the organism has a tumor that expresses the specific antigen (e.g., PSCA expressing tumor). In one embodiment, the gene edited, modified TCR/CAR T cell library will be able to clear a significant portion of the tumor from the tumor-bearing organism. In one embodiment, the gene edited, modified TCR/CAR T cell library will be able to fully clear the tumor from the tumor-bearing organism. In one embodiment, the gene edited, modified TCR/CAR T cell library will be able to clear the tumor from the tumor-bearing organism to levels that are undetectable using standard methods. Once the gene edited, modified TCR/CAR T cell library clears the tumor from the tumor-bearing organism, tumor re-inoculation is performed to re-introduce tumor cells into the cleared tumor-bearing organism. The re-inoculated tumor may be controlled by memory library T cells. Tumor infiltrating lymphocytes are then isolated from the re-inoculated organism, thereby resulting in an enriched TCR/CAR T cell library.

Once an enriched TCR/CAR immune cell library (e.g., an enriched TCR/CAR T cell library) is isolated, standard sequencing methods may be used to identify the gene that regulates immune cell function, immune cell memory, and/or immune cell persistence (e.g., T cell function, T cell memory, and/or T cell persistence). Several methods of DNA extraction and analysis are encompassed in the methods of the invention. As used herein "deep sequencing" indicates that the depth of the process is many times larger than the length of the sequence under study. Deep sequencing is encompassed in next generation sequencing methods which include but are not limited to single molecule realtime sequencing (Pacific Bio), Ion semiconductor (Ion torrent sequencing), Pyrosequencing (454), Sequencing by synthesis (Illumina), Sequencing by ligations (SOLiD sequencing) and Chain termination (Sanger sequencing). The skilled artisan would be able to determine the targeted gene that is enriched in the enriched TCR/CAR immune cell library.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The following experimental examples are not intended to be limiting, and relates to compositions and methods for generating a T cell gene knockout library by using a One-shot type II CRISPR system. One aspect includes a method for generating a One-shot sgRNA library encoding a T cell receptor (TCR) and/or chimeric antigen receptor (CAR) gene together with sgRNA library. Another aspect includes generating modified T cells by transduction of one-shot sgRNA library and subsequent electroporation of Cas9 endonuclease capable of altering endogenous gene expression. Also described are methods for in vitro and in vivo whole genome wide gene screening, by screening two CRISPR/Cas9 T cell libraries with either a NY-ESO-1 TCR or PSCA CAR in multiple NSG tumor mouse models. Deep sequencing of DNA from tumor infiltrating lymphocytes (TIL) isolated from treated mice identify the a panel of enriched gRNAs that target genes of hsa-mir-4508, C1orf141, PAGR1, CEACAM19, MFSD5, SIX2, KLF4, USP27X, CCDC33 and ZNF124. CAR-T or TCR-T cells with endogenous C1orf141, PAGR1, CEACAM19, SIX2, KLF4, USP27X or CCDC33 downregulated were tested in NSG mouse tumor models of prostate cancer (PC3-PASC), pancreatic cancer (CaPan1) or lung cancer (A549-ESO). Without being bound by any theory, tt was found that PAGR1, SIX2, and Klf4 downregulation could improve T cell function both in vitro and in vivo in different mouse tumor models.

Materials and Methods

Primary human lymphocytes. Primary lymphocytes were stimulated with microbeads coated with CD3 and CD28 stimulatory antibodies (Life Technologies, Grand Island, NY, Catalog) as described (Human gene therapy 2011, 22(12):1575-1586). T cells were cryopreserved at day 10 in a solution of 90% fetal calf serum and 10% dimethylsulfoxide (DMSO) at $1 \times 10^8$ cells/vial.

Propagation of primary T cells. Primary human T cells were cultured in RPMI 1640 supplemented with 10% FCS, 100-U/ml penicillin, 100-g/ml streptomycin sulfate, 10-mM Hepes, and stimulated with magnetic beads coated with anti-CD3/anti-CD28 at a 1:3 cell to bead ratio. Cells were counted and fed every 2 days and once T cells appeared to rest down, as determined by both decreased growth kinetics and cell size, the T cells were either used for functional assays or cryopreserved.

Generation of PSCA CAR one-shot constructs for lentiviral transduction. PSCA CAR was synthesized and subcloned into Human GeCKO Lentiviral sgRNA Library v2 (lentiGuide-Puro). The library was amplified and lentiviral vector was generated for transducing T cells.

CAR T cell gene editing with one-shot CRISPR. Cas9 mRNA was transcribed in vitro using mMESSAGE mMACHINE T7 ULTRA kits (Life Technologies, AM1345, Carlsbad, CA). gRNA were transcribed using a HiScribe™ T7 High Yield RNA Synthesis Kit. Cas9 protein was purchased from PNA Bio (CP01). Electroporation of CRISPR reagents with one-shot CAR or CAR T cells was performed with a BTX830 electroporator.

Briefly, T cells were washed three times with OPTI-MEM and re-suspended in OPTI-MEM (Invitrogen) at a final concentration of $1-3 \times 10^8$ cells/ml. Subsequently, 0.1 ml of the cells was mixed with IVT RNA and electroporated in a 2 mm cuvette. Twenty micrograms of Cas9 mRNA was electroporated into the cells using a BTX830 (Harvard Apparatus BTX) at 360 V and 1 ms. Following electroporation, the cells were immediately placed in 2 ml of pre-warmed culture media and cultured in the presence of IL-2 (100 IU/ml) at 37° C. and 5% $CO_2$.

Flow cytometry. The following monoclonal antibodies and reagents were used with indicated specificity and the appropriate isotype controls. From BD Biosciences (San Jose, CA): APC-conjugated anti-CD3 (555335). Data was acquired on a FACS Accuri (BD Biosciences, San Jose, CA) using CellQuest version 3.3 (BD Biosciences, San Jose, CA) and analyzed by FCS Express version 3.00 (De Novo Software, Los Angeles, CA) or FlowJo version 7.6.1 (Tree Star, Inc. Ashland, OR).

Mouse xenograft studies. All animal experiment protocols were approved and conducted in accordance with the Institutional Animal Care and Use Committee. Studies were performed as previously described with certain modifications. Briefly, for the Nalm6 tumor model, 6- to 10-week-old NSG mice were injected with 1×106 Nalm6 tumors cells through the tail vein on day 0. The T cell treatment began on day 7 after the tumor inoculation. T cells were administered at a dose of 2×10$^6$ cells/mouse (2M).

Figure 1B:
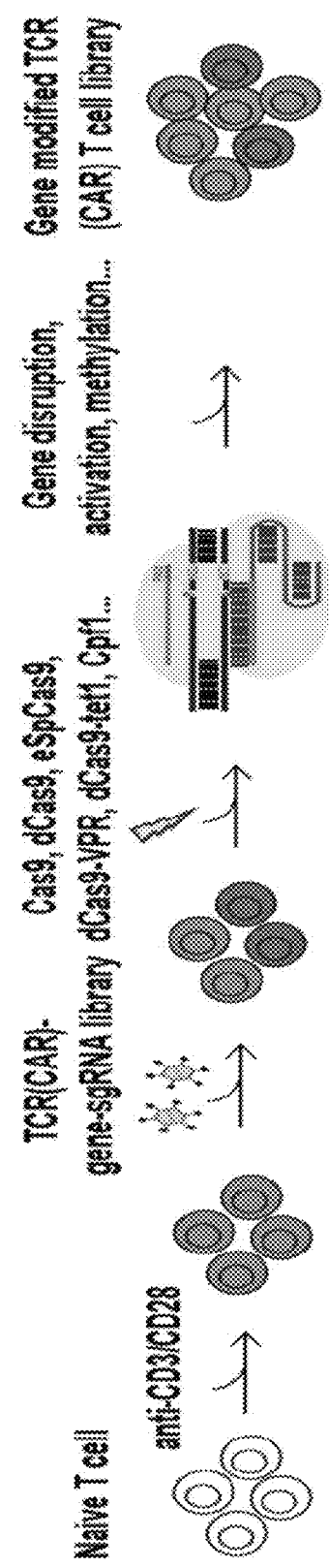
Figure 5B:
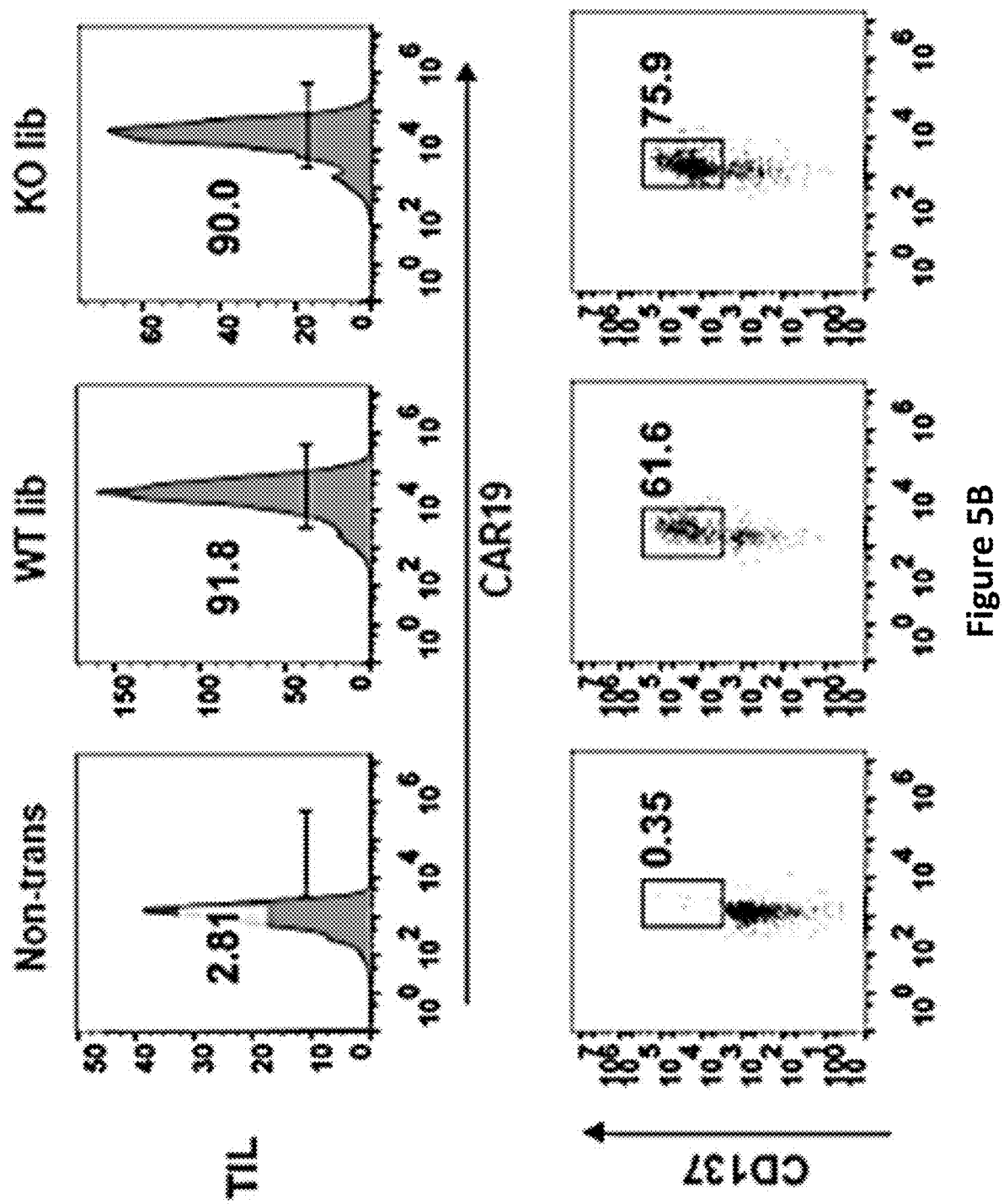

Example 1: Genome-Wide Functional Screening in TCR- or CAR-T Cells with CRISPR Library Gene modified TCR- or CAR-T cell libraries comprising the one-shot CRISPR system can be used for genome wide functional screen in vitro or in vivo. Gene modified TCR- or CAR-T cell CRISPR libraries are made using a construct as depicted in FIG. 1A, according to an embodiment of the present invention. The preparation of the libraries was performed according to the process depicted in FIG. 1B. In vitro genome wide screening was performed as depicted in FIG. 2, and in vivo genome wide screening was performed as depicted in FIGS. 3A and 3B. FIGS. 4A and 4B show the fold expansion of CAR-T cell libraries stimulated in vitro with irradiated target tumor cells for a CD19-directed CAR-T cell library (FIG. 4A) and a PSCA directed CAR-T cell library (FIG. 4B). FIG. 5 shows the functional analysis of a CD19-directed CAR-T cell library and a PSCA-directed CAR-T cell library. CD19-directed CAR-T cell library tumor infiltrating lymphocytes (TILs) were able to eliminate Nalm6-GFP tumor cells (FIG. 5A). PSCA-directed CAR-T cell library TILs were able to upregulate the T cell activation marker CD137 after co-culture with PC3-PSCA tumor cells (FIG. 5B).

Figure 6:
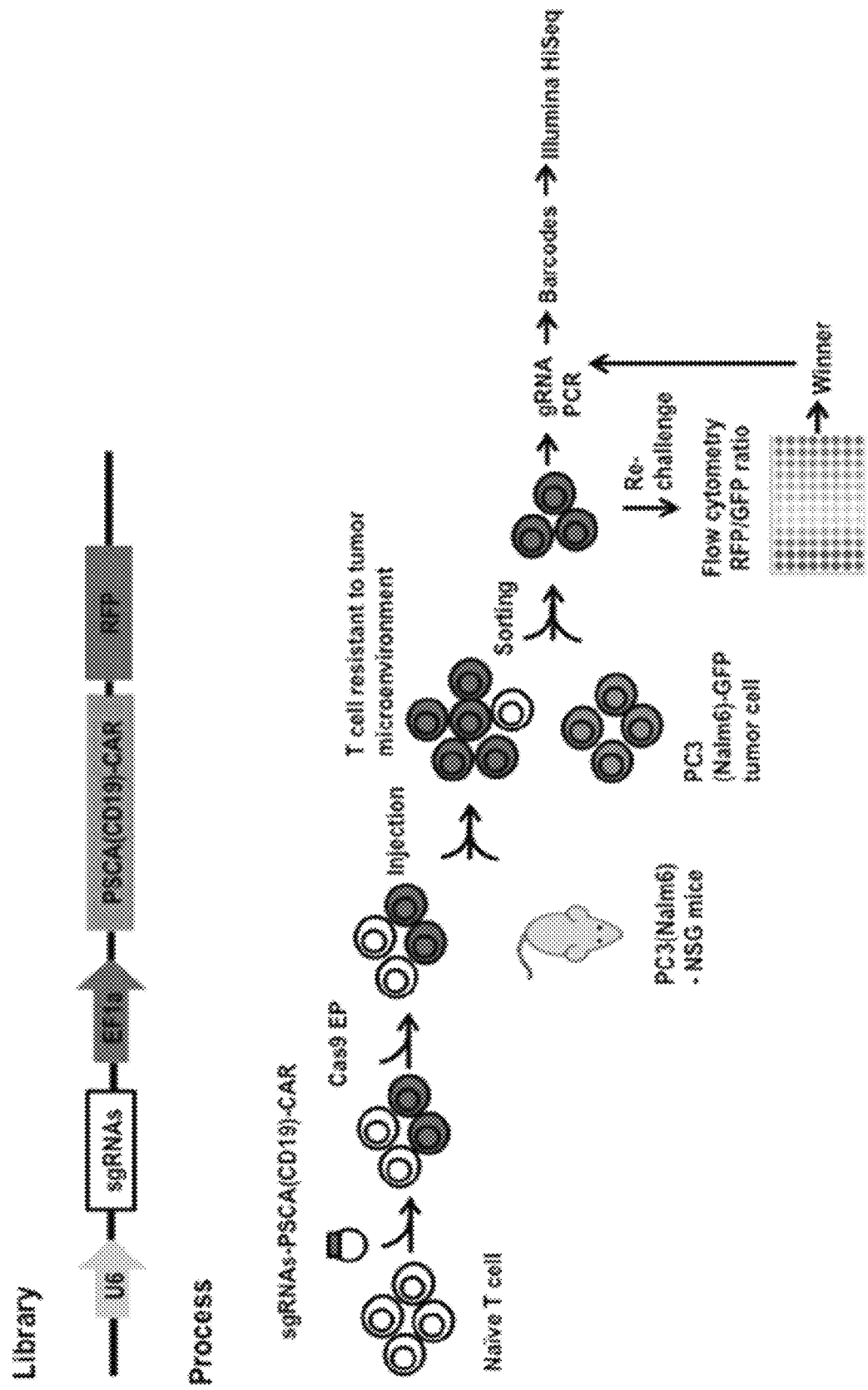
FIG. 6 depicts a schematic showing the library and selection process for an in vivo genome wide screen to identify inhibitory pathways of CAR-T cell therapy.

Example 2: Genome-Wide Functional Screening in CAR-T Cells with CRISPR Library CAR-T cell libraries underwent in vivo selections. Briefly, selection was directly carried out in vivo by injecting CAR-T cells into mice bearing PC3-PSCA tumor. 14 days post CAR-T cell infusion, tumor-infiltrating CAR-T cells were collected (FIG. 6).

Example 3: Deep Sequencing and Data Analysis

Preparation of barcoded DNA libraries was achieved by incorporating barcode and adaptor sequences into PCR primers. Miseq was performed to identify the enrichment of each guide RNA. Over 240 guide RNAs were found to show relative enrichment more than 5 times, including 40 guide RNAs enriched more than 10 times (FIG. 7). Top candidates identified by the in vivo screen included Klf4, Bach, and PTGIR which were found to show sgRNA enrichment of 50 to 100 times (FIGS. 8A and 8B). Without being bound by any theory, these results indicate that a One-shot CRISPR system is a potent and reliable system for in vivo screening of CAR-T cell negative regulatory genes.

Example 4: Identifying Common CAR-T Cell Regulatory Genes Among Different Tumor Types To further verify the candidates, another in vivo screen was conducted in a native PSCA antigen bearing pancreatic cancer-CaPan1, which has relatively low antigen expression compared to PC3-PSCA tumor. A similar screening approach was performed, and enriched sgRNAs were measured by deep sequencing. The top 20 enriched candidates did not have any overlap with the previous screen (FIG. 9).

Figure 10A:
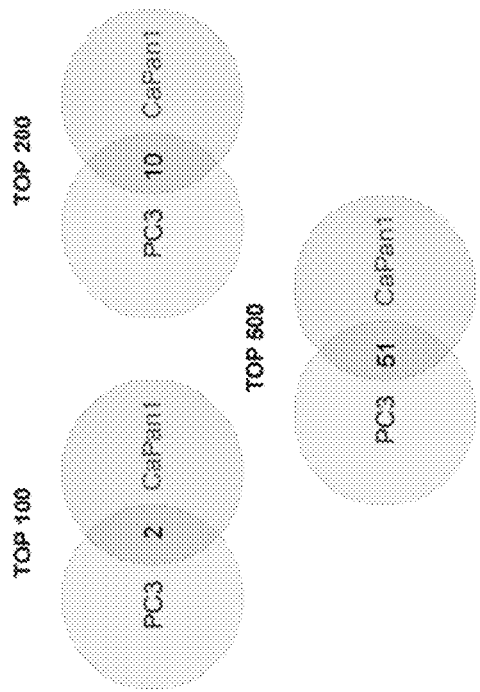
FIGS. 10A-10B depict the overlapping top candidates among different tumors.
Figure 10B:
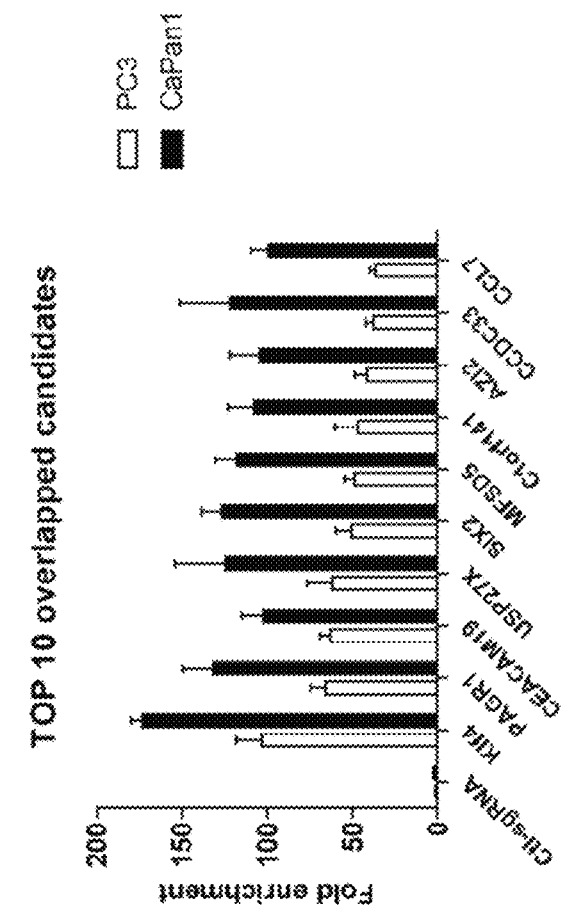
Figure 11:
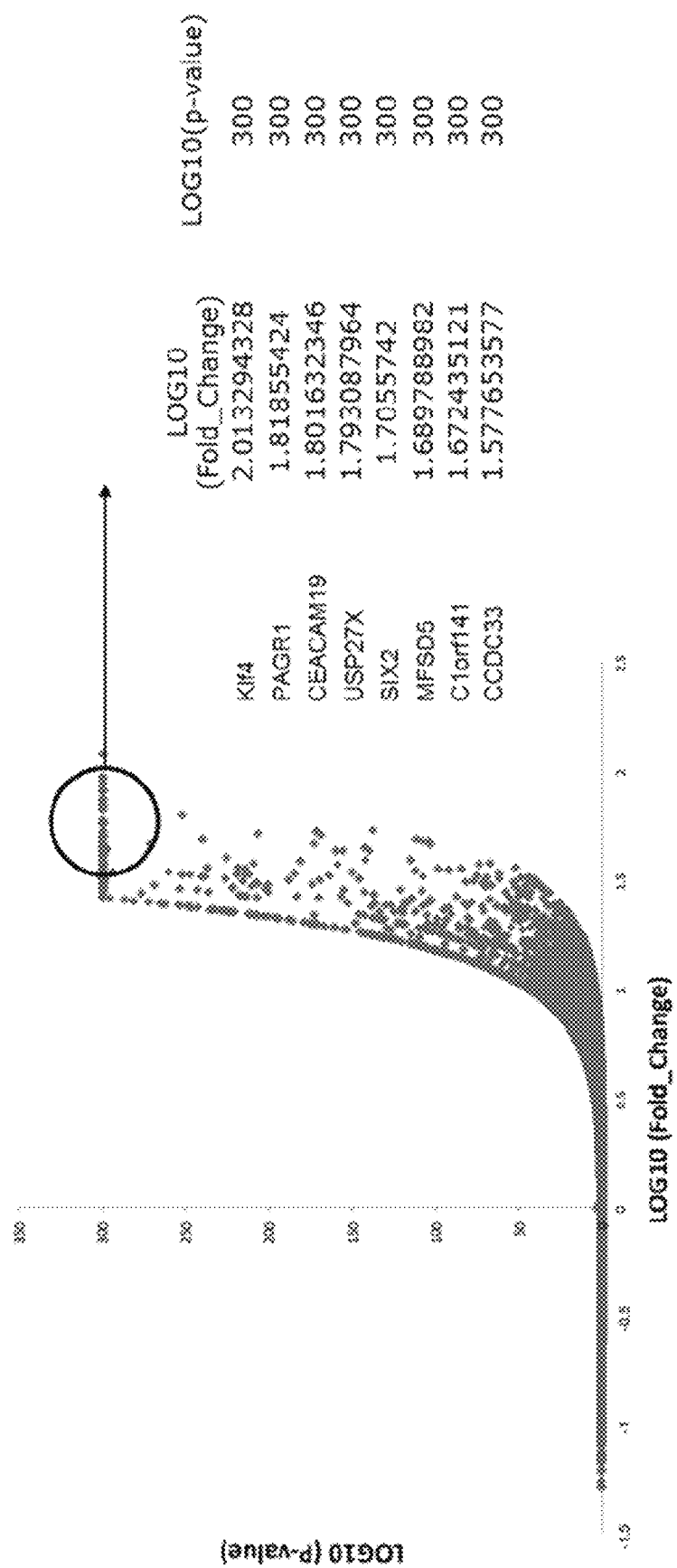
FIG. 11 depicts a plot of rank and fold change of the TOP candidates.

Without being bound by any theory, these differences may be due to different metabolic pathway preferences, inhibitory molecules profiles, and/or micro-environments among different tumor types. By comparing the top 100 candidates, two candidates were found to be highly enriched in both screens: Klf4 and PAGR1. Ten overlapping candidates were found among the top 200 in both screens. All ten candidates were found to have been enriched 50 to 100 times in the PC3-PSCA model and even higher in the CaPan1 model (FIGS. 10A and 10B). FIG. 11 shows the rank and fold change of the top candidates.

Table 2 sets forth top 10 enriched target genes in two separate experiments.

TABLE 2

| | Folds in Exp-1 | Folds in Exp-2 | Rank in Exp-1 | Rank in Exp-2 | p Rank in Exp-1 | p Rank in Exp-2 |
|---|---|---|---|---|---|---|
| Hsa-mir-4508 | 167 | 134 | 7 | 5 | 1884 | 10 |
| C1orf141 | 121 | 137 | 10 | 4 | 106 | 12 |
| PAGR1 | 85 | 66 | 32 | 13 | 273 | 35 |
| CEACAM19 | 82 | 52 | 39 | 25 | 300 | 70 |
| MFSD5 | 80 | 42 | 40 | 38 | 11276 | 109 |
| SIX2 | 74 | 25 | 53 | 114 | 47 | 313 |
| KLF4 | 71 | 102 | 57 | 6 | 111 | 17 |
| USP27X | 69 | 59 | 64 | 16 | 216 | 43 |
| CCDC33 | 63 | 68 | 82 | 11 | 431 | 27 |
| ZNF124 | 87 | 35 | 29 | 54 | 2858 | 122 |

Table 3 sets forth selected candidate target genes in tumor animal models.

TABLE 3

| Candidates | Rank in Exp-3 (in vivo) | Rank in Exp-4 (In vitro) |
|---|---|---|
| PAGR1 | 81 | 163 |
| C1orf141 | 11477 | 2138 |
| CEACAM19 | 11285 | 6429 |
| CCDC33 | 14710 | 812 |
| USP27X | 8541 | 23895 |
| SIX2 | 129 | 837 |
| KLF4 | 26 | 302 |

Example 5: Candidate Validation in Tumor Models

Figure 12B:
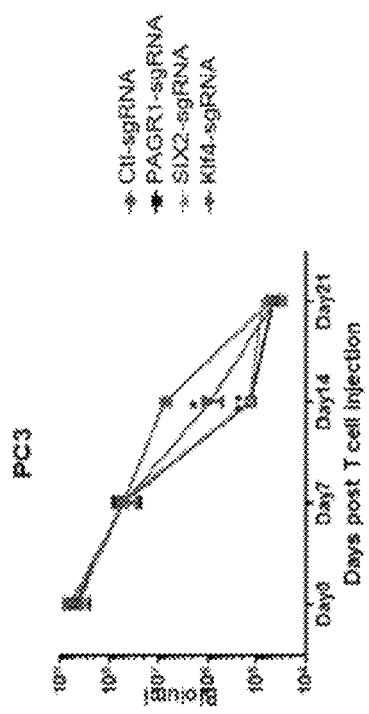
Figure 12C:
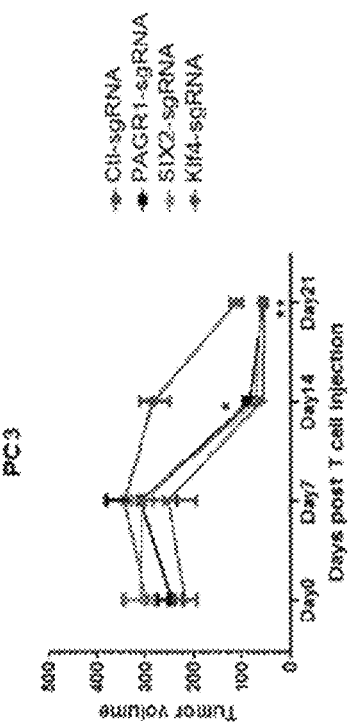
Figure 13C:
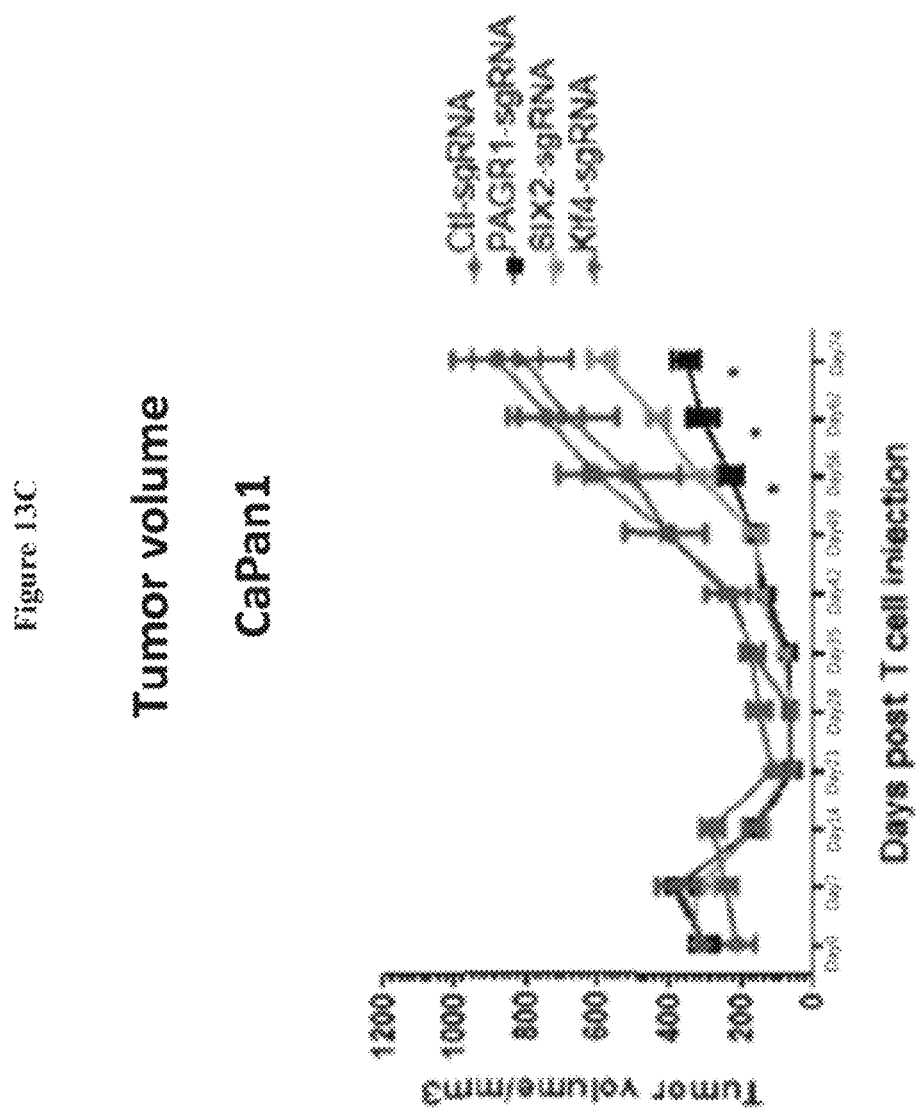
Figure 14B:
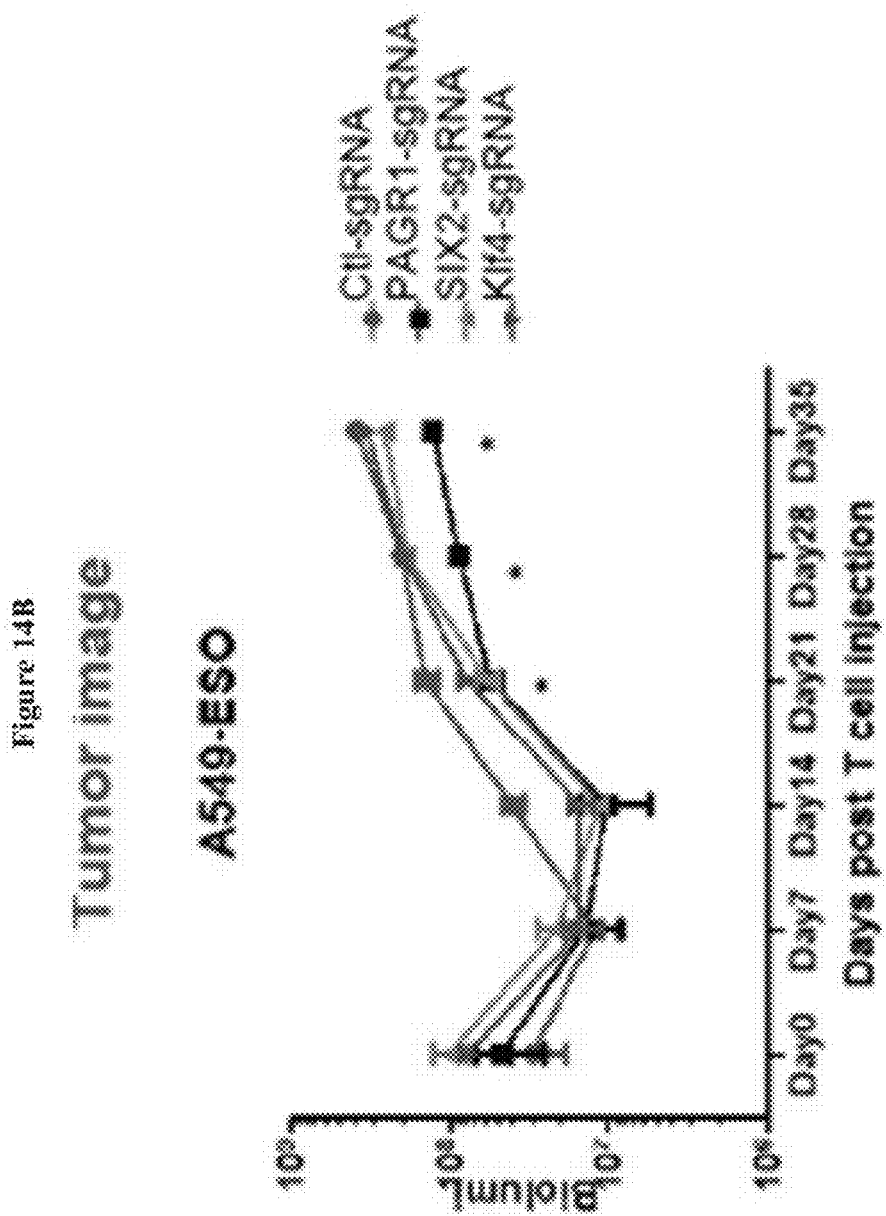
Figure 14C:
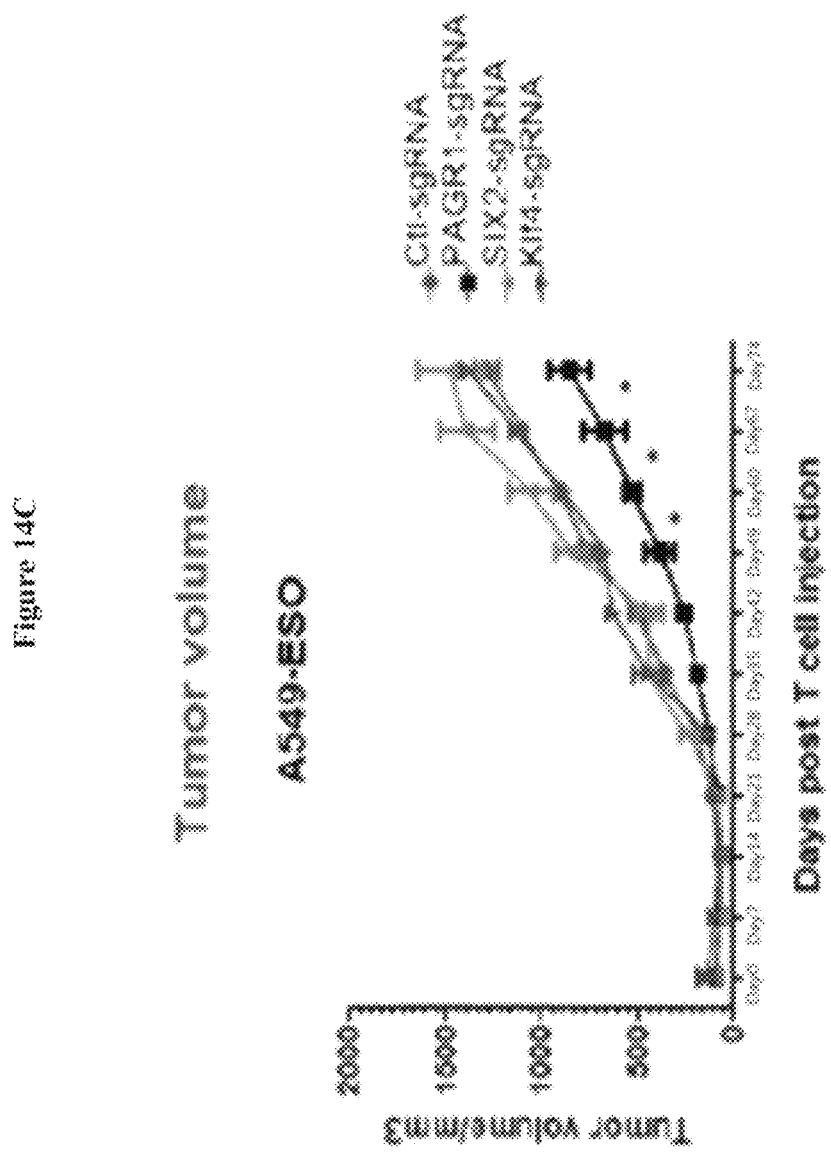

To validate the function in tumor models, six potential candidates were individually knocked-out in CAR-T cells, and tested in PSCA-expressing PC3-PSCA and CaPan1 tumor mouse models. Accelerated tumor clearance was observed in the PAGR1, Klf4 and SIX2 KO groups (FIGS. 12A-12C). When tested in PSCA low-expressing tumor model, PAGR1 and SIX2 KO augmented CAR-T cell function (FIGS. 13A-13C). To test whether these candidates enhance the function of TCR-T cells, another validation with NY-ESO-1 TCR T cells in a A549-NY-ESO lung cancer was performed. PAGR1 KO NY-ESO-1 TCR-T cells demonstrated better tumor control than wild type counterparts (FIGS. 14A-14C).

Figure 15A:
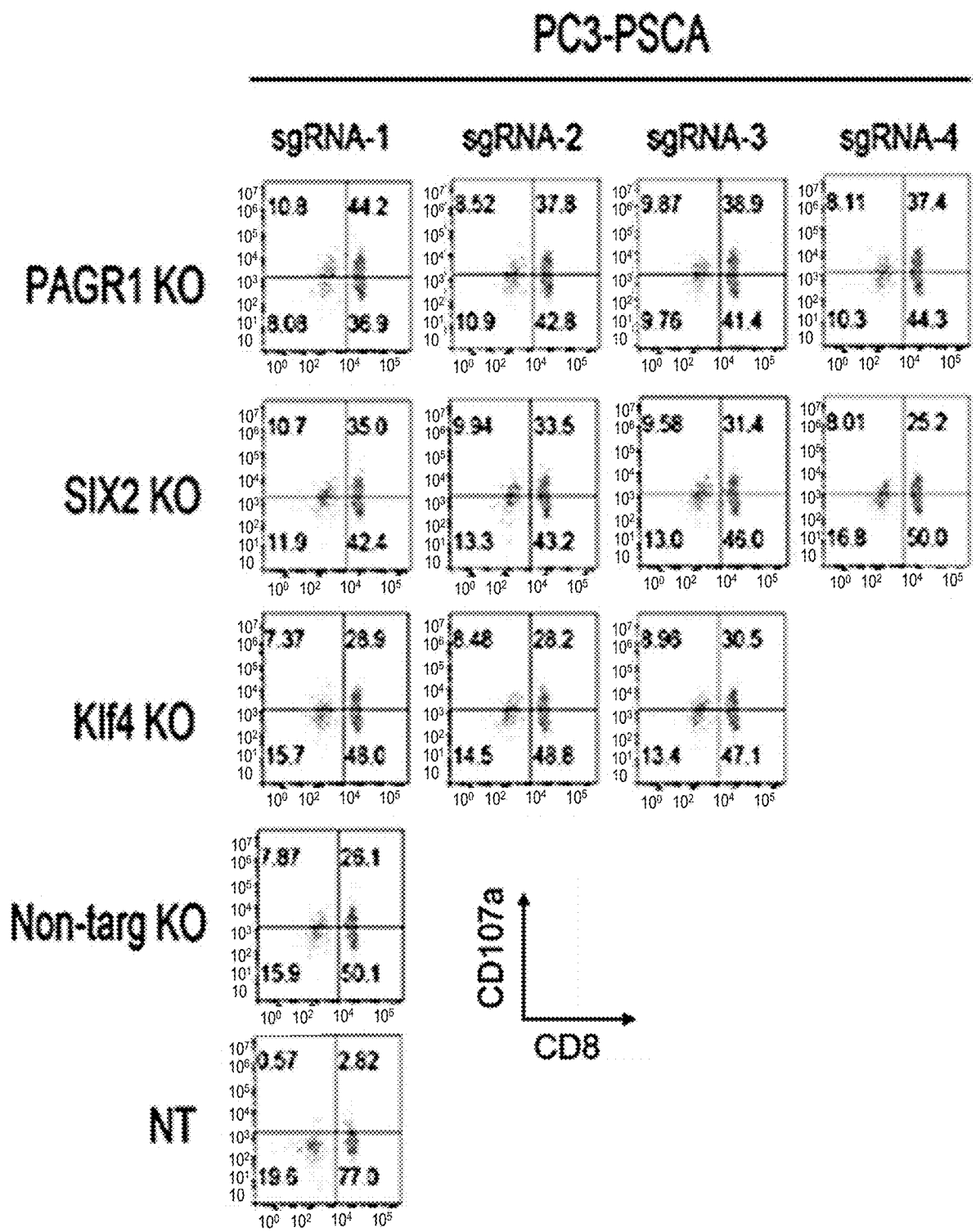
FIGS. 15A-15E depict data showing that PAGR1, Klf4, and SIX2 KO enhance in vitro tumor control.
Figure 15B:
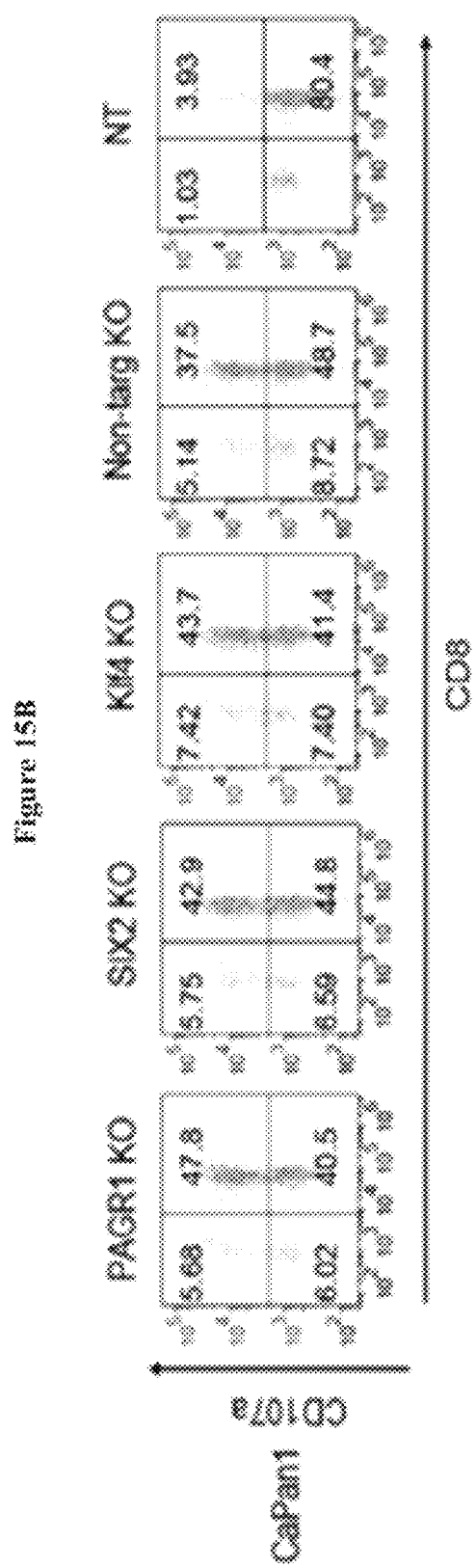
Figure 15C:
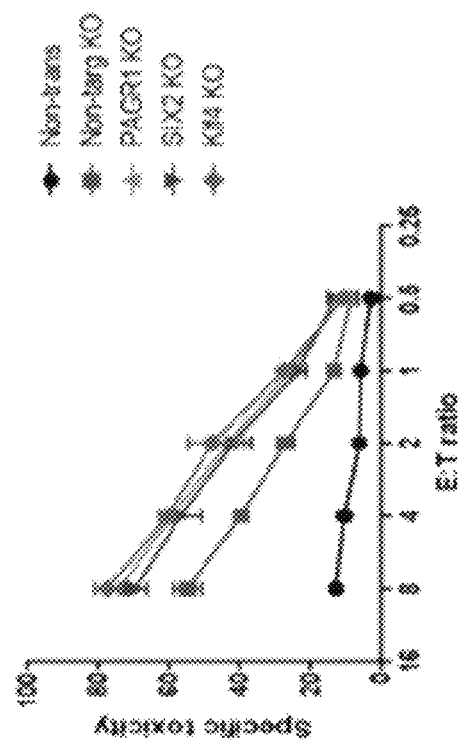
Figure 15D:
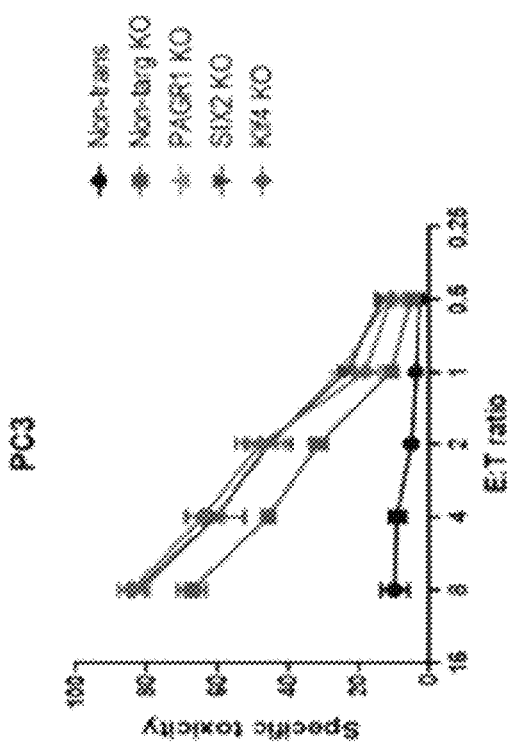
Figure 15E:
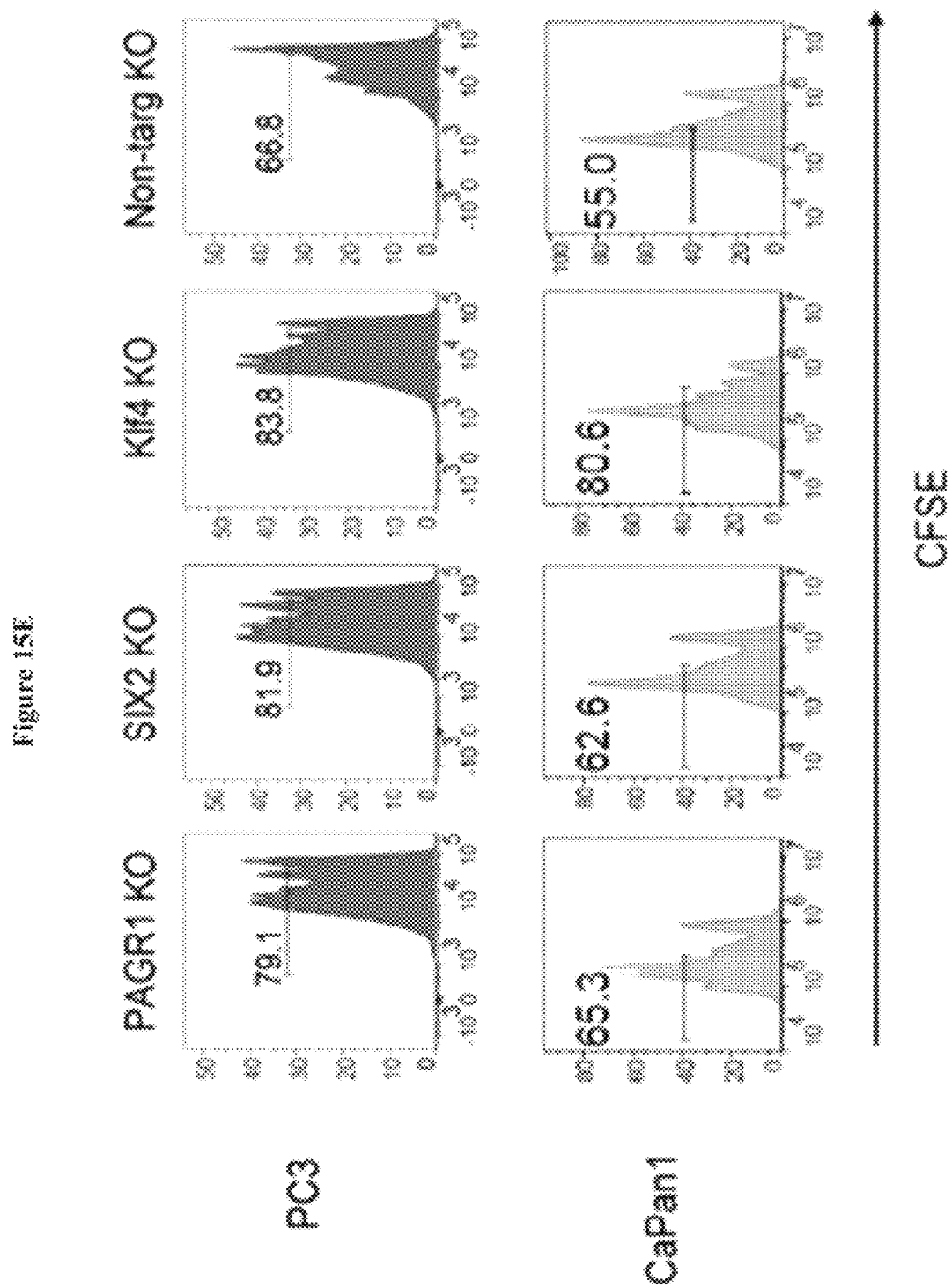
Figure 16A:
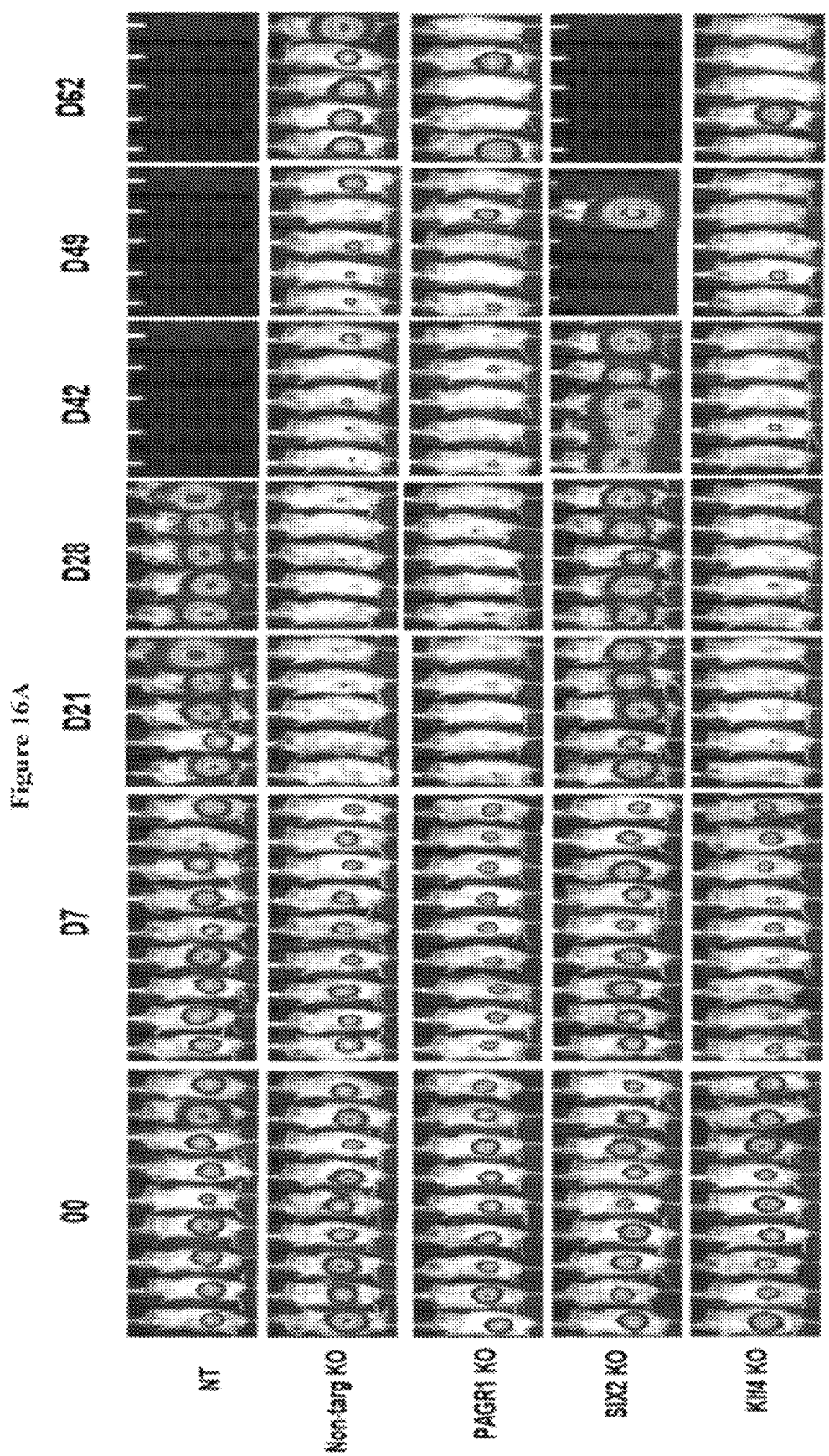
FIGS. 16A-16C depict results showing that PAGR1 and Klf4 KO enhances PC3-PSCA tumor control.
Figure 16C:
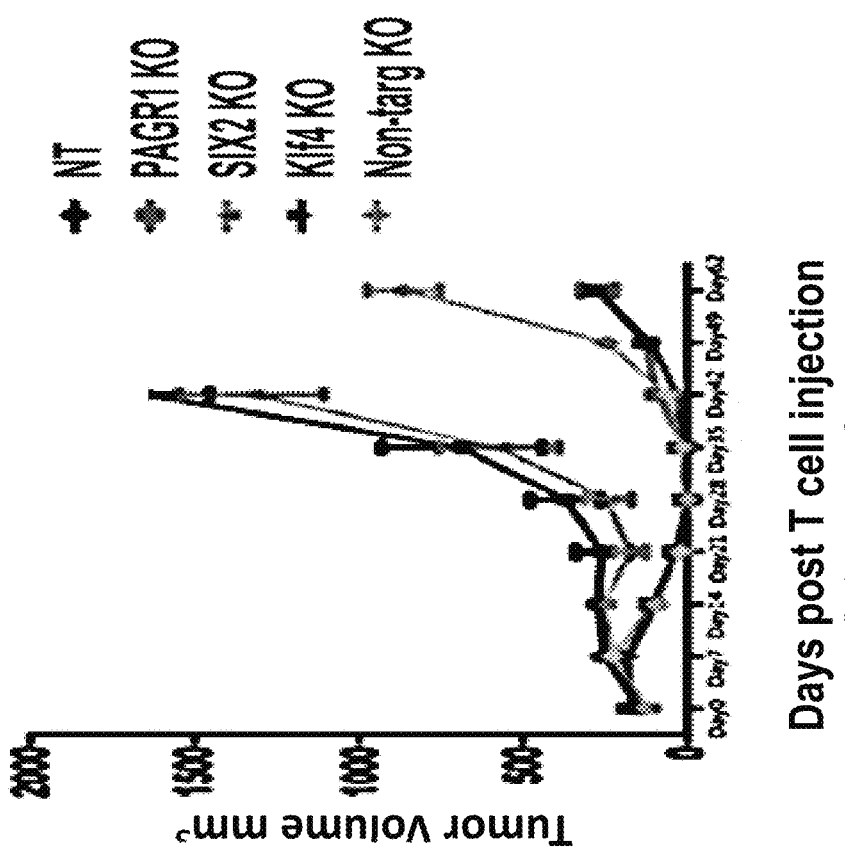
Figure 16B:
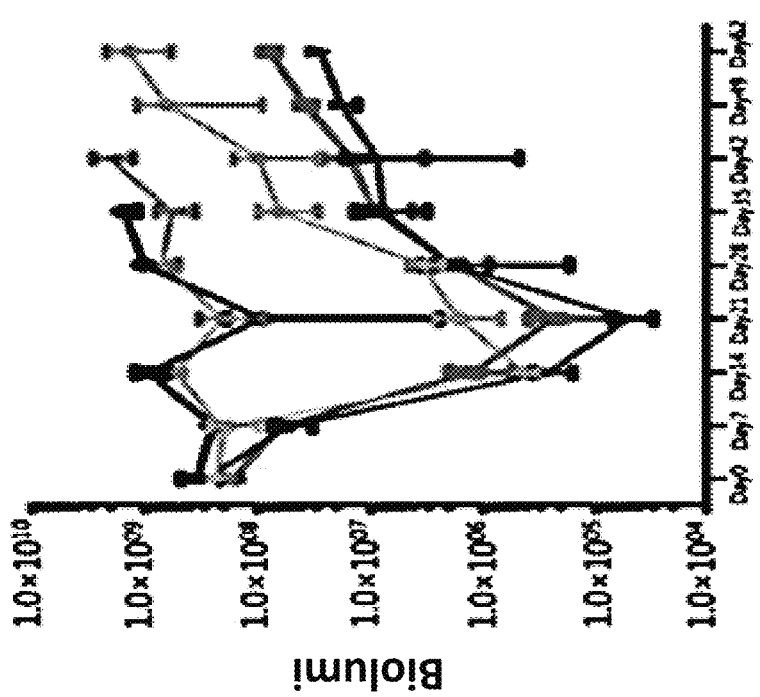
Figure 17B:
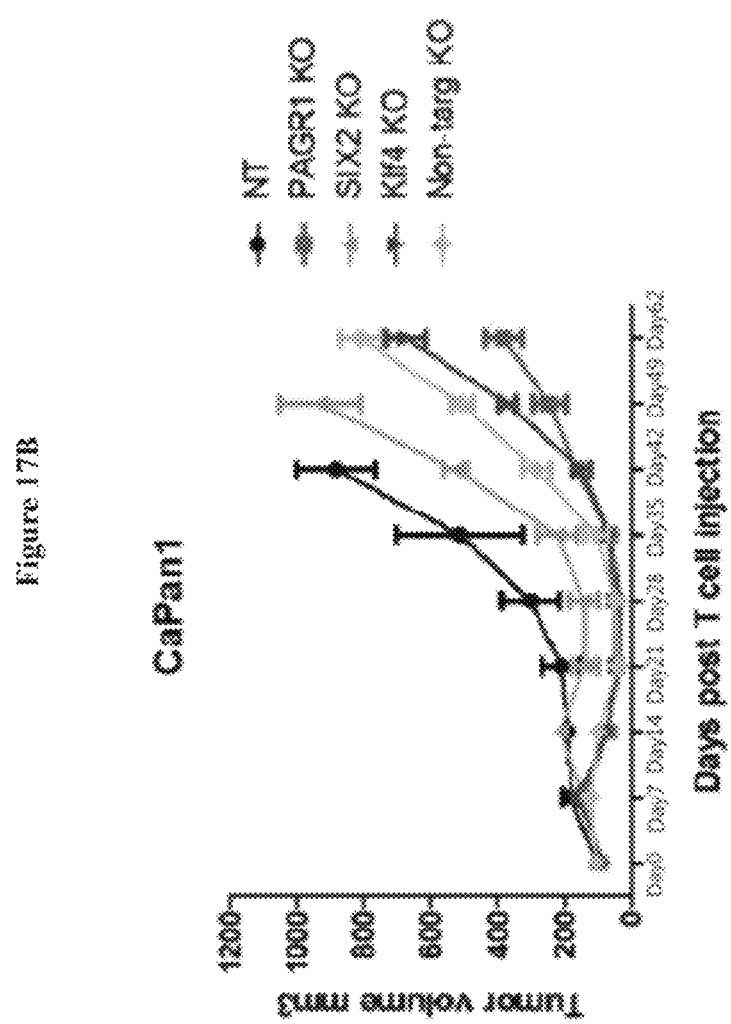

Based on superior tumor clearance in the tumor models, PAGR1, Klf4, and SIX2 were further investigated. To test how these genes regulate CAR-T cell function, functions of gene knockout CAR-T cells were tested in vitro. Significant elevated degranulation was observed in all of the three gene knockout CAR-T cells, no matter the sgRNA used (FIGS. 15A and 15B). This observation is consistent with elevated tumor cytotoxicity of the knockout CAR-T cells, compared with the wild type control (FIGS. 15C and 15D). The three candidates, when knocked-out, also enhanced CAR-T cell proliferation, which was confirmed by a CSFE assay (FIG. 15E). A second validation was performed in PC3-PSCA and CaPan1 models. PAGR1 KO showed superior tumor control in both models and Klf4 KO exhibits enhanced tumor control in the PC3-PSCA model (FIGS. 16A-16C and FIGS. 17A-17B).

Figure 18C:
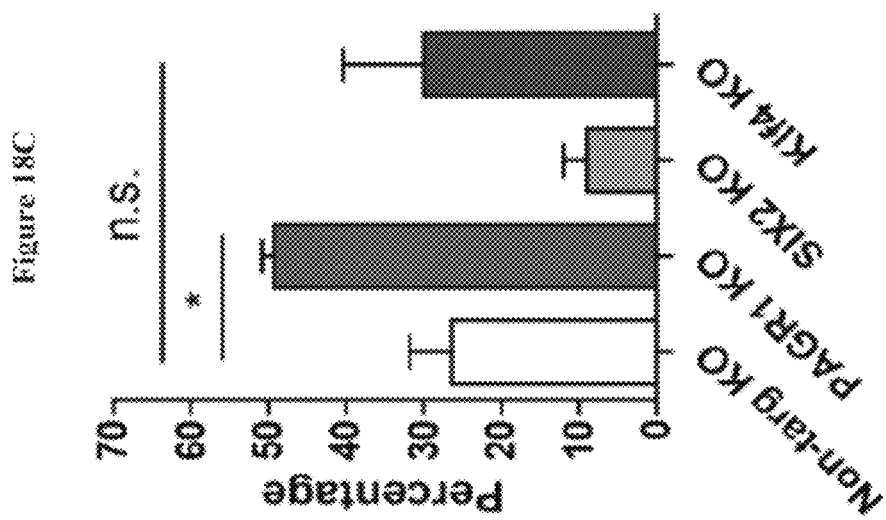
Figure 18B:
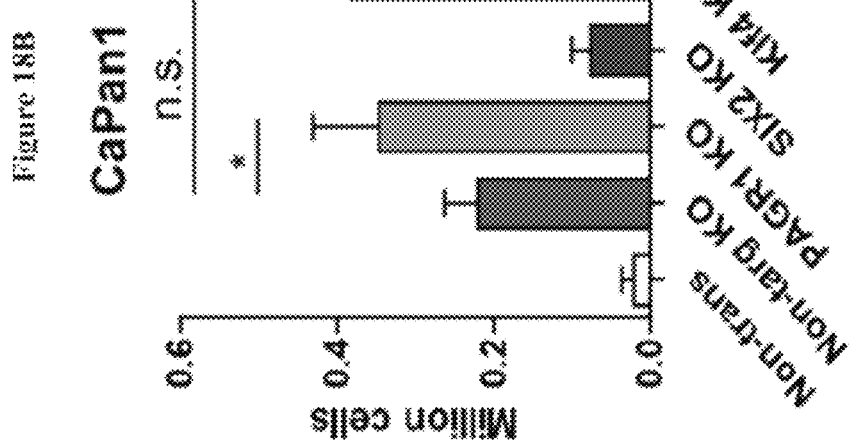
Figure 18A:
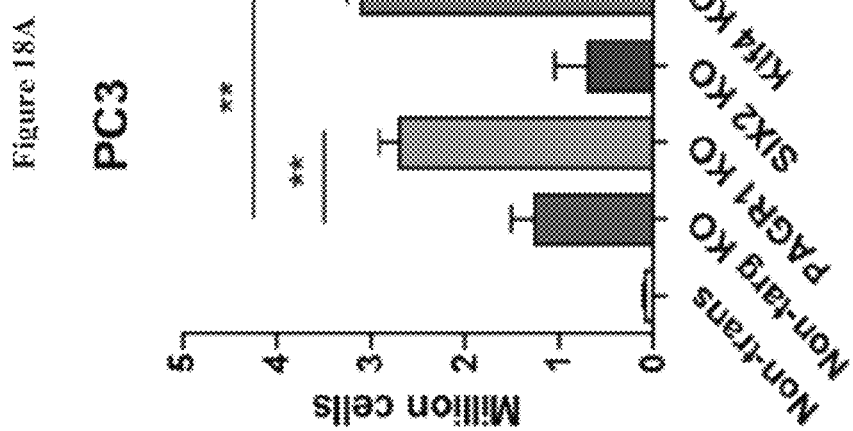

Example 6: PAGR1 KO Enhances CAR-T Cell Tumor Accumulation and Suppression Resistance Both PAGR1 and Klf4 KO significantly enhanced the number of PC3-PSCA tumor infiltrating CART cells. It was further found that PAGR1 KO CAR-T cells infiltrated significantly more than wild type CAR-T cells (FIGS. 18A and 18B). PAGR1 KO tumor infiltrating CAR-T cells were found to demonstrate superior tumor clearance in vitro (FIG. 18C). Without being bound by any theory, these findings may indicate that PAGR1 KO conferred inhibitory resistance to CAR-T cells. Indeed, it was found that tumor infiltrating PAGR1 KO CAR-T cells expressed less inhibitory molecules than the other groups (FIGS. 18D-18G). FIG. 18H also shows that PAGR1 KO enhances killing ability of the tumor infiltrating cells.

Figure 19B:
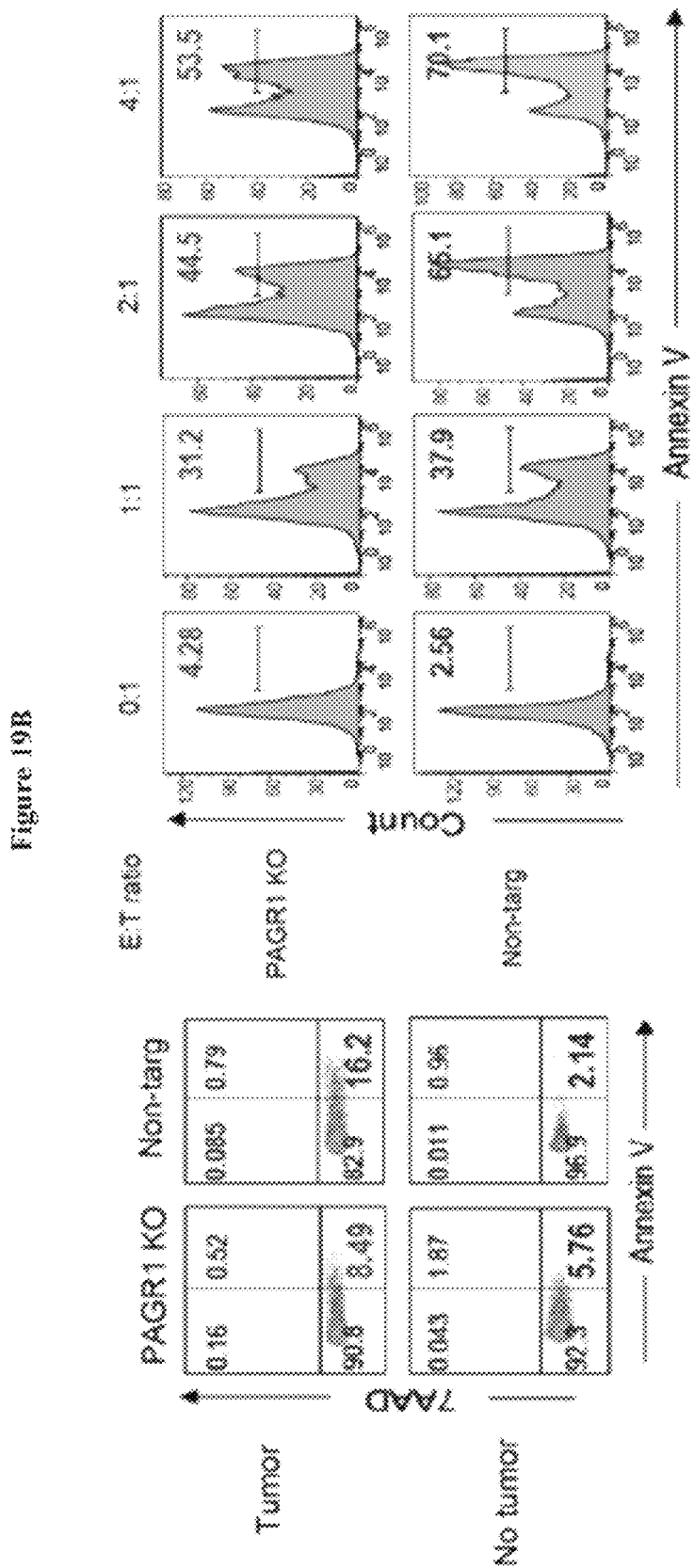
Figure 20B:
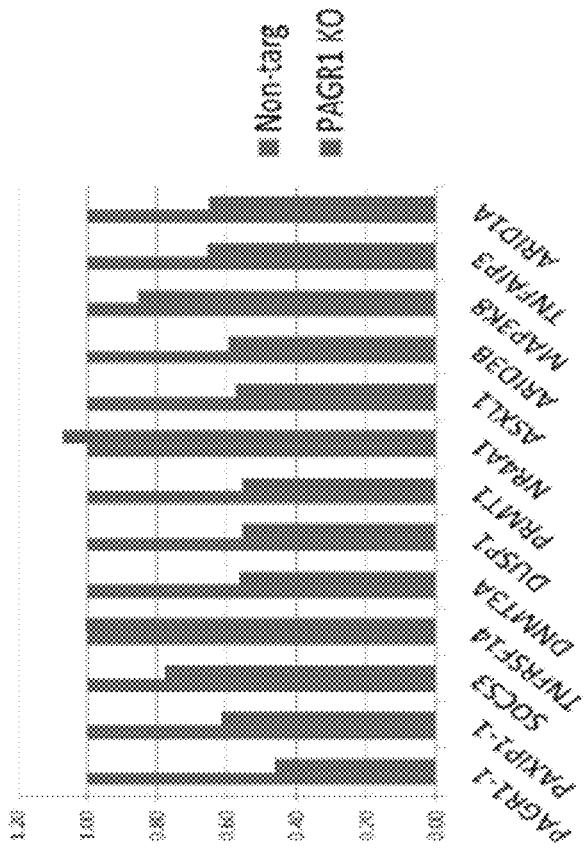
Figure 20A:
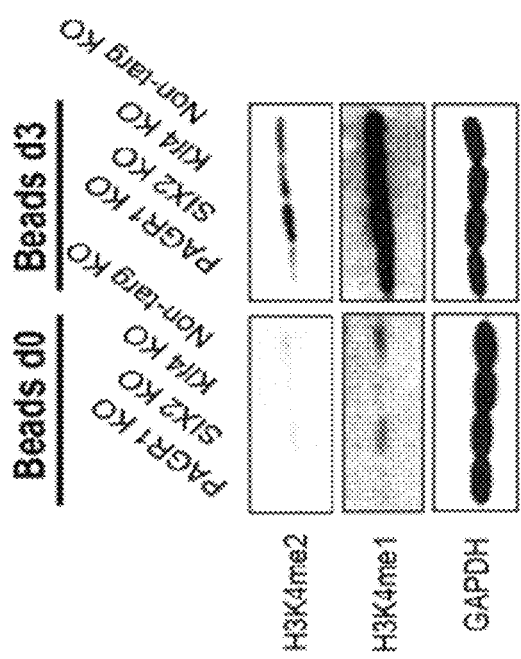

Example 7: PAGR1 KO Reduces Apoptosis by Epigenetic Regulation of Histone Methylation PAGR1 KO significantly reduced CAR-T cell apoptosis compared to wild type CAR-T cells, either with CD3/CD28 beads stimulation or antigen exposure by co-culturing with target tumor cells (FIGS. 19A and 19B). PAGR1 was reported to be a component of the histone methylation complex Histone-lysine N-methyltransferase 2D (KMT2D). PAGR1 KO demonstrated reduced H3K4 mono-methylation and di-methylation, consistent with the phenotype of KMT2D loss-of-function in B cell lymphoma (FIG. 20A). Reduced expression of downstream genes regulated by KMT2D was observed in PAGR1 KO CAR-T cells (FIG. 20B). H3K4 mono-methylation occupancy at the negative regulators of cell survival ARID1A and PRMT1 promoters was found to be greatly reduced (FIG. 20C). RNA levels of pro-survival factors, such as Bcl2 and Myc were found to be up-regulated (FIG. 20D).

Example 8: PAGR1 KO Enhances Adoptive T Cell Therapy in a Syngeneic Model

To test whether the downregulation of these candidates enhances the function of adoptive T cell therapy in an immunocompetent model, PAGR1 and Klf4 KO OT-I mouse T cells were infused into B16-OVA tumor bearing mice. As confirmed by the tumor size, PAGR1 KO significantly enhanced the function of OT-I mouse T cells than the wild type control (FIG. 21).

TABLE 4

| SEQ ID NO: | Protein or Nucleic Acid | Sequence |
|---|---|---|
| 1 | PRT | SLLMWITQC |
| 2 | PRT | GSGGS repeat 1-5, n at least 1 |
| 3 | PRT | GGGS repeat 1-4, n at least 1 |
| 4 | PRT | GGGGS repeat 1-5, n at least 1 |
| 5 | PRT | GGSG |
| 6 | PRT | GGSGG |
| 7 | PRT | GSGSG |
| 8 | PRT | GSGGG |
| 9 | PRT | GGGSG |
| 10 | PRT | GSSSG |
| 11 | PRT | GGGGS |
| 12 | PRT | GGGGSGGGGSGGGGS |
| 13 | DNA | GGTGGCGGTGGCTCGGGCGGTGGTGGGTCGGGTGGCGGCGGATCT |
| 14 | PRT | DKTHT |
| 15 | PRT | CPPC |
| 16 | PRT | CPEPKSCDTPPPCPR |
| 17 | PRT | ELKTPLGDTTHT |
| 18 | PRT | KSCDKTHTCP |
| 19 | PRT | KCCVDCP |
| 20 | PRT | KYGPPCP |
| 21 | PRT | EPKSCDKTHTCPPCP |
| 22 | PRT | ERKCCVECPPCP |
| 23 | PRT | ELKTPLGDTTHTCPRCP |
| 24 | PRT | SPNMVPHAHHAQ |
| 25 | PRT | EPKSCDKTYTCPPCP |
| 26 | PRT | RXKR x is any amino acid |
| 27 | PRT | RXRR x is any amino acid |
| 28 | PRT | XRXXR x1 is R/K, x2 is any amino acid, x3 is R/K |
| 29 | PRT | RXXR x is any amino acid |
| 30 | PRT | RQKR x is any amino acid |
| 31 | gRNA target | AATCAGTATTTCCGCTGCCG |
| 32 | gRNA target | TTGTACCTGGGGTGCGTCTC |
| 33 | gRNA target | AGGAGCAGATCCTTCGTACC |
| 34 | gRNA target | CCGGTAAGGCCGAGGACGAG |
| 35 | gRNA target | CCCCTCGTCCTCGGCCTTAC |

TABLE 4-continued

| SEQ ID NO: | Protein or Nucleic Acid | Sequence |
|---|---|---|
| 36 | gRNA target | ATTGACCGGAGACGCACCCC |
| 37 | gRNA target | GCGGGAATTTGCGGCGCACG |
| 38 | gRNA target | ACCCCGCGAGAAGCGTGAGC |
| 39 | gRNA target | GAGTGGTCTGGCGTCCCCGA |
| 40 | gRNA target | AACAGCCACAACCCGCTGAA |
| 41 | gRNA target | TTGCTCCTGCGTGAAGCCGA |
| 42 | gRNA target | CAAGGCACACTACATCGAGG |
| 43 | gRNA target | GTGGTGGCGCCCTACAACGG |
| 44 | gRNA target | AGCCCGCGTAATCACAAGTG |
| 45 | gRNA target | GCGCGGCGGCCCGCCGTTGT |
| 46 | gRNA target | TCTTTCTCCACGTTCGCGTC |
| 47 | gRNA target | CACCCACACTTGTGATTACG |
| 48 | gRNA target | GAGAAGACACTGCGTCAAGC |
| 49 | gRNA target | CGCGGCGCACGACTGCGACG |
| 50 | gRNA target | GTGAGATGTCGTCGCTGTTT |
| 51 | gRNA target | CTCGATGCCAGTTGTAGTAT |
| 52 | gRNA target | GTCCAGTACGTCCTTAATAC |
| 53 | gRNA target | TCTTAAACCGATCGTAAAGC |
| 54 | gRNA target | ACTGCTTGCGGAGGTTTACG |
| 55 | gRNA target | CTCTGAGGCCGTTGTATCCC |
| 56 | gRNA target | ATACAACGGCCTCAGAGGGA |
| 57 | gRNA target | GATCCCTGGCCCCTCGGAGC |
| 58 | gRNA target | CATGTGCTGGGCGTCACTGA |
| 59 | gRNA target | GGCCGCCAGGATCCCAGCGT |
| 60 | gRNA target | ATCCTGGCGGCCACCATCAT |
| 61 | gRNA target | TCTTGCTACATCCGCGTCTA |
| 62 | gRNA target | CTTTGATATTGCCTTAGACG |
| 63 | gRNA target | GATTCTGTTGGTCTCTTAGA |
| 64 | gRNA target | AATAAAGAAAGTGAGTCAAC |
| 65 | gRNA target | AAGAGACCAACAGAATCCAA |
| 66 | gRNA target | ACATTTGTTTGAATAAAGAA |

TABLE 5

| gRNA name | gRNA sequence | SEQ ID NO: |
|---|---|---|
| PAGR1 | AATCAGTATTTCCGCTGCCG | 31 |
| PAGR1 | TTGTACCTGGGGTGCGTCTC | 32 |
| PAGR1 | AGGAGCAGATCCTTCGTACC | 33 |
| PAGR1 | CCGGTAAGGCCGAGGACGAG | 34 |
| PAGR1 | CCCCTCGTCCTCGGCCTTAC | 35 |
| PAGR1 | ATTGACCGGAGACGCACCCC | 36 |
| SIX2 | GCGGGAATTTGCGGCGCACG | 37 |
| SIX2 | ACCCCGCGAGAAGCGTGAGC | 38 |
| SIX2 | GAGTGGTCTGGCGTCCCCGA | 39 |
| SIX2 | AACAGCCACAACCCGCTGAA | 40 |
| SIX2 | TTGCTCCTGCGTGAAGCCGA | 41 |
| SIX2 | CAAGGCACACTACATCGAGG | 42 |
| KLF4 | GTGGTGGCGCCCTACAACGG | 43 |
| KLF4 | AGCCCGCGTAATCACAAGTG | 44 |
| KLF4 | GCGCGGCGGCCCGCCGTTGT | 45 |
| KLF4 | TCTTTCTCCACGTTCGCGTC | 46 |
| KLF4 | CACCCACACTTGTGATTACG | 47 |
| KLF4 | GAGAAGACACTGCGTCAAGC | 48 |
| USP27X | CGCGGCGCACGACTGCGACG | 49 |
| USP27X | GTGAGATGTCGTCGCTGTTT | 50 |
| USP27X | CTCGATGCCAGTTGTAGTAT | 51 |
| USP27X | GTCCAGTACGTCCTTAATAC | 52 |
| USP27X | TCTTAAACCGATCGTAAAGC | 53 |
| USP27X | ACTGCTTGCGGAGGTTTACG | 54 |
| CEACAM19 | CTCTGAGGCCGTTGTATCCC | 55 |
| CEACAM19 | ATACAACGGCCTCAGAGGGA | 56 |

TABLE 5-continued

| gRNA name | gRNA sequence | SEQ ID NO: |
|---|---|---|
| CEACAM19 | GATCCCTGGCCCCTCGGAGC | 57 |
| CEACAM19 | CATGTGCTGGGCGTCACTGA | 58 |
| CEACAM19 | GGCCGCCAGGATCCCAGCGT | 59 |
| CEACAM19 | ATCCTGGCGGCCACCATCAT | 60 |
| C1orf141 | TCTTGCTACATCCGCGTCTA | 61 |
| C1orf141 | CTTTGATATTGCCTTAGACG | 62 |
| C1orf141 | GATTCTGTTGGTCTCTTAGA | 63 |
| C1orf141 | AATAAAGAAAGTGAGTCAAC | 64 |
| C1orf141 | AAGAGACCAACAGAATCCAA | 65 |
| C1orf141 | ACATTTGTTTGAATAAAGAA | 66 |

Example 9: Generating DNMT3A Knockout CAR T Cells for Adoptive Immunotherapy

Examples 9-12 describe a method of generating exhaustion-resistant T cells for adoptive immunotherapy by knocking out the DNMT3A gene. gRNAs targeting DNMT3A were screened, and then CRISPR/Cas9 and AAV mediated homologous recombination was used to knockin GFP into the DNMT3A locus, which ablated the DNMT3A gene. Donor DNA comprised of EGFP and homologous arms flanking the gRNA target, was introduced into T cells via AAV infection. A CD19BBz CAR was also transduced into T cells via lentivirus infection. CD19BBz+ T cells that have GFP knockin were selected by FACS sorting and expanded in vitro. These cells exhibited enhanced production of cytokines (IL2, INFγ, and TNFα) and degranulation when cocultured with cancer cells. Knockout of DNMT3A also increased the proliferation and anti-tumor effect of CD19BBz CAR T cells upon repeated stimulation by cancer cells.

Materials and Methods

Primary human lymphocytes: Primary human CD4 and CD8 T cells were isolated from healthy volunteer donors following leukapheresis by negative selection using RosetteSep kits (Stem Cell Technologies, Vancouver BC, Canada). Primary lymphocytes were stimulated with anti-CD3/CD28 Dynabeads (Life Technologies, Grand Island, NY).

Design and construction of CRISPRs: Cas9 DNA was synthesized by PCR as previously described (Cong, L. et al. (2013) Science 339, 819-823; Slaymaker, I. M. et al. (2016) Science 351, 84-88) and cloned into an RNA in vitro transcription (IVT) vector, pD-A vector (Zhao, Y. et al. (2010) *Cancer Research* 70, 9053-9061). gRNAs were selected using web-based CRISPR algorithms (crispr.mit.edu and chopchop.rc.fas.harvard.edu). The selected sgRNAs were cloned into the MSGV vector under the control of a T7 promoter, and then synthesized by in vitro transcription. Chemically modified gRNAs (S1, S2, S3 and S4) were made by Synthego (Menlo Park, CA). The in vitro transcribed Cas9 mRNA and sgRNAs were generated and stored as described (Ren, J. et al. (2017) *Clinical cancer research*, 23(9), 2255-2266).

Lentivirus and AAV transduction: T cells were stimulated by CD3/CD28 dynabeads on day 0, and transduced by CD19BBz lentivirus on day 1. AAV vectors were added to cells three hours after electroporation of gRNAs on day 4.

Analysis of DNMT3A gene editing and knockin: CRISPR/Cas9 gene editing was performed as previously described (Ren, J. et al. (2017) *Clinical cancer research*, 23(9), 2255-2266). Genomic DNA was extracted from cells 2 or 3 days after RNA electroporation. The PCR primers used to amplify genomic DNA fragments and analyze DNMT3A knockout efficiencies are listed in Table 6. TIDE (Tracking of Indels by Decomposition) and ICE (Inference of CRISPR Editing) tools were used to quantify indel frequencies. Knockin was confirmed by sequencing the junction of DNMT3A DNA and PGK-EGFP-WPRE-BGH PolyA transgene. Knockin at the 5' end was PCR amplified using primers CTTCTGTCACTGTTCCGGGTTTTG (SEQ ID NO:67) and GCCACTCCCACTGTCCTTTCCTA (SEQ ID NO:68). Knockin at the 3' end was PCR amplified using primers CACAAGGGTAGCGGCGAAGATC (SEQ ID NO:69) and ACATGCCCAGAAGCGGTGGA (SEQ ID NO:70).

TABLE 6

PCR primers used to amplify genomic DNA fragments and analyze DNMT3A knockout efficiencies

| Exon(s) | Forward Primer | Reverse Primer | Sequencing Primer |
|---|---|---|---|
| 7 | TTTCCATTTTTCACGGCAAG (SEQ ID NO: 71) | CACCCCAATTCCAGACTGC (SEQ ID NO: 72) | GGAGCTCCATCTGAATGAGG (SEQ ID NO: 73) |
| 8 | TTTTGCTCTGTCTTGCCTCA (SEQ ID NO: 74) | ACTTCCAGGCCTCCTAGTGC (SEQ ID NO: 75) | TTTTGCTCTGTCTTGCCTCA (SEQ ID NO: 76) |
| 9 and 10 | ACTGTATCTGGTCCCCTCCA (SEQ ID NO: 77) | CCAACAGAGAGCAGGTCATTC (SEQ ID NO: 78) | ACTGTATCTGGTCCCCTCCA (SEQ ID NO: 79) and CCAACAGAGAGCAGGTCATTC (SEQ ID NO: 80) |
| 11 and 12 | CTGGGGTCAGGACTTGAATG (SEQ ID NO: 81) | CCATTGACAGGAGAGCAGAA (SEQ ID NO: 82) | CTGGGGTCAGGACTTGAATG (SEQ ID NO: 83) and CCATTGACAGGAGAGCAGAA (SEQ ID NO: 84) |
| 13 | AGATGATGGCGTTCGAGACT (SEQ ID NO: 85) | CAAAAGCTTGAAACCCAAGG (SEQ ID NO: 86) | CAAAAGCTTGAAACCCAAGG (SEQ ID NO: 87) |

TABLE 6-continued

PCR primers used to amplify genomic DNA fragments and analyze DNMT3A knockout efficiencies

| Exon(s) | Forward Primer | Reverse Primer | Sequencing Primer |
|---|---|---|---|
| 14 and 15 | CTGACCCTGGCTAAGGTGGT (SEQ ID NO: 88) | AGGGTCCTAAGCAGTGAGCA (SEQ ID NO: 89) | CTGACCCTGGCTAAGGTGGT (SEQ ID NO: 90) and AGGGTCCTAAGCAGTGAGCA (SEQ ID NO: 91) |
| 19 | GACAGCTATTCCCGATGACC (SEQ ID NO: 92) | TGCAAAGCAGAAGTCACCAG (SEQ ID NO: 93) | TGCAAAGCAGAAGTCACCAG (SEQ ID NO: 94) |

Constructs: The PAAV6-MCS plasmid (Cell Biolabs, Inc) was digested by MluI and PmlI, and the 2907 bp fragment was used as the backbone. DNA fragments of DNMT3A 5' arm, WPRE-BGH PolyA, and DNMT3A 3' arm were synthesized by IDT. Target sequences of DNMT3A gRNAs 8-2, 8-3 and 8-4 (aaggcacccgctgggtcatgtggttcggagacgg) (SEQ ID NO:95) was added to the 5' ends of both 5' arm and 3' arm. PGK promoter-EGFP was PCR amplified. The fragment DNMT3A 5' arm-PGK promoter-EGFP-WPRE-BGH PolyA-DNMT3A 3' arm was assembled by overlapping PCR, digested by MluI and PmlI, and then ligated with PAAV6 backbone. AAV vectors were produced by Genecopoeia (Rockville, MD).

Rapid T cell expansion protocol: 0.1 million T cells were mixed with 25 million irradiated allogeneic peripheral blood mononuclear cells in 25 ml R10 medium with 30 ng/ml mouse anti-Human CD3 monoclonal antibody (Thermo Fisher Scientific 16-0037-85) on day 0. 300 IU/ml Interleukin-2 was added to the culture on day 2. 20 ml medium was replaced with fresh medium containing 300 IU/ml IL-2 on day 5. Cells were split and fed with fresh medium containing 300 IU/ml IL-2 on day 8 and day 11, and were cryopreserved on day 14.

Flow cytometry: The following monoclonal antibodies and reagents were used with the indicated specificity and the appropriate isotype controls. From BD Biosciences (San Jose, CA): APC-conjugated anti-CD3 (555335), FITC-anti-CD8 (555366), PE-anti-CD8 (555635), PE-anti-CD107a (555801), PECy7-anti-TNF (557647) and V450-anti-INFγ (560371). From Jackson ImmunoResearch Laboratories, Inc. (West Grove, PA): Biotin-SP AffiniPure Goat Anti-Mouse IgG (115-065-072). From Biolegend (San Diego, CA): BV785-anti-CD45 (304048), AF700-anti-CD8a (300920), AF647-anti-Granzyme B (515406), and BV605-anti-IL-2 (500332).

For intracellular cytokine staining, cells were first stained using LIVE/DEAD™ Fixable Aqua Dead Cell Stain Kit (Thermo Fisher Scientific) in order to exclude dead cells. Next, the cells were stained for surface antigens, fixed and permeabilized using FIX & PERM Cell Fixation & Cell Permeabilization Kit (Thermo Fisher Scientific), and then stained for cytokines. Data were acquired on a Fortessa (BD Biosciences, San Jose, CA) and data were analyzed with FlowJo version 7.6.1 (Tree Star, Inc., Ashland, OR).

Sequential killing assay: 0.1 million T cells were cocultured with 0.2 million K562, K562-CD19, Raji, or Nalm6 cells on Day 1. Medium was removed and 0.2 million tumor cells in fresh medium were added on Day 4 and Day 7. Cells were stained with LIVE/DEAD™ Fixable Aqua (Invitrogen), CD4 and CD8, and Countbright Absolute Counting Beads (Invitrogen) were used to count CD4 cells, CD8 cells and tumor cells.

Example 10: Screening gRNAs Targeting DNMT3A

Figure 22:
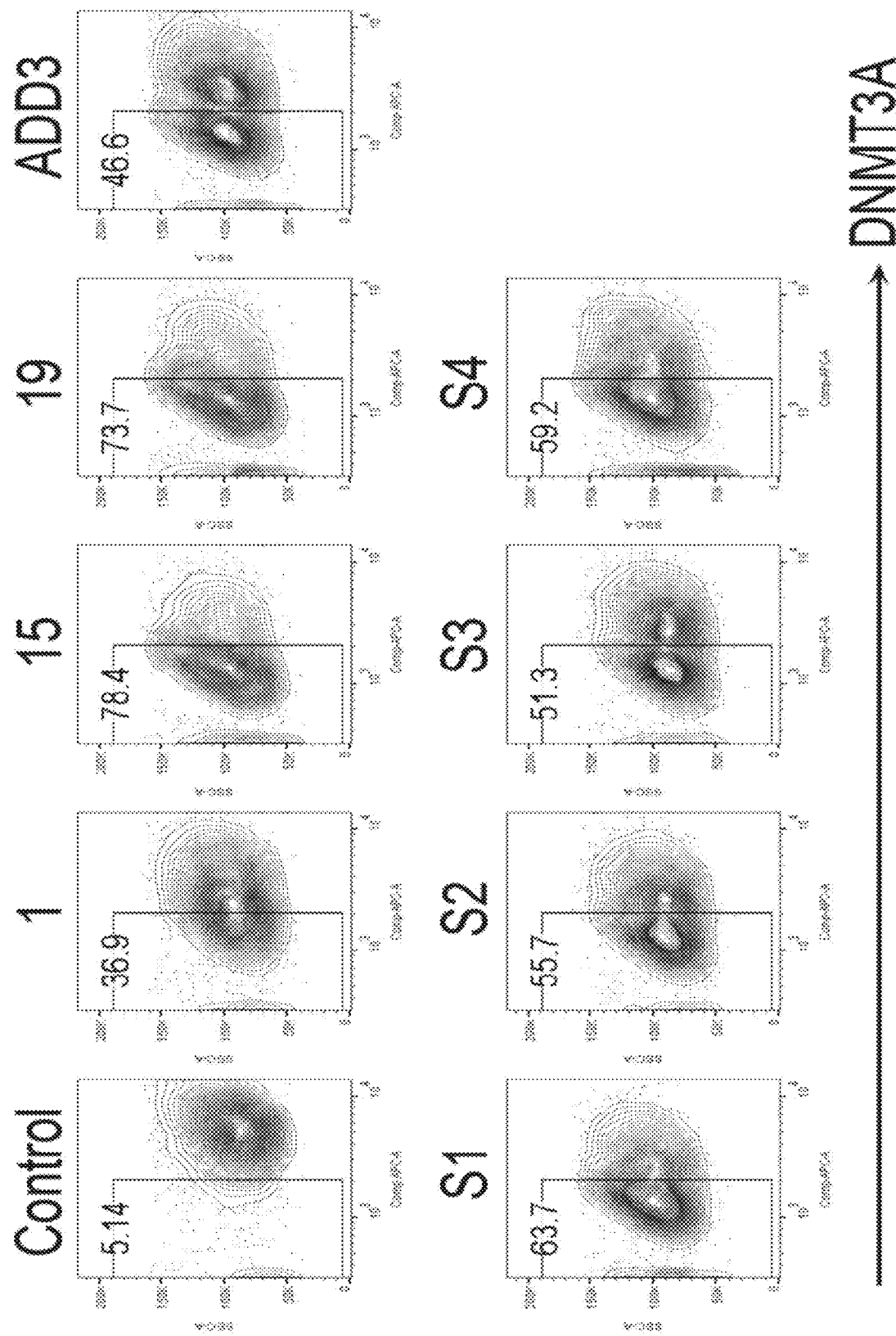
FIG. 22 depicts results from intracellular staining for DNMT3A performed to confirm knockout efficiencies for selected gRNAs.

Knockout efficiencies of gRNAs targeting DNMT3A exons 7-15 and 19 were evaluated using TIDE and ICE tools (Tables 7-10). Intracellular staining for DNMT3A was performed to confirm knockout efficiencies for selected gRNAs. (FIG. 22).

TABLE 7

Sequences and gene editing efficiencies of gRNAs targeting DNMT3A exon 7.

| | gRNA Name | gRNA sequence | TIDE % | ICE % | SEQ ID NO: |
|---|---|---|---|---|---|
| Exon 7 | X2 | CTCGTCATCGCCTGCTTTGG | 1.3 | 0 | 96 |
| | X5 | TCAGGCGTGGTAGCCACAGT | 0.3 | 0 | 97 |
| | X7 | TGGCTCGTCATCGCCTGCTT | 0.2 | 0 | 98 |
| | X10 | CTACCACGCCTGAGCCCGTG | 0.7 | 0 | 99 |
| | X14 | GACAAGAATGCCACCAAAGC | 0.1 | 0 | 100 |
| | 4 | CGATGACGAGCCAGAGTACG | 4.3 | 0 | 101 |
| | 10 | AAGCCGCTCACCTCGTACTC | 1.1 | 0 | 102 |
| | 30 | GCTACCACGCCTGAGCCCGT | 14.2 | 16 | 103 |
| | 31 | GAGCCCGTGGGGTCCGATGC | 4.2 | 0 | 104 |
| | 34 | GGCTACCACGCCTGAGCCCG | 0.8 | 0 | 105 |
| | 7.1 | GGGGCCCGGGGAGTCTCAGA | 10.9 | | 106 |
| | 7.2 | GCCCGTGGGGTCCGATGCTG | 17 | | 107 |
| | 15original | TGTCTTGGTGGATGACGGGC | 1.5 | | 108 |
| | S1 | TCTGAGACTCCCCGGGCCCC | 74.2 | 88 | 109 |
| | S2 | CTCGTCATCGCCTGCTTTGG | 30.1* | 87 | 110 |
| | S3 | CAGGCGTGGTAGCCACAGTG | 54.6 | 58 | 111 |
| | S4 | GGAAGAAAACCAGGGGCCCG | 61.9 | 83 | 112 |

TABLE 8

Sequences and gene editing efficiencies of gRNAs targeting DNMT3A exons 8 and 9.

| | gRNA Name | gRNA sequence | TIDE % | ICE % | SEQ ID NO: |
|---|---|---|---|---|---|
| Exon 8 | X3 | TCCGAACCACATGACCCAGC | 3.6 | 3 | 113 |
| | X4 | CGGAGACGGCAAATTCTCAG | 2 | 1 | 114 |
| | 32 | GACGGCCGGGGCTTTGGCAT | 2.2 | 1 | 115 |
| | 33 | GGCCAGGCCGCATTGTGTCT | 4.6 | 4 | 116 |
| | 35 | TGGGTCATGTGGTTCGGAGA | 2 | 1 | 117 |
| | 37 | TGGGTCATGTGGTTCGGAGA | 8.1 | 9 | 118 |
| | 8.1 | CGGCCGGGGCTTTGGCATTG | 7.4 | | 119 |
| | 8.2 | TGGGTCATGTGGTTCGGAGA | 12.8 | | 120 |
| | 8.3 | ACCCGCTGGGTCATGTGGTT | 1.9 | | 121 |
| | 16original | TCCCCAGCATCGGACCCCAC | 4.4 | | 122 |

TABLE 8-continued

Sequences and gene editing efficiencies of gRNAs targeting DNMT3A exons 8 and 9.

|  | gRNA Name | gRNA sequence | TIDE % | ICE % | SEQ ID NO: |
|---|---|---|---|---|---|
| Exon 9 | 9 | CATGGGCTGCTTGTTGTACG | 3.4 | 3 | 123 |
|  | 12 | GCTGCTTGTTGTACGTGGCC | 1.3 | 0 | 124 |
|  | 15 | GCACTGCAAAACGAGCTCAG | 82.5 | 83 | 125 |
|  | 25 | GTTTTGCAGTGCGTTCCACC | 4.1 | 5 | 126 |
|  | 27 | GCTTGTTGTACGTGGCCTGG | 1.9 | 3 | 127 |

TABLE 9

Sequences and gene editing efficiencies of gRNAs targeting DNMT3A exons 10, 11, and 12.

|  | gRNA Name | gRNA sequence | TIDE % | ICE % | SEQ ID NO: |
|---|---|---|---|---|---|
| Exon 10 | ADD1 | AGAACAAGCCCATGATTGAA | 2.7 | 8 | 128 |
|  | 13 | CATCGCTGTCGTGGCACACC | 2.7 | 4 | 129 |
|  | 14 | CCGGGAACAGCTTCCCCGCG | 7.6 | 4 | 130 |
|  | 24 | CCCAGGGCCCATTCAATCAT | 2.2 | 2 | 131 |
| Exon 11 | ADD3 | AAAGCCCCGGAAGAGCACAG | 36.2 | 40 | 132 |
|  | ADD12 | AGAAGTGTACACGGACATG | 9.3 | 3 | 133 |
|  | 3 | ATTATTGATGAGCGCACAAG | 3.8 | 1 | 134 |
|  | ADD2 | AAGAAGTGTACACGGACATG | 6 | 1 | 135 |
|  | 26 | TTCTCCGCTGTGCTCTTCCG | 9.7 | 2 | 136 |
| Exon 12 | ADD9 | AGCGGCTGGTGTACGAGGTG | 2.9 | 1 | 137 |
|  | ADD10 | ACGAGGTGCGGCAGAAGTGC | 3.7 | 2 | 138 |
|  | 18 | TGCAGAGCGGCTGGTGTACG | 2.2 | 3 | 139 |
|  | 29 | CAGAAGTGCCGGAACATTGA | 14.2 | 11 | 140 |

TABLE 10

Sequences and gene editing efficiencies of gRNAs targeting DNMT3A exons 13, 14, 15 and 19.

|  | gRNA Name | gRNA sequence | TIDE % | ICE % | SEQ ID NO: |
|---|---|---|---|---|---|
| Exon 13 | 16 | GGCACATTCCTCCAACGAAG | 0 | 1 | 141 |
|  | 28 | GCACATTCCTCCAACGAAGA | 10.7 | 10 | 142 |
| Exon 14 | 1 | GCGTACCAGTACGACGACGA | 31.1 | 39 | 143 |
|  | 5 | GGTAGCCGTCGTCGTCGTAC | 2.7 | 3 | 144 |
|  | 8 | GCGGAAACAACAACTGCTGC | 2 | 1 | 145 |
| Exon 15 | 2 | CTTCGCTAATAACCACGACC | 1.2 | 2 | 146 |
|  | 6 | TGCGGGCACAAGGGTACCTA | 0.5 | 1 | 147 |
|  | 11 | TGCTACATGTGCGGGCACAA | 0.8 | 1 | 148 |
|  | 17 | CCGCACATGTAGCAGTTCCA | 0.8 | 1 | 149 |
|  | 19 | GCGGGCACAAGGGTACCTAC | 68.3 | 72 | 150 |
|  | 21 | CACTCACAAATTCCTGGTCG | 0.8 | 1 | 151 |
|  | 22 | GGTTATTAGCGAAGAACATC | 3 | 4 | 152 |
|  | 23 | GTACCTACGGGCTGCTGCGG | 9.6 | 17 | 153 |
| Exon 19 | ADD11 | GCATGATGCGCGGCCCA | 1.7 | 1 | 154 |

TABLE 11

Sequences and gene editing efficiencies of gRNAs described in Patent WO 2017/079642 A1.

| gRNA Name | gRNA sequence | Exon | TIDE % | ICE % | SEQ ID NO: |
|---|---|---|---|---|---|
| ADD1 | AGAACAAGCCCATGATTGAA | Exon 10 | 2.7 | 8 | 155 |
| ADD2 | AAGAAGTGTACACGGACATG | Exon 11 | 6 | 1 | 156 |
| ADD3 | AAAGCCCCGGAAGAGCACAG | Exon 11 | 36.2 | 40 | 157 |
| ADD9 | AGCGGCTGGTGTACGAGGTG | Exon 12 | 2.9 | 1 | 158 |
| ADD10 | ACGAGGTGCGGCAGAAGTGC | Exon 12 | 3.7 | 2 | 159 |
| ADD11 | GCATGATGCGCGGCCCA | Exon 19 | 1.7 | 1 | 160 |
| ADD12 | AGAAGTGTACACGGACATG | Exon 11 | 9.3 | 3 | 161 |

Example 11: Knockin of GFP into DNMT3A Locus in CAR T Cells

Figure 23:
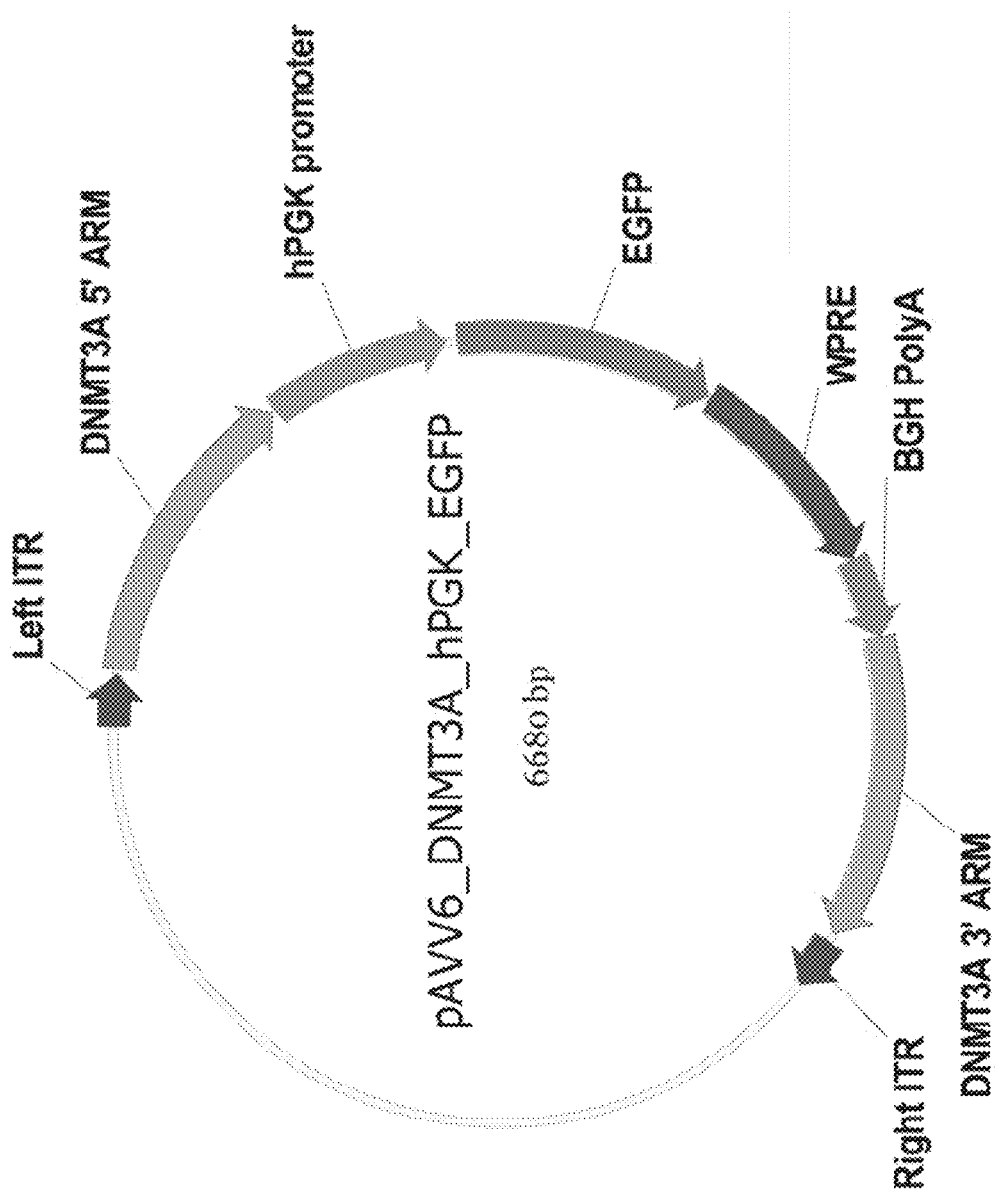
FIG. 23 depicts a map of the AAV plasmid that carries the donor template for homology-directed repair.
Figure 24:
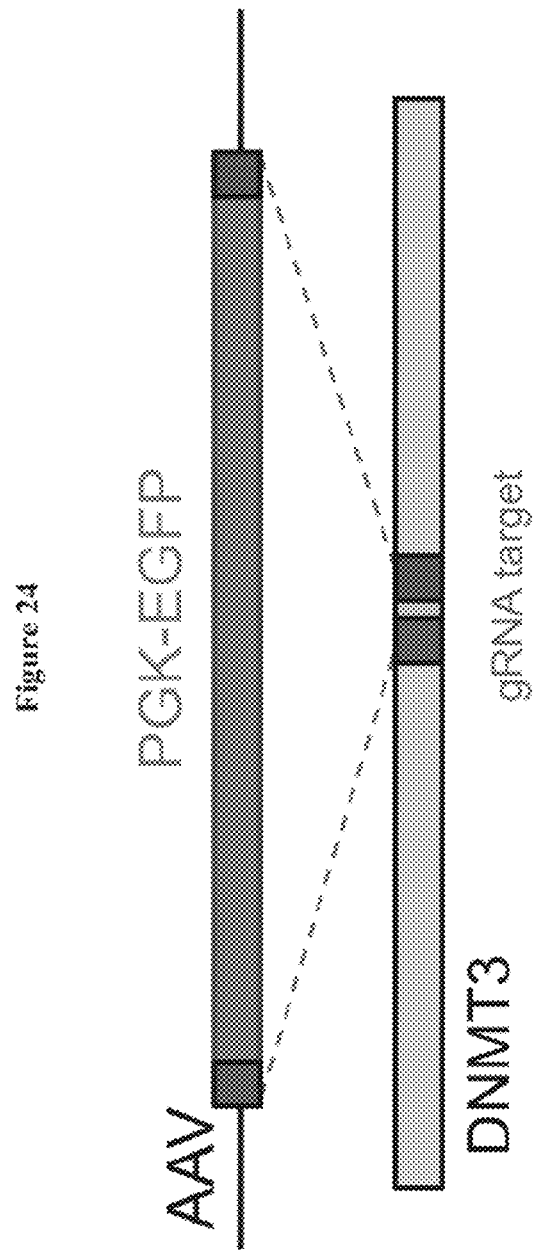
FIG. 24 depicts a schematic of CRISPR/Cas9 and AAV mediated homologous recombination to knockin GFP into the DNMT3A locus. Boxes represent homologous arms, and the gRNA target locus.
Figure 25:
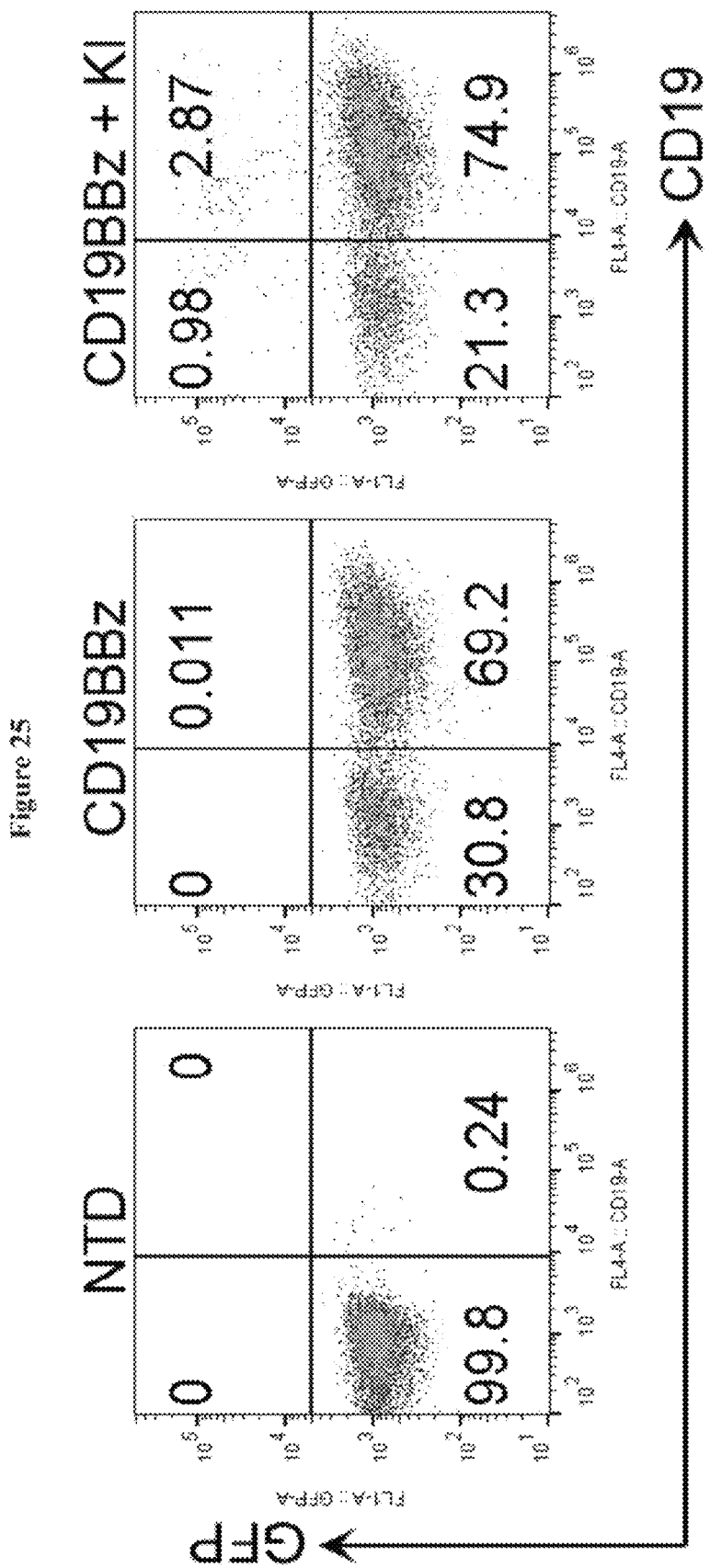
FIG. 25 depicts expression of CD19BBz and EGFP after lentivirus/AAV infection.
Figure 26:
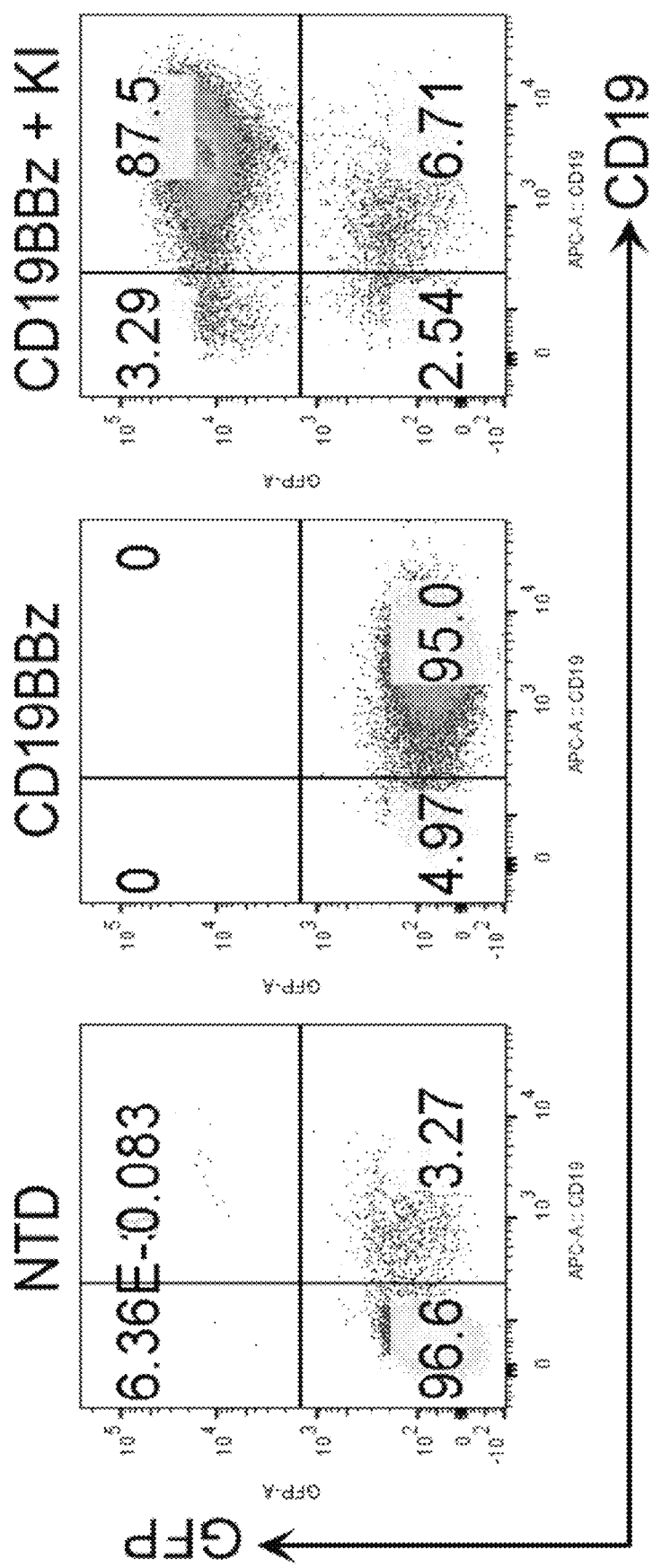
FIG. 26 depicts expression of CD19BBz and EGFP in T cells that were sorted and expanded using the REP protocol described herein.
Figure 27:
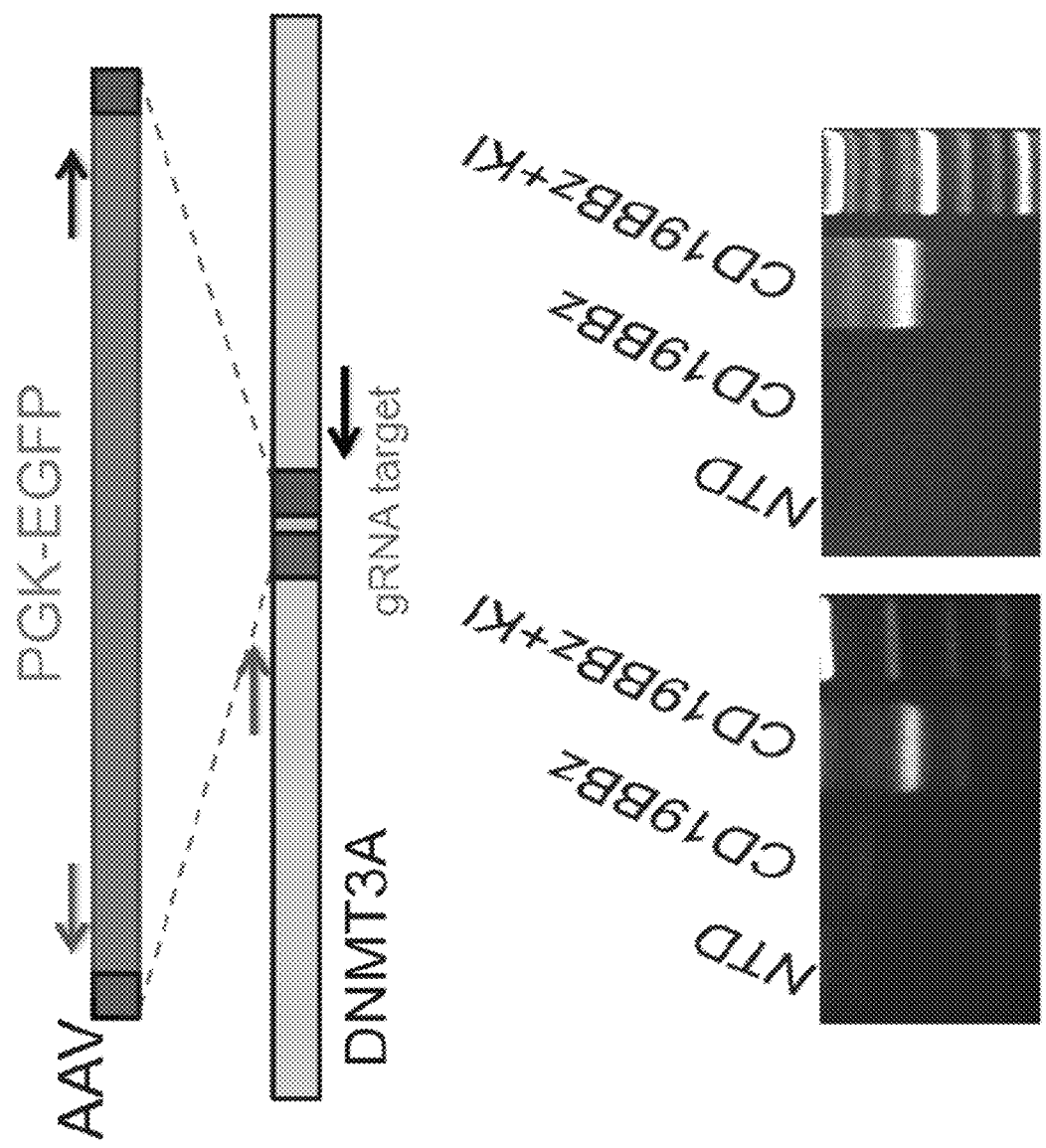
FIG. 27 depicts results from knockin of EGFP into the DNMT3A gRNA target region confirmed by PCR amplification of the junction between DNMT3A DNA and transgene. Boxes represent the homologous arms of DNMT3A and the gRNA target locus. Arrows represent PCR primers.

T cells were first transduced with CD19BBz lentivirus, followed by CRISPR/Cas9 gene editing at the DNMT3A locus using gRNAs 8.2 and 8.3. AAVs vector harboring DNMT3A homologous arms and EGFP (FIGS. 23-24) were used to infect T cells and served as the template for homology-directed repair in order to knockin EGFP. FACS was performed on day 10 to examine the expression of CD19BBz and EGFP (FIG. 25). Untransduced cells (NTD) did not express CD19BBz and EGFP. CD19BBz cells were only transduced by CD19BBz lentivirus. 69.2% of the cells expressed CD19BBz, but they did not express EGFP. These CAR T cells were sorted by FACS. For T cells transduced by both lentivirus and AAV (CD19BBz+KI), 77.77% of cells expressed CD19BBz and 3.85% cells expressed EGFP. The 2.87% double positive cells were sorted by FACS. NTD, sorted CD19BBz T cells, and sorted CD19BBz+EGFP+ cells were expanded using the Rapid T cell Expansion Protocol (REP). After expansion with the REP protocol, 95% of the cells expressed CD19BBz in the CD19BBz group, and 87.5% of the cells expressed both CD19BBz and EGFP in the CD19BBz+KI group (FIG. 26). Knockin of EGFP into the DNMT3A gRNA target region was confirmed by PCR amplification of the junction between DNMT3A DNA and the transgene (FIG. 27).

Example 12: Knockout of DNMT3A Enhanced the Function of CD19BBz T Cells

Figure 28:
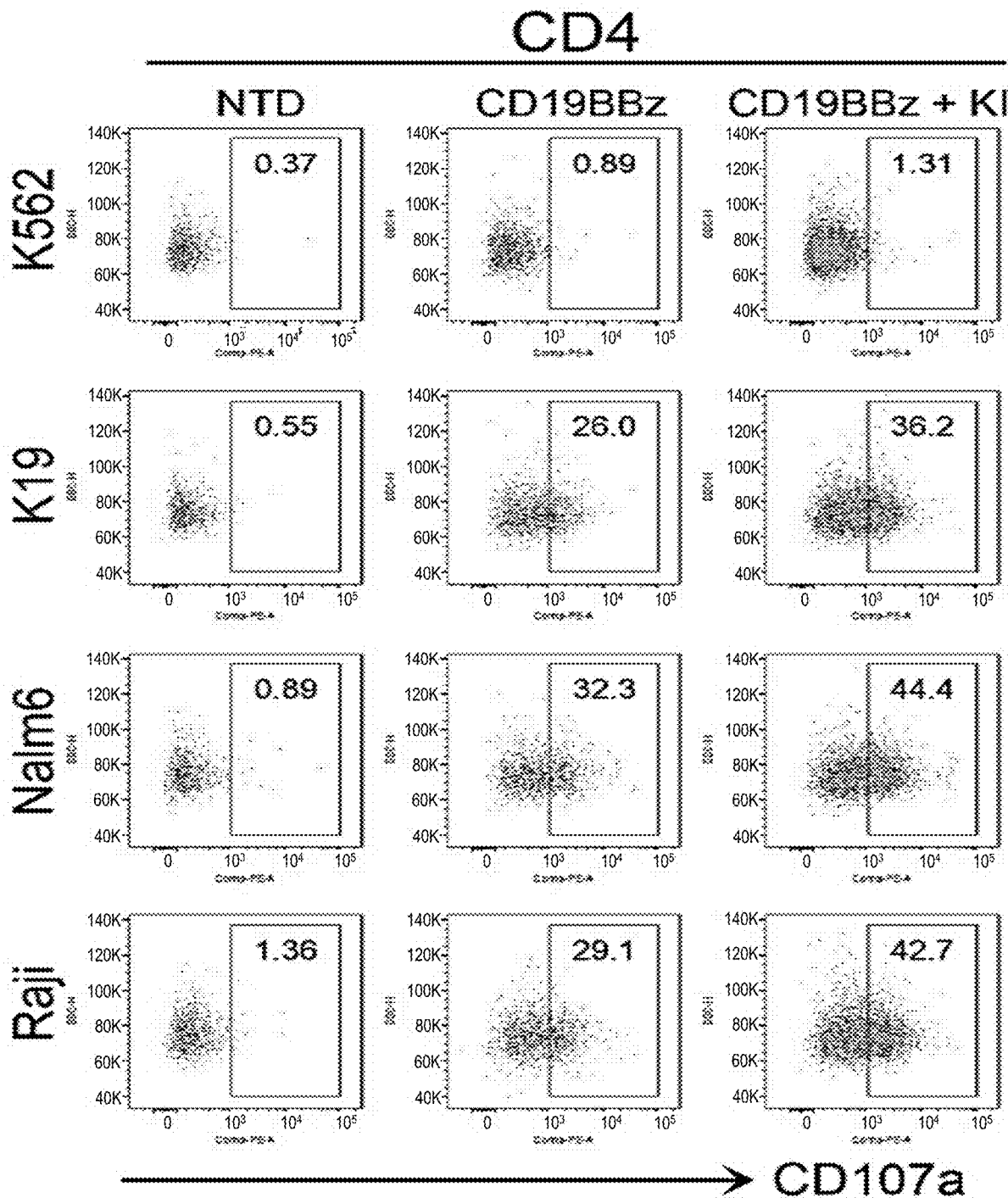
FIG. 28 depicts results showing that CD107a is expressed at significant levels in both CD4 and CD8 CD19BBz+KI cells.
Figure 29:
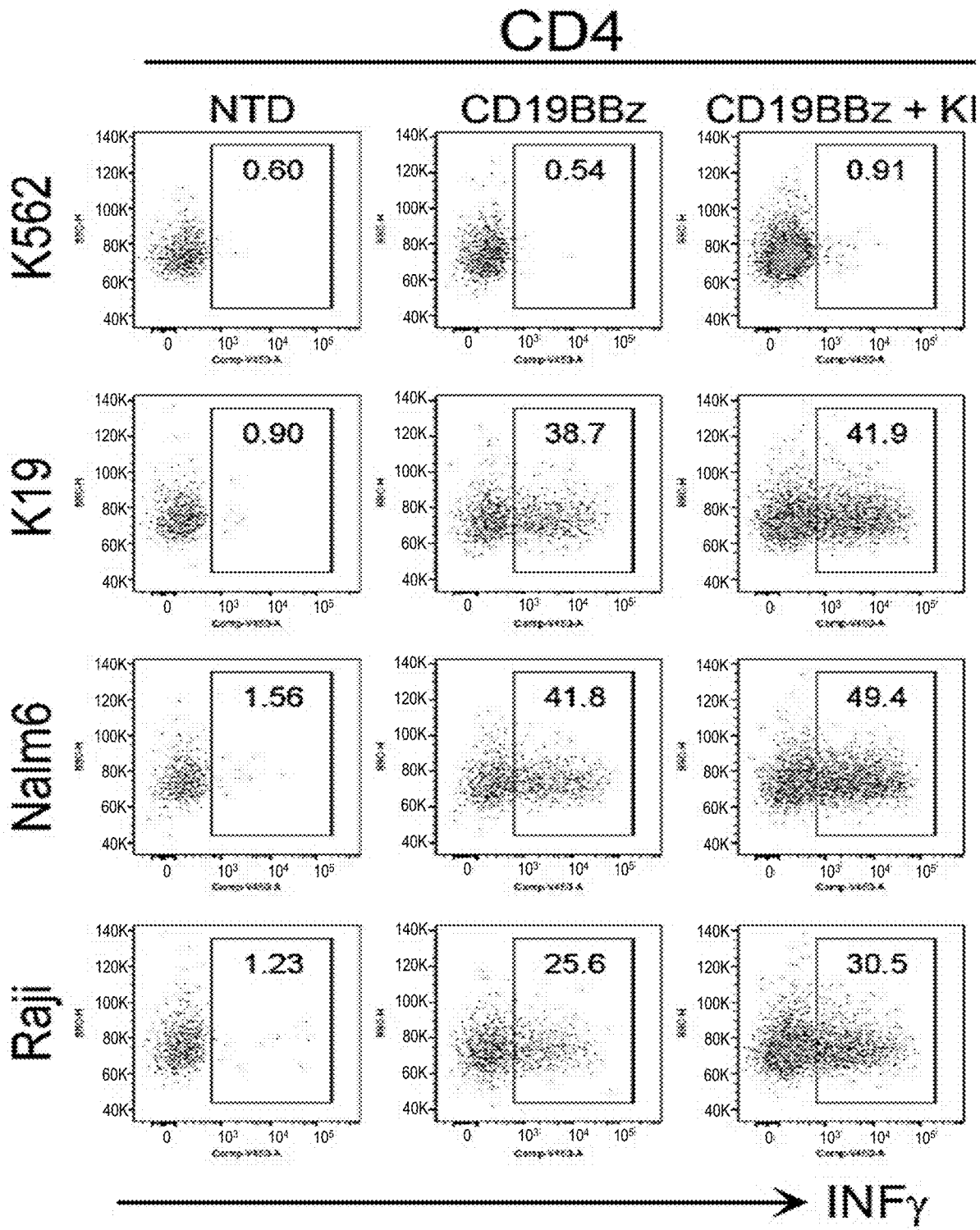
FIG. 29 depicts results showing that INFγ is expressed at significant levels in both CD4 and CD8 CD19BBz+KI cells.
Figure 31:
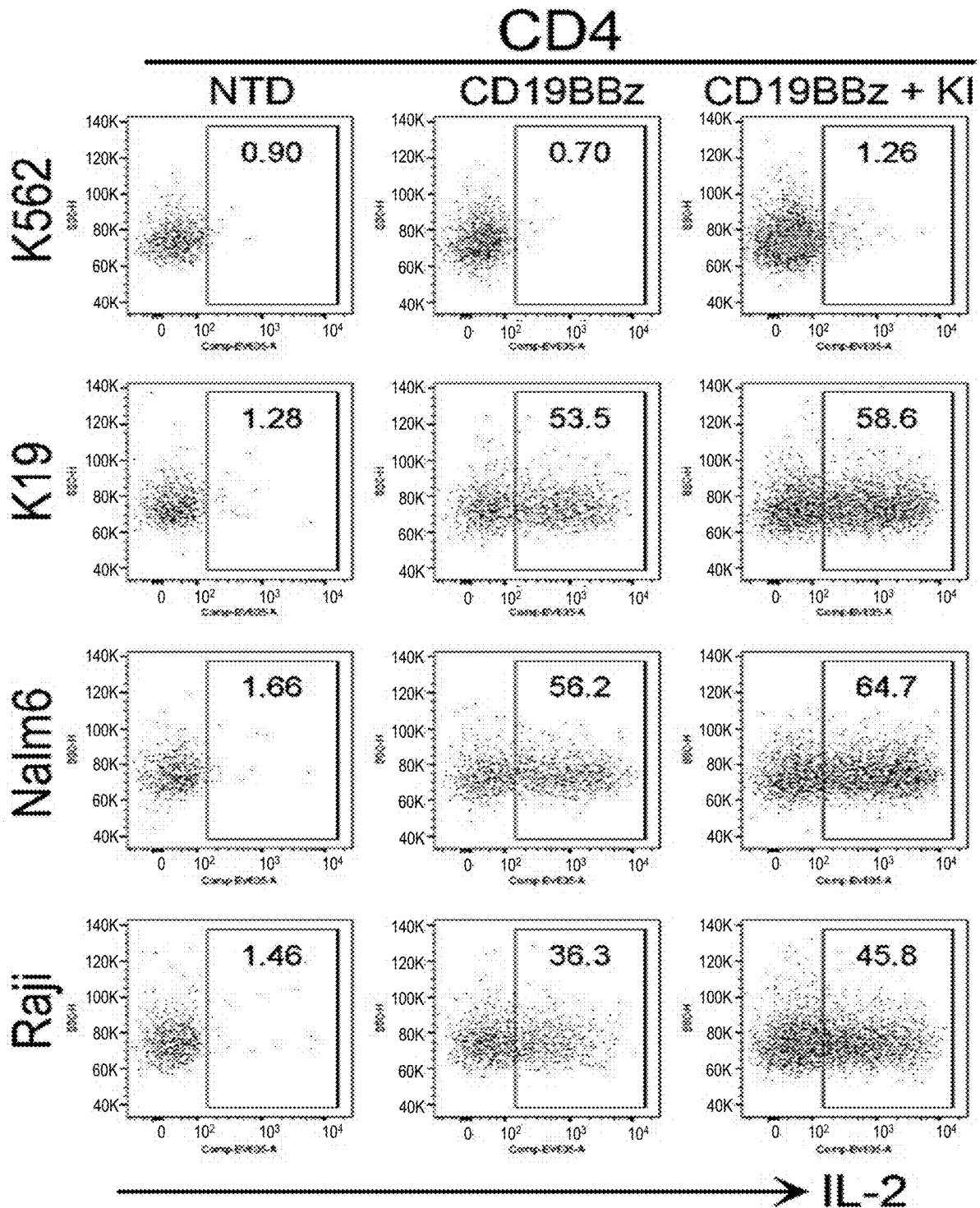
FIG. 31 depicts results showing that IL-2 is expressed at higher levels in CD4 CD19BBz+KI cells, but is expressed at lower levels in CD8 cells than that in CD19BBz T cells.
Figure 32:
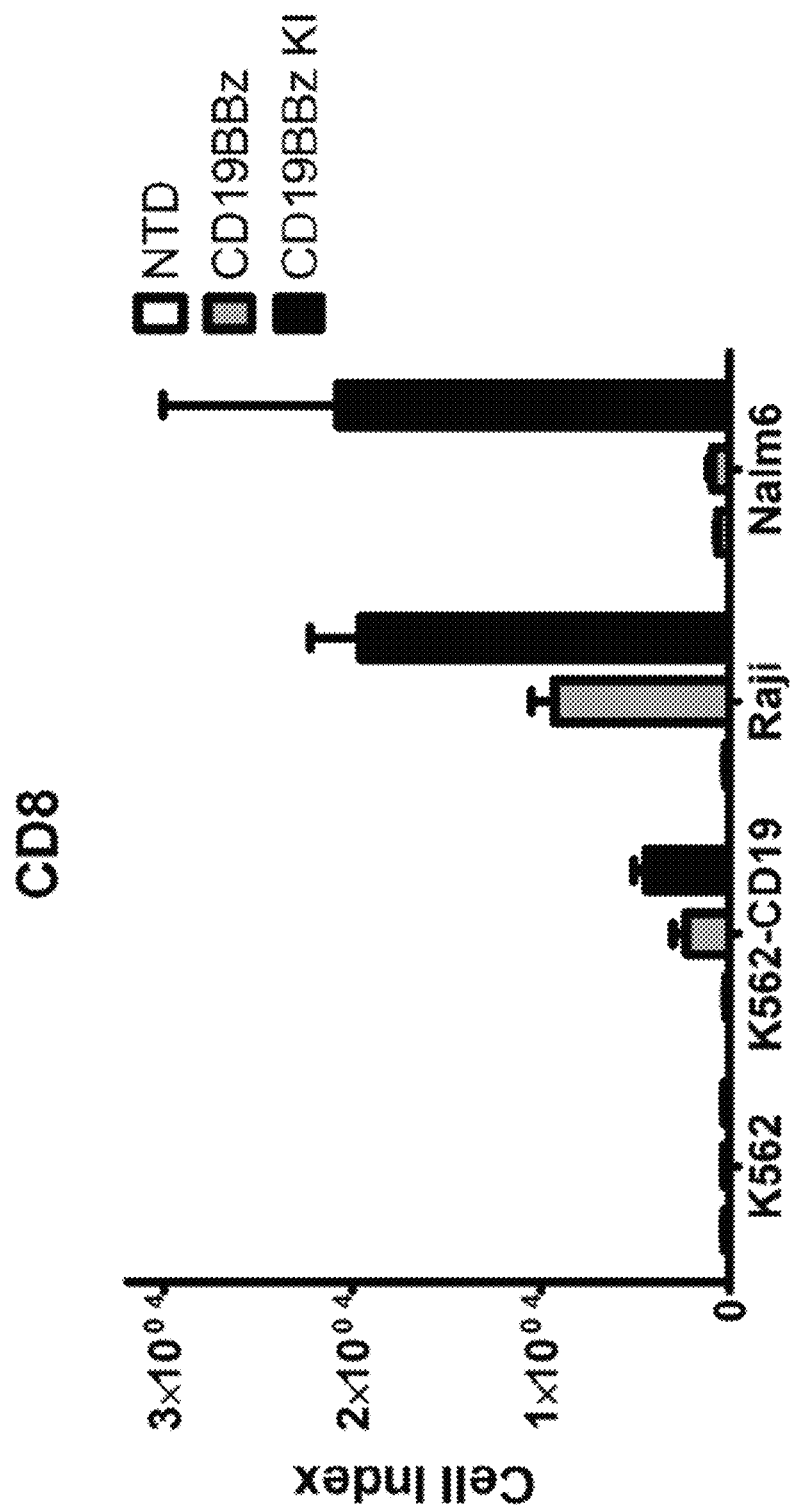
FIG. 32 depicts results showing the number of CD8 cells after repeated stimulations.

NTD, CD19BBz, and CD19BBz+KI T cells were cocultured with K562 cancer cells that do not express CD19, and three cancer cell lines that express CD19: K19 (Forced expression of CD19 in K562 cells), Nalm6 and Raji. CD107a was expressed at significant levels suggesting degranulation is increased in CD19BBz+KI cells (FIG. 28). INFγ and TNFα were induced at higher levels in both CD4 and CD8 CD19BBz+KI cells (FIGS. 29-30). Although IL-2 was expressed at lower levels in CD8 cells, it was expressed at higher levels in CD4 CD19BBz+KI cells (FIG. 31). T cells were repeatedly challenged by tumor cells on Day 1, Day 4 and Day 7 and then the number of CD8 T cells and tumor cells were counted on Day 10. Significantly more CD19BBz KI T cells were present than CD19BBz T cells when cocultured with CD19+ tumor cells (FIG. 32), indicating knockout of DNMT3A increased cell proliferation upon antigen stimulation. More importantly, CD19BBz KI T cells almost completely eliminated Nalm6 cells, while CD19BBz T cells failed to efficiently control Nalm6 cells after repeated stimulations (FIG. 33).

CRISPR/Cas9 gene editing technology combined with donor DNA delivery by AAV vectors successfully generated knockin of EGFP into the DNMT3A gene in T cells. The EGFP+ knockin cells could be sorted and expanded in vitro, and they exhibited increased cytokine production, proliferation and cytotoxicity in response to cancer cells. DNMT3A is required for de novo DNA methylation that is involved in the development of T cell exhaustion. This approach created DNMT3A knockout CAR T cells that have stronger antitumor function.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed:

1. A method for generating a modified immune cell or precursor cell thereof, comprising:
   a) introducing into the immune cell a first nucleic acid comprising a nucleic acid sequence encoding an exogenous T cell receptor (TCR) and/or a chimeric antigen receptor (CAR) comprising affinity for an antigen on a target cell; and
   b) introducing into the immune cell one or more polypeptides and/or nucleic acids that downregulate a gene expression of an endogenous transcriptional modulator; wherein the endogenous transcriptional modulator is downregulated with a CRISPR system-mediated insertion and/or deletion in a gene locus encoding for the endogenous transcriptional modulator; and wherein the endogenous transcriptional modulator is selected from the group consisting of AZI2, C1orf141, CCDC33, CCL7, CEACAM19, KLF4, MFSD5, PAGR1, SIX2, and USP27X.

2. A method for generating a modified immune cell or precursor cell thereof, comprising:
   a) introducing into the immune cell a first nucleic acid comprising a nucleic acid sequence encoding an exogenous T cell receptor (TCR) and/or an exogenous chimeric antigen receptor (CAR) comprising affinity for an antigen on a target cell; and
   b) introducing into the immune cell one or more polypeptides and/or nucleic acids that downregulate a gene expression of an endogenous transcriptional modulator; wherein the endogenous transcriptional modulator is downregulated with an insertion and/or deletion in a gene locus encoding for the endogenous transcriptional modulator; and wherein the endogenous transcriptional modulator is a transcription factor or an epigenetic regulator, wherein the transcription factor is SIX Homeobox 2 (SIX2) or Kruppel-like factor 4 (KLF4), and wherein the epigenetic regulator is a histone-lysine-N-methyltransferase 2D (KMT2D), or PAXIPI Associated Glutamate Rich Protein 1 (PAGR1).

3. The method of claim 2, wherein the insertion and/or deletion in a gene locus encoding for PAGR1 or KMT2D downregulates the gene expression of (a) PAGR1 or KMT2D, and/or (b) one or more downstream targets of the KMT2D- or PAGR1-associated histone methyltransferase complex.

4. The method of claim 3, wherein the one or more downstream targets of the PAGR1-associated histone methyltransferase complex is selected from the group consisting of ARID1A, ARID3B, ASXL1, DNMT3A, DUSP1, MAP3K8, PAXIP1, PRMT1, SOCS3, and TNFAIP3.

5. The method of claim 2, wherein the insertion and/or deletion in the gene locus encoding for the endogenous transcriptional modulator is mediated by:
   (a) a CRISPR-related system;
   (b) a CRISPR nuclease and a guide RNA; and/or
   (c) a CRISPR/Cas9.

6. The method of claim 5, wherein the guide RNA comprises a guide sequence that is complementary to a target sequence of the endogenous transcriptional modulator.

7. The method of claim 2, wherein the insertion and/or deletion is in one or more gene loci encoding for the endogenous transcriptional modulator further comprises AZI2, C1orf141, CCDC33, CCL7, CEACAM19, KLF4, MFSD5, PAGR1, SIX2 or USP27X.

8. The method of claim 7, wherein the endogenous transcriptional modulator is:
   (a) the PAGR1 gene and the guide RNA comprises a nucleic acid sequence set forth in any one of SEQ ID NOs: 31-36;
   (b) the SIX2 gene and the guide RNA comprises a nucleic acid sequence set forth in any one of SEQ ID NOs:37-42;
   (c) the Klf4 gene and the guide RNA comprises a nucleic acid sequence set forth in any one of SEQ ID NOs:43-48;
   (d) the USP27X gene and the guide RNA comprises a nucleic acid sequence set forth in any one of SEQ ID NOs:49-54;
   (e) the CEACAM19 gene and the guide RNA comprises a nucleic acid sequence set forth in any one of SEQ ID NOs:55-60; or (f) the C1orf141 gene and the guide RNA comprises a nucleic acid sequence set forth in any one of SEQ ID NOs:61-66.

9. The method of claim 6, wherein the guide RNA comprises a nucleic acid sequence set forth in any one of SEQ ID NOs: 31-66.

10. The method of claim 2, wherein each of the one or more polypeptides and/or nucleic acids that downregulates gene expression is introduced by electroporation.

11. The method of claim 2, wherein the first nucleic acid is introduced by viral transduction, and wherein the viral transduction comprises contacting the immune cell or precursor cell thereof with a viral vector.

12. The method of claim 11, wherein the viral vector is selected from the group consisting of a retroviral vector, a lentiviral vector, an adenoviral vector, and an adeno-associated viral vector.

13. The method of claim 12, wherein the antigen on a target cell is a tumor associated antigen (TAA).

14. The method of claim 12, wherein the modified cell is:
(a) an autologous cell;
(b) derived from a human; or
(c) a modified T cell.

15. The method of claim 12, wherein the exogenous TCR is selected from the group consisting of a wild-type TCR, a high affinity TCR, and a chimeric TCR;
comprises at least one disulfide bond; and/or
comprises a TCR alpha chain and a TCR beta chain.

16. The method of claim 2, wherein the exogenous CAR comprises an antigen-binding domain, a transmembrane domain, a co-stimulatory domain and an intracellular domain, wherein:
the antigen-binding domain is selected from the group consisting of an antibody, an scFv, and a Fab;
the transmembrane domain is selected from the group consisting of an artificial hydrophobic sequence and transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, CD134, CD137, and CD154;
the co-stimulatory domain is selected from at least one of the group consisting of co-stimulatory domains of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3; and/or
the intracellular domain is selected from the group consisting of cytoplasmic signaling domains of a human CD3 zeta chain, FcγRIII, FcsRI, a cytoplasmic tail of an Fc receptor, an immunoreceptor tyrosine-based activation motif (ITAM) bearing cytoplasmic receptors, TCR zeta, FcRgamma, FcR beta, CD3 gamma, CD3 delta, CD3 epsilon, CD5, CD22, CD79a, CD79b, and CD66d.

17. The method of claim 16, wherein the exogenous CAR further comprises a hinge domain, and wherein the hinge domain is selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof.

18. A method for generating a modified immune cell or precursor cell thereof, comprising:
a) introducing into the immune cell a first nucleic acid comprising a nucleic acid sequence encoding an exogenous T cell receptor (TCR) and/or a chimeric antigen receptor (CAR) comprising affinity for an antigen on a target cell; and
b) introducing into the immune cell one or more polypeptides and/or nucleic acids that downregulate a gene expression of an endogenous transcriptional modulator; wherein the endogenous transcriptional modulator is downregulated with a CRISPR system-mediated insertion and/or deletion in a gene locus encoding for the endogenous transcriptional modulator; and wherein the endogenous transcriptional modulator is:
(i) a transcription factor selected from the group consisting of SIX Homeobox 2 (SIX2) and Krüppel-like factor 4 (KLF4); or
(ii) an epigenetic regulator selected from the group consisting of histone-lysine-N-methyltransferase 2D (KMT2D) or PAXIP1 Associated Glutamate Rich Protein 1 (PAGR1).

19. The method of claim 18, wherein the insertion and/or deletion in the gene locus encoding for SIX2 or KLF4 downregulates gene expression of SIX2 or KLF4, or one or more downstream targets of SIX2 or KLF4.

* * * * *

SEQUENCE LISTING

<160> NUMBER OF SEQ ID NOS: 165

<210> SEQ ID NO 1
<211> LENGTH: 9
<212> TYPE: PRT
<213> ORGANISM: Artificial Sequence
<220> FEATURE:
<223> OTHER INFORMATION: NY-ESO157-165

<400> SEQUENCE: 1

Ser Leu Leu Met Trp Ile Thr Gln Cys
1               5

<210> SEQ ID NO 2
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: Repeat n times, where n is at least 1

<400> SEQUENCE: 2

Gly Ser Gly Gly Ser
1               5

<210> SEQ ID NO 3
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)..(4)
<223> OTHER INFORMATION: Repeat n times, where n is at least 1

<400> SEQUENCE: 3

Gly Gly Gly Ser
1

<210> SEQ ID NO 4
<211> LENGTH: 5
<212> TYPE: PRT

```
<213> ORGANISM: Artificial Sequence
<220> FEATURE:
<223> OTHER INFORMATION: linker
<220> FEATURE:
<221> NAME/KEY: REPEAT
<222> LOCATION: (1)..(5)
<223> OTHER INFORMATION: Repeat n times, where n is at least 1

<400> SEQUENCE: 4

Gly Gly Gly Gly Ser
1               5

<210> SEQ ID NO 5
<211> LENGTH: 4
<212> TYPE: PRT
<213> ORGANISM: Artificial Sequence
<220> FEATURE:
<223> OTHER INFORMATION: linker

<400> SEQUENCE: 5

Gly Gly Ser Gly
1

<210> SEQ ID NO 6
<211> LENGTH: 5
<212> TYPE: PRT
<213> ORGANISM: Artificial Sequence
<220> FEATURE:
<223> OTHER INFORMATION: linker

<400> SEQUENCE: 6

Gly Gly Ser Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: linker

<400> SEQUENCE: 7

Gly Ser Gly Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: linker

<400> SEQUENCE: 8

Gly Ser Gly Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: linker

<400> SEQUENCE: 9

Gly Gly Gly Ser Gly
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: linker

<400> SEQUENCE: 10

Gly Ser Ser Ser Gly
1               5

<210> SEQ ID NO 11
<211> LENGTH: 5
<212> TYPE: PRT
<213> ORGANISM: Artificial Sequence
<220> FEATURE:
<223> OTHER INFORMATION: linker

<400> SEQUENCE: 11

Gly Gly Gly Gly Ser
1               5

<210> SEQ ID NO 12
<211> LENGTH: 15
<212> TYPE: PRT
<213> ORGANISM: Artificial Sequence
<220> FEATURE:
<223> OTHER INFORMATION: linker

<400> SEQUENCE: 12

Gly Gly Gly Gly Ser Gly Gly Gly Ser Gly Gly Gly Gly Ser
1               5                   10                  15

<210> SEQ ID NO 13
<211> LENGTH: 45
<212> TYPE: DNA
<213> ORGANISM: Artificial Sequence
<220> FEATURE:
<223> OTHER INFORMATION: linker

<400> SEQUENCE: 13
ggtggcggtg gctcgggcgg tggtgggtcg ggtggcggcg gatct            45

<210> SEQ ID NO 14
<211> LENGTH: 5
<212> TYPE: PRT
<213> ORGANISM: Artificial Sequence
<220> FEATURE:
<223> OTHER INFORMATION: hinge

<400> SEQUENCE: 14

Asp Lys Thr His Thr
1               5

<210> SEQ ID NO 15
<211> LENGTH: 4
<212> TYPE: PRT
<213> ORGANISM: Artificial Sequence
<220> FEATURE:
<223> OTHER INFORMATION: hinge

<400> SEQUENCE: 15

Cys Pro Pro Cys
1

<210> SEQ ID NO 16
<211> LENGTH: 15
```

<212> TYPE: PRT
<213> ORGANISM: Artificial Sequence
<220> FEATURE:
<223> OTHER INFORMATION: hinge

<400> SEQUENCE: 16

Cys Pro Glu Pro Lys Ser Cys Asp Thr Pro Pro Pro Cys Pro Arg
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: hinge

<400> SEQUENCE: 17

Glu Leu Lys Thr Pro Leu Gly Asp Thr Thr His Thr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: hinge

<400> SEQUENCE: 18

Lys Ser Cys Asp Lys Thr His Thr Cys Pro
1               5                   10

<210> SEQ ID NO 19
<211> LENGTH: 7
<212> TYPE: PRT
<213> ORGANISM: Artificial Sequence
<220> FEATURE:
<223> OTHER INFORMATION: hinge

<400> SEQUENCE: 19

Lys Cys Cys Val Asp Cys Pro
1               5

<210> SEQ ID NO 20
<211> LENGTH: 7
<212> TYPE: PRT
<213> ORGANISM: Artificial Sequence
<220> FEATURE:
<223> OTHER INFORMATION: hinge

<400> SEQUENCE: 20

Lys Tyr Gly Pro Pro Cys Pro
1               5

<210> SEQ ID NO 21
<211> LENGTH: 15
<212> TYPE: PRT
<213> ORGANISM: Artificial Sequence
<220> FEATURE:
<223> OTHER INFORMATION: hinge

<400> SEQUENCE: 21

Glu Pro Lys Ser Cys Asp Lys Thr His Thr Cys Pro Pro Cys Pro
1               5                   10                  15

<210> SEQ ID NO 22
<211> LENGTH: 12
<212> TYPE: PRT

```
<213> ORGANISM: Artificial Sequence
<220> FEATURE:
<223> OTHER INFORMATION: hinge

<400> SEQUENCE: 22

Glu Arg Lys Cys Cys Val Glu Cys Pro Pro Cys Pro
1               5                   10

<210> SEQ ID NO 23
<211> LENGTH: 17
<212> TYPE: PRT
<213> ORGANISM: Artificial Sequence
<220> FEATURE:
<223> OTHER INFORMATION: hinge

<400> SEQUENCE: 23

Glu Leu Lys Thr Pro Leu Gly Asp Thr Thr His Thr Cys Pro Arg Cys
1               5                   10                  15

Pro

<210> SEQ ID NO 24
<211> LENGTH: 12
<212> TYPE: PRT
<213> ORGANISM: Artificial Sequence
<220> FEATURE:
<223> OTHER INFORMATION: hinge

<400> SEQUENCE: 24

Ser Pro Asn Met Val Pro His Ala His His Ala Gln
1               5                   10

<210> SEQ ID NO 25
<211> LENGTH: 15
<212> TYPE: PRT
<213> ORGANISM: Artificial Sequence
<220> FEATURE:
<223> OTHER INFORMATION: hinge

<400> SEQUENCE: 25

Glu Pro Lys Ser Cys Asp Lys Thr Tyr Thr Cys Pro Pro Cys Pro
1               5                   10                  15

<210> SEQ ID NO 26
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid

<400> SEQUENCE: 26

Arg Xaa Lys Arg
1

<210> SEQ ID NO 27
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid
```

```
<400> SEQUENCE: 27

Arg Xaa Arg Arg
1

<210> SEQ ID NO 28
<211> LENGTH: 5
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (1)..(1)
<223> OTHER INFORMATION: Xaa is Arg or Lys
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is Arg or Lys

<400> SEQUENCE: 28

Xaa Arg Xaa Xaa Arg
1               5

<210> SEQ ID NO 29
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 29

Arg Xaa Xaa Arg
1

<210> SEQ ID NO 30
<211> LENGTH: 4
<212> TYPE: PRT
<213> ORGANISM: Artificial Sequence
<220> FEATURE:
<223> OTHER INFORMATION: furin cleavage site

<400> SEQUENCE: 30

Arg Gln Lys Arg
1

<210> SEQ ID NO 31
<211> LENGTH: 20
<212> TYPE: DNA
<213> ORGANISM: Artificial Sequence
<220> FEATURE:
<223> OTHER INFORMATION: gRNA

<400> SEQUENCE: 31
aatcagtatt tccgctgccg                                                 20

<210> SEQ ID NO 32
<211> LENGTH: 20
<212> TYPE: DNA
<213> ORGANISM: Artificial Sequence
<220> FEATURE:
<223> OTHER INFORMATION: gRNA
```

```
<400> SEQUENCE: 32
ttgtacctgg ggtgcgtctc                                                      20

<210> SEQ ID NO 33
<211> LENGTH: 20
<212> TYPE: DNA
<213> ORGANISM: Artificial Sequence
<220> FEATURE:
<223> OTHER INFORMATION: gRNA

<400> SEQUENCE: 33
aggagcagat ccttcgtacc                                                      20

<210> SEQ ID NO 34
<211> LENGTH: 20
<212> TYPE: DNA
<213> ORGANISM: Artificial Sequence
<220> FEATURE:
<223> OTHER INFORMATION: gRNA

<400> SEQUENCE: 34
ccggtaaggc cgaggacgag                                                      20

<210> SEQ ID NO 35
<211> LENGTH: 20
<212> TYPE: DNA
<213> ORGANISM: Artificial Sequence
<220> FEATURE:
<223> OTHER INFORMATION: gRNA

<400> SEQUENCE: 35
cccctcgtcc tcggccttac                                                      20

<210> SEQ ID NO 36
<211> LENGTH: 20
<212> TYPE: DNA
<213> ORGANISM: Artificial Sequence
<220> FEATURE:
<223> OTHER INFORMATION: gRNA

<400> SEQUENCE: 36
attgaccgga gacgcacccc                                                      20

<210> SEQ ID NO 37
<211> LENGTH: 20
<212> TYPE: DNA
<213> ORGANISM: Artificial Sequence
<220> FEATURE:
<223> OTHER INFORMATION: gRNA

<400> SEQUENCE: 37
gcgggaattt gcggcgcacg                                                      20

<210> SEQ ID NO 38
<211> LENGTH: 20
<212> TYPE: DNA
<213> ORGANISM: Artificial Sequence
<220> FEATURE:
<223> OTHER INFORMATION: gRNA

<400> SEQUENCE: 38
accccgcgag aagcgtgagc                                                      20

<210> SEQ ID NO 39
```

<211> LENGTH: 20
<212> TYPE: DNA
<213> ORGANISM: Artificial Sequence
<220> FEATURE:
<223> OTHER INFORMATION: gRNA

<400> SEQUENCE: 39
gagtggtctg gcgtccccga                                          20

<210> SEQ ID NO 40
<211> LENGTH: 20
<212> TYPE: DNA
<213> ORGANISM: Artificial Sequence
<220> FEATURE:
<223> OTHER INFORMATION: gRNA

<400> SEQUENCE: 40
aacagccaca acccgctgaa                                          20

<210> SEQ ID NO 41
<211> LENGTH: 20
<212> TYPE: DNA
<213> ORGANISM: Artificial Sequence
<220> FEATURE:
<223> OTHER INFORMATION: gRNA

<400> SEQUENCE: 41
ttgctcctgc gtgaagccga                                          20

<210> SEQ ID NO 42
<211> LENGTH: 20
<212> TYPE: DNA
<213> ORGANISM: Artificial Sequence
<220> FEATURE:
<223> OTHER INFORMATION: gRNA

<400> SEQUENCE: 42
caaggcacac tacatcgagg                                          20

<210> SEQ ID NO 43
<211> LENGTH: 20
<212> TYPE: DNA
<213> ORGANISM: Artificial Sequence
<220> FEATURE:
<223> OTHER INFORMATION: gRNA

<400> SEQUENCE: 43
gtggtggcgc cctacaacgg                                          20

<210> SEQ ID NO 44
<211> LENGTH: 20
<212> TYPE: DNA
<213> ORGANISM: Artificial Sequence
<220> FEATURE:
<223> OTHER INFORMATION: gRNA

<400> SEQUENCE: 44
agcccgcgta atcacaagtg                                          20

<210> SEQ ID NO 45
<211> LENGTH: 20
<212> TYPE: DNA
<213> ORGANISM: Artificial Sequence
<220> FEATURE:
<223> OTHER INFORMATION: gRNA

<400> SEQUENCE: 45
gcgcggcggc ccgccgttgt                                              20

<210> SEQ ID NO 46
<211> LENGTH: 20
<212> TYPE: DNA
<213> ORGANISM: Artificial Sequence
<220> FEATURE:
<223> OTHER INFORMATION: gRNA

<400> SEQUENCE: 46
tctttctcca cgttcgcgtc                                              20

<210> SEQ ID NO 47
<211> LENGTH: 20
<212> TYPE: DNA
<213> ORGANISM: Artificial Sequence
<220> FEATURE:
<223> OTHER INFORMATION: gRNA

<400> SEQUENCE: 47
cacccacact tgtgattacg                                              20

<210> SEQ ID NO 48
<211> LENGTH: 20
<212> TYPE: DNA
<213> ORGANISM: Artificial Sequence
<220> FEATURE:
<223> OTHER INFORMATION: gRNA

<400> SEQUENCE: 48
gagaagacac tgcgtcaagc                                              20

<210> SEQ ID NO 49
<211> LENGTH: 20
<212> TYPE: DNA
<213> ORGANISM: Artificial Sequence
<220> FEATURE:
<223> OTHER INFORMATION: gRNA

<400> SEQUENCE: 49
cgcggcgcac gactgcgacg                                              20

<210> SEQ ID NO 50
<211> LENGTH: 20
<212> TYPE: DNA
<213> ORGANISM: Artificial Sequence
<220> FEATURE:
<223> OTHER INFORMATION: gRNA

<400> SEQUENCE: 50
gtgagatgtc gtcgctgttt                                              20

<210> SEQ ID NO 51
<211> LENGTH: 20
<212> TYPE: DNA
<213> ORGANISM: Artificial Sequence
<220> FEATURE:
<223> OTHER INFORMATION: gRNA

<400> SEQUENCE: 51
ctcgatgcca gttgtagtat                                              20

<210> SEQ ID NO 52
<211> LENGTH: 20
<212> TYPE: DNA

```
<213> ORGANISM: Artificial Sequence
<220> FEATURE:
<223> OTHER INFORMATION: gRNA

<400> SEQUENCE: 52
gtccagtacg tccttaatac                                              20

<210> SEQ ID NO 53
<211> LENGTH: 20
<212> TYPE: DNA
<213> ORGANISM: Artificial Sequence
<220> FEATURE:
<223> OTHER INFORMATION: gRNA

<400> SEQUENCE: 53
tcttaaaccg atcgtaaagc                                              20

<210> SEQ ID NO 54
<211> LENGTH: 20
<212> TYPE: DNA
<213> ORGANISM: Artificial Sequence
<220> FEATURE:
<223> OTHER INFORMATION: gRNA

<400> SEQUENCE: 54
actgcttgcg gaggtttacg                                              20

<210> SEQ ID NO 55
<211> LENGTH: 20
<212> TYPE: DNA
<213> ORGANISM: Artificial Sequence
<220> FEATURE:
<223> OTHER INFORMATION: gRNA

<400> SEQUENCE: 55
ctctgaggcc gttgtatccc                                              20

<210> SEQ ID NO 56
<211> LENGTH: 20
<212> TYPE: DNA
<213> ORGANISM: Artificial Sequence
<220> FEATURE:
<223> OTHER INFORMATION: gRNA

<400> SEQUENCE: 56
atacaacggc ctcagaggga                                              20

<210> SEQ ID NO 57
<211> LENGTH: 20
<212> TYPE: DNA
<213> ORGANISM: Artificial Sequence
<220> FEATURE:
<223> OTHER INFORMATION: gRNA

<400> SEQUENCE: 57
gatccctggc ccctcggagc                                              20

<210> SEQ ID NO 58
<211> LENGTH: 20
<212> TYPE: DNA
<213> ORGANISM: Artificial Sequence
<220> FEATURE:
<223> OTHER INFORMATION: gRNA

<400> SEQUENCE: 58
catgtgctgg gcgtcactga                                              20
```

```
<210> SEQ ID NO 59
<211> LENGTH: 20
<212> TYPE: DNA
<213> ORGANISM: Artificial Sequence
<220> FEATURE:
<223> OTHER INFORMATION: gRNA

<400> SEQUENCE: 59
ggccgccagg atcccagcgt                                                 20

<210> SEQ ID NO 60
<211> LENGTH: 20
<212> TYPE: DNA
<213> ORGANISM: Artificial Sequence
<220> FEATURE:
<223> OTHER INFORMATION: gRNA

<400> SEQUENCE: 60
atcctggcgg ccaccatcat                                                 20

<210> SEQ ID NO 61
<211> LENGTH: 20
<212> TYPE: DNA
<213> ORGANISM: Artificial Sequence
<220> FEATURE:
<223> OTHER INFORMATION: gRNA

<400> SEQUENCE: 61
tcttgctaca tccgcgtcta                                                 20

<210> SEQ ID NO 62
<211> LENGTH: 20
<212> TYPE: DNA
<213> ORGANISM: Artificial Sequence
<220> FEATURE:
<223> OTHER INFORMATION: gRNA

<400> SEQUENCE: 62
ctttgatatt gccttagacg                                                 20

<210> SEQ ID NO 63
<211> LENGTH: 20
<212> TYPE: DNA
<213> ORGANISM: Artificial Sequence
<220> FEATURE:
<223> OTHER INFORMATION: gRNA

<400> SEQUENCE: 63
gattctgttg gtctcttaga                                                 20

<210> SEQ ID NO 64
<211> LENGTH: 20
<212> TYPE: DNA
<213> ORGANISM: Artificial Sequence
<220> FEATURE:
<223> OTHER INFORMATION: gRNA

<400> SEQUENCE: 64
aataaagaaa gtgagtcaac                                                 20

<210> SEQ ID NO 65
<211> LENGTH: 20
<212> TYPE: DNA
<213> ORGANISM: Artificial Sequence
<220> FEATURE:
```

<223> OTHER INFORMATION: gRNA

<400> SEQUENCE: 65
aagagaccaa cagaatccaa                                              20

<210> SEQ ID NO 66
<211> LENGTH: 20
<212> TYPE: DNA
<213> ORGANISM: Artificial Sequence
<220> FEATURE:
<223> OTHER INFORMATION: gRNA

<400> SEQUENCE: 66
acatttgttt gaataaagaa                                              20

<210> SEQ ID NO 67
<211> LENGTH: 24
<212> TYPE: DNA
<213> ORGANISM: Artificial Sequence
<220> FEATURE:
<223> OTHER INFORMATION: primer

<400> SEQUENCE: 67
cttctgtcac tgttccgggt tttg                                         24

<210> SEQ ID NO 68
<211> LENGTH: 23
<212> TYPE: DNA
<213> ORGANISM: Artificial Sequence
<220> FEATURE:
<223> OTHER INFORMATION: primer

<400> SEQUENCE: 68
gccactccca ctgtcctttc cta                                          23

<210> SEQ ID NO 69
<211> LENGTH: 22
<212> TYPE: DNA
<213> ORGANISM: Artificial Sequence
<220> FEATURE:
<223> OTHER INFORMATION: primer

<400> SEQUENCE: 69
cacaagggta gcggcgaaga tc                                           22

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
acatgcccag aagcggtgga                                              20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
tttccatttt tcacggcaag                                              20

```
<210> SEQ ID NO 72
<211> LENGTH: 19
<212> TYPE: DNA
<213> ORGANISM: Artificial Sequence
<220> FEATURE:
<223> OTHER INFORMATION: primer

<400> SEQUENCE: 72
caccccaatt ccagactgc                                                  19

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
ggagctccat ctgaatgagg                                                 20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
ttttgctctg tcttgcctca                                                 20

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
acttccaggc ctcctagtgc                                                 20

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
ttttgctctg tcttgcctca                                                 20

<210> SEQ ID NO 77
<211> LENGTH: 20
<212> TYPE: DNA
<213> ORGANISM: Artificial Sequence
<220> FEATURE:
<223> OTHER INFORMATION: primer

<400> SEQUENCE: 77
actgtatctg gtcccctcca                                                 20

<210> SEQ ID NO 78
<211> LENGTH: 21
<212> TYPE: DNA
<213> ORGANISM: Artificial Sequence
<220> FEATURE:
<223> OTHER INFORMATION: primer
```

```
<400> SEQUENCE: 78
ccaacagaga gcaggtcatt c                                      21

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
actgtatctg gtcccctcca                                        20

<210> SEQ ID NO 80
<211> LENGTH: 21
<212> TYPE: DNA
<213> ORGANISM: Artificial Sequence
<220> FEATURE:
<223> OTHER INFORMATION: primer

<400> SEQUENCE: 80
ccaacagaga gcaggtcatt c                                      21

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
ctggggtcag gacttgaatg                                        20

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
ccattgacag gagagcagaa                                        20

<210> SEQ ID NO 83
<211> LENGTH: 20
<212> TYPE: DNA
<213> ORGANISM: Artificial Sequence
<220> FEATURE:
<223> OTHER INFORMATION: primer

<400> SEQUENCE: 83
ctggggtcag gacttgaatg                                        20

<210> SEQ ID NO 84
<211> LENGTH: 20
<212> TYPE: DNA
<213> ORGANISM: Artificial Sequence
<220> FEATURE:
<223> OTHER INFORMATION: primer

<400> SEQUENCE: 84
ccattgacag gagagcagaa                                        20

<210> SEQ ID NO 85
<211> LENGTH: 20
```

```
<212> TYPE: DNA
<213> ORGANISM: Artificial Sequence
<220> FEATURE:
<223> OTHER INFORMATION: primer

<400> SEQUENCE: 85
agatgatggc gttcgagact                                          20

<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86
caaaagcttg aaacccaagg                                          20

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
caaaagcttg aaacccaagg                                          20

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
ctgaccctgg ctaaggtggt                                          20

<210> SEQ ID NO 89
<211> LENGTH: 20
<212> TYPE: DNA
<213> ORGANISM: Artificial Sequence
<220> FEATURE:
<223> OTHER INFORMATION: primer

<400> SEQUENCE: 89
agggtcctaa gcagtgagca                                          20

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
ctgaccctgg ctaaggtggt                                          20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
```
agggtcctaa gcagtgagca                                              20

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
gacagctatt cccgatgacc                                              20

<210> SEQ ID NO 93
<211> LENGTH: 20
<212> TYPE: DNA
<213> ORGANISM: Artificial Sequence
<220> FEATURE:
<223> OTHER INFORMATION: primer

<400> SEQUENCE: 93
tgcaaagcag aagtcaccag                                              20

<210> SEQ ID NO 94
<211> LENGTH: 20
<212> TYPE: DNA
<213> ORGANISM: Artificial Sequence
<220> FEATURE:
<223> OTHER INFORMATION: primer

<400> SEQUENCE: 94
tgcaaagcag aagtcaccag                                              20

<210> SEQ ID NO 95
<211> LENGTH: 34
<212> TYPE: DNA
<213> ORGANISM: Artificial Sequence
<220> FEATURE:
<223> OTHER INFORMATION: artificial sequence

<400> SEQUENCE: 95
aaggcacccg ctgggtcatg tggttcggag acgg                              34

<210> SEQ ID NO 96
<211> LENGTH: 20
<212> TYPE: DNA
<213> ORGANISM: Artificial Sequence
<220> FEATURE:
<223> OTHER INFORMATION: gRNA

<400> SEQUENCE: 96
ctcgtcatcg cctgctttgg                                              20

<210> SEQ ID NO 97
<211> LENGTH: 20
<212> TYPE: DNA
<213> ORGANISM: Artificial Sequence
<220> FEATURE:
<223> OTHER INFORMATION: gRNA

<400> SEQUENCE: 97
tcaggcgtgg tagccacagt                                              20

<210> SEQ ID NO 98
<211> LENGTH: 20
<212> TYPE: DNA
<213> ORGANISM: Artificial Sequence

```
<220> FEATURE:
<223> OTHER INFORMATION: gRNA

<400> SEQUENCE: 98
tggctcgtca tcgcctgctt                                                    20

<210> SEQ ID NO 99
<211> LENGTH: 20
<212> TYPE: DNA
<213> ORGANISM: Artificial Sequence
<220> FEATURE:
<223> OTHER INFORMATION: gRNA

<400> SEQUENCE: 99
ctaccacgcc tgagcccgtg                                                    20

<210> SEQ ID NO 100
<211> LENGTH: 20
<212> TYPE: DNA
<213> ORGANISM: Artificial Sequence
<220> FEATURE:
<223> OTHER INFORMATION: gRNA

<400> SEQUENCE: 100
gacaagaatg ccaccaaagc                                                    20

<210> SEQ ID NO 101
<211> LENGTH: 20
<212> TYPE: DNA
<213> ORGANISM: Artificial Sequence
<220> FEATURE:
<223> OTHER INFORMATION: gRNA

<400> SEQUENCE: 101
cgatgacgag ccagagtacg                                                    20

<210> SEQ ID NO 102
<211> LENGTH: 20
<212> TYPE: DNA
<213> ORGANISM: Artificial Sequence
<220> FEATURE:
<223> OTHER INFORMATION: gRNA

<400> SEQUENCE: 102
aagccgctca cctcgtactc                                                    20

<210> SEQ ID NO 103
<211> LENGTH: 20
<212> TYPE: DNA
<213> ORGANISM: Artificial Sequence
<220> FEATURE:
<223> OTHER INFORMATION: gRNA

<400> SEQUENCE: 103
gctaccacgc ctgagcccgt                                                    20

<210> SEQ ID NO 104
<211> LENGTH: 20
<212> TYPE: DNA
<213> ORGANISM: Artificial Sequence
<220> FEATURE:
<223> OTHER INFORMATION: gRNA

<400> SEQUENCE: 104
gagcccgtgg ggtccgatgc                                                    20
```

```
<210> SEQ ID NO 105
<211> LENGTH: 20
<212> TYPE: DNA
<213> ORGANISM: Artificial Sequence
<220> FEATURE:
<223> OTHER INFORMATION: gRNA

<400> SEQUENCE: 105
ggctaccacg cctgagcccg                                                 20

<210> SEQ ID NO 106
<211> LENGTH: 20
<212> TYPE: DNA
<213> ORGANISM: Artificial Sequence
<220> FEATURE:
<223> OTHER INFORMATION: gRNA

<400> SEQUENCE: 106
ggggcccggg gagtctcaga                                                 20

<210> SEQ ID NO 107
<211> LENGTH: 20
<212> TYPE: DNA
<213> ORGANISM: Artificial Sequence
<220> FEATURE:
<223> OTHER INFORMATION: gRNA

<400> SEQUENCE: 107
gcccgtgggg tccgatgctg                                                 20

<210> SEQ ID NO 108
<211> LENGTH: 20
<212> TYPE: DNA
<213> ORGANISM: Artificial Sequence
<220> FEATURE:
<223> OTHER INFORMATION: gRNA

<400> SEQUENCE: 108
tgtcttggtg gatgacgggc                                                 20

<210> SEQ ID NO 109
<211> LENGTH: 20
<212> TYPE: DNA
<213> ORGANISM: Artificial Sequence
<220> FEATURE:
<223> OTHER INFORMATION: gRNA

<400> SEQUENCE: 109
tctgagactc cccgggcccc                                                 20

<210> SEQ ID NO 110
<211> LENGTH: 20
<212> TYPE: DNA
<213> ORGANISM: Artificial Sequence
<220> FEATURE:
<223> OTHER INFORMATION: gRNA

<400> SEQUENCE: 110
ctcgtcatcg cctgctttgg                                                 20

<210> SEQ ID NO 111
<211> LENGTH: 20
<212> TYPE: DNA
<213> ORGANISM: Artificial Sequence
<220> FEATURE:
<223> OTHER INFORMATION: gRNA
```

```
<400> SEQUENCE: 111
caggcgtggt agccacagtg                                              20

<210> SEQ ID NO 112
<211> LENGTH: 20
<212> TYPE: DNA
<213> ORGANISM: Artificial Sequence
<220> FEATURE:
<223> OTHER INFORMATION: gRNA

<400> SEQUENCE: 112
ggaagaaaac caggggcccg                                              20

<210> SEQ ID NO 113
<211> LENGTH: 20
<212> TYPE: DNA
<213> ORGANISM: Artificial Sequence
<220> FEATURE:
<223> OTHER INFORMATION: gRNA

<400> SEQUENCE: 113
tccgaaccac atgacccagc                                              20

<210> SEQ ID NO 114
<211> LENGTH: 20
<212> TYPE: DNA
<213> ORGANISM: Artificial Sequence
<220> FEATURE:
<223> OTHER INFORMATION: gRNA

<400> SEQUENCE: 114
cggagacggc aaattctcag                                              20

<210> SEQ ID NO 115
<211> LENGTH: 20
<212> TYPE: DNA
<213> ORGANISM: Artificial Sequence
<220> FEATURE:
<223> OTHER INFORMATION: gRNA

<400> SEQUENCE: 115
gacggccggg gctttggcat                                              20

<210> SEQ ID NO 116
<211> LENGTH: 20
<212> TYPE: DNA
<213> ORGANISM: Artificial Sequence
<220> FEATURE:
<223> OTHER INFORMATION: gRNA

<400> SEQUENCE: 116
ggccaggccg cattgtgtct                                              20

<210> SEQ ID NO 117
<211> LENGTH: 20
<212> TYPE: DNA
<213> ORGANISM: Artificial Sequence
<220> FEATURE:
<223> OTHER INFORMATION: gRNA

<400> SEQUENCE: 117
tgggtcatgt ggttcggaga                                              20

<210> SEQ ID NO 118
```

```
<211> LENGTH: 20
<212> TYPE: DNA
<213> ORGANISM: Artificial Sequence
<220> FEATURE:
<223> OTHER INFORMATION: gRNA

<400> SEQUENCE: 118
tgggtcatgt ggttcggaga                                        20

<210> SEQ ID NO 119
<211> LENGTH: 20
<212> TYPE: DNA
<213> ORGANISM: Artificial Sequence
<220> FEATURE:
<223> OTHER INFORMATION: gRNA

<400> SEQUENCE: 119
cggccggggc tttggcattg                                        20

<210> SEQ ID NO 120
<211> LENGTH: 20
<212> TYPE: DNA
<213> ORGANISM: Artificial Sequence
<220> FEATURE:
<223> OTHER INFORMATION: gRNA

<400> SEQUENCE: 120
tgggtcatgt ggttcggaga                                        20

<210> SEQ ID NO 121
<211> LENGTH: 20
<212> TYPE: DNA
<213> ORGANISM: Artificial Sequence
<220> FEATURE:
<223> OTHER INFORMATION: gRNA

<400> SEQUENCE: 121
acccgctggg tcatgtggtt                                        20

<210> SEQ ID NO 122
<211> LENGTH: 20
<212> TYPE: DNA
<213> ORGANISM: Artificial Sequence
<220> FEATURE:
<223> OTHER INFORMATION: gRNA

<400> SEQUENCE: 122
tccccagcat cggaccccac                                        20

<210> SEQ ID NO 123
<211> LENGTH: 20
<212> TYPE: DNA
<213> ORGANISM: Artificial Sequence
<220> FEATURE:
<223> OTHER INFORMATION: gRNA

<400> SEQUENCE: 123
catgggctgc ttgttgtacg                                        20

<210> SEQ ID NO 124
<211> LENGTH: 20
<212> TYPE: DNA
<213> ORGANISM: Artificial Sequence
<220> FEATURE:
<223> OTHER INFORMATION: gRNA

<400> SEQUENCE: 124
```
gctgcttgtt gtacgtggcc                                                20

<210> SEQ ID NO 125
<211> LENGTH: 20
<212> TYPE: DNA
<213> ORGANISM: Artificial Sequence
<220> FEATURE:
<223> OTHER INFORMATION: gRNA

<400> SEQUENCE: 125
gcactgcaaa acgagctcag                                                20

<210> SEQ ID NO 126
<211> LENGTH: 20
<212> TYPE: DNA
<213> ORGANISM: Artificial Sequence
<220> FEATURE:
<223> OTHER INFORMATION: gRNA

<400> SEQUENCE: 126
gttttgcagt gcgttccacc                                                20

<210> SEQ ID NO 127
<211> LENGTH: 20
<212> TYPE: DNA
<213> ORGANISM: Artificial Sequence
<220> FEATURE:
<223> OTHER INFORMATION: gRNA

<400> SEQUENCE: 127
gcttgttgta cgtggcctgg                                                20

<210> SEQ ID NO 128
<211> LENGTH: 20
<212> TYPE: DNA
<213> ORGANISM: Artificial Sequence
<220> FEATURE:
<223> OTHER INFORMATION: gRNA

<400> SEQUENCE: 128
agaacaagcc catgattgaa                                                20

<210> SEQ ID NO 129
<211> LENGTH: 20
<212> TYPE: DNA
<213> ORGANISM: Artificial Sequence
<220> FEATURE:
<223> OTHER INFORMATION: gRNA

<400> SEQUENCE: 129
catcgctgtc gtggcacacc                                                20

<210> SEQ ID NO 130
<211> LENGTH: 20
<212> TYPE: DNA
<213> ORGANISM: Artificial Sequence
<220> FEATURE:
<223> OTHER INFORMATION: gRNA

<400> SEQUENCE: 130
ccgggaacag cttccccgcg                                                20

<210> SEQ ID NO 131
<211> LENGTH: 20
<212> TYPE: DNA

```
<213> ORGANISM: Artificial Sequence
<220> FEATURE:
<223> OTHER INFORMATION: gRNA

<400> SEQUENCE: 131
cccagggccc attcaatcat                                               20

<210> SEQ ID NO 132
<211> LENGTH: 20
<212> TYPE: DNA
<213> ORGANISM: Artificial Sequence
<220> FEATURE:
<223> OTHER INFORMATION: gRNA

<400> SEQUENCE: 132
aaagccccgg aagagcacag                                               20

<210> SEQ ID NO 133
<211> LENGTH: 19
<212> TYPE: DNA
<213> ORGANISM: Artificial Sequence
<220> FEATURE:
<223> OTHER INFORMATION: gRNA

<400> SEQUENCE: 133
agaagtgtac acggacatg                                                19

<210> SEQ ID NO 134
<211> LENGTH: 20
<212> TYPE: DNA
<213> ORGANISM: Artificial Sequence
<220> FEATURE:
<223> OTHER INFORMATION: gRNA

<400> SEQUENCE: 134
attattgatg agcgcacaag                                               20

<210> SEQ ID NO 135
<211> LENGTH: 20
<212> TYPE: DNA
<213> ORGANISM: Artificial Sequence
<220> FEATURE:
<223> OTHER INFORMATION: gRNA

<400> SEQUENCE: 135
aagaagtgta cacggacatg                                               20

<210> SEQ ID NO 136
<211> LENGTH: 20
<212> TYPE: DNA
<213> ORGANISM: Artificial Sequence
<220> FEATURE:
<223> OTHER INFORMATION: gRNA

<400> SEQUENCE: 136
ttctccgctg tgctcttccg                                               20

<210> SEQ ID NO 137
<211> LENGTH: 20
<212> TYPE: DNA
<213> ORGANISM: Artificial Sequence
<220> FEATURE:
<223> OTHER INFORMATION: gRNA

<400> SEQUENCE: 137
agcggctggt gtacgaggtg                                               20
```

```
<210> SEQ ID NO 138
<211> LENGTH: 20
<212> TYPE: DNA
<213> ORGANISM: Artificial Sequence
<220> FEATURE:
<223> OTHER INFORMATION: gRNA

<400> SEQUENCE: 138
acgaggtgcg gcagaagtgc                                               20

<210> SEQ ID NO 139
<211> LENGTH: 20
<212> TYPE: DNA
<213> ORGANISM: Artificial Sequence
<220> FEATURE:
<223> OTHER INFORMATION: gRNA

<400> SEQUENCE: 139
tgcagagcgg ctggtgtacg                                               20

<210> SEQ ID NO 140
<211> LENGTH: 20
<212> TYPE: DNA
<213> ORGANISM: Artificial Sequence
<220> FEATURE:
<223> OTHER INFORMATION: gRNA

<400> SEQUENCE: 140
cagaagtgcc ggaacattga                                               20

<210> SEQ ID NO 141
<211> LENGTH: 20
<212> TYPE: DNA
<213> ORGANISM: Artificial Sequence
<220> FEATURE:
<223> OTHER INFORMATION: gRNA

<400> SEQUENCE: 141
ggcacattcc tccaacgaag                                               20

<210> SEQ ID NO 142
<211> LENGTH: 20
<212> TYPE: DNA
<213> ORGANISM: Artificial Sequence
<220> FEATURE:
<223> OTHER INFORMATION: gRNA

<400> SEQUENCE: 142
gcacattcct ccaacgaaga                                               20

<210> SEQ ID NO 143
<211> LENGTH: 20
<212> TYPE: DNA
<213> ORGANISM: Artificial Sequence
<220> FEATURE:
<223> OTHER INFORMATION: gRNA

<400> SEQUENCE: 143
gcgtaccagt acgacgacga                                               20

<210> SEQ ID NO 144
<211> LENGTH: 20
<212> TYPE: DNA
<213> ORGANISM: Artificial Sequence
<220> FEATURE:
```

<223> OTHER INFORMATION: gRNA

<400> SEQUENCE: 144
ggtagccgtc gtcgtcgtac                                               20

<210> SEQ ID NO 145
<211> LENGTH: 20
<212> TYPE: DNA
<213> ORGANISM: Artificial Sequence
<220> FEATURE:
<223> OTHER INFORMATION: gRNA

<400> SEQUENCE: 145
gcggaaacaa caactgctgc                                               20

<210> SEQ ID NO 146
<211> LENGTH: 20
<212> TYPE: DNA
<213> ORGANISM: Artificial Sequence
<220> FEATURE:
<223> OTHER INFORMATION: gRNA

<400> SEQUENCE: 146
cttcgctaat aaccacgacc                                               20

<210> SEQ ID NO 147
<211> LENGTH: 20
<212> TYPE: DNA
<213> ORGANISM: Artificial Sequence
<220> FEATURE:
<223> OTHER INFORMATION: gRNA

<400> SEQUENCE: 147
tgcgggcaca agggtaccta                                               20

<210> SEQ ID NO 148
<211> LENGTH: 20
<212> TYPE: DNA
<213> ORGANISM: Artificial Sequence
<220> FEATURE:
<223> OTHER INFORMATION: gRNA

<400> SEQUENCE: 148
tgctacatgt gcgggcacaa                                               20

<210> SEQ ID NO 149
<211> LENGTH: 20
<212> TYPE: DNA
<213> ORGANISM: Artificial Sequence
<220> FEATURE:
<223> OTHER INFORMATION: gRNA

<400> SEQUENCE: 149
ccgcacatgt agcagttcca                                               20

<210> SEQ ID NO 150
<211> LENGTH: 20
<212> TYPE: DNA
<213> ORGANISM: Artificial Sequence
<220> FEATURE:
<223> OTHER INFORMATION: gRNA

<400> SEQUENCE: 150
gcgggcacaa gggtacctac                                               20

```
<210> SEQ ID NO 151
<211> LENGTH: 20
<212> TYPE: DNA
<213> ORGANISM: Artificial Sequence
<220> FEATURE:
<223> OTHER INFORMATION: gRNA

<400> SEQUENCE: 151
cactcacaaa ttcctggtcg                                                   20

<210> SEQ ID NO 152
<211> LENGTH: 20
<212> TYPE: DNA
<213> ORGANISM: Artificial Sequence
<220> FEATURE:
<223> OTHER INFORMATION: gRNA

<400> SEQUENCE: 152
ggttattagc gaagaacatc                                                   20

<210> SEQ ID NO 153
<211> LENGTH: 20
<212> TYPE: DNA
<213> ORGANISM: Artificial Sequence
<220> FEATURE:
<223> OTHER INFORMATION: gRNA

<400> SEQUENCE: 153
gtacctacgg gctgctgcgg                                                   20

<210> SEQ ID NO 154
<211> LENGTH: 17
<212> TYPE: DNA
<213> ORGANISM: Artificial Sequence
<220> FEATURE:
<223> OTHER INFORMATION: gRNA

<400> SEQUENCE: 154
gcatgatgcg cggccca                                                      17

<210> SEQ ID NO 155
<211> LENGTH: 20
<212> TYPE: DNA
<213> ORGANISM: Artificial Sequence
<220> FEATURE:
<223> OTHER INFORMATION: gRNA

<400> SEQUENCE: 155
agaacaagcc catgattgaa                                                   20

<210> SEQ ID NO 156
<211> LENGTH: 20
<212> TYPE: DNA
<213> ORGANISM: Artificial Sequence
<220> FEATURE:
<223> OTHER INFORMATION: gRNA

<400> SEQUENCE: 156
aagaagtgta cacggacatg                                                   20

<210> SEQ ID NO 157
<211> LENGTH: 20
<212> TYPE: DNA
<213> ORGANISM: Artificial Sequence
<220> FEATURE:
<223> OTHER INFORMATION: gRNA
```

```
<400> SEQUENCE: 157
aaagccccgg aagagcacag                                                    20

<210> SEQ ID NO 158
<211> LENGTH: 20
<212> TYPE: DNA
<213> ORGANISM: Artificial Sequence
<220> FEATURE:
<223> OTHER INFORMATION: gRNA

<400> SEQUENCE: 158
agcggctggt gtacgaggtg                                                    20

<210> SEQ ID NO 159
<211> LENGTH: 20
<212> TYPE: DNA
<213> ORGANISM: Artificial Sequence
<220> FEATURE:
<223> OTHER INFORMATION: gRNA

<400> SEQUENCE: 159
acgaggtgcg gcagaagtgc                                                    20

<210> SEQ ID NO 160
<211> LENGTH: 17
<212> TYPE: DNA
<213> ORGANISM: Artificial Sequence
<220> FEATURE:
<223> OTHER INFORMATION: gRNA

<400> SEQUENCE: 160
gcatgatgcg cggccca                                                       17

<210> SEQ ID NO 161
<211> LENGTH: 19
<212> TYPE: DNA
<213> ORGANISM: Artificial Sequence
<220> FEATURE:
<223> OTHER INFORMATION: gRNA

<400> SEQUENCE: 161
agaagtgtac acggacatg                                                     19

<210> SEQ ID NO 162
<211> LENGTH: 835
<212> TYPE: DNA
<213> ORGANISM: Artificial Sequence
<220> FEATURE:
<223> OTHER INFORMATION: Artificial Sequence

<400> SEQUENCE: 162
aaggcacccg ctgggtcatg tggttcggag acggacattg aggctcccac aggagatgca        60
gatgtctgga aagcagaggg aggggatggg gtgagagtgc cagagttccc aggcaacaaa       120
cttaccctca atgttccggc acttctgccg cacctcgtac accagccgct ctgcaagggg       180
aggagagctg gcgtcagagg tgccacccct tccagaagca ggccaactac ctcttgtgcg       240
ctcatcaata atctccttga ccttgggctt ctccgctgtg ctcttccggg cttttttggc       300
tggtggaggt ggtgcgtagg cagctgcctc aggttccacc cacatgtccg tgtacacttc       360
tttgtaggga ttcttctctt ctggaggagg aaagcaggtg ccaaggtcag ggtcccagaa       420
agctgggtgc cctcatttac cttctggtgg ctccaggccc ttagggccag aaggctggaa       480 gcccccagg gcccattcaa tcatgggctt gttctgcacc tccacggcct tggcagtgtc        540
```

```
actctcatcg ctgtcgtggc acaccgggaa cagcttcccc gcgcggctgc tggccacctg      600
gagggtgaca cgccagggtt ggggttgctc ctccgagctc ccagcaggga cactcacctg      660
caggacctcg tagatggctt tgcggtacat gggctgcttg ttgtacgtgg cctggtggaa      720
cgcactgcaa aacgagctca gcggcatcag cttctcaaca cacacctggg gggacaagcc      780
aggccttgtt tgccgcccag gctactgcca aaccccacaa cttaccactg agaat          835
```

<210> SEQ ID NO 163
<211> LENGTH: 2082
<212> TYPE: DNA
<213> ORGANISM: Artificial Sequence
<220> FEATURE:
<223> OTHER INFORMATION: Artificial Sequence

<400> SEQUENCE: 163

```
ggggttgggg ttgcgccttt tccaaggcag ccctgggttt gcgcagggac gcggctgctc       60
tgggcgtggt tccgggaaac gcagcggcgc cgaccctggg tctcgcacat tcttcacgtc      120
cgttcgcagc gtcacccgga tcttcgccgc tacccttgtg ggccccccgg cgacgcttcc      180
tgctccgccc ctaagtcggg aaggttcctt gcggttcgcg gcgtgccgga cgtgacaaac      240
ggaagccgca cgtctcacta gtaccctcgc agacggacag cgccagggag caatggcagc      300
gcgccgaccg cgatgggctg tggccaatag cggctgctca gcaggcgcg ccgagagcag       360 cggccgggaa ggggcggtgc gggaggcggg gtgtggggcg gtagtgtggg ccctgttcct      420 gcccgcgcg tgttccgcat tctgcaagcc tccgagcgc acgtcggcag tcggctccct        480
cgttgaccga atcaccgacc tctctcccca gggggatcat cgaattacct ctagagccac      540
catggtgagc aagggcgagg agctgttcac cggggtggtg cccatcctgg tcgagctgga      600
cggcgacgta aacggccaca gttcagcgt gtccggcgag ggcgagggcg atgccaccta      660
cggcaagctg accctgaagt tcatctgcac caccggcaag ctgcccgtgc cctggcccac      720
cctcgtgacc accctgacct acggcgtgca gtgcttcagc cgctaccccg accacatgaa      780
gcagcacgac ttcttcaagt ccgccatgcc cgaaggctac gtccaggagc gcaccatctt      840
cttcaaggac gacggcaact acaagacccg cgccgaggtg aagttcgagg gcgacaccct      900
ggtgaaccgc atcgagctga agggcatcga cttcaaggag gacggcaaca tcctggggca      960
caagctggag tacaactaca acagccacaa cgtctatatc atggccgaca gcagaagaa     1020 cggcatcaag gtgaacttca gatccgcca caacatcgag gacggcagcg tgcagctcgc     1080
cgaccactac cagcagaaca cccccatcgg cgacggcccc gtgctgctgc ccgacaacca     1140
ctacctgagc acccagtccg ccctgagcaa agaccccaac gagaagcgcg atcacatggt     1200
cctgctggag ttcgtgaccg ccgccgggat cactctcggc atggacgagc tgtacaagta     1260
agtcgacatc aacctctgga ttacaaaatt tgtgaaagat tgactggtat tcttaactat     1320
gttgctcctt ttacgctatg tggatacgct gctttaatgc ctttgtatca tgctattgct     1380
tcccgtatgg ctttcatttt ctcctccttg tataaatcct ggttgctgtc tctttatgag     1440
gagttgtggc ccgttgtcag gcaacgtggc gtggtgtgca ctgtgtttgc tgacgcaacc     1500
cccactggtt ggggcattgc caccacctgt cagctccttt ccgggacttt cgctttcccc     1560
ctccctattg ccacggcgga actcatcgcc gcctgccttg cccgctgctg acaggggct      1620 cggctgttgg gcactgacaa ttccgtggtg ttgtcgggga agctgacgtc ctttccttgg     1680
ctgctcgcct gtgttgccac ctggattctg cgcgggacgt ccttctgcta cgtcccttcg     1740
```

```
gccctcaatc cagcggacct tccttcccgc ggcctgctgc cggctctgcg gcctcttccg    1800
cgtcttcgcc ttcgccctca gacgagtcgg atctcccttt gggccgcctc cccgcctgct    1860
gtgccttcta gttgccagcc atctgttgtt tgcccctccc ccgtgccttc cttgaccctg    1920
gaaggtgcca ctcccactgt cctttcctaa taaaatgagg aaattgcatc gcattgtctg    1980
agtaggtgtc attctattct gggggtggg gtggggcagg acagcaaggg ggaggattgg     2040
gaagacaata gcaggcatgc tggggatgcg gtgggctcta tg                       2082

<210> SEQ ID NO 164
<211> LENGTH: 834
<212> TYPE: DNA
<213> ORGANISM: Artificial Sequence
<220> FEATURE:
<223> OTHER INFORMATION: Artificial Sequence

<400> SEQUENCE: 164
gacccagcgg gtgccttcag ctgctcggct ccggcccgtc atccaccaag acacaatgcg      60
gcctggccac caggagaagc cccgcagttt cccccacacc agctccccaa tgccaaagcc     120
ccggccgtcc tggagcccca aggagcagaa atcattacac tggccacggc tggtgaagaa     180
gccgctcacc tcgtactctg gctcgtcatc gcctgctttg gtggcattct gtccccagc     240 atcggacccc acgggctcag gcgtggtagc cacagtgggg gatgcggggt cagtgggctg     300
ctgcacagca ggagggctgg cctcctccac cttctgagac tccccgggcc cctggttttc     360
ttccacagca ttcattcctg caatgacctt ggctttcttc tcagcctggg gaaacaaaaa     420
acaaaaagtc accttggctg gggcccaggc cagaaggcgc ctcacctccc ttttccagcg     480
tgccagccac tcgtcccgct tgcgcttgct gatgtagtag gggtccccg cctggaaggt      540 gagcctcggc atgggccgct gacggaggct ggactcccag cccaagccac cccgcagccg    600
gccccgggag ccctaggaca gagagacaga cattagggca ttccacagag cccctggggg    660
tggaacactt gcctccattt tcatggattc gatgttggtc tccttctgtt ctttgcctgt    720
ggagagggaa gaacaaaggg accagtaaga ggctgcccct ggtgctgagg actcacccgc    780
ttctgcaggg gctcctcggc ccgtctccga accacatgac ccagcgggtg cctt          834

<210> SEQ ID NO 165
<211> LENGTH: 3759
<212> TYPE: DNA
<213> ORGANISM: Artificial Sequence
<220> FEATURE:
<223> OTHER INFORMATION: Artificial Sequence

<400> SEQUENCE: 165
aaggcacccg ctgggtcatg tggttcggag acggacattg aggctcccac aggagatgca      60
gatgtctgga aagcagaggg aggggatggg gtgagagtgc cagagttccc aggcaacaaa    120
cttaccctca atgttccggc acttctgccg cacctcgtac accagccgct ctgcaagggg    180
aggagagctg gcgtcagagg tgccaccctc tccagaagca ggccaactac ctcttgtgcg    240
ctcatcaata atctccttga ccttgggctt ctccgctgtg ctcttccggg gcttttttggc   300 tggtggaggt ggtgcgtagg cagctgcctc aggttccacc cacatgtccg tgtacacttc     360
tttgtaggga ttcttctctt ctggaggagg aaagcaggtg ccaaggtcag ggtcccagaa     420
agctgggtgc cctcatttac cttctggtgg ctccaggccc ttagggccag aaggctggaa     480 gcccccagg gccattcaa tcatgggctt gttctgcacc tccacggcct tggcagtgtc      540
actctcatcg ctgtcgtggc acaccgggaa cagcttcccc gcgcggctgc tggccacctg    600
```

-continued

```
gagggtgaca cgccagggtt ggggttgctc ctccgagctc ccagcaggga cactcacctg      660
caggacctcg tagatggctt tgcggtacat gggctgcttg ttgtacgtgg cctggtggaa      720
cgcactgcaa aacgagctca gcggcatcag cttctcaaca cacacctggg gggacaagcc      780
aggccttgtt tgccgcccag gctactgcca aaccccacaa cttaccactg agaatgcgat      840
cgcggggttg gggttgcgcc ttttccaagg cagccctggg tttgcgcagg acgcggctg      900 ctctgggcgt ggttccggga aacgcagcgg cgccgaccct gggtctcgca cattcttcac      960
gtccgttcgc agcgtcaccc ggatcttcgc cgctacccct gtgggccccc cggcgacgct     1020
tcctgctccg cccctaagtc gggaaggttc cttgcggttc gcggcgtgcc ggacgtgaca     1080
aacggaagcc gcacgtctca ctagtaccct cgcagacgga cagcgccagg gagcaatggc     1140
agcgcgccga ccgcgatggg ctgtggccaa tagcggctgc tcagcagggc gcgccgagag     1200
cagcggccgg gaaggggcgg tgcgggaggc ggggtgtggg gcggtagtgt gggccctgtt     1260
cctgcccgcg cggtgttccg cattctgcaa gcctccggag cgcacgtcgg cagtcggctc     1320
cctcgttgac cgaatcaccg acctctctcc caggggat catcgaatta cctctagagc     1380
caccatggtg agcaagggcg aggagctgtt caccggggtg gtgcccatcc tggtcgagct     1440
ggacggcgac gtaaacggcc acaagttcag cgtgtccggc gagggcgagg gcgatgccac     1500
ctacggcaag ctgaccctga agttcatctg caccaccggc aagctgcccg tgccctggcc     1560 cacccctcgtg accaccctga cctacggcgt gcagtgcttc agccgctacc ccgaccacat     1620
gaagcagcac gacttcttca gtccgccat gcccgaaggc tacgtccagg agcgcaccat     1680
cttcttcaag gacgacggca actacaagac ccgcgccgag gtgaagttcg agggcgacac     1740
cctggtgaac cgcatcgagc tgaagggcat cgacttcaag gaggacggca acatcctggg     1800
gcacaagctg gagtacaact acaacagcca caacgtctat atcatggccg acaagcagaa     1860
gaacggcatc aaggtgaact tcaagatccg ccacaacatc gaggacggca gcgtgcagct     1920
cgccgaccac taccagcaga acacccccat cggcgacggc cccgtgctgc tgcccgacaa     1980
ccactacctg agcacccagt ccgccctgag caaagacccc aacgagaagc gcgatcacat     2040
ggtcctgctg gagttcgtga ccgccgccgg gatcactctc ggcatggacg agctgtacaa     2100
gtaagtcgac atcaacctct ggattacaaa atttgtgaaa gattgactgg tattcttaac     2160
tatgttgctc cttttacgct atgtggatac gctgctttaa tgcctttgta tcatgctatt     2220
gcttcccgta tggctttcat tttctcctcc ttgtataaat cctggttgct gtctctttat     2280
gaggagttgt ggcccgttgt caggcaacgt ggcgtggtgt gcactgtgtt tgctgacgca     2340
acccccactg gttggggcat tgccaccacc tgtcagctcc tttccgggac tttcgctttc     2400
cccctcccta ttgccacggc ggaactcatc gccgcctgcc ttgcccgctg ctggacaggg     2460
gctcggctgt tgggcactga caattccgtg gtgttgtcgg ggaagctgac gtcctttcct     2520
tggctgctcg cctgtgttgc cacctggatt ctgcgcggga cgtccttctg ctacgtccct     2580
tcggccctca atccagcgga ccttccttcc cgcggcctgc tgccggctct gcggcctctt     2640
ccgcgtcttc gccttcgccc tcagacgagt cggatctccc tttgggccgc ctccccgcct     2700
gctgtgcctt ctagttgcca gccatctgtt gtttgcccct cccccgtgcc ttccttgacc     2760
ctggaaggtg ccactcccac tgtcctttcc taataaaatg aggaaattgc atcgcattgt     2820
ctgagtaggt gtcattctat tctgggggggt ggggtggggc aggacagcaa ggggaggat     2880 tgggaagaca atagcaggca tgctggggat gcggtgggct ctatggaccc agcgggtgcc     2940
```

```
ttcagctgct cggctccggc ccgtcatcca ccaagacaca atgcggcctg gccaccagga    3000 gaagcccgc agtttccccc acaccagctc cccaatgcca aagccccggc cgtcctggag    3060
ccccaaggag cagaaatcat tacactggcc acggctggtg aagaagccgc tcacctcgta    3120
ctctggctcg tcatcgcctg ctttggtggc attcttgtcc ccagcatcgg accccacggg    3180
ctcaggcgtg gtagccacag tgggggatgc ggggtcagtg ggctgctgca cagcaggagg    3240
gctggcctcc tccaccttct gagactcccc gggccctgg tttcttcca cagcattcat    3300 tcctgcaatg accttggctt tcttctcagc ctggggaaac aaaaaacaaa aagtcacctt    3360
ggctggggcc caggccagaa ggcgcctcac ctcccttttc cagcgtgcca gccactcgtc    3420
ccgcttgcgc ttgctgatgt agtaggggtc ccccgcctgg aaggtgagcc tcggcatggg    3480
ccgctgacgg aggctggact cccagcccaa gccacccgc agccggcccc gggagccccta    3540 ggacagagag acagacatta gggcattcca cagagcccct ggggtggaa cacttgcctc    3600 cattttcatg gattcgatgt tggtctcctt ctgttctttg cctgtggaga gggaagaaca    3660
aagggaccag taagaggctg cccctggtgc tgaggactca cccgcttctg caggggctcc    3720
tcggcccgtc tccgaaccac atgacccagc gggtgcctt                           3759
```